United States Patent
Mestas

(10) Patent No.: US 9,943,724 B2
(45) Date of Patent: *Apr. 17, 2018

(54) ACTIVITY MONITORING, TRACKING AND SYNCHRONIZATION

(71) Applicant: NIKE, Inc., Beaverton, OR (US)

(72) Inventor: Alex Mestas, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/605,503

(22) Filed: May 25, 2017

(65) Prior Publication Data

US 2017/0259116 A1    Sep. 14, 2017

Related U.S. Application Data

(63) Continuation of application No. 14/186,425, filed on Feb. 21, 2014, now Pat. No. 9,682,281.

(60) Provisional application No. 61/768,279, filed on Feb. 22, 2013.

(51) Int. Cl.
  *G06F 19/00*   (2011.01)
  *A63B 24/00*   (2006.01)
  *A61B 5/11*    (2006.01)

(52) U.S. Cl.
  CPC ...... *A63B 24/0062* (2013.01); *G06F 19/3481* (2013.01); *A61B 5/1118* (2013.01)

(58) Field of Classification Search
  CPC ... A63B 220/10; A63B 220/20; A63B 220/30; A63B 220/40; A63B 220/50; A63B 220/62; A63B 220/80; A63B 220/836
  USPC .......................... 463/36, 42; 700/91
  See application file for complete search history.

(56) References Cited

U.S. PATENT DOCUMENTS

| | | | | |
|---|---|---|---|---|
| 4,371,945 A | * | 2/1983 | Karr | G01C 22/006 235/105 |
| 4,408,183 A | * | 10/1983 | Wills | G08B 5/36 340/323 R |
| 6,018,705 A | * | 1/2000 | Gaudet | A61B 5/1121 235/105 |
| 6,032,108 A | * | 2/2000 | Seiple | A63B 24/0021 702/158 |
| 6,305,221 B1 | * | 10/2001 | Hutchings | A63B 24/00 73/488 |
| 6,356,856 B1 | * | 3/2002 | Damen | A43B 3/00 482/3 |

(Continued)

FOREIGN PATENT DOCUMENTS

| | | |
|---|---|---|
| CN | 101713660 A | 5/2010 |
| JP | 2009517168 A | 4/2009 |

(Continued)

OTHER PUBLICATIONS

Jul. 3, 2014(WO)—ISR and WO—App. No. PCT/US2014/017665.
Jul. 3, 2014—(EP)—Search Report—App. No. 14156267.8.

*Primary Examiner* — Michael Cuff
(74) *Attorney, Agent, or Firm* — Banner & Witcoff, Ltd.

(57) ABSTRACT

A physical activity monitoring method and system may include a competition component requiring users to compete based on various metrics. The challenge may be device-specific, activity type-specific, user-type specific and the like. In some examples, the users' performance might only affect the status of the competition if the user synchronizes the information to an activity monitoring system.

16 Claims, 171 Drawing Sheets

(56) References Cited

U.S. PATENT DOCUMENTS

| | | | |
|---|---|---|---|
| 6,585,622 B1* | 7/2003 | Shum | A63B 24/0084 482/8 |
| 7,107,180 B2* | 9/2006 | Karason | A61B 5/1038 702/160 |
| 7,519,327 B2* | 4/2009 | White | A63B 24/0021 455/41.1 |
| 7,532,977 B2* | 5/2009 | Chen | G01C 17/02 342/357.57 |
| 7,698,101 B2* | 4/2010 | Alten | A43B 3/0005 340/5.8 |
| 7,827,000 B2* | 11/2010 | Stirling | A61B 5/1038 702/141 |
| 7,831,199 B2* | 11/2010 | Ng | H04L 67/06 455/3.01 |
| 7,841,966 B2* | 11/2010 | Aaron | A63B 24/0006 482/8 |
| 7,927,253 B2* | 4/2011 | Vincent | A63B 24/0021 482/1 |
| 8,028,443 B2* | 10/2011 | Case, Jr. | A43B 1/0036 36/132 |
| 8,073,984 B2* | 12/2011 | Lydon | G06F 1/3209 710/10 |
| 8,360,904 B2* | 1/2013 | Oleson | A63B 24/0062 463/36 |
| 8,652,009 B2* | 2/2014 | Ellis | A61B 5/1038 482/1 |
| 8,702,430 B2* | 4/2014 | Dibenedetto | G06F 19/3418 434/247 |
| 8,827,815 B2* | 9/2014 | Burroughs | G06F 19/3481 463/1 |
| 9,415,265 B2* | 8/2016 | Aaron | A63B 24/0006 |
| 2007/0100595 A1* | 5/2007 | Earles | G06Q 30/02 703/13 |
| 2013/0238106 A1* | 9/2013 | Ellis | A61B 5/1038 700/91 |

FOREIGN PATENT DOCUMENTS

| | | |
|---|---|---|
| KR | 20090132019 A | 12/2009 |
| WO | 2009021147 A1 | 2/2009 |
| WO | 2012061438 A2 | 5/2012 |
| WO | 2012161768 A1 | 11/2012 |

* cited by examiner

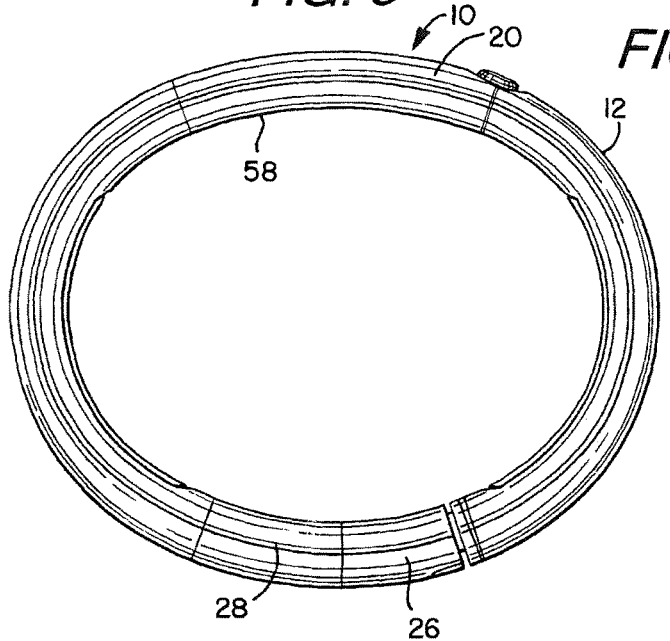
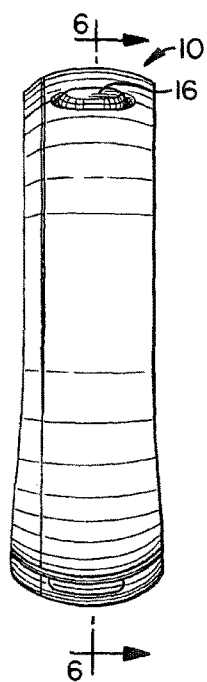
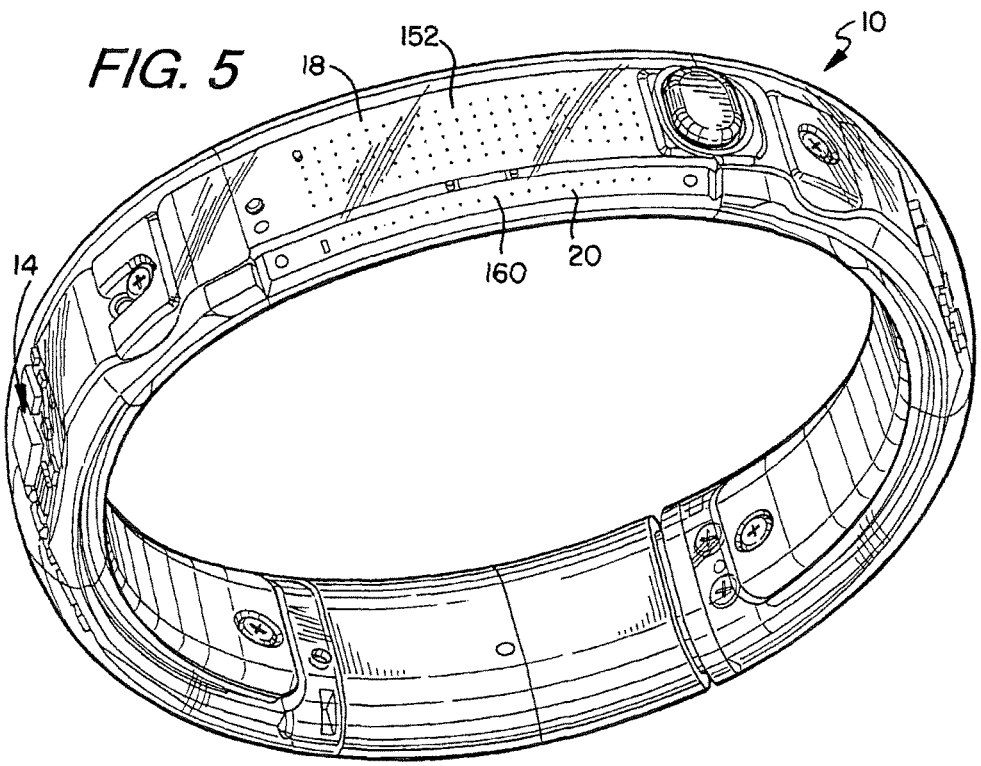

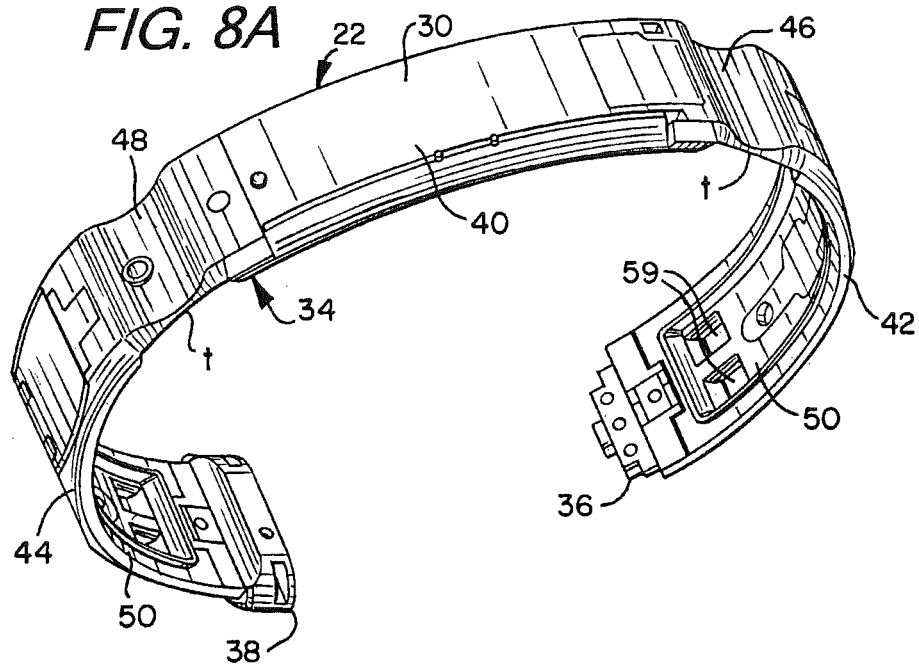
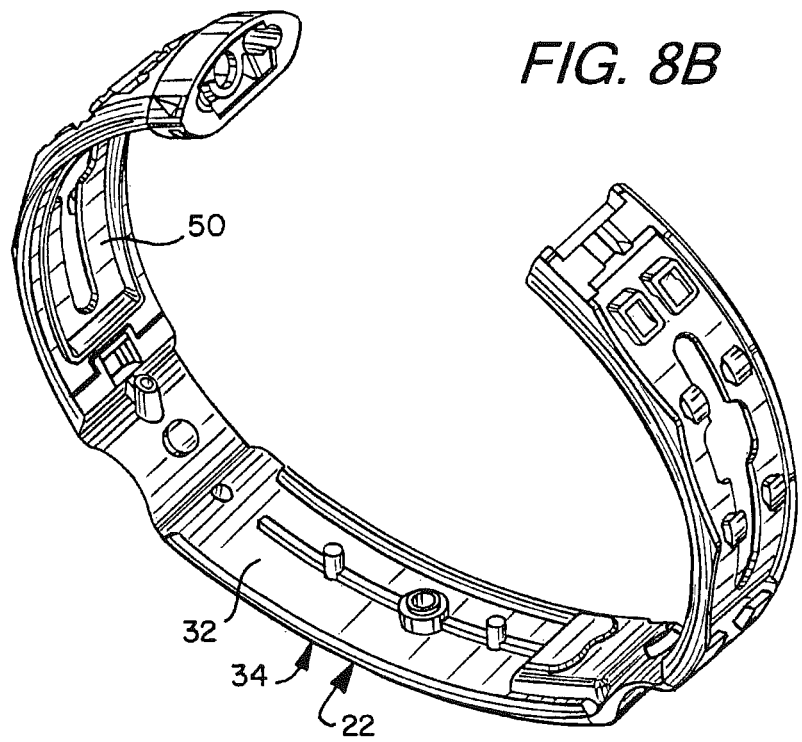

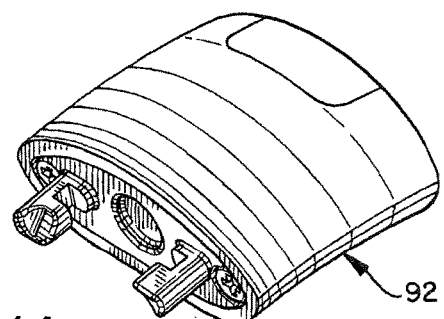
FIG. 11A
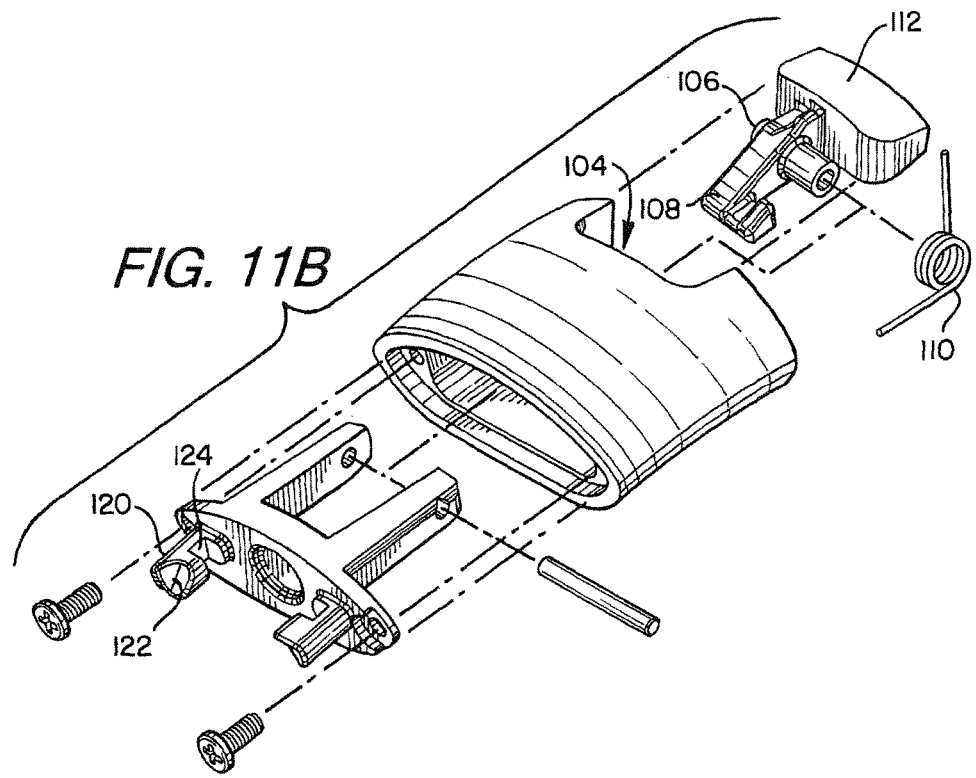
FIG. 11B
FIG. 11C
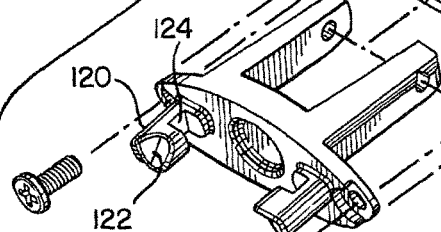
FIG. 11D
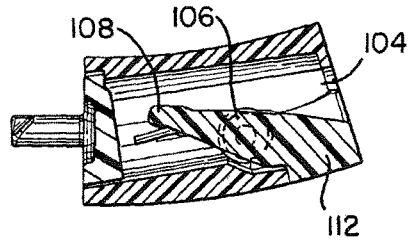

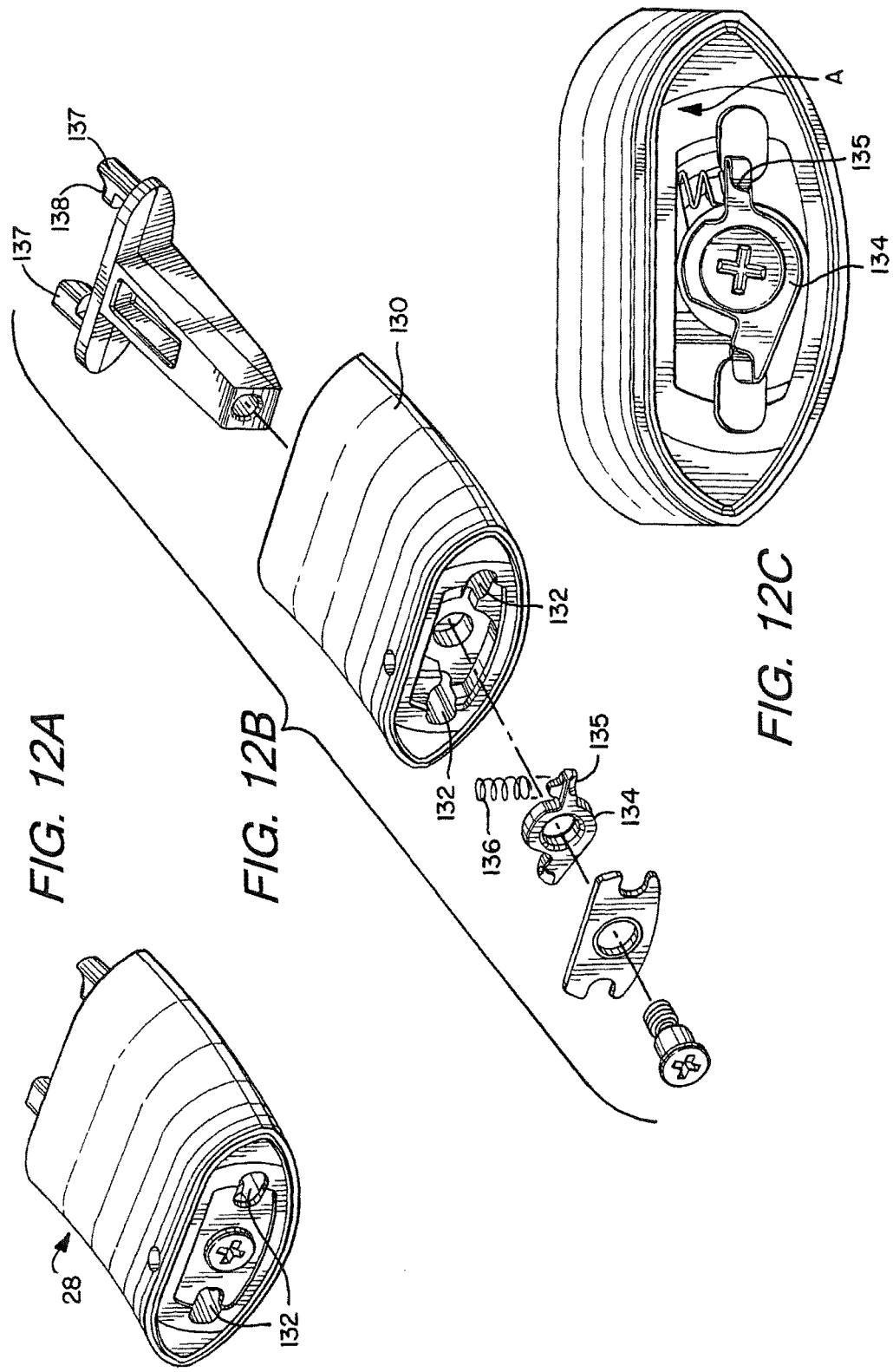

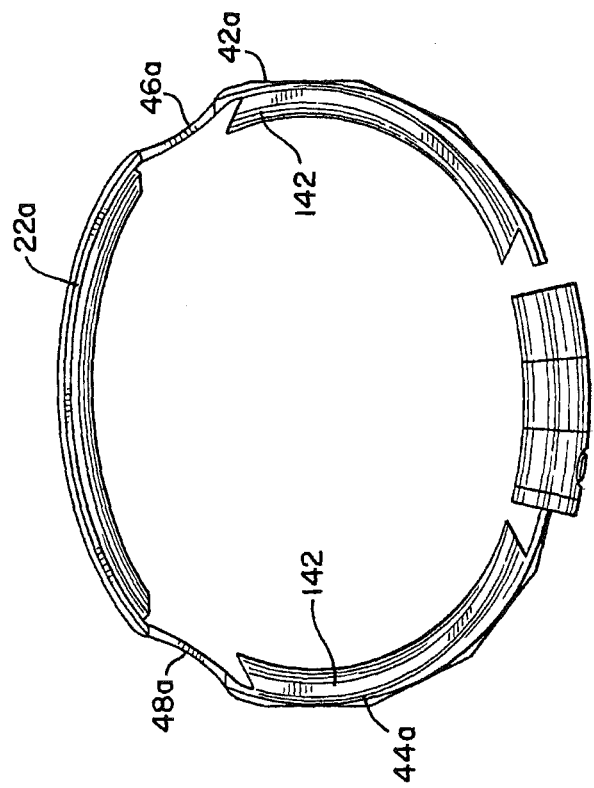
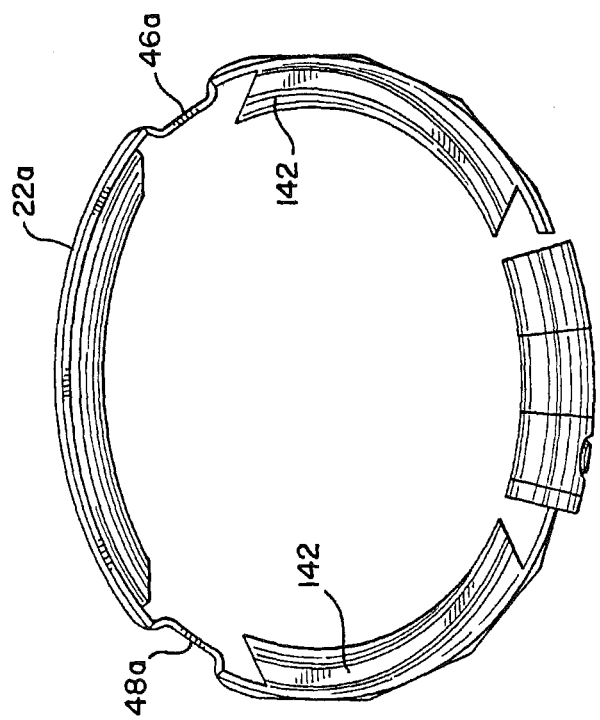

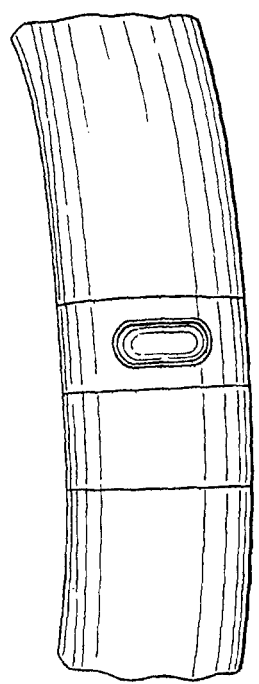
FIG. 34B
FIG. 34A

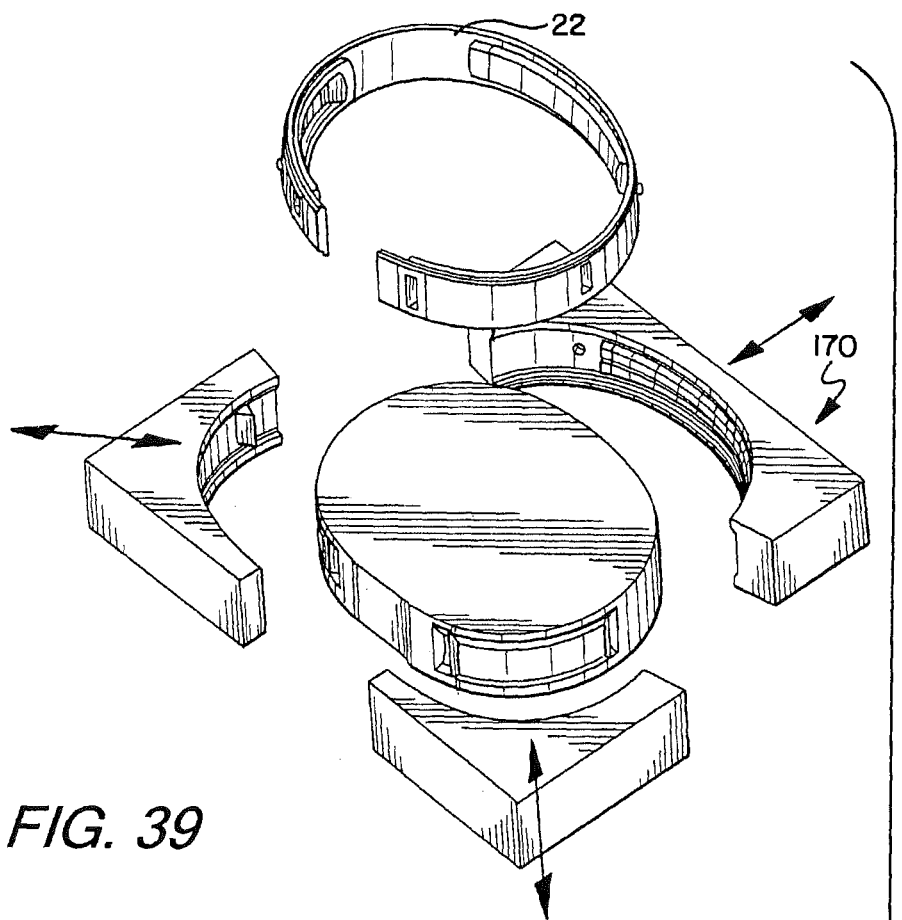
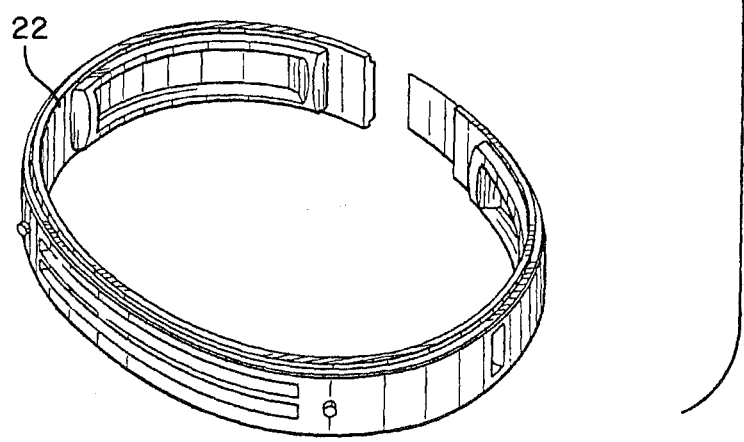
FIG. 39

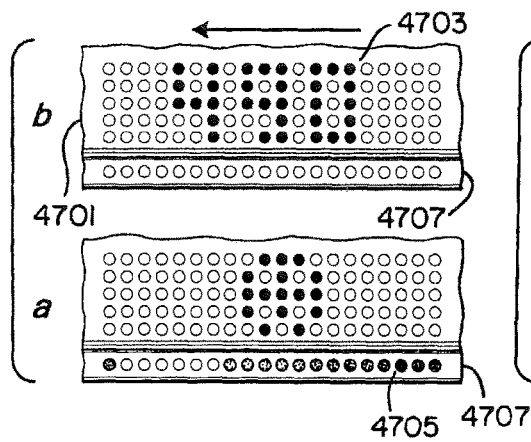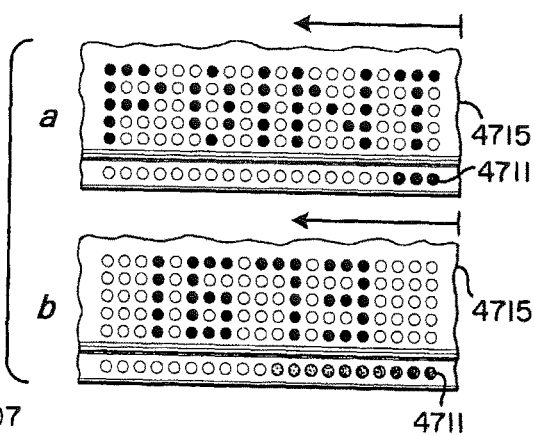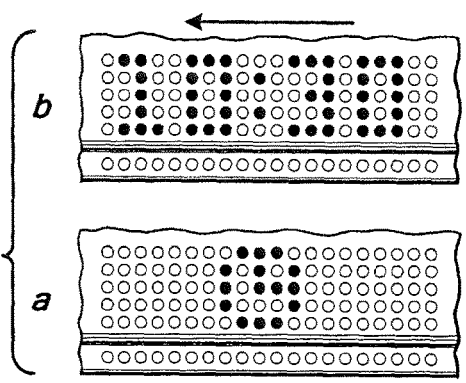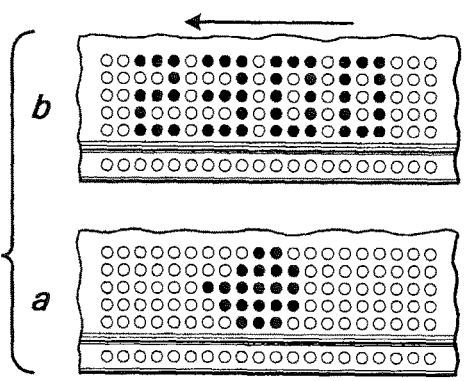

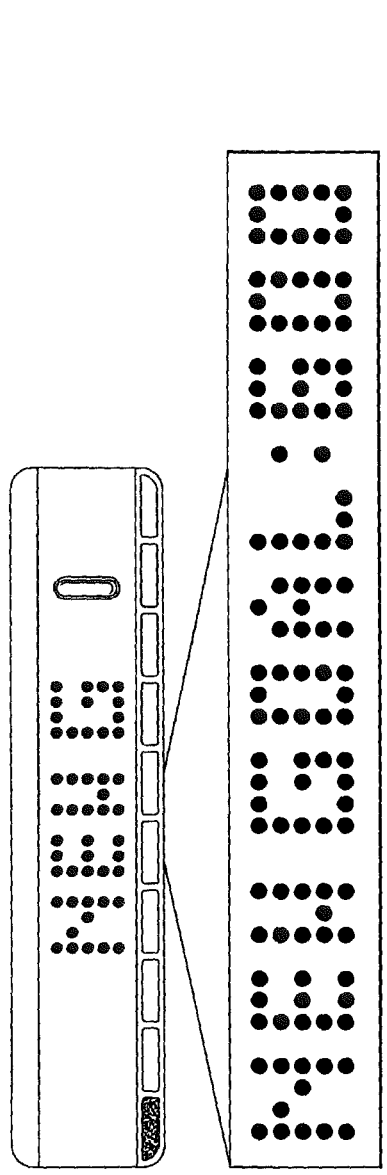
FIG. 55
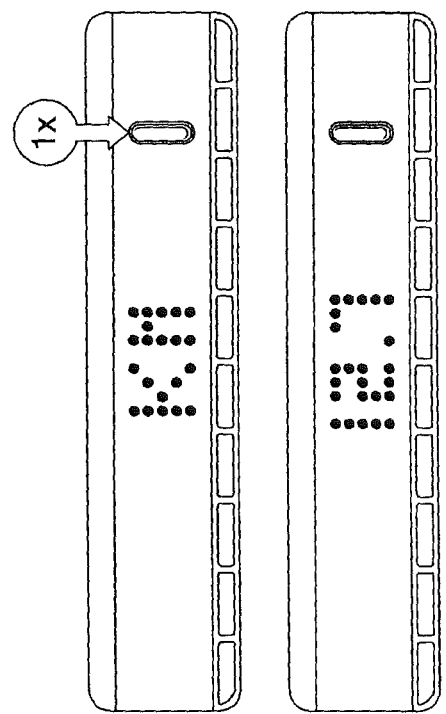
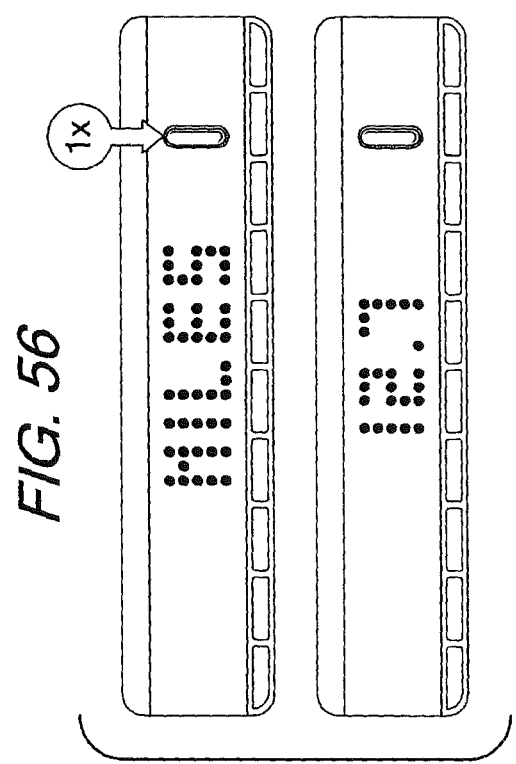
FIG. 56

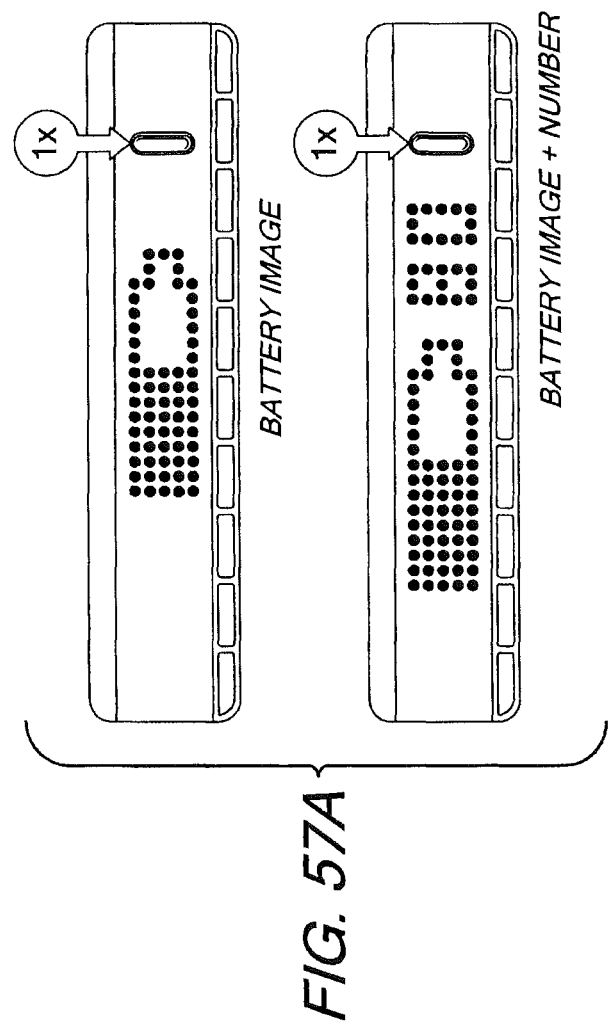

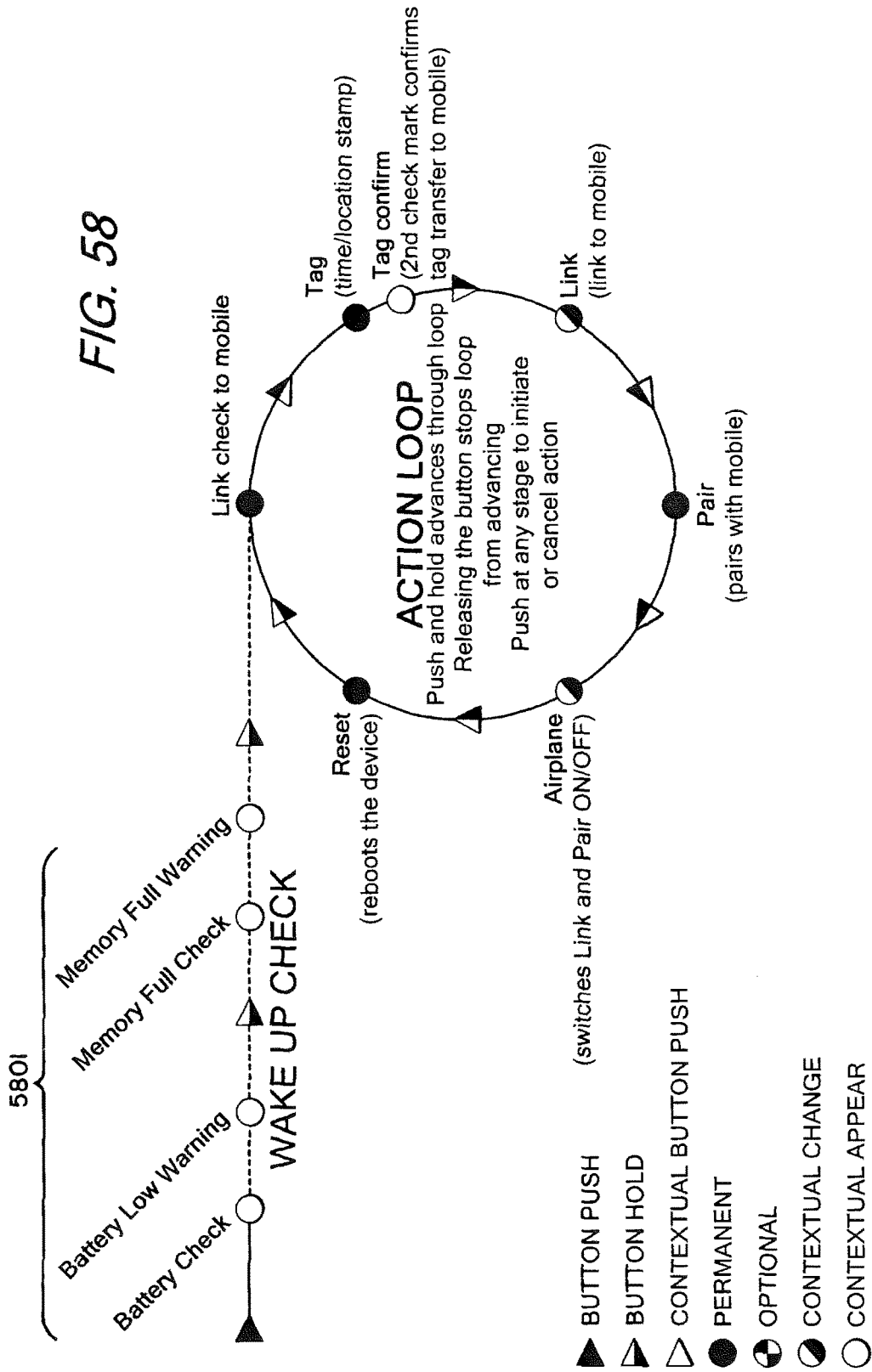

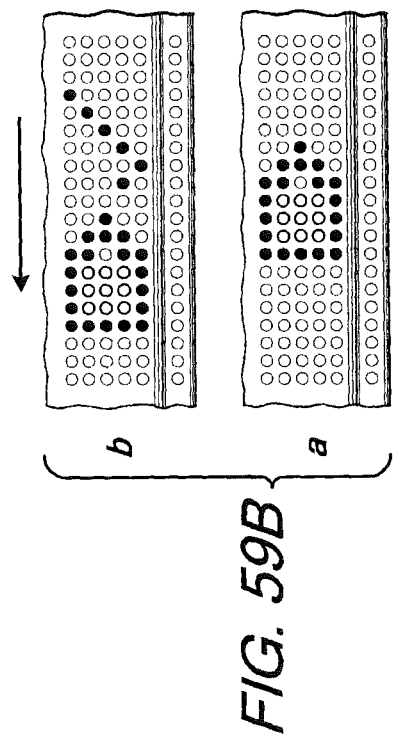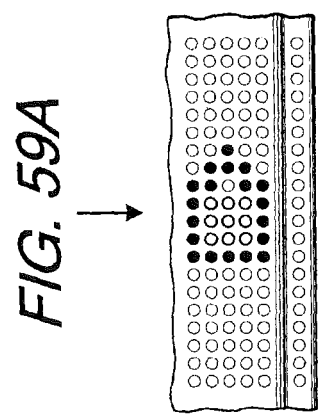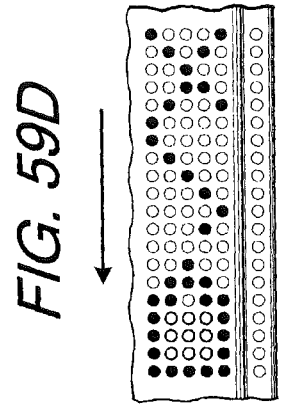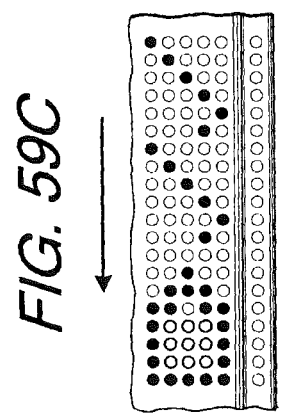

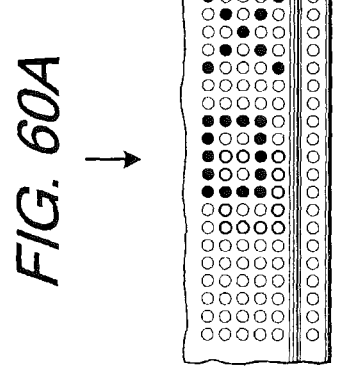
FIG. 60A
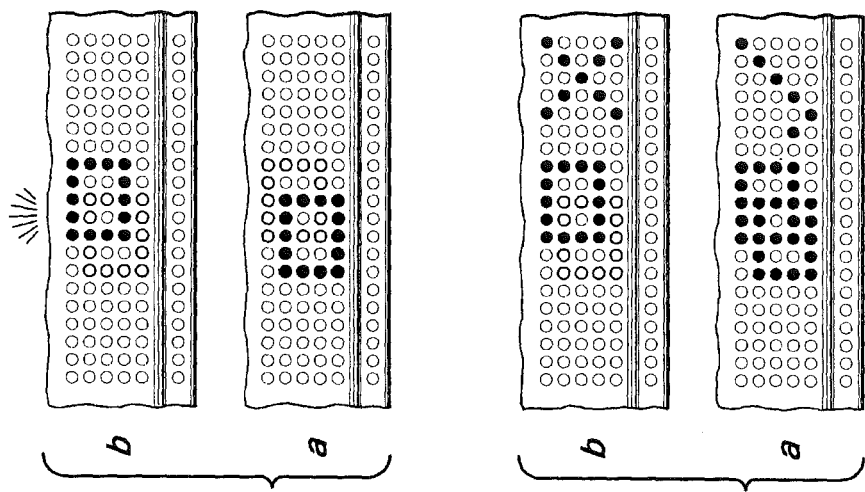
FIG. 60C
FIG. 60D
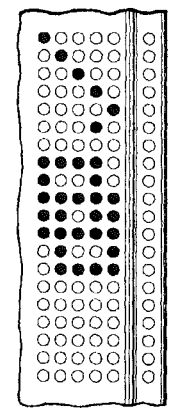
FIG. 60B

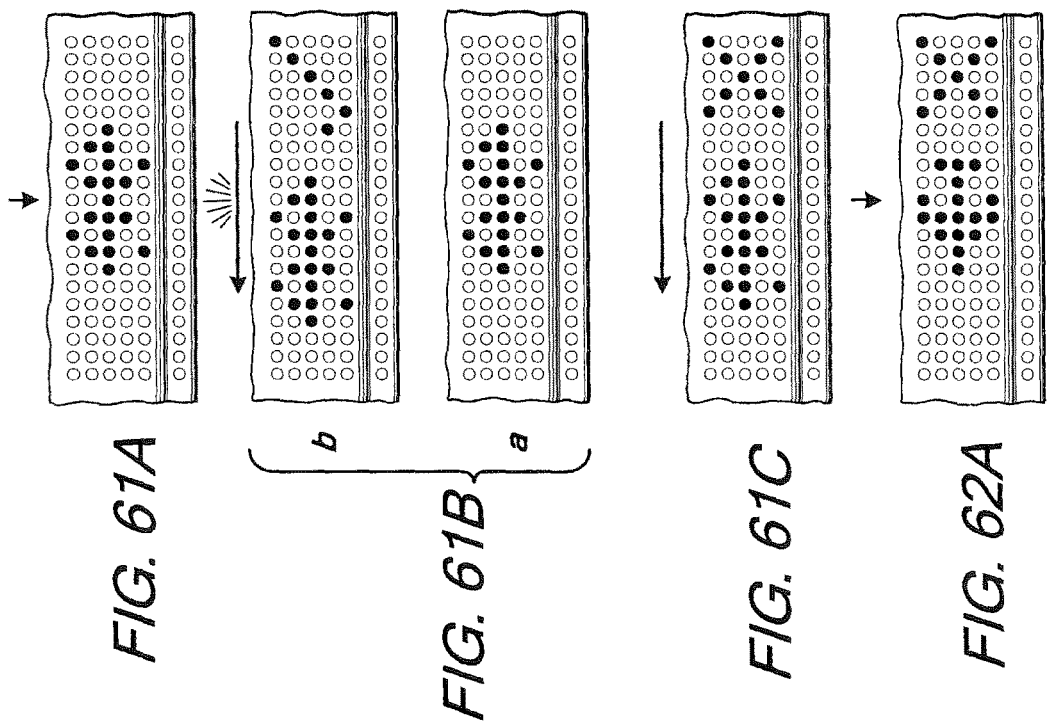
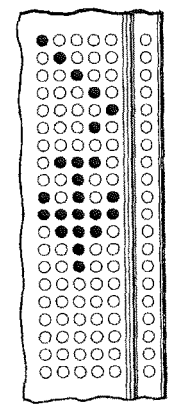
FIG. 61A  FIG. 61B  FIG. 61C  FIG. 62A  FIG. 62B

[opponent name replaces "tug of war" game title]

[scroll left to show game score]

[scroll to left]

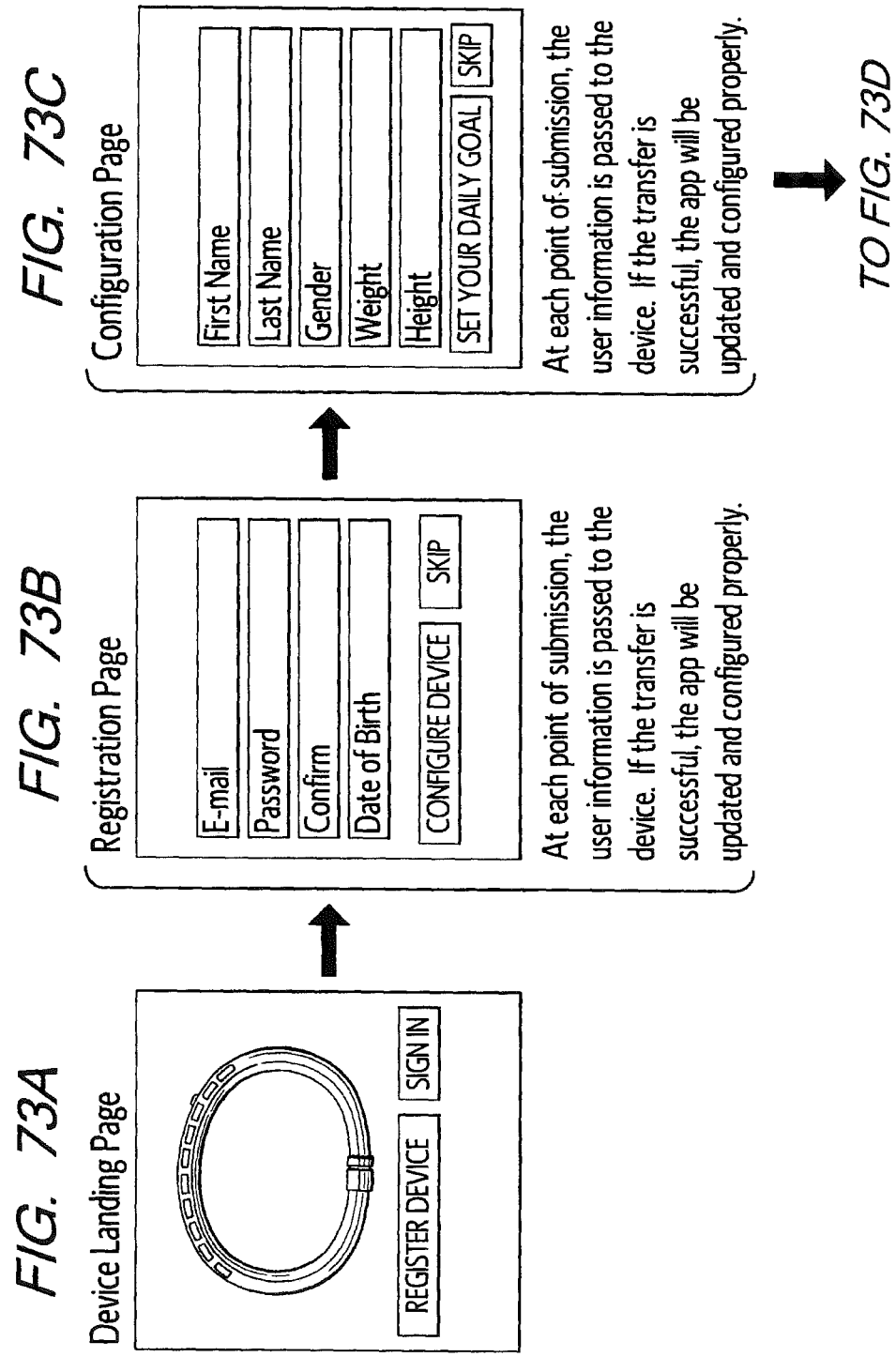

FIG. 73E
Display Setup
- ☐ Steps
- ☐ Calories
- ☐ Distance
- ☑ Daily Goal
- ☐ Play (games)
- ☐ Battery

[SAVE SETTINGS] [SKIP]

At each point of submission, the user information is passed to the device. If the transfer is successful, the app will be updated and configured properly.

FIG. 73G
Device Dashboard

Device Name

FIG. 73D
FROM FIG. 73C

Daily Goal Setup

My goal is to earn
[300]
points each day

[CUSTOMIZE DISPLAY] [SKIP]

At each point of submission, the user information is passed to the device. If the transfer is successful, the app will be updated and configured properly.

FIG. 73F
Setup Complete Page

You're ready to go
- ∿ Track your progress
- ○ Earn rewards
- ⩙ Find friends & rivals

[VIEW MY DASHBOARD]

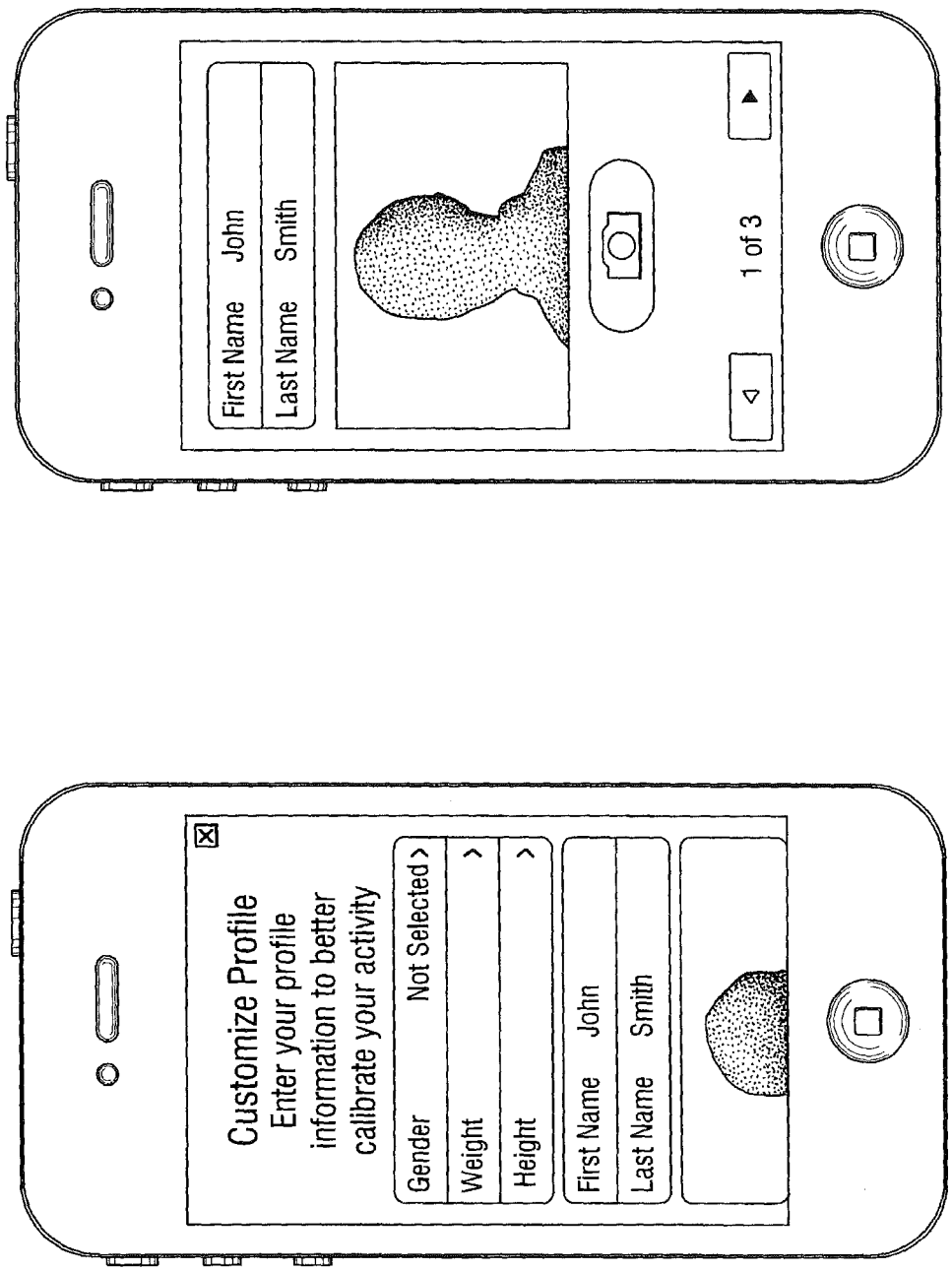

READY TO GO MESSAGE

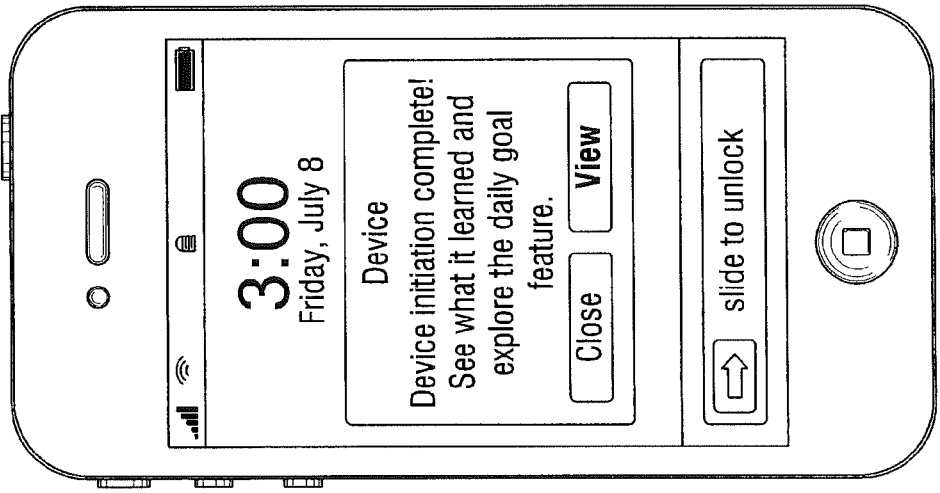
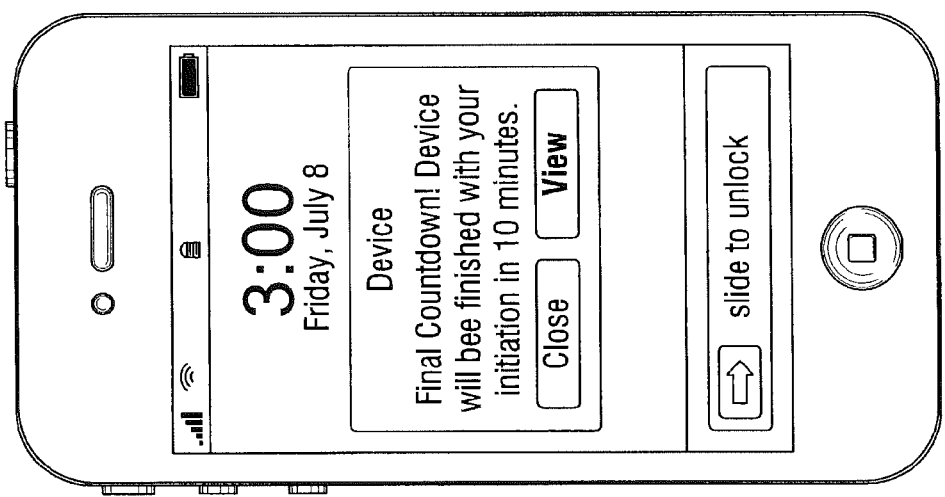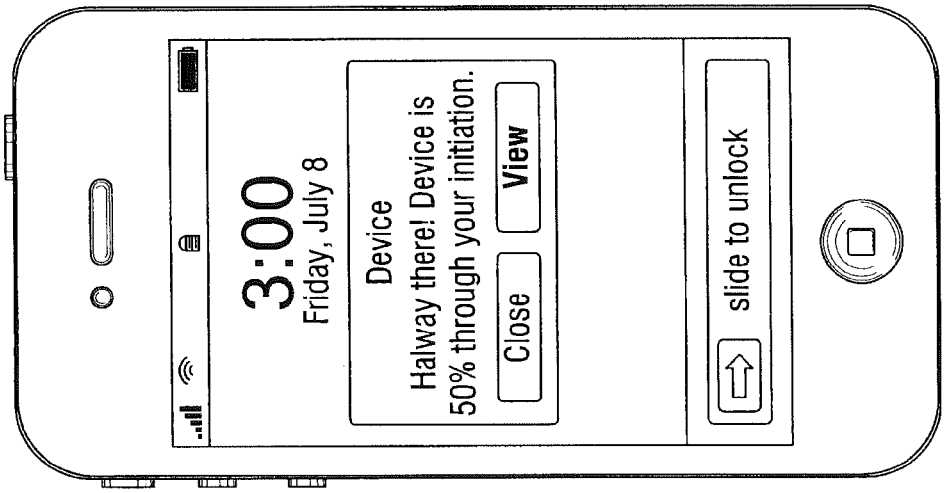

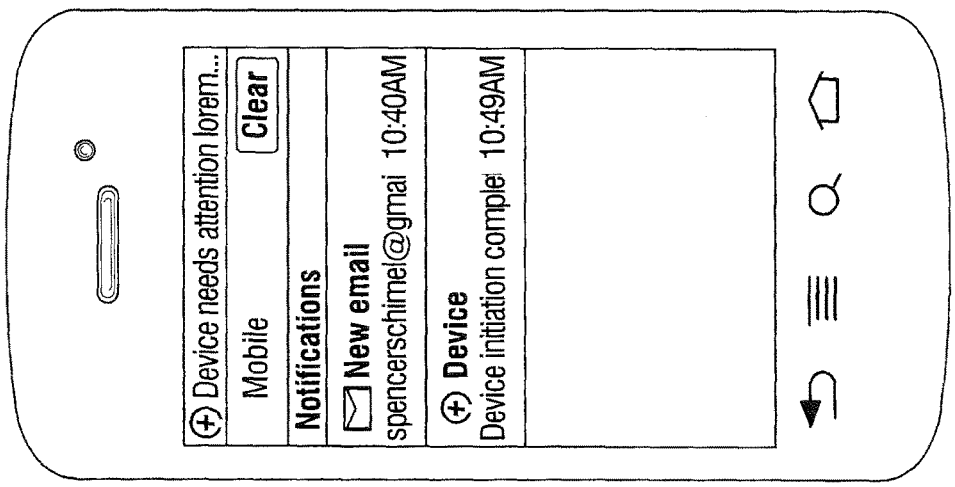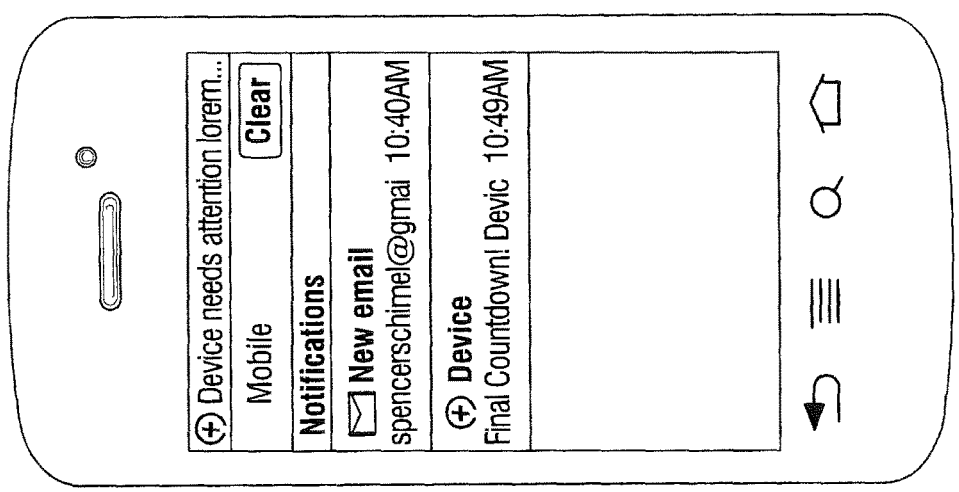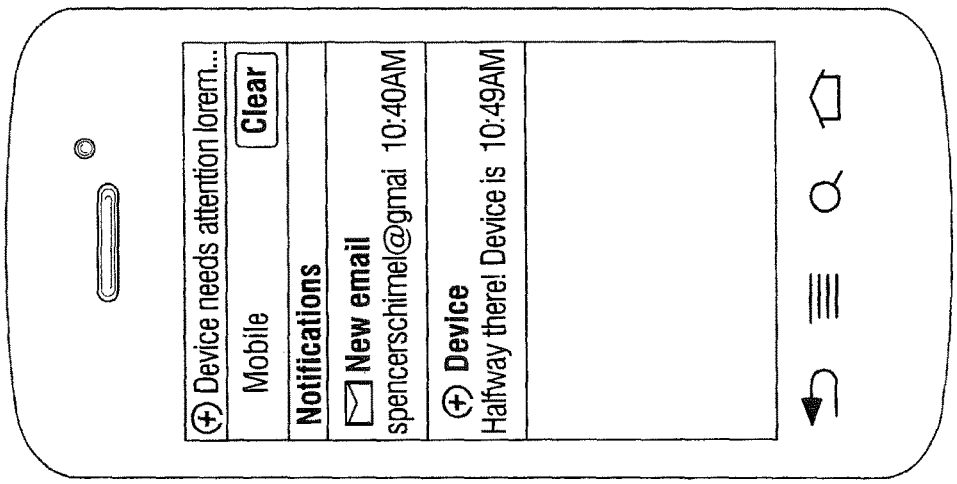

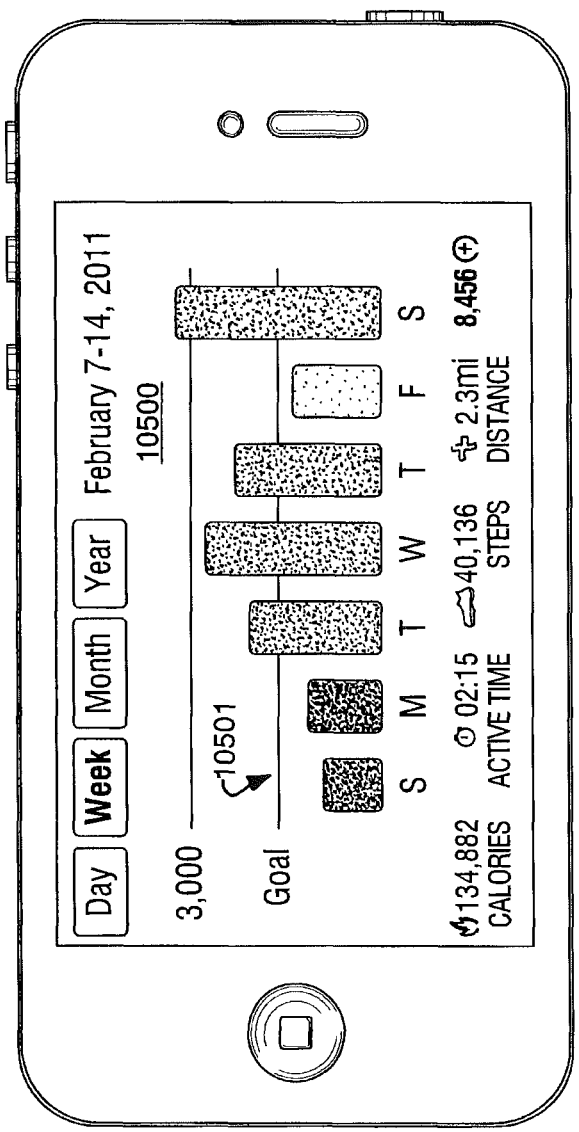

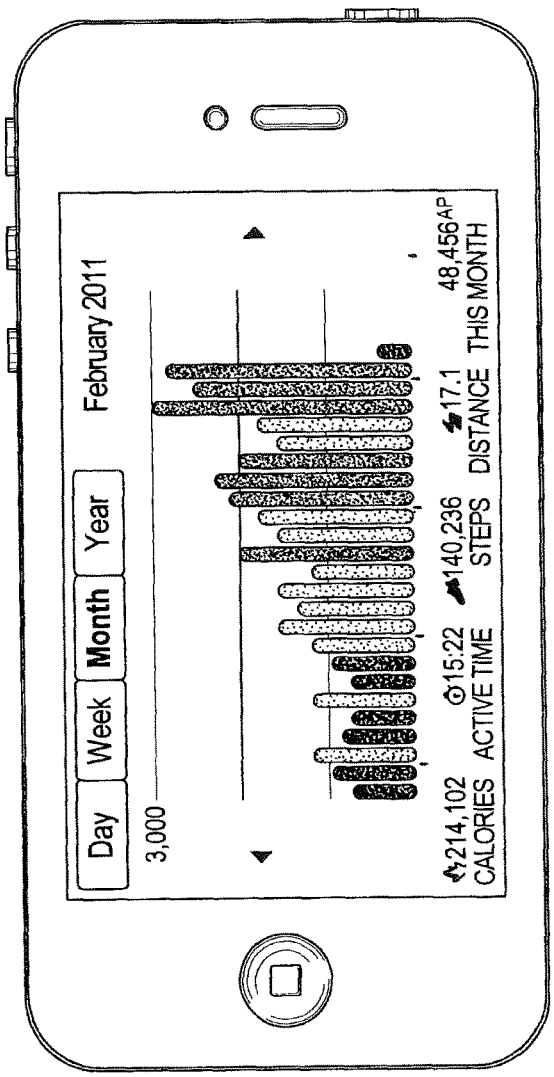
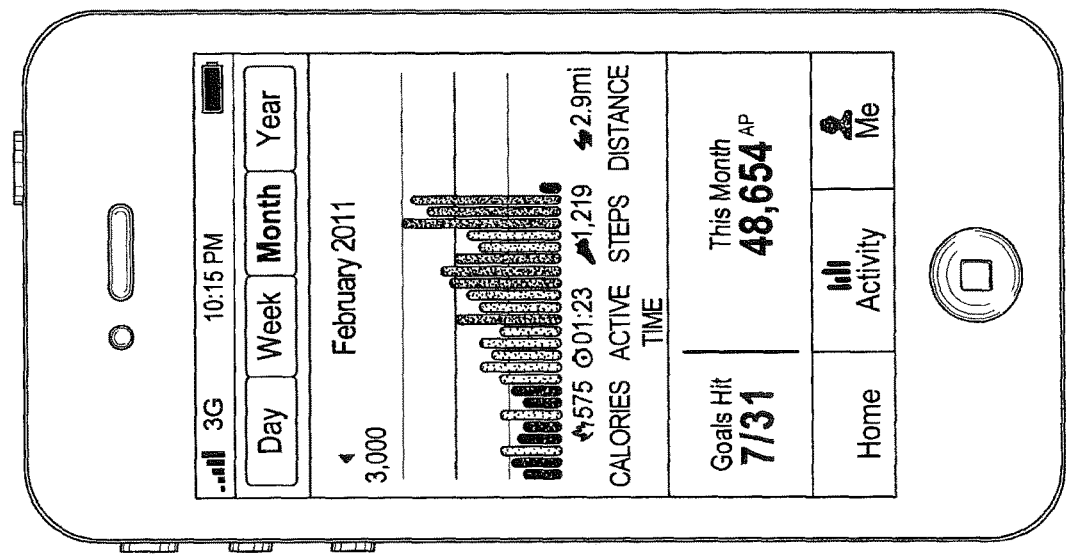
FIG. 105A
FIG. 105B

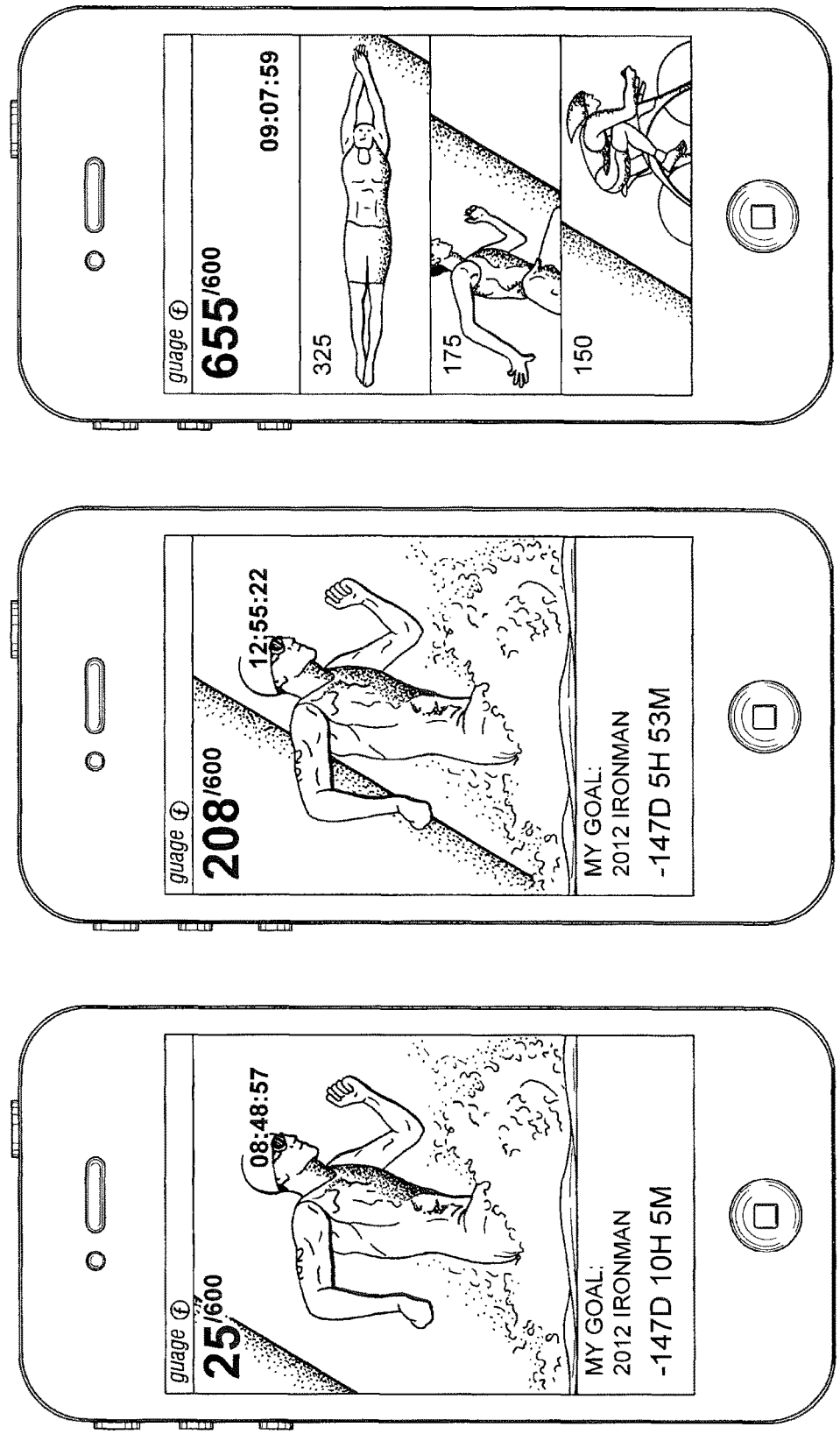

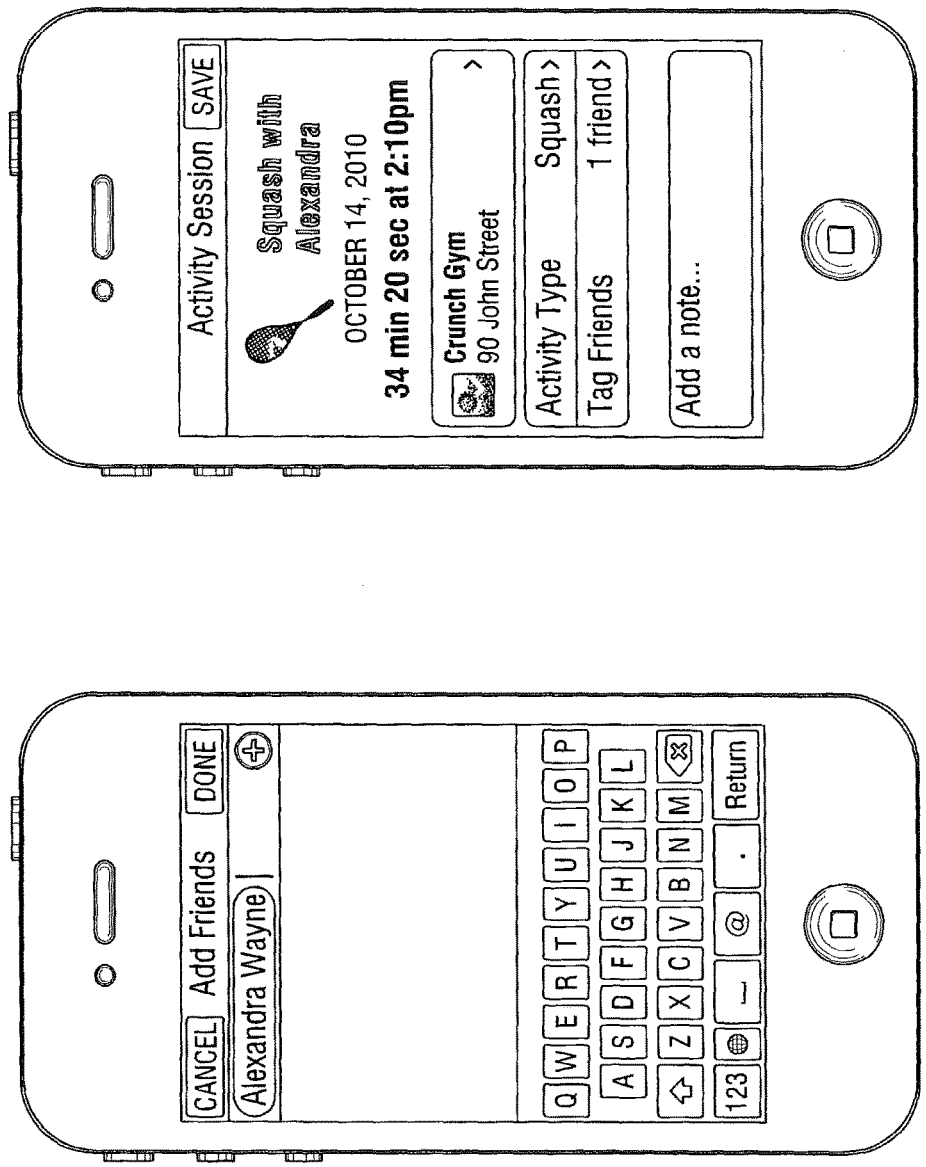

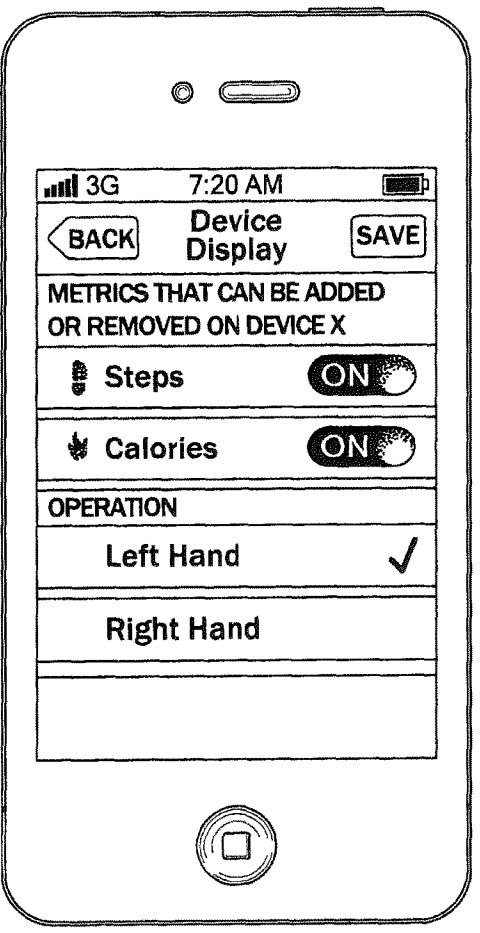
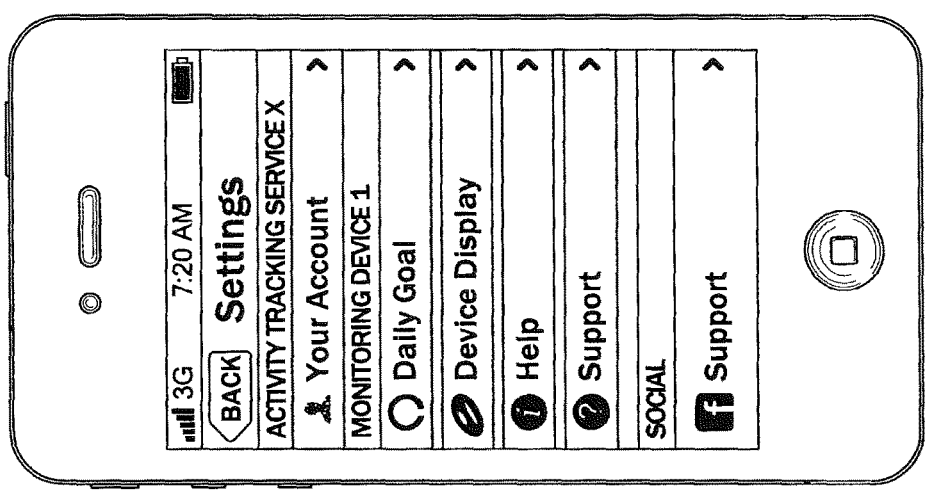
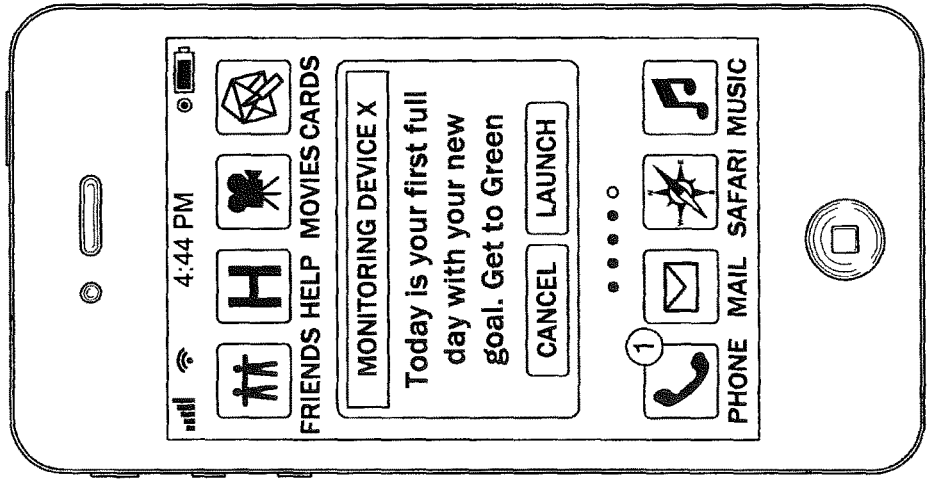

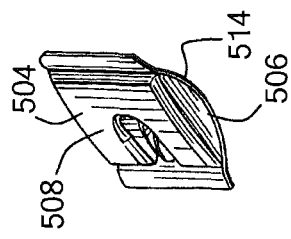
FIG. 147A
FIG. 147B
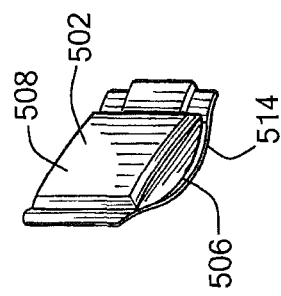
FIG. 146E
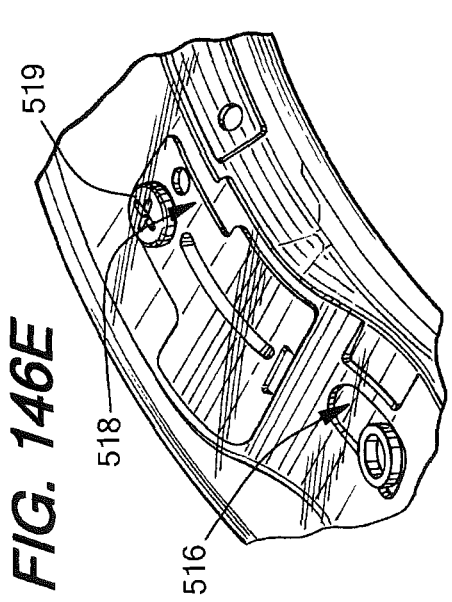
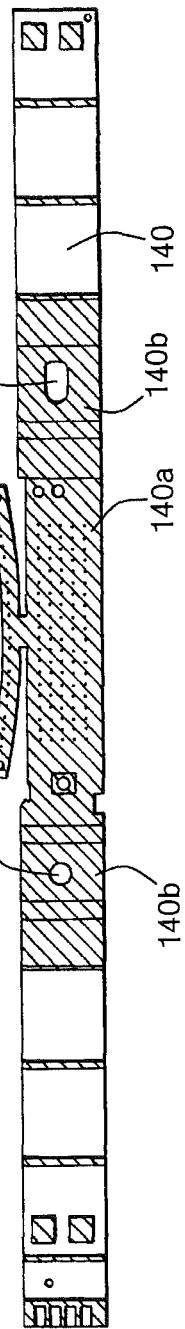
FIG. 146F

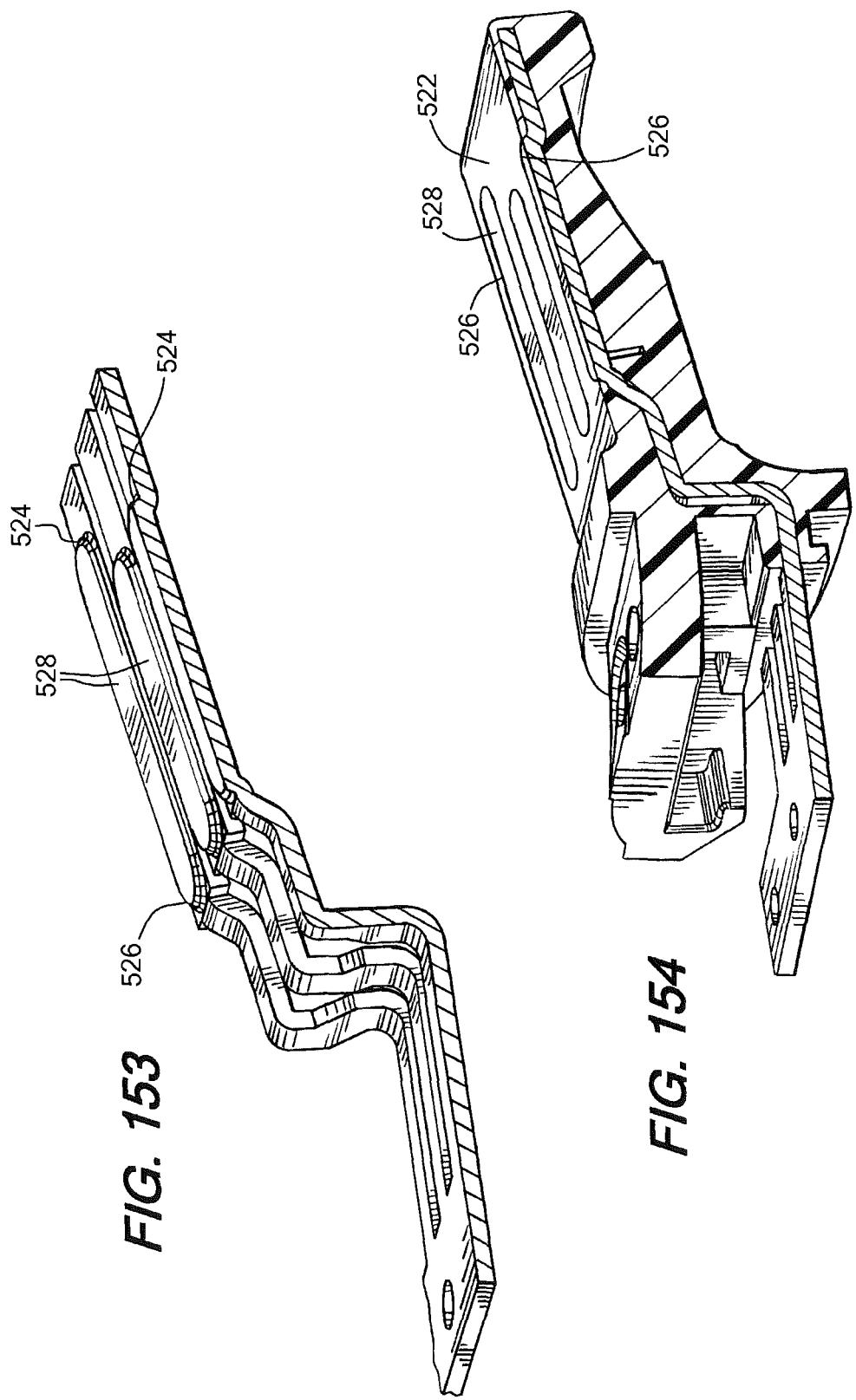

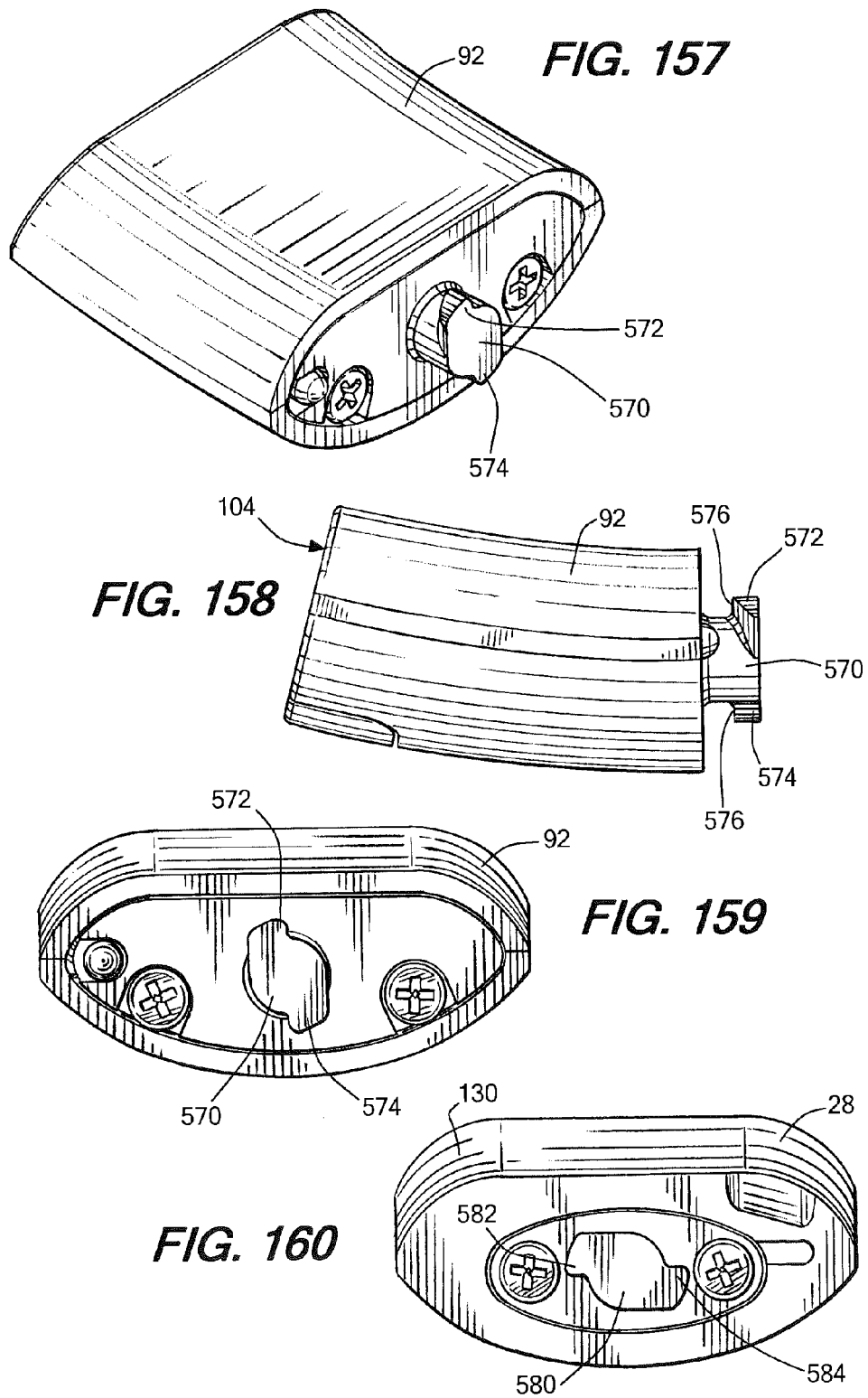

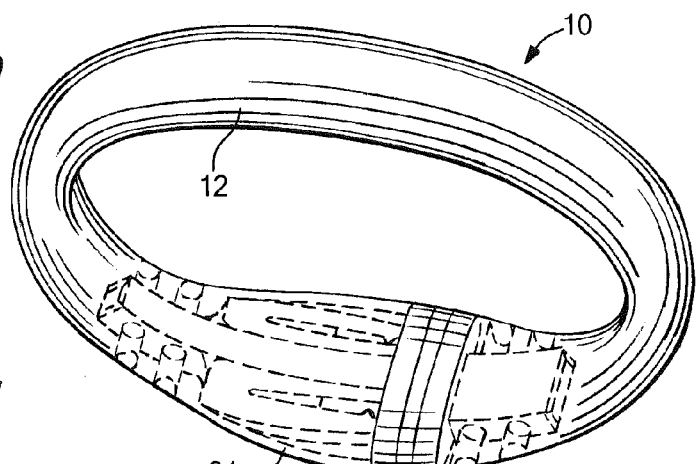
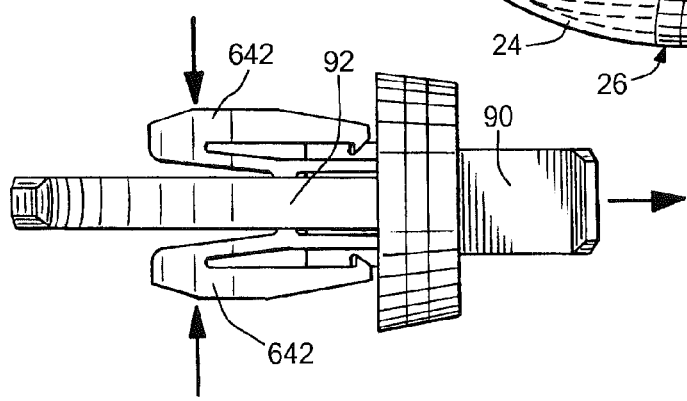
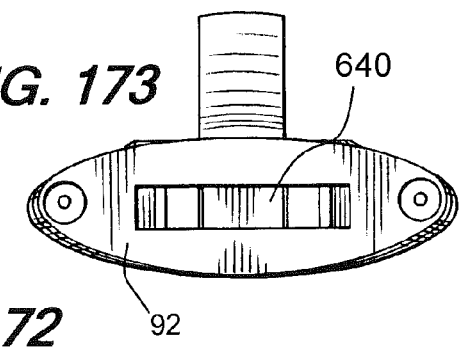
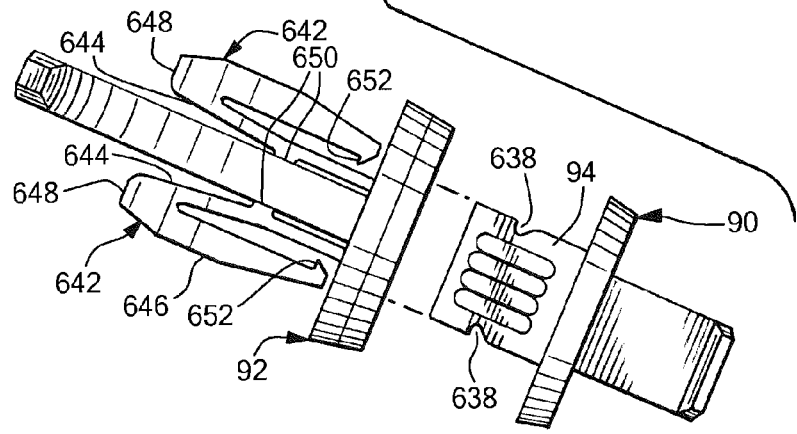

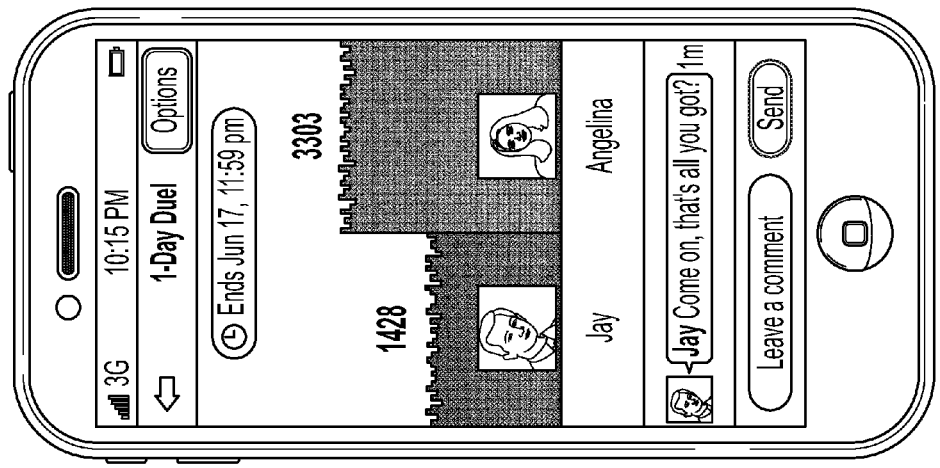
FIG. 180C Post-sync Game Status
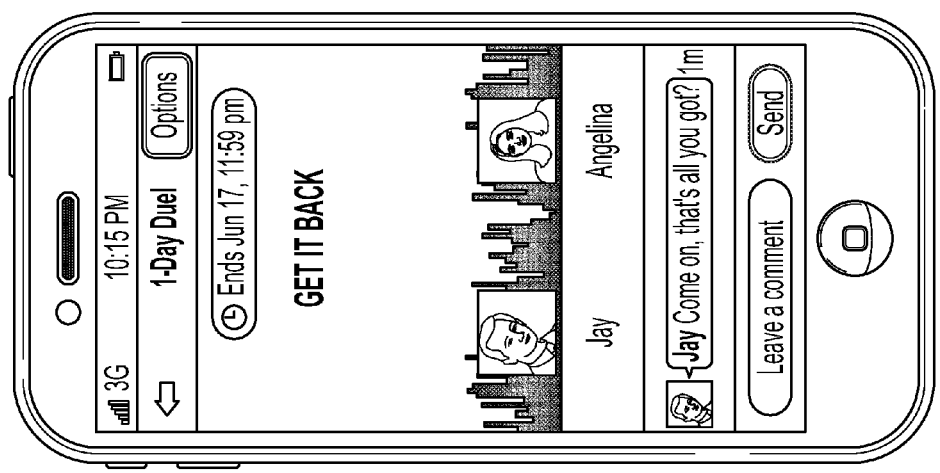
FIG. 180B Game Status Message
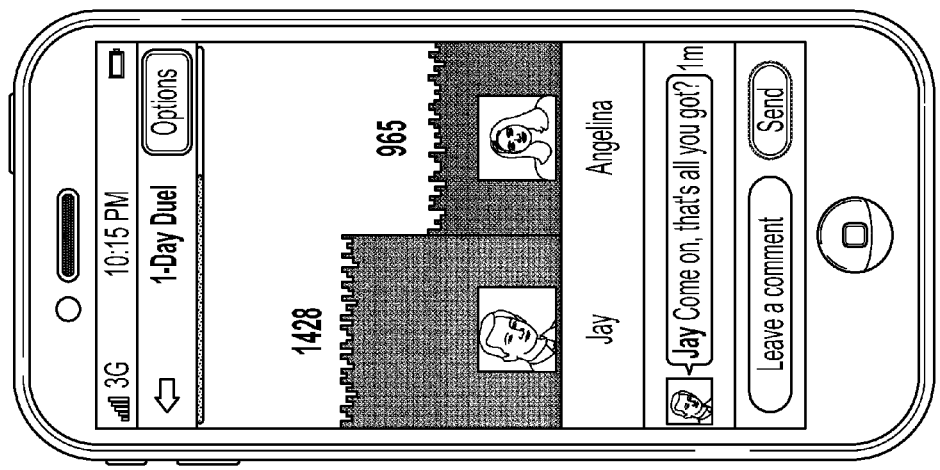
FIG. 180A Syncing

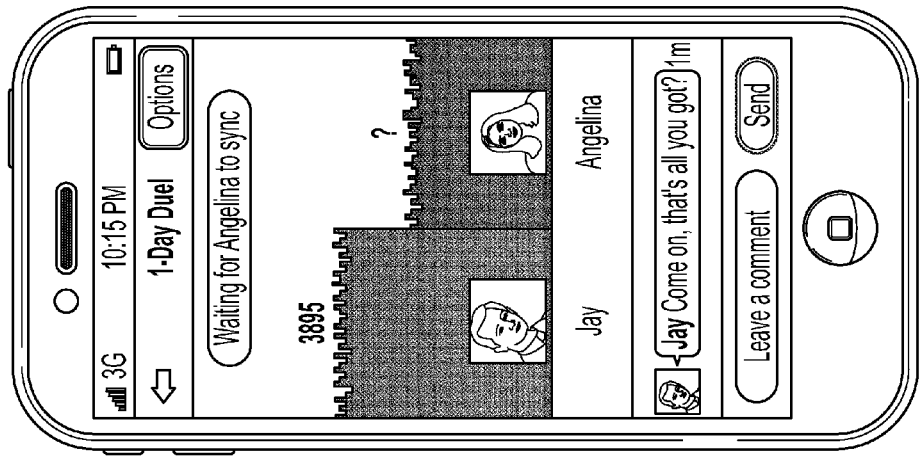
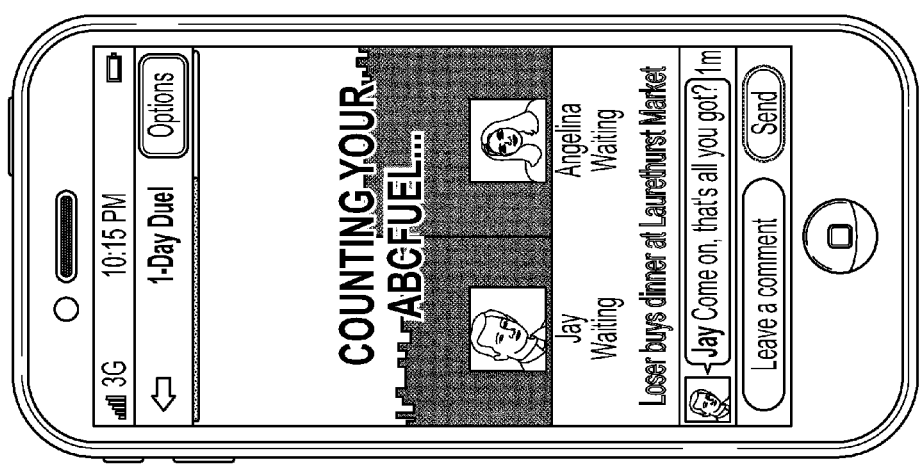
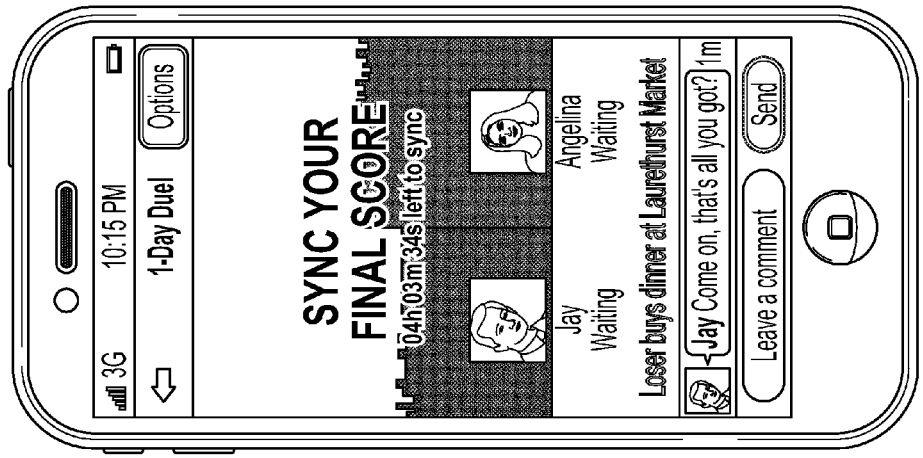

Final Sync

Sync In Progress

Results Transition Animation

ACTIVITY MONITORING, TRACKING AND SYNCHRONIZATION

CROSS-REFERENCE TO RELATED APPLICATION

The present application is a continuation of U.S. application Ser. No. 14/186,425 filed Feb. 21, 2014, which claims the benefit of and priority to U.S. provisional application Ser. No. 61/768,279, filed Feb. 22, 2013 and entitled "ACTIVITY MONITORING, TRACKING AND SYNCHRONIZATION." The content of the above noted applications are hereby incorporated by reference in their entirety for any and all non-limiting purposes.

BACKGROUND

Exercise and fitness have become increasingly popular and the benefits from such activities are well known. Various types of technology have been incorporated into fitness and other athletic activities. For example, a wide variety of portable electronic devices are available for use in fitness activity such as MP3 or other audio players, radios, portable televisions, DVD players, or other video playing devices, watches, GPS systems, pedometers, mobile telephones, pagers, beepers, etc. Many fitness enthusiasts or athletes use one or more of these devices when exercising or training to keep them entertained, record and provide performance data or to keep them in contact with others, etc.

Advances in technology have also provided more sophisticated athletic performance monitoring systems. Athletic performance monitoring systems enable easy and convenient monitoring of many physical or physiological characteristics associated with exercise and fitness activity, or other athletic performances including, for example, speed and distance data, altitude data, GPS data, heart rate, pulse rate, blood pressure data, body temperature, steps taken etc. This data can be provided to a user through a portable electronic device carried by the user. For example, one athletic performance monitoring system may incorporate an audio player wherein data can be incorporated for display or further communication on the audio player. Other systems may have a device having its own display or the ability to display information on a separate mobile device such as a smartphone. While athletic performance monitoring systems according to the prior art provide a number of advantageous features, they nevertheless have certain limitations. For example, some users prefer not to use a portable audio player or prefer to obtain and display performance data separately from an audio player. Other athletic performance monitoring systems have limited ability to further upload data to a personal computer or other location for further review and consideration, or such data transfer is cumbersome for the user. Still other systems can only monitor a single type of athletic activity and cannot record the accumulation of various types of activity during a day or predetermined time period. Other systems also do not offer sufficient and creative feedback regarding the activity recorded and monitored.

A full discussion of the features and advantages of aspects of the present disclosure is referred to in the following detailed description, which proceeds with reference to the accompanying drawings.

SUMMARY

The following presents a general summary of aspects of the invention in order to provide a basic understanding of at least some of its aspects. This summary is not an extensive overview of the invention. It is not intended to identify key or critical elements of the invention or to delineate the scope of the invention. The following summary merely presents some concepts of the invention in a general form as a prelude to the more detailed description provided below.

Aspects described herein provide a system whereby competitions may be defined between a plurality of users. The competition may be user, device and/or activity type specific. In other examples, the competition might only register a user's activity if the activity data is synchronized to a specified system, site, device, etc. In various arrangements, a competition may require the user to achieve a specified amount of activity in a shortest amount of time. This may encourage a user to synchronize data as frequently as possible to win the challenge. In other examples, a challenge may require a user to achieve the most amount of activity within a specified time period. This may also encourage the user to synchronize data as frequently as possible.

Other aspects and features are described throughout the disclosure.

BRIEF DESCRIPTION OF THE DRAWINGS

To understand the present invention, it will now be described by way of example, with reference to the accompanying drawings in which:

FIG. 3 is a front view of the wearable device assembly shown in FIG. 2;

FIG. 4 is a side view of the wearable device assembly shown in FIG. 2;

FIG. 5 is a perspective view of the wearable device assembly shown in FIG. 2 wherein portions of the assembly are shown in transparent form to show internal components;

FIG. 8a is a front perspective view of the spine member;

FIG. 8b is an underside perspective view of the spine member;

FIGS. 11a-f are views of a receiver member and other components for a fastening mechanism used in the wearable device assembly and using the USB connector;

FIGS. 12a-c are views of a spacer member or expansion element used in the wearable device assembly;

FIGS. 21a-21d disclose various spine member and battery configurations according to one or more aspects described herein;

FIGS. 34a-34b are views of a spacer assembly of an alternative embodiment of the device;

FIGS. 39-42 are schematic views showing a process of forming the device of the present invention;

FIGS. 47A, 47B and 48-56 illustrate example user interfaces for a wearable device assembly in an information display mode;

FIGS. 57A and 57B illustrate example battery indication interfaces for a wearable device assembly;

FIGS. 58 and 58a are example process flows for an action mode of a wearable device assembly;

FIGS. 59A-59D, 60A-60D, 61A-61C, 62A, 62B, 63A-63D, 64 and 65 illustrate example user interfaces for a wearable device in an action mode;

FIGS. 73A-73G illustrate example registration and configuration user interfaces;

FIGS. 84A-84F illustrate example notifications for tracking activity levels and goals;

FIGS. 104A-104F, 105 and 105A-105D illustrate example activity summary interfaces;

FIGS. 124A-124C, 125A-125C, 126A-126C, 127A-127C, 128A-128C, 129A-129C, 130A-130C, 131A-131C, 132A-132C, 133A-133C, 134A-134C illustrate example activity summary interfaces including a breakdown of activity by activity type;

FIGS. 135A-135D illustrate example interfaces for tracking activity along with activity partners;

FIG. 142 illustrates an example notification for indicating the start of a first goal period;

FIGS. 143 and 144 illustrate example application and device setting interfaces;

FIG. 146e is a partial perspective view of the spine member and PCB member and having a flex clamp;

FIG. 146f is a plan view of the PCB member;

FIGS. 147a-147b are perspective views of plug members;

FIG. 153 is a partial perspective cross-sectional view of the USB leads of FIG. 152;

FIG. 154 is a partial cross-sectional view of the USB connector of FIG. 151;

FIG. 157 is a perspective view of the second receiver member of FIGS. 156a-156b;

FIG. 158 is a side elevation view of the second receiver member of FIGS. 156a-156b;

FIG. 159 is an end elevation view of the second receiver member of FIGS. 156a-156b;

FIG. 160 is an end elevation view of the spacer member of FIGS. 156a-156b;

FIG. 170 is a perspective view of an alternative embodiment of a wearable device assembly having an alternative fastening mechanism;

FIG. 171 is a perspective view of the alternative fastening mechanism of FIG. 170

FIG. 172 is an exploded perspective view of the alternative fastening mechanism of FIG. 171;

FIG. 173 is an end view of a second receiver member of the alternative fastening mechanism shown in FIGS. 170-172;

FIG. 174 is a perspective view of a wearable device assembly having an alternative input button;

FIG. 175 is a perspective view of a spine member of the wearable device assembly of FIG. 174 and showing an actuation post of the input button;

FIG. 176 is a partial exploded perspective view of the input button;

FIG. 177 is a partial perspective view of components of the input button supported by the spine member;

FIG. 178 is a partial cross-sectional view of the input button;

FIG. 179 illustrates an example physical activity competition interface;

FIGS. 180A-180C illustrate example user interfaces for synchronizing game data and receiving status messages; and FIGS. 181A-181F illustrate further examples user interfaces for synchronizing game data.

DETAILED DESCRIPTION

Figure 1:
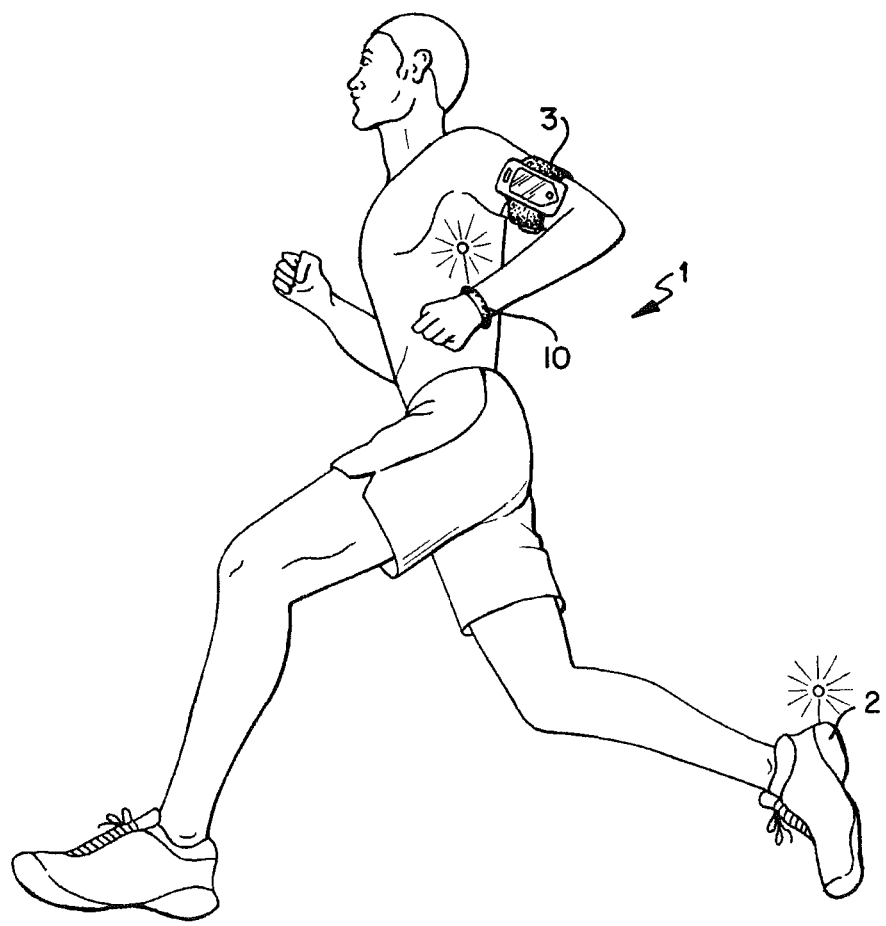
FIG. 1 is a view of a person utilizing an athletic performance monitoring and feedback system that in one exemplary embodiment of the invention includes a wearable device assembly having athletic functionality.

In the following description of various example embodiments of the invention, reference is made to the accompanying drawings, which form a part hereof, and in which are shown by way of illustration various example devices, systems, and environments in which aspects of the invention may be practiced. It is to be understood that other specific arrangements of parts, example devices, systems, and environments may be utilized and structural and functional modifications may be made without departing from the scope of the present invention. Also, while the terms "top," "bottom," "front," "back," "side," and the like may be used in this specification to describe various example features and elements of the invention, these terms are used herein as a matter of convenience, e.g., based on the example orientations shown in the figures. Nothing in this specification should be construed as requiring a specific three dimensional orientation of structures in order to fall within the scope of this invention.

General Description of Aspects of the Invention

The present invention provides a wearable electronic device assembly having athletic functionality. In one exemplary embodiment, the wearable electronic athletic device assembly may comprise illuminable portions that convey athletic information to a wearer. Additionally, the wearable electronic athletic device may include a data transmission portion configured to connect to (directly or indirectly) another device. In one example, the wearable electronic athletic device may include a USB connector and storage device that may be connectable to a USB port of another device to transmit and receive data.

In one arrangement, the wearable electronic athletic device may include a USB storage device that may also be configured to act as a connector to secure two ends of the wearable electronic athletic device assembly to one another. The USB device is connected to a carrier that, in one exemplary embodiment, is a wristband.

The electronic wearable device assembly may further include a housing portion that supports a controller therein. The controller has associated components such as a power supply and circuitry. Various sensors may be operably associated with the controller including a three-axis accelerometer. The housing has a structural configuration wherein the housing is water-resistant as well as impact resistant.

In one or more arrangements, the controller may utilize a user interface having certain features to enhance the functionality of the device. For example, the wearable electronic athletic device assembly may include a display that may include an indicator system wherein performance data can be displayed or otherwise conveyed to the user. The display may include an LCD screen, a display comprised of a series of LED lights, an LED graphical user interface and the like. The data displayed on the display may be stored in an internal non-removable memory or a removable USB storage device. Additionally, the USB device of the wearable electronic athletic device may be plugged into a computer wherein performance data can be automatically uploaded to a remote site or mobile device for further processing, display and review. The device may also be configured for the user to be prompted in order to commence a data transfer operation. The device may also be capable of general wireless communication with other mobile devices or remote web sites.

In addition, the wearable athletic device may be worn in a variety of locations on a user's body including on a user's chest (e.g., a chest strap), around a user's wrist, around a user's arm, on a user's head, on a user's ankle or thigh, and the like.

In one exemplary embodiment, the display may include a display and an indicator system. The indicator system may display information corresponding to a level of activity of the user wearing the device assembly. The indicator system may include a plurality of light elements that are selectively illuminable to provide information. Each of the plurality of light elements may be illuminated in a plurality of colors. The display and indicator system may operate separately or in tandem to display indicia to the user.

In an additional exemplary embodiment, the device may include a spacer member that can adjust the size of the device to accommodate various users.

In still further exemplary embodiments, the device may interact with mobile devices and remote web sites to provide enhanced experiences to the user.

Specific Examples of the Invention

While aspects of the invention generally have been described above, the following detailed description, in conjunction with the Figures, provides even more detailed examples of athletic performance monitoring systems and methods in accordance with examples of this invention. Those skilled in the art should understand, of course, that the following description constitutes descriptions of examples of the invention and should not be construed as limiting the invention in any way.

FIG. 1 generally discloses a person utilizing an athletic performance monitoring and feedback system 1 that in one exemplary embodiment of the invention includes a wearable device assembly 10 having athletic functionality. As explained in greater detail below, the wearable device assembly 10 has a sensor associated therewith such as a three-axis accelerometer wherein the device 10 is capable of monitoring athletic activity or overall activity of the user. As shown in FIG. 1, the athletic performance monitoring and feedback system 1 may also include a further module or sensor 2, such as one carried by or embedded in a shoe, as well as a mobile device 3. It is understood that the system 1 could also employ other types of sensors and devices if desired including a heart-rate monitor. As discussed in greater detail below, various components of the system 1 including the wearable device 10 may wirelessly communicate with one another to record and monitor athletic performance or overall user activity. It is further understood that the person may utilize only the wearable device 10 to record and monitor athletic performance or overall activity. The athletic performance data or overall activity can include a variety of different parameters, metrics or physiological characteristics including but not limited to speed, distance, steps taken, and energy expenditure such as calories, heart rate and sweat detection. Such parameters may also be expressed in terms of activity points (e.g., sometimes referred herein as "AP") or currency earned by the user based on the activity of the user.

The shoe-based sensor 2 may have various electronic components including a power supply, magnetic sensor element, microprocessor, memory, transmission system and other suitable electronic devices. The sensor 2 in one exemplary embodiment is mounted on the shoe of a user as shown in FIG. 1. The sensor 2 is used in conjunction with the other components of the system to record data such as speed and distance among other parameters of athletic performance. The sensor 2 can be a sensor as disclosed in U.S. Publication Nos. 2007/0006489; 2007/0011919 and 2007/0021269. These U.S. Publications are incorporated by reference and made a part hereof. The sensor 2 could also take the form of a force-sensor array to collect additional data associated with the user, such as disclosed in U.S. Publication Nos. 2010/0063778 and 2010/0063779, which are incorporated by reference and made a part hereof. The mobile device may be a smartphone or other types of portable display devices. The wearable device assembly 10 may also interact and communicate with other types of sensors including apparel based sensors or sensors associated with events such as running competitions or other athletic competitions.

FIGS. 2-6 illustrate different views of the wearable device assembly 10 of FIG. 1. The wearable device assembly 10 generally includes a housing 12, a controller 14, an input button 16, a display 18, and an indicator system 20. It is understood that the controller 14 has and/or is operably connected to various associated components including power supplies, sensors and associated circuitry. FIG. 2*a* discloses an alternative device 10 having a larger indicator system 20. The structure of the device 10 will first be described followed by a further description of the operation of the device and additional user experiences provided by the device and related systems.

The housing 12 is in the form of a wearable band such as a wristband and generally includes an inner spine member 22 (FIGS. 6-9) having compartments for power supplies, an outer encasement member 24, and a fastening mechanism 26 or latch member 26. In certain exemplary embodiments, the housing 12 may have one or more spacer members 28 to adjust the size of the device 10 to be discussed in greater detail below.

As further shown in FIGS. 2-6, the wearable device assembly 10 is annular or generally circular in shape and, in this illustrative example, is configured for wearing around a user's wrist. The wearable device assembly 10 may be formed in various other shapes without departing from the invention, such as oval, oblong, octagonal, rectangular, and the like. The device 10 may also be configured to be attached to a clip or other device that can be removably attached to a person, or incorporated into other apparel. The wearable device assembly 10 and the housing 12 may include a generally planar portion and rounded or beveled edges along the sides. The beveled edge may only be included on one side of the housing 12 in an exemplary embodiment. Ends of the housing are configured to join with one another via the fastening mechanism 26. In one or more arrangements, an outward or exterior facing side of housing 12 of the wearable device assembly 10 may include a smooth texture while an interior facing side (e.g., contacting the wearer's body) may include frictional features. In one example, the interior facing side of the wearable device assembly 10 may be ribbed to improve traction and prevent slippage around a user's wrist or other body part. The texture may be even throughout the interior side or may be uneven. For example, the ribs or other texture may become more pronounced as the texture progresses away from the fastening mechanism formed at the ends of the housing. In other arrangements, texture might also be added to an exterior side of the wearable device assembly 14 and the interior side may be smooth. Various combinations and configurations of textures may be used. In still other embodiments, the housing 12 may incorporate sweat absorption members on an inner diameter of the device 10 or wicking elements.

Figure 9:
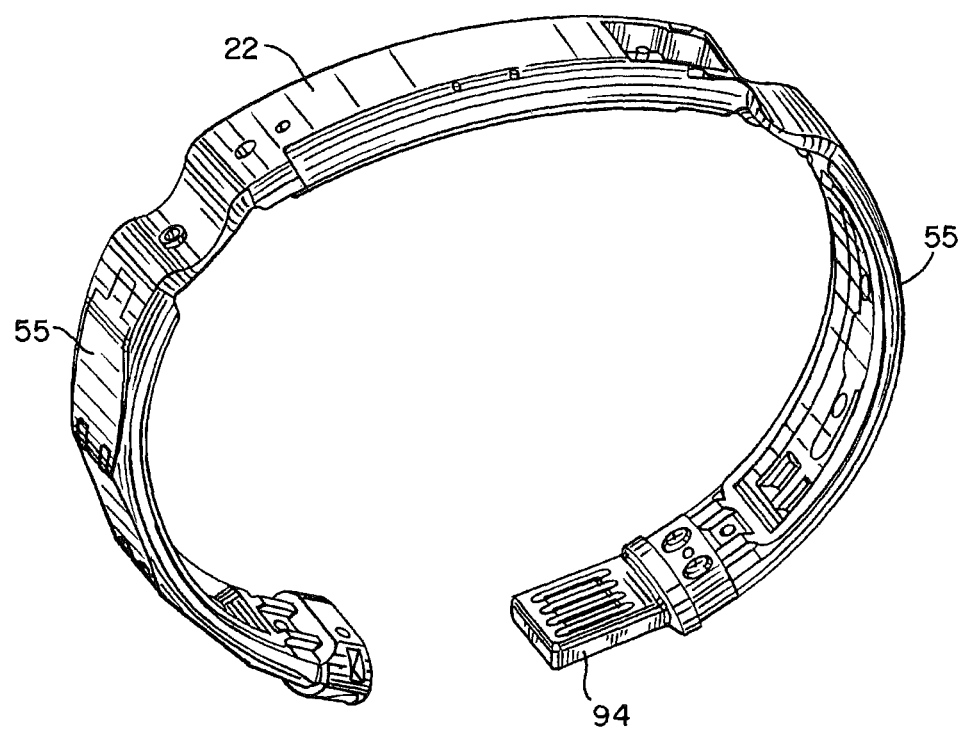
FIG. 9 is a perspective view of the spine member having a USB connector attached.

As shown in FIGS. 7-9, the inner spine member 22 is a member having substantially rigid portions and certain flexible portions or zones. The spine member 22 generally supports components of the controller 14 as described further herein. The spine member 22 may be considered a chassis member having various components attached thereto. The spine member 22 has a general curvilinear configuration and has an outer surface 30 and an inner surface 32. The spine member 22 has an intermediate portion 34 that extends to a first distal end 36 and a second distal end 38. The intermediate portion 34 has a central portion or central segment 40 as well as a first segment 42 and a second segment 44. The intermediate portion 34 further has a first flexible zone 46 or member that connects one end of the central portion 40 to the first segment 42, and has a second flexible zone 48 or member that connects the other end of the central portion 40 to the second segment 44. The flexible zones 46,48 provide for more easy flexing of the spine member 22 at these zones and also the overall device while the first segment 42 and second segment 44, and central portion 40, are considered rigid zones or substantially rigid zones. In an exemplary embodiment, the flexible zones 46,48 may be considered flexible hinge zones and are curved segments in a generally concave shape. Thus, the flexible zones have a central portion or base portion with a pair of members extending away from the base portion, and therefore define an inwardly curved portion. The curved segments have a thinned out thickness at the base or central portion of the concave configuration to enhance the flexible characteristics of the flexible zones 46,48. Thus, the spine member 22 has a general thickness or first thickness along its length (e.g., the rigid central portion and rigid first and second segments) while the flexible zones have a lesser, second thickness "t" to assist in the flexible characteristics of the spine member 22 and overall housing 12. In particular, the base portion of the flexible zone has a lesser thickness than the rigid central portion and first and second rigid segments. As explained in greater detail below, the flexible zones 46,48 assist in the components supported by the spine member 22 to be closest to a neutral axis wherein stresses are minimized when the device 10 is flexed such as when placing on a user's wrist or removing the device 10 from a user's wrist.

Figure 7A:
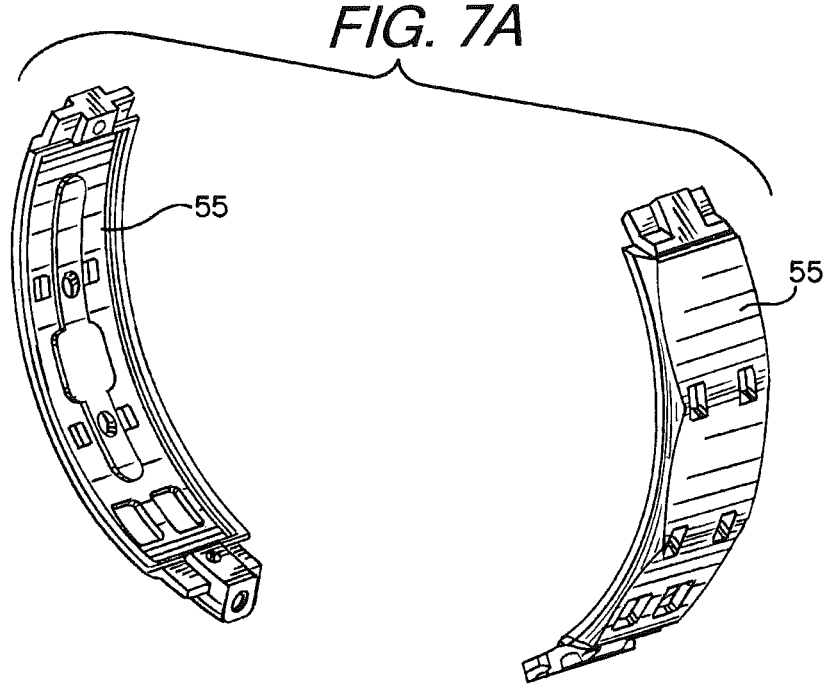
FIG. 7a is a perspective view of battery compartments used in a spine member of the wearable device assembly.
Figure 7B:
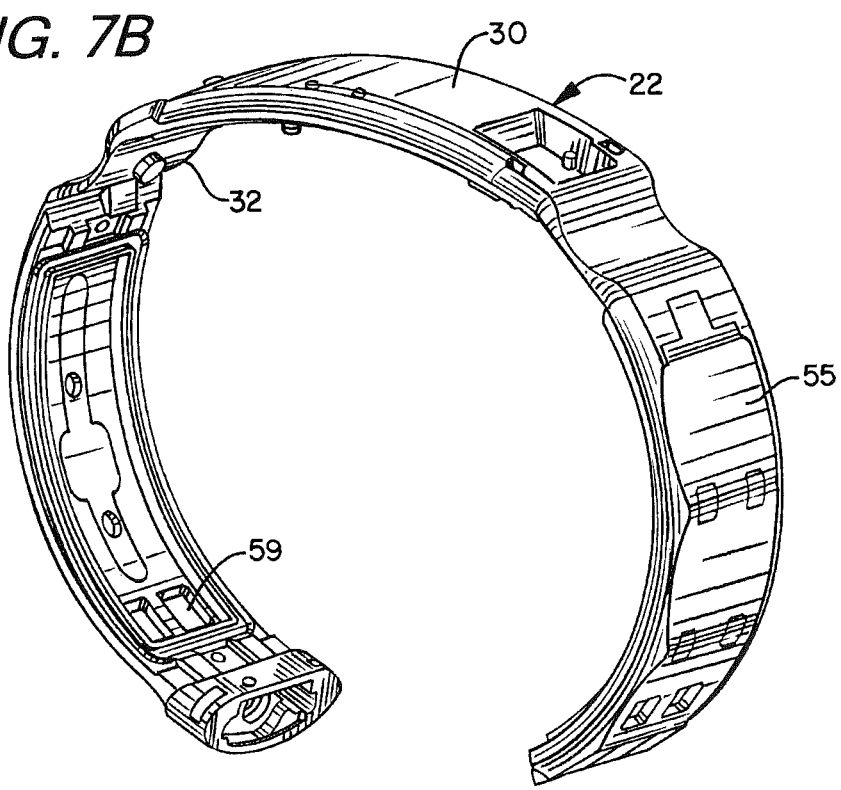
FIG. 7b is a perspective view of the battery compartments as part of the spine member.

As shown in FIGS. 7-9, the first segment 42 of the intermediate portion 34 has a first recessed compartment 50 and the second segment 44 of the intermediate portion 34 has a second recessed compartment 52. These segments have a curvilinear configuration. The recessed compartments 50,52 are dimensioned to receive power supplies associated with the controller 14. In an exemplary embodiment as shown in FIGS. 7*a* and 7*b*, the recessed compartments 50,52 are initially formed from a metal enclosure such as a thixo-molded metal member 55. A thixo-molded member is utilized in one exemplary embodiment while other members could also be used such as any cast metal members, die cast members or any metal injected molded members. Metal cover or closure members in the form of metal caps are also provided as described below to provide a metal enclosure for the power supplies. It is desirable to form a metal enclosure for the battery or batteries 142 and it is understood that the enclosure may include confronting metal members that may not form a complete chamber, but substantially surround the battery. It is understood that the thixo-molded compartments can be initially formed wherein the remaining portions of the spine member 22 are formed over the thixo-molded compartments. Portions of the spine member may be formed over the thixo-molded members that define a bottom portion of the compartments 50,52. The compartments 50,52 further have a pair of openings 59 to receive battery terminals or contacts to be described. The recessed compartments 50,52 may vary in size generally or with respect to one another. Thus, the recessed compartments 50,52 may have an increased size to accommodate larger power supplies having increased capacity. Such features will be described in greater detail below.

The intermediate portion 34 further supports other components of the controller 14 proximate the outer surface 30 as well as the display 18 and indicator system 20 as described further below. The spine member 22 may have a beveled edge that supports the indicator system 20 thereon. The spine member 22 has certain openings to receive fastening mechanisms such as adhesives and screw fasteners to fixedly attach controller components to the spine member 22. The first distal end 36 and the second distal end 38 support the fastening mechanism 26 and optional spacers 28.

In one exemplary embodiment, the thixo-molded members 55 that help form the compartments 50,52 are made from magnesium wherein the remaining portion of the spine member 22 is made from a polypropylene material that is formed over the members 55. It is understood that other materials could be used for the spine member 22 as well as the battery enclosures.

As shown in FIGS. 2, 3, 6 and 19, the outer encasement member 24 is positioned around the spine member 22 and encases the controller 14, the display 18 and the indicator system 20. In an exemplary embodiment, the outer encasement member 24 is a thermoplastic elastomer member that is formed in an injection molding process described in greater detail below. Accordingly, the outer casement member 24 has resilient elasticity while maintaining an annular shape. The outer encasement member 24 has a generally rounded outer surface 56 and a generally planar inner surface 58, and may be considered to have an inner portion defining an inner diameter of the device 10 and an outer portion defining an outer diameter of the device 10. The outer surface 56 has a substantially large radius to form a curvature while almost appearing planar. The side edges have a smaller radius than the outer surface and the beveled side edge further has a small radius. The surfaces of the outer encasement member 24 cooperate to form an internal volume to house the various components of the device while maintaining a minimal cross-sectional dimension. The outer encasement member further has a beveled side edge 60. The indicator system 20 is positioned proximate the beveled side edge 60. It is understood that the housing 12 could have beveled edges on each side edge if desired. The outer encasement member 24 has an aperture 62 to accommodate the input button for interaction with the controller 14. The outer encasement member 24 has a first region 64 to accommodate viewing of the display 18 and a second region 66 to accommodate viewing of the indicator system 20. It is understood that the first region 64 is structured and dimensioned such that indicia projected by the display 18 can be viewed through the first region 64 of the outer encasement member 24. It is further understood that the second region 66 is structured and dimensioned such that indicia projected by the indicator system 20 can be viewed through the second region 66 of the outer encasement member 24. The outer encasement member 24 may include a colorant providing a dark appearance. The amount of colorant is controlled such that the components encased by the outer encasement member 24 cannot be seen. However, when the display 18 and indicator system 20 are activated, light easily projects through the outer encasement member 24 and is visually perceptible. For example, in one exemplary embodiment, the outer encasement member is translucent thermoplastic elastomer with a certain percentage of colorant. The outer encasement member 24 may further be considered generally transparent but having a tint provided by a certain amount of black pigmented material. In this configuration, the internal components within the outer encasement member 24 are generally not seen, however, when the display 18 and/or indicator system 20 are activated, the light members are clearly seen through the outer encasement member 24. Thus, the internal components are not seen via the naked eye, but the display and/or indicator system can be seen through the outer encasement member when activated. The device 10 may further be configured such that one of the display and indictor system is always visible while the other one of the display and indicator system is viewable only upon activation. For example, the display may always be viewable such as to show time of day, while the indicator system is only viewable when activated. It is further understood that the outer encasement member 24 may be a clear material or include a variety of different colorants, or multiple colorants. Certain colors may indicate a device 10 is specifically designed for certain types of uses or events. The first region 64 and the second region 66 may be constructed to be transparent. In an exemplary embodiment, these regions are tinted to a darker color wherein the display 18 and indicator system 20 are illuminated therethrough. It is understood that alternatively, openings can be provided at the first region 64 and the second region 66 for viewing the display 18 and indicator system 20. The inner surface 58 of the outer encasement member 24 has a first opening 68 and a second opening 70 proximate to the location of the power supplies supported by the spine member 22. The first opening 68 is covered by a first cap 72 or closure member secured over the first opening 68 by fasteners, and the second opening 70 is covered by a second cap 74 or closure member secured over the second opening 70 by fasteners. The first cap 72 and the second cap 74 are formed from metal materials to cooperate with the metal battery compartments 50,52 to provide a metal enclosure for the power supplies to be described. The outer encasement member 24 may be composed of a variety of materials including a variety of polymers, plastics or rubbers, thermoplastic elastomer members, thermoplastic urethane members, liquid silicone members, and rubber composites, and other moldable elastic members, and/or synthetics such as neoprene, plastics, textiles, metals and/or combinations thereof. In one or more examples, the material may include thermo polyurethane and/or thermoplastic rubber. The material used may also offer some flexibility so that the size of the loop formed by the wearable device assembly 10 may be enlarged without fracturing or breaking the assembly 10. As explained in greater detail below, an adhesion promoter may be used on the spine member 22 and components supported thereon to assist in adhesion of the outer encasement member 24. The spine member 22 and outer casement member 24 will be described in further detail below when describing the process of forming the device 10 below.

Figure 6:
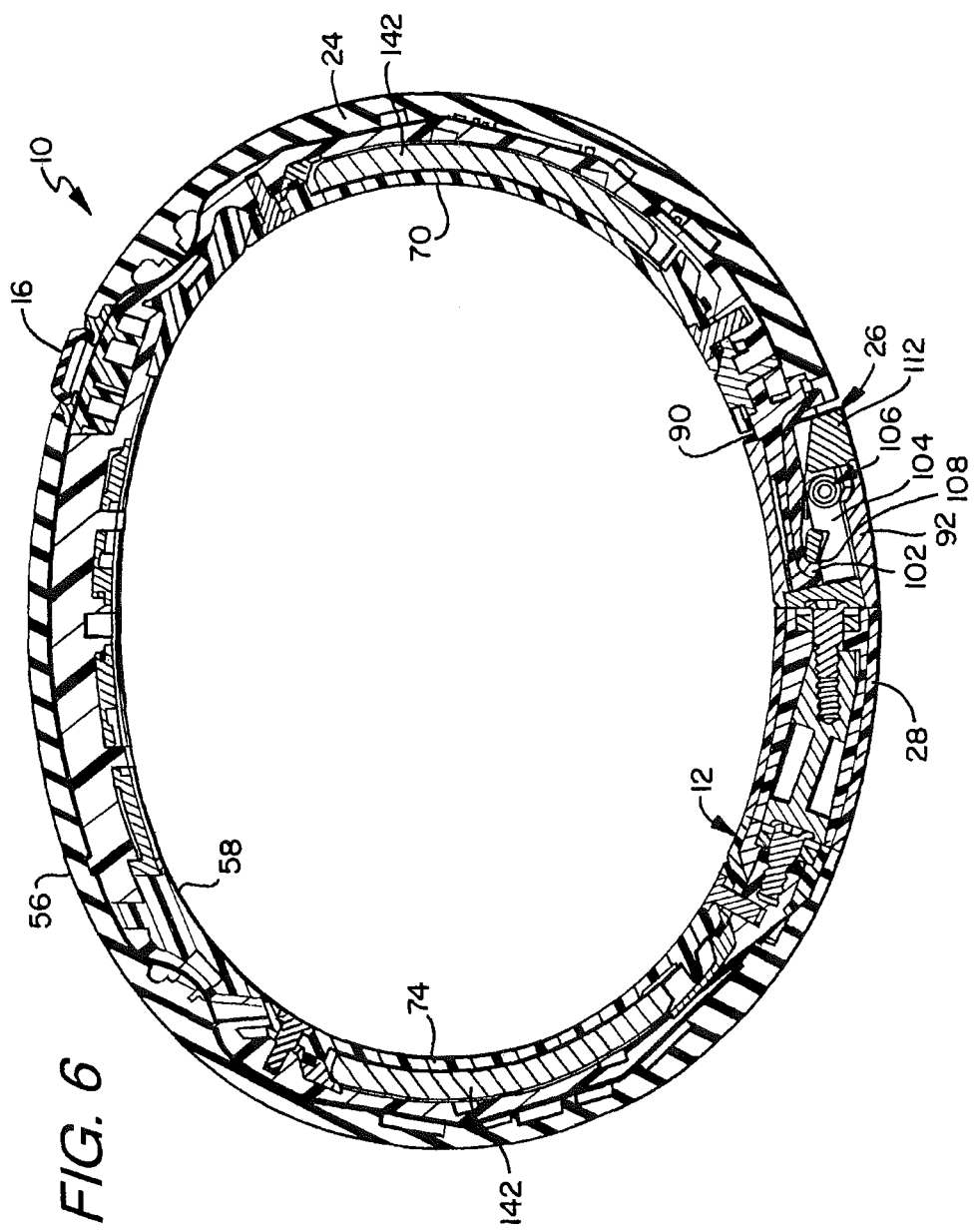
FIG. 6 is a schematic cross-sectional view of the wearable device assembly taken along Lines 6-6 of FIG. 4.
Figure 10A:
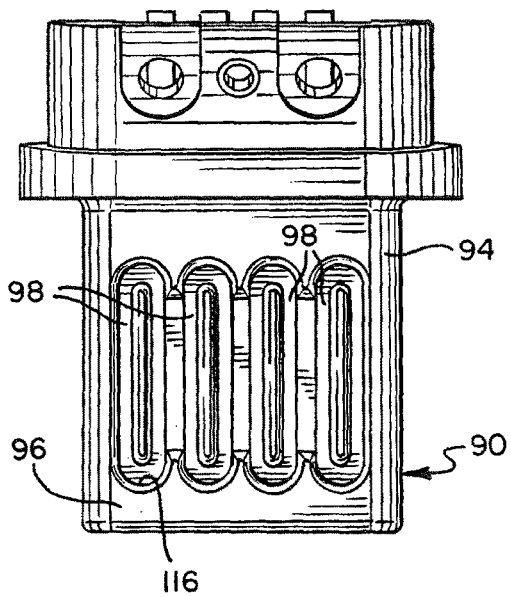
FIGS. 10a-10c are views of the USB connector.
Figure 10B:
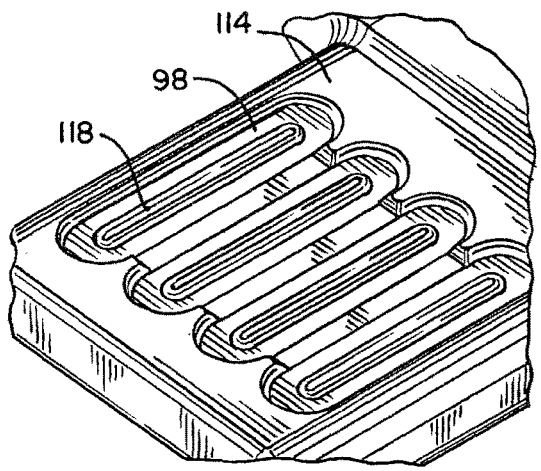
Figure 10C:
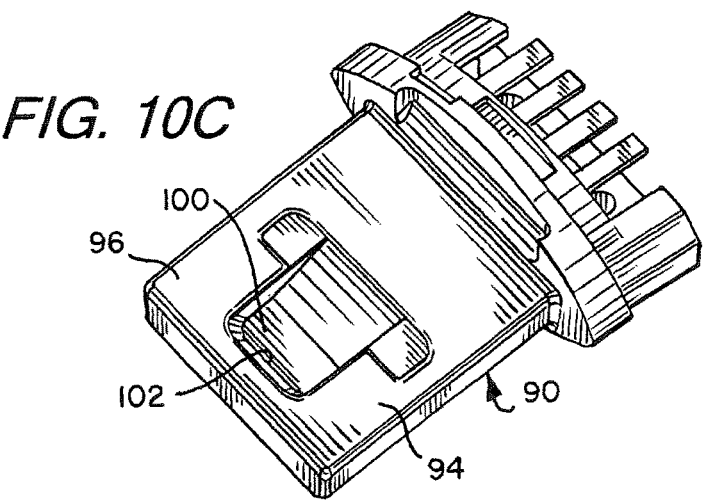
Figure 11E:
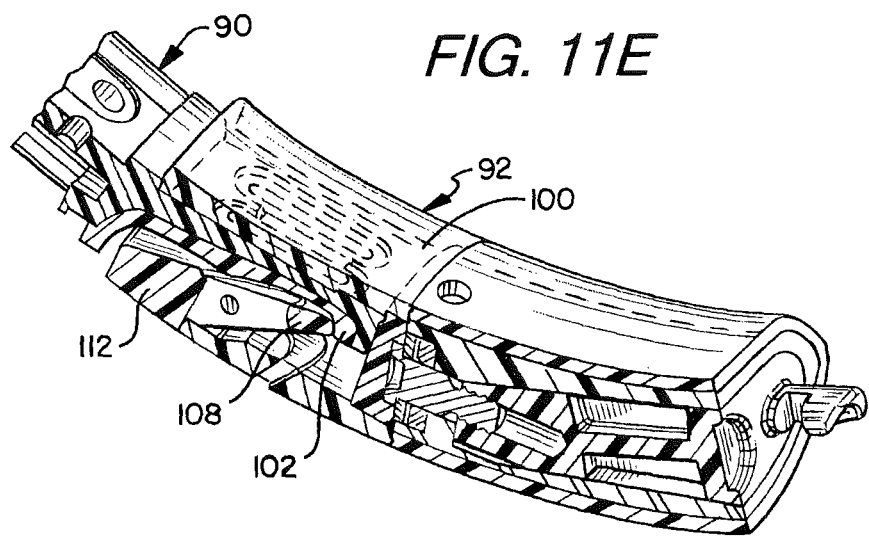
Figure 11F:
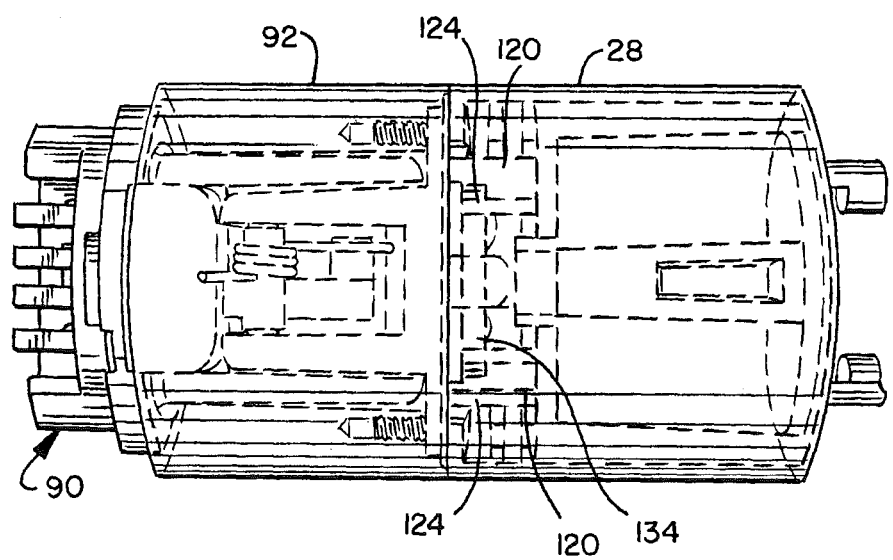

As shown in FIGS. 6 and 10-11, the fastening mechanism 26 or latch member 26 generally includes a first projection member 90 and a second receiver member 92. The first projection member 90 is positioned proximate the first end of the housing 12, and the second receiver member 92 is positioned proximate the second end of the housing 12. It is understood that the members 90,92 could be placed on opposite ends of the housing 12 if desired. The first projection member 90 incorporates an input/output member 94 for data transfer and in an exemplary embodiment, takes the form of a USB connector 94 having a substantially rigid body 96. The USB connector 94 includes a plurality of leads 98 embedded in a top surface of the rigid body 96. The leads 98 have connectors that are operably connected to the controller 14. As shown in FIG. 10c, the first projection member 90 further has a recess 100 positioned in a bottom surface of the rigid body 96 generally opposite of the USB leads 98. The bottom recess 100 defines an engagement surface 102.

As shown in FIGS. 6 and 11a-f, the second receiver member 92 defines an opening 104 therein and supports a pivoting member 106. The pivoting member 106 has a finger portion 108 and includes a spring 110 to bias the finger portion 108 towards a latching position. The pivoting member further includes a depressible button 112 to move the finger portion 108 away from the latching position. The second receiver member 92 further has a pair of prong members 120 at an opposite end from the opening 104. The prong member 120 has an inclined or curved cam surface 122. A slot 124 is defined along the length of the prong member 120.

As further shown in FIGS. 11*a-f*, the first projection member 90 is received into the second receiver member 92 that may be connected to one end of the spine member 22 in an embodiment. Initially, the finger portion 108 is pivoted and biased away from the latching position. Once the finger portion 108 passes into the recess 100, the finger portion 108 is biased by the spring 110 into the recess 100 and to the latching position. The device 10 is then in a closed position wherein the finger portion 108 can abut the engagement surface 102 to maintain the device 10 in a closed, annular configuration. While in an exemplary embodiment, the fastening mechanism 26 incorporates a traditional USB connector 94, it is understood that other types of connection configurations for communication could also be employed. For example, the device 10 may utilize a micro USB connector, a Firewire port, a 16-pin pit, or other type of physical contact-based connection, or may include a wireless or contactless communication interface, such as an interface for Wi-Fi, Bluetooth, near-field communication, RFID, Bluetooth Low Energy, Zigbee, or other wireless communication technique, or an interface for infrared or other optical communication technique. It is further understood that the device 10 can be configured to communicate and data transfer completely from a data transfer member such as the USB connector 94, or completely via wireless communication, or a combination of both wireless communication and various types of plug-in communication.

FIGS. 10*a*-10*c* disclose additional views of the USB connector 94. The USB connector 94 has structural features that provide a cleaner, more aesthetically pleasing configuration while maintaining operability. In conventional USB connectors, the leads are spaced apart unevenly, are rectangular in shape, and respective ends of the leads are not aligned. As shown in FIG. 10*a*, the leads 98 of the USB connector 94 are evenly spaced a distance across the rigid body 96. In addition, the leads 98 are recessed with respect to a top surface 114 of the rigid body 96. In addition, the rigid body 96 defines rounded openings 116 that are evenly spaced and wherein the ends of the openings 116 are aligned. The leads 98 are exposed by the openings 116. Because the leads 98 are recessed with respect the top surface 114 of the rigid body 96, each lead 98 has a raised rib 118 that extends proximate the top surface 114 of the rigid body 96. In an exemplary embodiment, the leads 98 are placed in a mold wherein material is injection molded around the leads 98 to form the rigid body having the uniform and aligned rounded openings 116. Such structure provides an enhanced USB connector 94.

Figure 13:
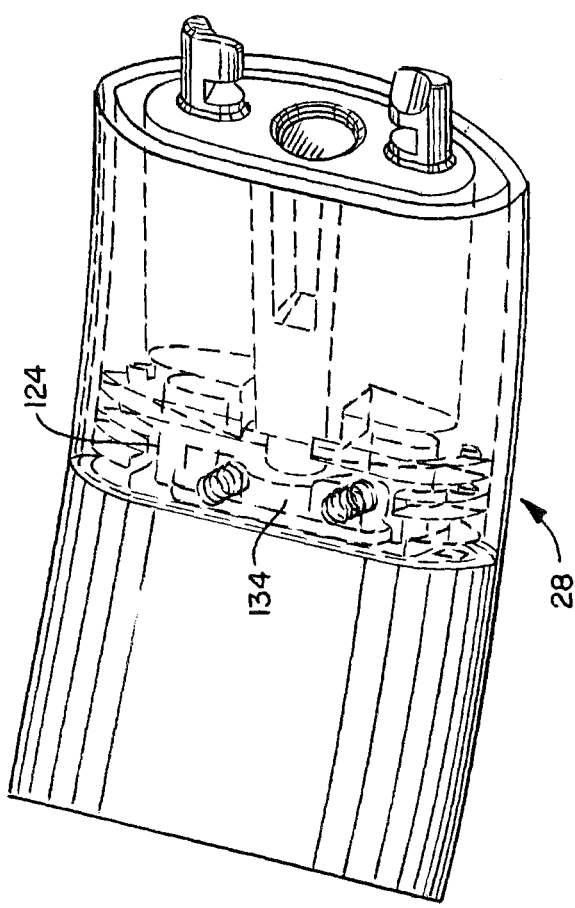
FIG. 13 is a perspective view of the spacer member attached to the wearable device assembly.

The device 10 may be varied in circumferential size wherein the device 10 can define smaller and larger loop configurations to accommodate, for example, different wrist sizes of users. To this end, the housing 12 may incorporate a spacer member 28 or expansion member or element 28 as shown in FIGS. 12-13. It is understood that a single spacer member 28 may be used or multiple spacer members 28 may be used, or not used at all wherein the device 10 simply has the latch mechanism connected at ends of the housing 12. The spacer member 28 cooperates with one end of the housing 12 and one end of the receiver member 92 of the fastening mechanism 26 to increase the circumferential size of the device 10. The spacer member 28 has a body 130 having one end having a pair of openings 132 dimensioned to receive the pair of prong members 120 positioned on the receiver member 92 of the fastening mechanism 26. The body 130 supports a rotary pawl 134 proximate the openings 132. The rotary pawl 134 has a curved cam surface 135 and has a biasing spring 136. The rotary pawl 134 is secured generally at a central location to the body 130 by a fastener and cover plate shown in FIG. 12*b*. The rotary pawl 134 generally is rotatable about the central location. The other end of the body 130 supports a pair of prong members 137 having cam surfaces 138 similar to the prong members 120 of the receiver member 92. As can be appreciated from FIGS. 11*f* and 13, when using the spacer member 28, the prong members 137 of the spacer member 28 are received in and secured in openings in an end of the housing 12. This end of the housing 12 has corresponding structure to receive such prong members 137. The prong members 120 on the receiver member 92 of the fastening mechanism 26 are inserted into the pair of openings 132 on the body 130 of the spacer member 28. To this end, the inclined cam surface 122 on the receiver member 92 engages the cam surface 135 on the rotary pawl 134 wherein the rotary pawl 134 rotates (Arrow A in FIG. 12*c* having cover plate removed for clarity) allowing further insertion of the prongs 120 into the openings 132. Once the slots 124 on the prong members 120 align with the rotary pawl 134, ends of the rotary pawl 134 are received in the slots 124 thereby securing the spacer member to the receiver member 92 of the fastening mechanism 26 (See FIGS. 11*f* and 13). It is understood that access holes can be provided to rotate the rotary pawl 134 when desiring to remove the spacer member 28 from the device 10. It is understood that multiple spacer elements 28 may be used to increase size or spacer elements 28 could be removed to decrease size. The length of the spacer members 28 may vary and in some cases, may range from 5-10 mm. In one example, the length of the spacer elements 28 may be 8 mm each. In another example, the length of spacer members 28 may be 6 mm. It is further understood that if an expansion element 28 is not used, the prong members 120 on the receiver member 92 cooperate with an end of the housing 12 to be secured thereto. In an exemplary embodiment, the spacer element 28 may have similar construction as the housing such as a plastic body having a thermoplastic member positioned over the body. The prong member 120 may be part of a metal insert into the body. In certain exemplary embodiments, the inner diameters of devices 10 that may utilize spacer members can vary from approximately 147 mm to 221 mm.

Figure 43:
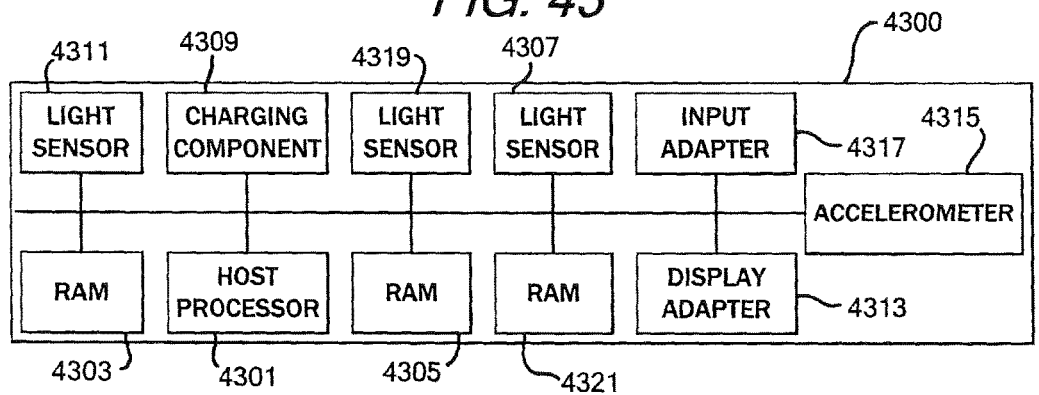
FIG. 43 is a schematic block diagram of the wearable device assembly.

The device 10 has the controller 14 that is supported by the housing 12. The controller 14 generally includes a printed circuit board 140 having various components including circuitry, processing units, data storage memory, connectors and other known components as understood in the art (FIG. 43). The controller 14 further includes a power supply 142 in the form of a battery pack(s) or batteries 142, an antenna assembly 144 and a sensor assembly 146. The controller 14 could also have other components such as a speaker for conveying audible information. FIG. 43 discloses a block diagram of the controller showing additional components associated therewith and will be described in greater detail below.

Figure 14:
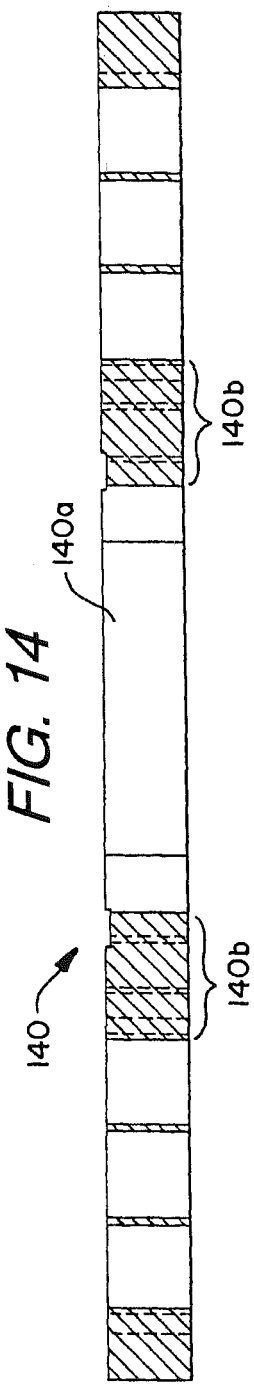
FIG. 14 is a schematic plan view of a flexible circuit member of a controller of the wearable device assembly described herein.
Figure 15:
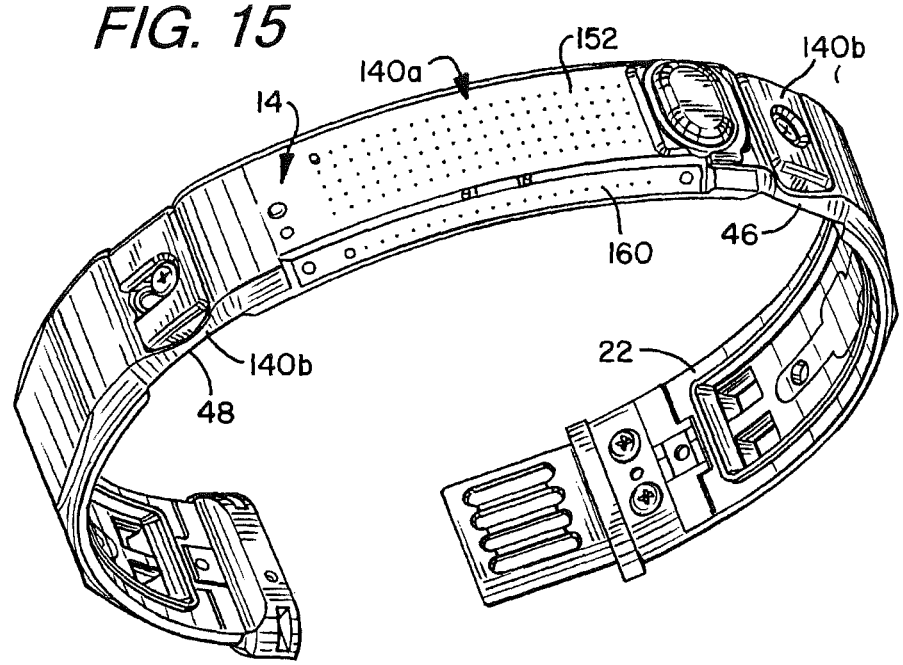
FIGS. 15 and 16 are perspective views of the spine member having certain components of the device attached thereto.
Figure 16:
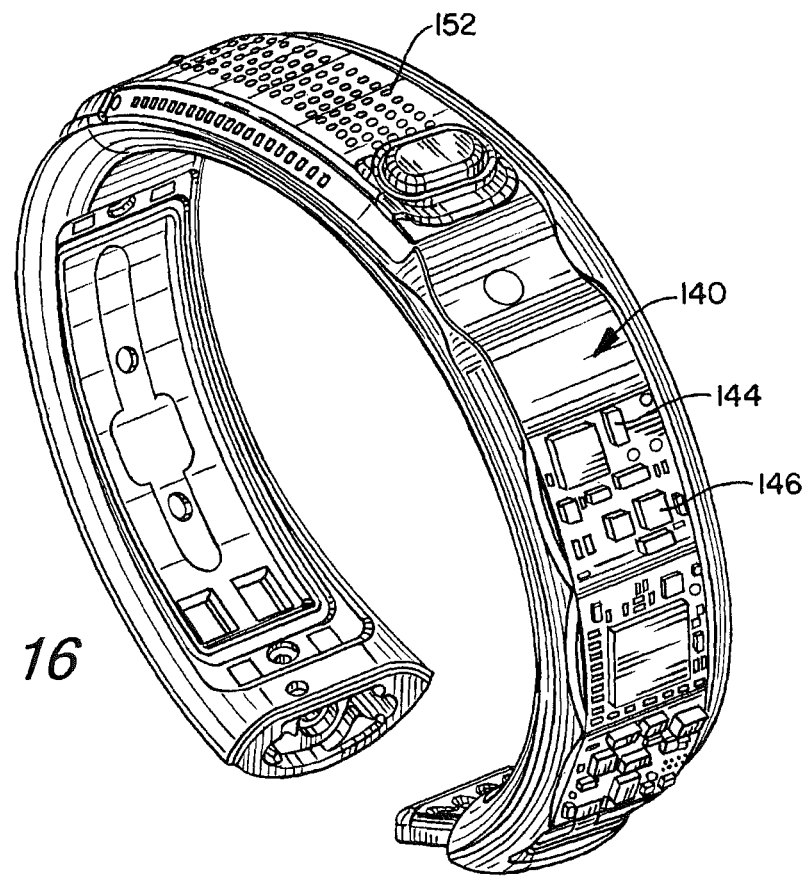

FIG. 14 shows a schematic view of the printed circuit board (PCB member) 140. In an exemplary embodiment, the PCB member 140 is a flexible circuit member. The PCB member has various regions or sections to support the various components thereon. The PCB member further has a central region 140*a* wherein the display 18 and indicator system 20 are operably connected thereto. The PCB member also has flex regions 140*b* that will correspond in position to the flexible zones 46,48 of the spine member 22. Other components described herein are also connected to the PCB member 140. As shown in FIGS. 15 and 16, the PCB member 140 is wrapped around and mounted to the spine member 22. Fasteners may be used to fixedly attach the PCB member to the spine member 22. It is understood that the central region 140a of the PCB member corresponds to the central portion 34 of the spine member 22 when connected. The PCB member 140 generally follows the contours of the spine member 22 including the contours of the flexible zones 46,48. Thus, the flex regions 140b are positioned at the flexible zones 46,48 of the spine member 22 and in general surface-to-surface engagement. This configuration allows the PCB member to be moved proximate a neutral axis wherein stress on the PCB member is minimized when the device 10 is flexed.

Figure 44:
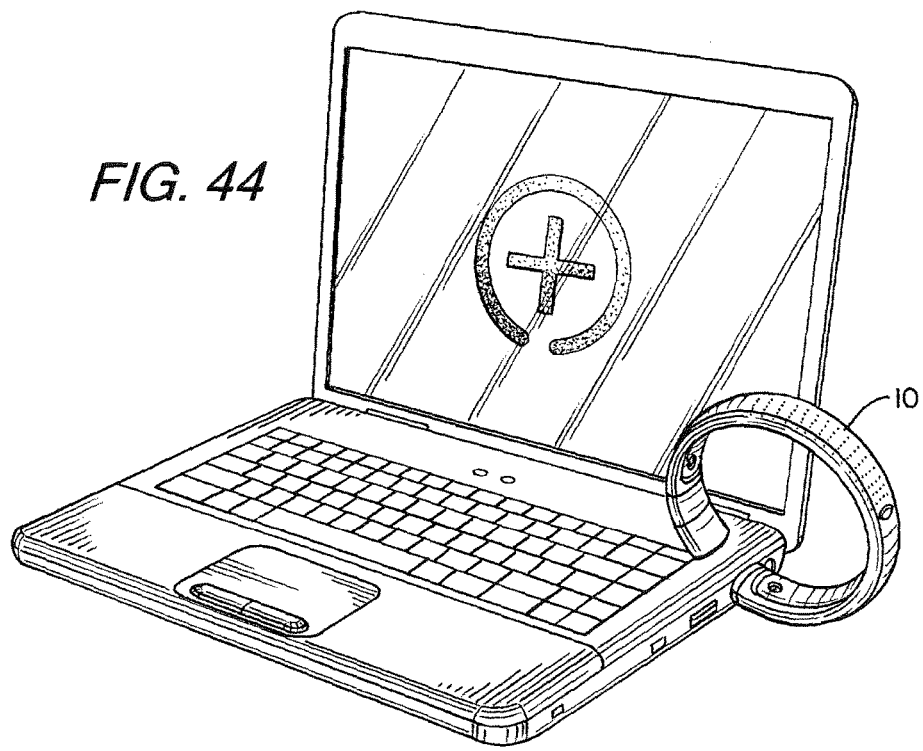
FIG. 44 is a perspective view of the wearable device assembly plugged into a USB port of a computer.

As discussed, the PCB member 140 supports the various components of the controller 14. For example, the PCB member 140 supports the antenna assembly 144 and the sensor assembly 146. The PCB member further supports data storage memory components. Data storage memory receives input from the sensor assembly and as well as receives inputs from the USB connector 94. Data stored by the controller 14 can also be transferred via the USB connector 94 to another device such as a computer and also to a remote site via the computer (FIG. 44).

The antenna assembly 144 supported by the PCB member 140 assists in communication with other mobile devices. Thus, the device 10 is capable of wirelessly communicating with mobile devices, and in one exemplary embodiment, the controller 14 utilizes Blue tooth wireless communication. The controller 14 may, therefore, have a Bluetooth radio and utilizes the antenna assembly 144 wherein the device 10 may wirelessly communicate with a mobile device. It is understood the device 10 is equipped with other necessary components for such wireless communication. Further examples of such communication will be described in greater detail below.

As discussed, the PCB member 140 supports a sensor assembly 146 thereon. The sensor assembly 146 may comprise a plurality of different sensors. In an exemplary embodiment, the sensor assembly 146 comprises an accelerometer in the form of a three-axis accelerometer. As explained in greater detail, the sensor 146 detects movement corresponding to activity of the user wearing the device 10. It is understood that the system 1 and/or controller 14 may also include other sensors as desired. For example, the system 1 utilized by the user may utilize shoe-based sensors that communicate with the device 10. The user may also have apparel based sensors that can communicate with the device 10. It is further understood that the sensor assembly 146 could include a heart rate sensor. The heart rate sensor could be chest mounted sensor if desired. It is understood that the heart rate sensor could also be incorporated into the housing 12 of the device 10 such as a sensor that detects heart rate proximate a wrist of the user. Other sensors could also be utilized such as GPS sensors. Additional sensors may also be incorporated into the device 10. In one exemplary embodiment, the sensor may include a gyroscope sensor. The sensor may be a microelectromechanical system (MEMS) type gyroscope device. Such a sensor may cooperate with other sensors in the device such as the accelerometer to provide enhanced functionality and capabilities as well to provide further differentiation of sensed movements of the user.

Figure 20:
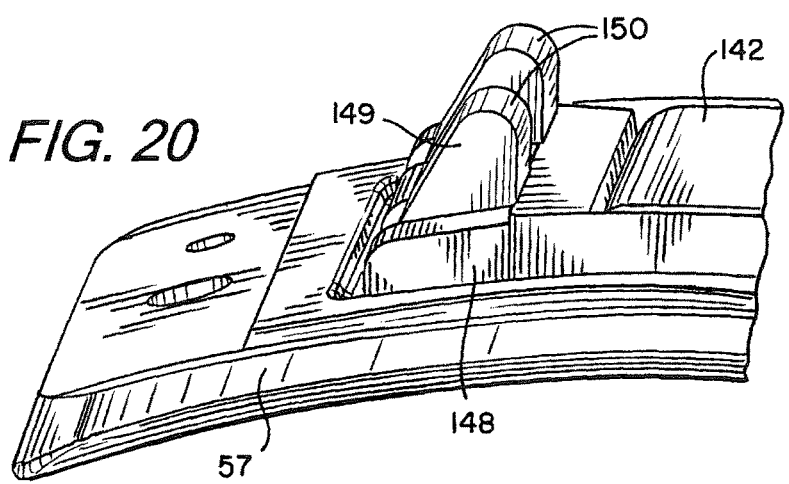
FIG. 20 is a partial perspective view of a battery and closure member and showing contacts of the battery.

As discussed, the controller 14 includes the power supply 142 in the form of batteries 142. It is understood that a single battery 142 could be utilized in the design. Such a design may allow for a flexible circuit member having additional areas to support additional components associated with the device 10. In an exemplary embodiment, however, the power supply 142 utilizes a pair of batteries 142. As can be appreciated from FIGS. 6 and 20, the batteries 142 have a curvilinear or curved configuration and are generally rigid members. The batteries 142 define curved planar surfaces. In an exemplary embodiment, the device 10 utilizes the pair of batteries 142. The first battery 142 is positioned in the first recessed compartment 50 of the spine member 22, and the second battery 142 is positioned in the second recessed compartment 52 of the spine member 22. The batteries 142 have a thickness that generally corresponds to a depth of the recesses 50,52. The batteries 142 are generally flush with the inner surface 32 of the spine member 22. It is understood that the batteries 142 are operably connected to the controller 14 to provide power to the device 10. As shown in FIG. 20, the batteries 142 have a resilient boot member 148 associated therewith. The boot member 148 has a pair of rounded protrusions 149 and battery contacts 150 of the batteries 142 are adhered over the round protrusions 149. The batteries are positioned in the recessed compartments 50,52 wherein the contacts 150 extend through the openings 59 in the compartments 50,52 and engage the PCB member 140 to provide power to the device 10. When the caps 70,74 are fastened down on the spine member 22, the round protrusions 149 and contacts 150 are resiliently pinched against the PCB member 140 providing an enhanced conductive connection. It is understood that each battery 142 utilizes a resilient boot member 148. In additional exemplary embodiments, a conductive epoxy member may be used to join the battery contacts. The overall size of the batteries 142 and respective recessed compartments 50,52 may vary such being larger to increase battery capacity and life of the device before requiring recharging. It is appreciated that the rigid batteries 142 are mounted in the more rigid first segment 42 and rigid second segment 44 of the spine member 22. The flexible zones 46,48 of the spine member 22 allow the segments 42,44 and batteries 142 to hingedly pivot about the flexible zones 46,48 to provide a generally flexible housing 12 and device 10.

As shown in FIGS. 2-6 and 16-19, the device 10 includes a depressible input button 16 assist in operation of the device 10. As can be appreciated from FIGS. 17 and 18, the input button 16 is operably connected to the controller 14 and supported by the housing 12 generally adjacent the display 18. The input button 16 is accessible to the user via the input button 16 extending past the outer encasement member 24 of the housing 12. The input button 16 has a rigid base member 76 and a flexible cap 78 integrally formed together in a two-shot molding process. An internal chamber 79 is defined by the input button 16 to support a tact switch that can interact with the controller 14. The rigid base member 76 has an upper ring 80 defining a first tool surface 82 and a lower ring 84 adjacent the flexible cap 78 and defining a second tool surface 86. During the process of forming the device 10, the first tool surface 82 and the second tool surface 86 engage a tool in tight surface-to-surface engagement when the outer encasement member 24 is injection molded around the spine member 22 and supported components. This engagement prevents the injection molded material from flowing into the internal chamber 79 of the input button 16 which would prevent the input button 16 from operating correctly. Operation of the device 10 from inputs provided via the input button 16 will be described in greater detail below.

Figure 2:
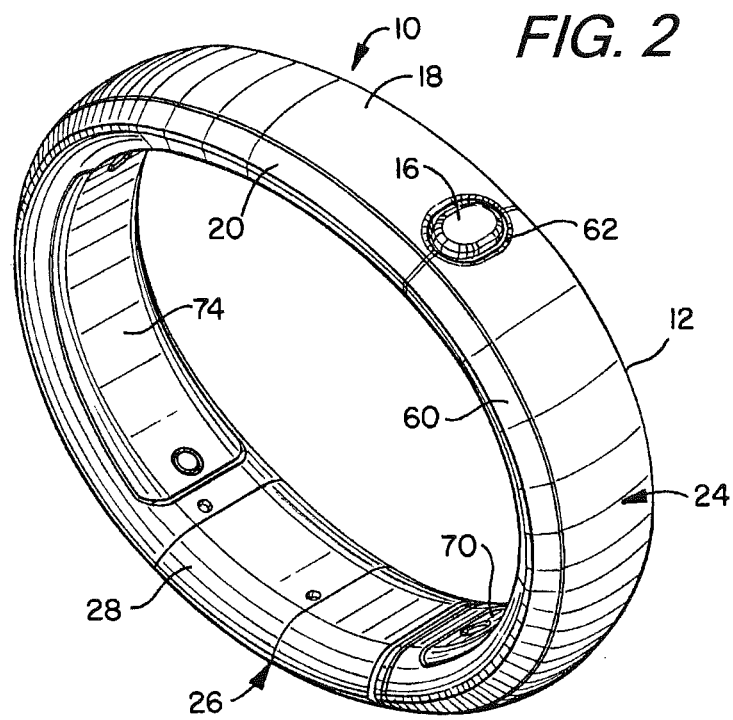
FIG. 2 is a perspective view of the wearable device assembly shown in FIG. 1.
Figure 2A:
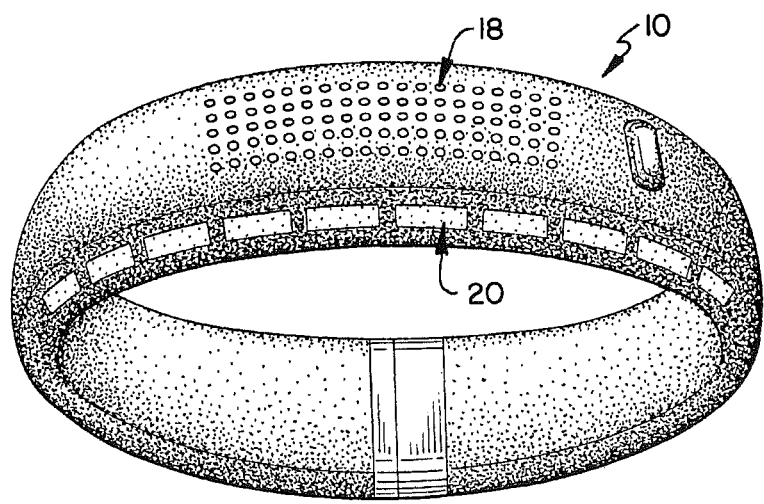
FIG. 2a is an alternative embodiment of the wearable device assembly.

As shown in FIGS. 2 and 15 and 16, the display system 18 or display 18 of the device 10 is supported by the housing 12 and operably connected to the controller 14. The display may be considered an illuminable portion of the device 10 or housing 12. The display system 18 may include a series of individual lighting elements or light members such as LED lights 152 in an exemplary embodiment. The LED lights may be formed in an array and operably connected to the PCB member 140 at the central location. The LED lights 152 may be arranged such that words, letters, numbers, symbols and the like may be produced by lighting various combinations of the individual discrete LED lights 152. For example, LED lights 152 may be arranged in a matrix formation having a specified number of rows and columns. The outer encasement member 24 of the housing 12 surrounds and protects the LED lights 152. As discussed, the outer encasement member 24 has the first region 64 (FIG. 19) and corresponds to the locations of the LED lights 152 so that once the LED lights are illuminated, the light is visible through outer encasement member 24 (in an alternative embodiment, the first region 64 could be made transparent or substantially transparent). It is understood that the first region may be individual and discrete. For example, each of the illumination regions may be surrounded by non-transparent or opaque portions of the outer encasement member 24 such that illumination from each of the LED lights 152 does not blend together. The display system 18 may span only a portion of the total circumference of the wearable device assembly 10. For example, as illustrated in FIG. 2, the display system 18 occupies a top portion or central portion of the device 10 opposite the fastening mechanism 26. The size of the display system 18 (e.g., the number of individual LED lights, number of rows and columns of lights, an overall width or length) may be determined based on a maximum amount of data to be displayed at any one time, a size of the font and/or characters to be used and/or combinations thereof. In one example, the display system 18 may be composed of 5 rows of 20 LED lights 152, wherein each row is substantially parallel to the length of wearable device assembly 10. Additionally or alternatively, the overall exterior circumference (e.g., of an outward facing surface of the device assembly 14) may range from 174-182 mm. It is also understood that the display 18 could include a light member indicating the device 10 is communicating via wireless connection such as Bluetooth communication with a mobile device.

As also shown in FIGS. 2 and 15 and 16, the indicator system 20 of the device 10 is supported by the housing 12 and operably connected to the controller 14. The indicator system 20 may also be considered a portion or component of the overall display 18. The display system of the device 10 may be considered to have a first display and a second display. It is understood that the indicator system 20 can operate and illuminate in conjunction with the display 18 or completely separate from the display 18. The indicator system 20 may also include a plurality of additional lighting elements 160 or light members 160, which may also take the form of LED lights in an exemplary embodiment. The light members 160 are operably connected to the controller 14 and supported by the PCB member 140. The indicator system 20 is positioned generally at the side edge of the housing 12. In one particular example, the indicator system 20 may include a series of twenty lighting elements 160. Optionally, lighting elements 41 may run along both side edges of the housing 12 of the wearable device assembly 10. The lighting elements 160 are also positioned in a generally linear configuration in an exemplary embodiment. The lighting elements 160 of the indicator system 20 may be differently shaped from lights 152 of the display system 18. The difference in shape, size or other appearance attribute may allow a user to identify the type of information being conveyed. The lighting elements 160 may, for example, line one or more of the beveled side edges 60 of the housing 12 of the wearable device assembly 10, allowing for ease of viewing by the user. In the example where the sides or edges of wearable device assembly 14 are rounded, the lighting elements 160 may be positioned on an outer curvature of the rounded edges such that light may be seen when worn (e.g., facing away from the user's wrist or other body part on which the device 14 is worn). Similar to the configuration of lights 152 of the display 18, the outer encasement member 24 has the second region 66 (FIG. 19) that is at locations corresponding to the position of lighting elements 160 of the indicator system 20. Light projected from the light members of the indicator system 20 are viewable through the outer encasement member 24 at the second region 66 (in alternative embodiments, the second region 64 could be transparent or substantially transparent). In one or more arrangements, the appearance of illumination produced by lighting elements 160 may be defined by the size, shape, transparency and other appearance attributes of a corresponding portion of the outer encasement member 24. For example, the lighting elements 160 might actually be circular (e.g., circular bulbs) but may be used to illuminate transparent rectangular regions of the outer encasement member 24, thereby producing rectangular indicators (See e.g., FIG. 2a). The plurality of lights 160 of the indicator system 20 may extend around a portion of the circumference of device assembly 10. In one example, the plurality of lights 160 of the indicator system 20 extend generally the same length of the length of the display 18. Spacing between the various plurality of lights of the indicator system 20 and display 18 may also be similar. In another example, the light members 160 may extend around approximately half of the circumference while in other examples, indicators light members 160 may extend around approximately a third of the circumference. In yet another example, the light members 160 may extend around three-quarters or substantially the entire circumference of the wearable device assembly 10. It is also understood that the plurality of lights 160 comprising the indicator system may be grouped together wherein the indicator system may have different segments. The different segments of the indicator system 20 may be illuminated in different configurations as described in greater detail below. Each lighting element 160 may also be considered a separate individual segment of the display. From the configuration of the display 18 and indicator system 20, it is understood that the display 18 may project light in a first direction, and the indicator system 20 may project light in a second direction 20, wherein the first direction is different from the second direction. In one exemplary embodiment, the second direction may be generally transverse to the first direction. It is also understood that the light members of the displays could take other various forms and structures that provide illuminable characteristics.

FIGS. 39-42 are schematic views illustrating a molding process for creating a wearable device assembly according to aspects of the invention. In FIG. 39, a first mold 170 may be used to create the spine member 22 of the wearable device assembly 10. As discussed, the structural features of the spine member 22 allow the attachment, insertion and mating of various electronic and non-electronic components of the wearable device assembly 10. The spine member 22 may be molded from a plastic material such as a thermoplastic material injected into the mold 170. The spine member 22 may be thinner in some portions such as the flexible zones to provide flexibility in those regions. In contrast, other portions such as the segments supporting the batteries may be thicker to provide more rigidity. In addition, the electronic components such as circuits and lighting elements (e.g., LEDs) may be attached to more rigid portions to prevent breakage. Subsequently, the spine member 22 may be assembled with other components as described above. For example, the battery packs 142, circuits, display 18 and indicator system 20 may be assembled with the spine member 22.

Figure 40:
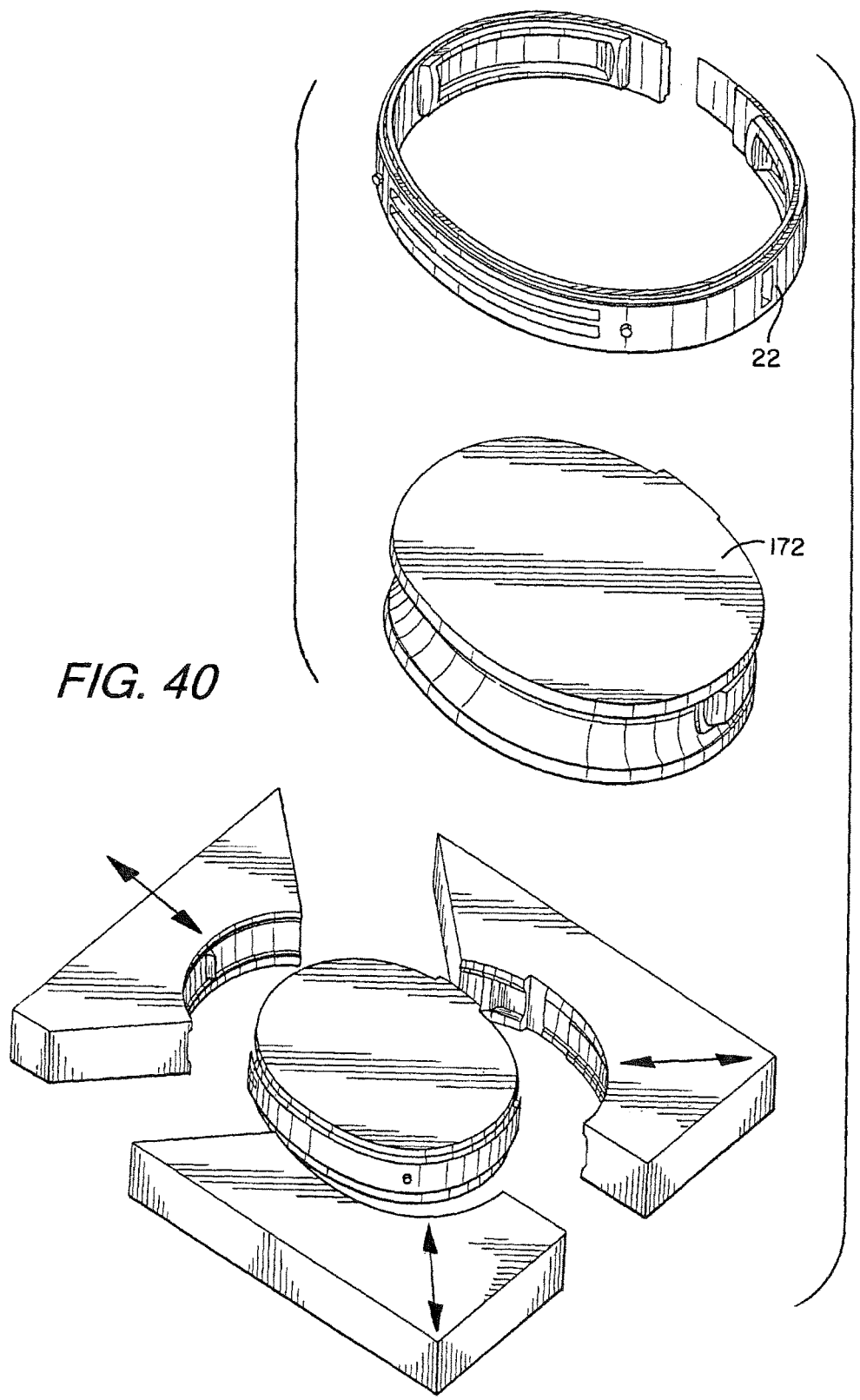
Figure 41:
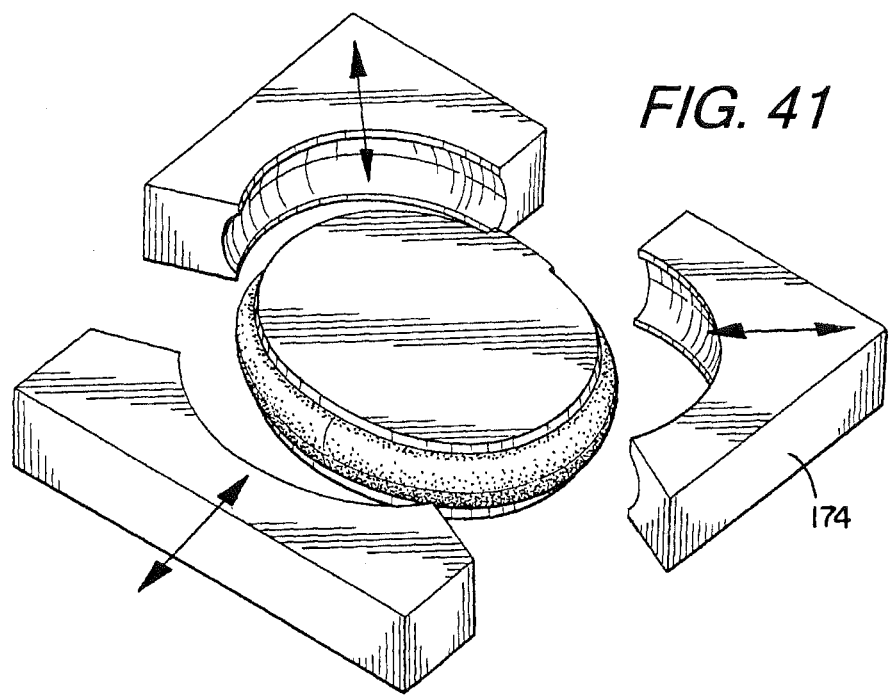
Figure 42:
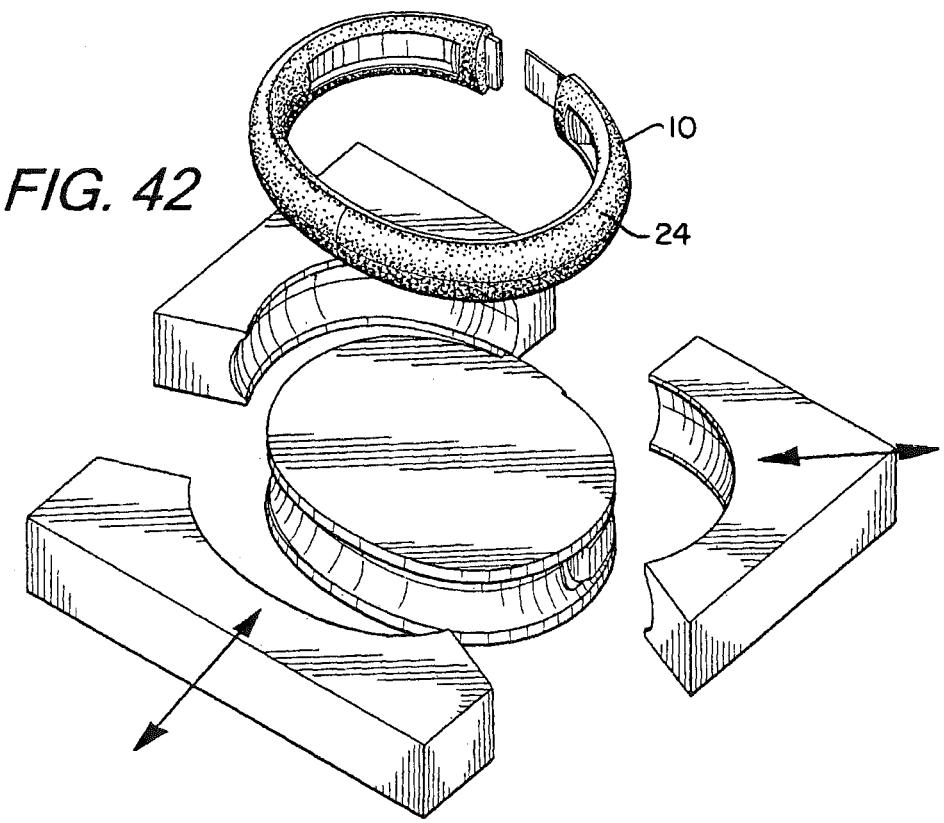

As further shown in FIG. 40, the assembled spine member 22 supporting certain of the various components may then be wrapped or loaded onto an insert core 172 for further injection molding. An interior diameter, or inner portion, may then be injection molded onto the spine member 22. In FIGS. 41 and 42, the molded assembly may then be inserted into an outer diameter mold 174 and an outer diameter, or outer portion, of the wearable device assembly 10 may be molded to completely form the outer encasement member 24 of the housing 12. The device assembly 10 can then be removed from the insert core 172.

It is understood that additional processes can be utilized in forming the device such as the device 10 shown in FIGS. 1-6. In an exemplary embodiment, a process of forming the spine member 22 initially includes forming the battery compartments. As can be appreciated from FIGS. 7a, 7b, 8a and 8b, a mold is provided wherein via a thixo-molding process, magnesium is injected into the mold to form the thixo-molded members 55. The magnesium thixo-molded members 55 cooperate with the metal battery caps 70,74 (FIG. 2) to provide a substantially metal enclosure for the batteries 142. As discussed, other metal forming processes can be used. Once formed, the thixo-molded members 55 are placed in a mold wherein material is injected into the mold to form the spine member 22. The material is overmolded around the thixo-molded members 55 wherein a certain amount of injected material extends over an internal surface of the members 55 (FIGS. 7-8). It is understood that the mold is designed to incorporate forms for the substantially rigid portions of the spine member 22, the flexible zones 46,48 of the spine member 22 as well as other structures for receiving, mounting or otherwise supporting the various components of the device 10 as described herein. In an exemplary embodiment, the material injected over the thixo-molded members 55 to form the remaining portions of the spine member 22 is polypropylene.

Once the spine member 22 is formed, additional components are connected to the spine member 22. For example, one end of the spine member 22 can be connected with connection structure that will cooperate with either one of the latch mechanism or a spacer element. It is further understood that the USB connector 94 is formed having the features described above. As can be appreciated from FIGS. 10a-10c, the USB leads 98 are provided having the raised ribs 118 formed such as through a stamping process. The leads 98 are placed in a mold wherein plastic injection molded material is formed around the leads 98 to form the rigid body 96 around the leads 98. It is understood that the mold is designed such that the rounded openings 116 are formed and wherein the leads 98 are then spaced apart equally and vertically aligned. While the leads 98 are recessed in the rounded openings, the raised ribs 118 extend to proximate a top surface 114 of the rigid body 96. The mold is also designed to form the recess 100 in the rigid body 96 of the USB connector 94. Once formed the USB connector 94 is connected to an end of the spine member 22 while ends of the leads will be ready to be connected to the controller (FIG. 9).

The spine member 22 with the attached components may then be inserted into a mold wherein an inner diameter portion of the device is overmolded. A thermoplastic elastomer material is injected into the mold to form the inner portion of the housing 12. It is understood that an adhesion promoter may be used wherein the adhesion promoter is applied to the inner surface of the spine member 22 prior to overmolding the thermoplastic elastomer material. The adhesion promoter assists enhances the bonding of the thermoplastic elastomer material to the spine member 22. In one exemplary embodiment, 3M Primer 94 sold by the 3M company is used as the adhesion promoter. It is also understood that the molds are designed such that openings are provided in the inner portion of the housing 12 that are in communication with the recessed compartments 50,52 that will receive the batteries 142.

Figure 17:
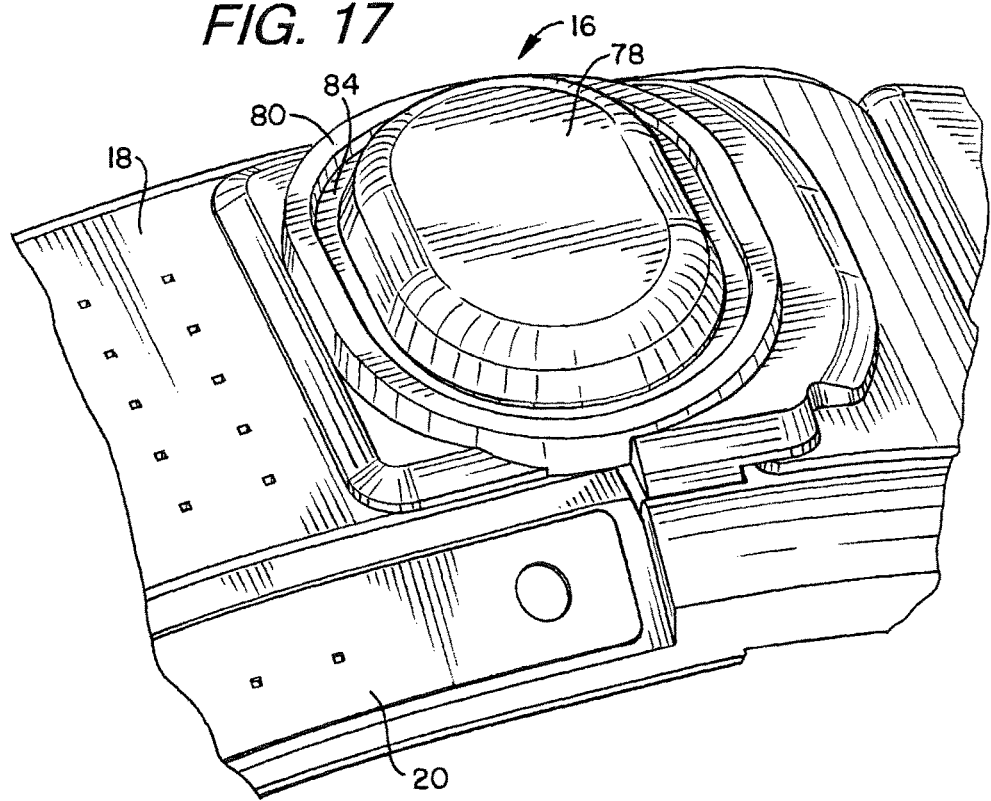
FIG. 17 is an enlarged view of an input button associated with the controller.
Figure 18:
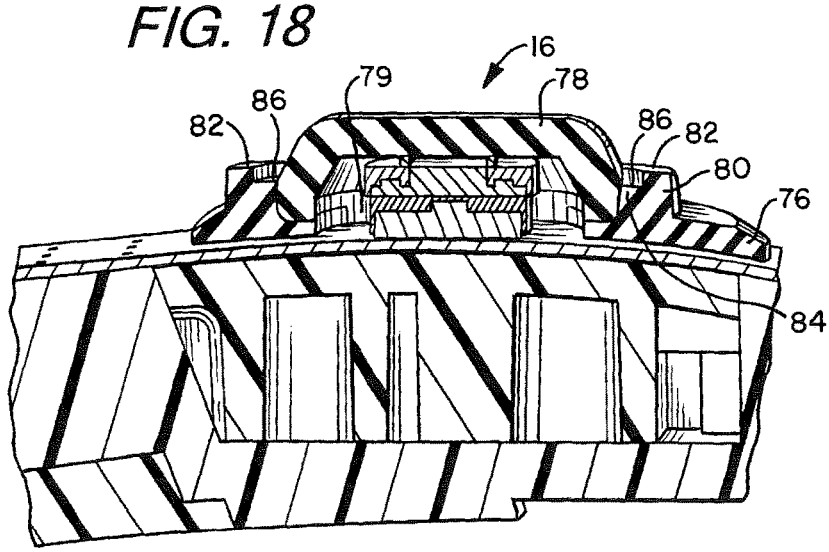
FIG. 18 is a partial cross-sectional view of the input button of FIG. 17.
Figure 19:
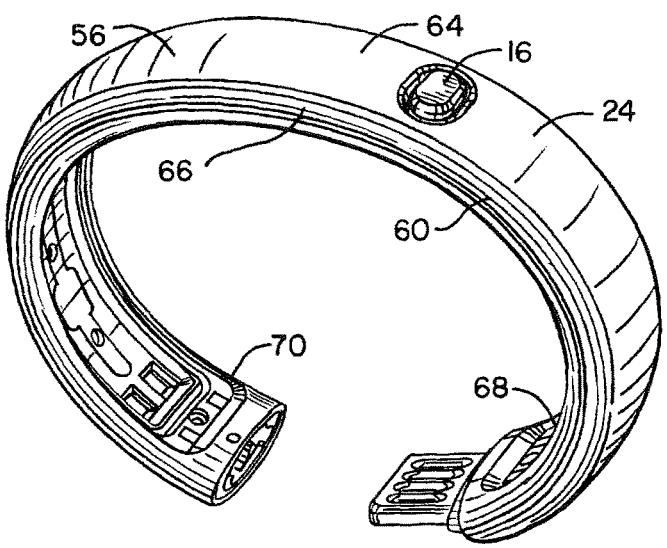
FIG. 19 is a perspective view of the spine member having an outer member formed thereon and showing battery compartments.

Additional components are then ready to be attached to the spine member. As can be appreciated from FIGS. 15 and 16, the PCB member 140 of the controller 14 is formed with the necessary circuitry, other electrical components, antennas, as well as the required sensors including the three-axis accelerometer. In addition, the display 18 and indicator system 20 components are also connected to the PCB member 140. It is further understood that the input button 16 is formed in a two-shot injection molding process wherein the rigid base member is integrally connected to the flexible cap (FIGS. 17-18). The input button is also connected to the PCB member 140. The PCB member 140 is connected to the spine member 22. The PCB member 140 is wrapped onto the spine member and follows the contours of the spine member 22 generally in surface-to-surface engagement including at the flexible zones 46,48 of the spine member 22. (FIGS. 6, 15, 16) The PCB member 140 is fixedly attached to the spine member 22. As discussed, this configuration assists in providing a more neutral axis wherein stresses from flexing are minimized. The ends of the leads of the USB connector 94 are also soldered onto the PCB member 140. The batteries 142 are inserted into the battery compartments (FIGS. 19-20). The raised contacts are positioned through the openings 59 in the battery compartment 50,52 wherein the contacts mate with receiving contacts on the printed circuit board. The battery closure members are fixedly attached to the inner portion of the device via screw fasteners (FIG. 2) wherein the battery contacts are biased against mating contacts associated with PCB member 140.

Figure 19A:
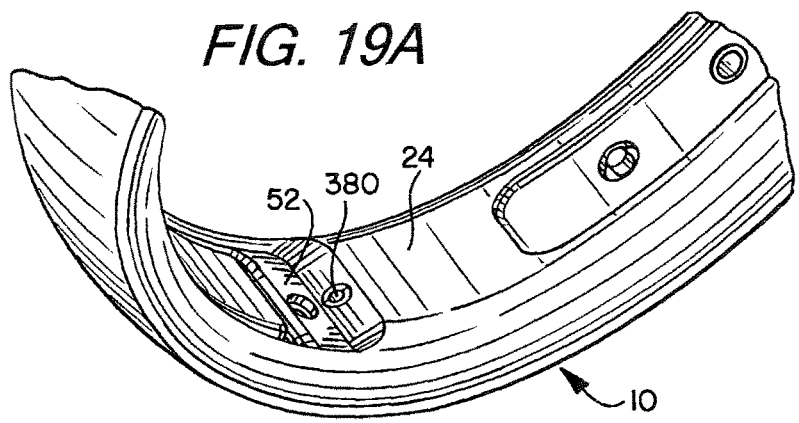
FIG. 19a is an underside perspective view of the device showing a portion of a battery compartment having a port opening.

This intermediate assembly is then inserted into an additional mold for an additional overmolding process. The mold includes a tool that engages the first ring surface 82 and the second ring surface 86 of the input button 16 to prevent the thermoplastic elastomer material from migrating into the internal portions of the input button 16 (FIGS. 17-18). The thermoplastic elastomer material is injected into the mold to complete formation of the outer encasement member 24. In one exemplary embodiment, the spine member 22 includes a tube structure having a port opening 380 wherein the material is injected through the tube structure to form the outer portion of the outer encasement member 24. As shown in FIG. 19a, the port opening 380 is provided in an inclined surface in the battery compartment 52 and is in communication with the tube structure through the spine member 22. Once placed in the appropriate mold member, the injected material is injected through the port opening 380 and flows in the mold to form the outer portion of the outer encasement member 24. It is understood that the port opening 380 could be located in either battery compartment or in other locations on the spine member 22. The port opening 380 could further include multiple port openings. Thus, the various components supported on the spine member 22 are encased in the outer encasement member 24. The thermoplastic elastomer material flows to and engages with a side surface of the input button 16 wherein further migration of the material is prevented by the tool (See FIG. 6). Once the overmolding process is complete, the receiver portion of the latch mechanism and any desired spacer element can be attached (FIGS. 2, 3 and 19). In such configuration, it is understood that the housing 12 is easily flexible to allow for placing the device on a wrist of a user. The device 10 flexes at the flexible zones 46,48 of the spine member 22 wherein it is understood that the rigid segments with the batteries 142 mounted thereon move together. The elastic properties of the outer encasement member 24 readily allow for such pivoting while providing sufficient structure to protect the components supported by the spine member 22.

The device 10 is then formed and ready for operation (FIG. 2). Operation and other user experiences are described below.

The device 10 of the present invention has numerous alternative structures and configurations. For example, FIGS. 21-38 disclose additional embodiments of various components of the housing 12, controller 14, display 18 and indicator system 20 that can be utilized in the device 10 and combined with features of the device 10 described above.

FIGS. 21*a-d* illustrate schematic side views of alternative embodiments of spine members and batteries that can be used with the device 10 of the present invention. Similar structures may be referred to with similar reference numerals. The spine member 22*a* has the multiple flexible zones 46*a*,48*a* along with the rigid or substantially rigid segments or zones 42*a*,44*a*. FIGS. 21*a-d* illustrate the flexible zones in the form of thinner portions of the spine member 22*a*. The thinner portions may correspond to more flexible regions while thicker portions of the spine member 22*a* may correspond to more inflexible areas or rigid zones. It is understood that the spine member 22*a* more easily flexes or hingedly pivots about the flexible zones. The rigid zones 42*a*,44*a* might not be flexible to allow for non-flexible components such as circuit boards, lighting systems, battery packs and other electronics assemblies to be secured. For example, the rigid zones 42*a*,44*a* may each include a battery pack 142. Additionally or alternatively, one or more of rigid zones 42*a*,44*a* may include circuitry for processing, storing and/or sensing athletic information. The display component may be disposed in an additional central rigid zone generally extending between the rigid zones 42*a*,44*a* supporting the batteries. The rigid zones 42*a*,44*a* may have a limited amount of flexibility to at least allow for a predefined amount of expansion of device assembly 10.

Figure 21B:
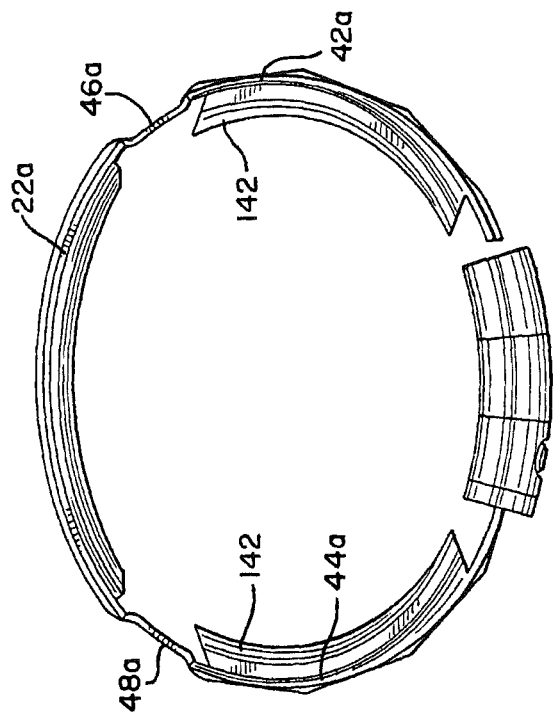
Figure 21A:
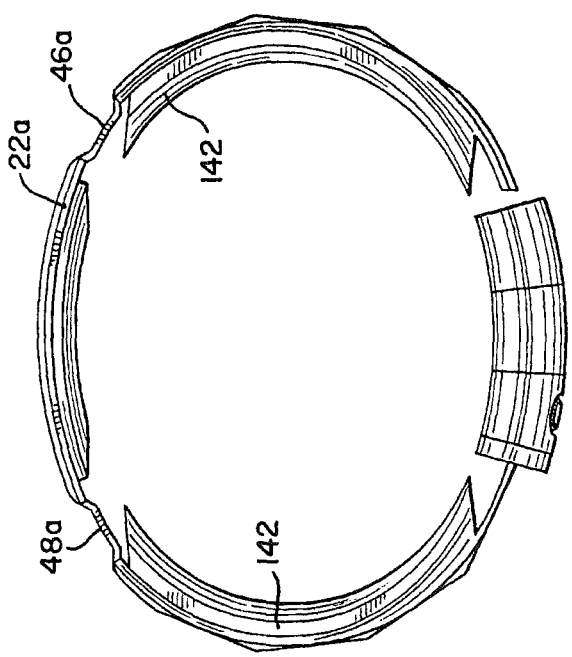

As further can be appreciated from FIGS. 21*a*-21*b*, the lengths of battery packs 142 can be adjusted to increase or decrease battery capacity. Due to the changes in the lengths of the battery packs 142, the length or other dimension of display components, indicator system components, or other controller components can also be affected. For example, if the length of battery packs 142 is increased, the size of the display or display may be decreased to compensate. Similarly, in FIGS. 21*c*-21*d*, the thickness of the battery packs 142 may be modified to adjust battery capacity and device life. By increasing thickness of the device rather than length, the size of flexible zones may be maximized since there is no expansion of the battery pack 142 along the length of device assembly 10. However, increasing thickness may also increase weight and/or device circumference. The batteries 142 and rigid segment or zones 42*a*,44*a* may be cooperatively dimensioned to provide a device 10 having a suitable capacity to record activity and display information prior to requiring recharging.

Figure 22:
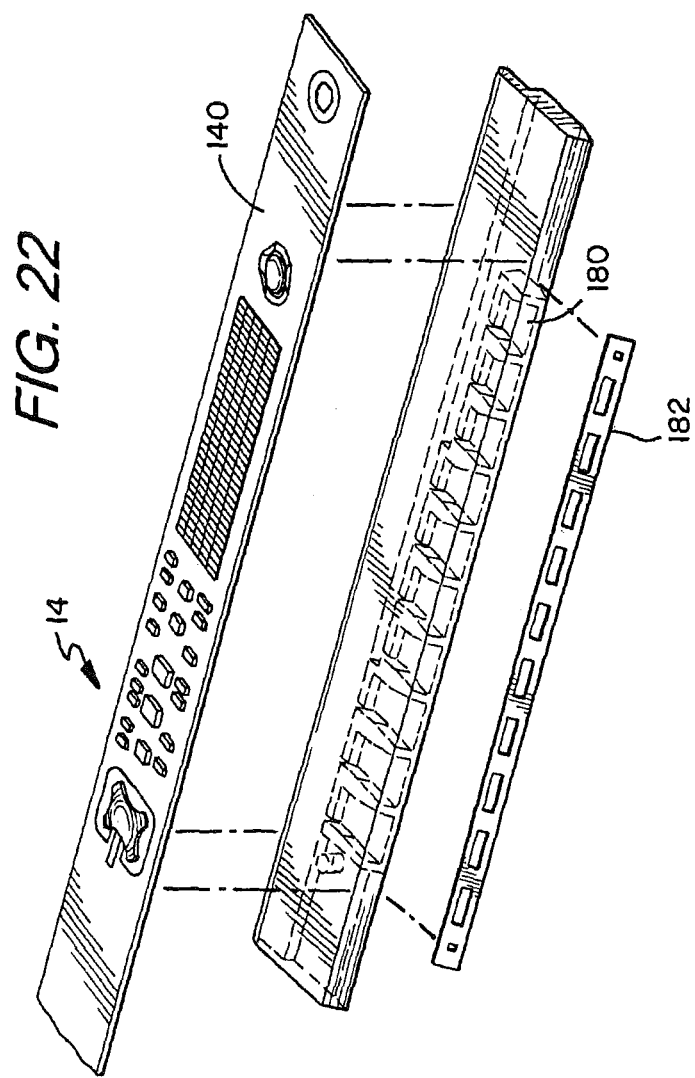
FIG. 22 is an exploded perspective view of an alternative embodiment of controller components of the device.
Figure 23:
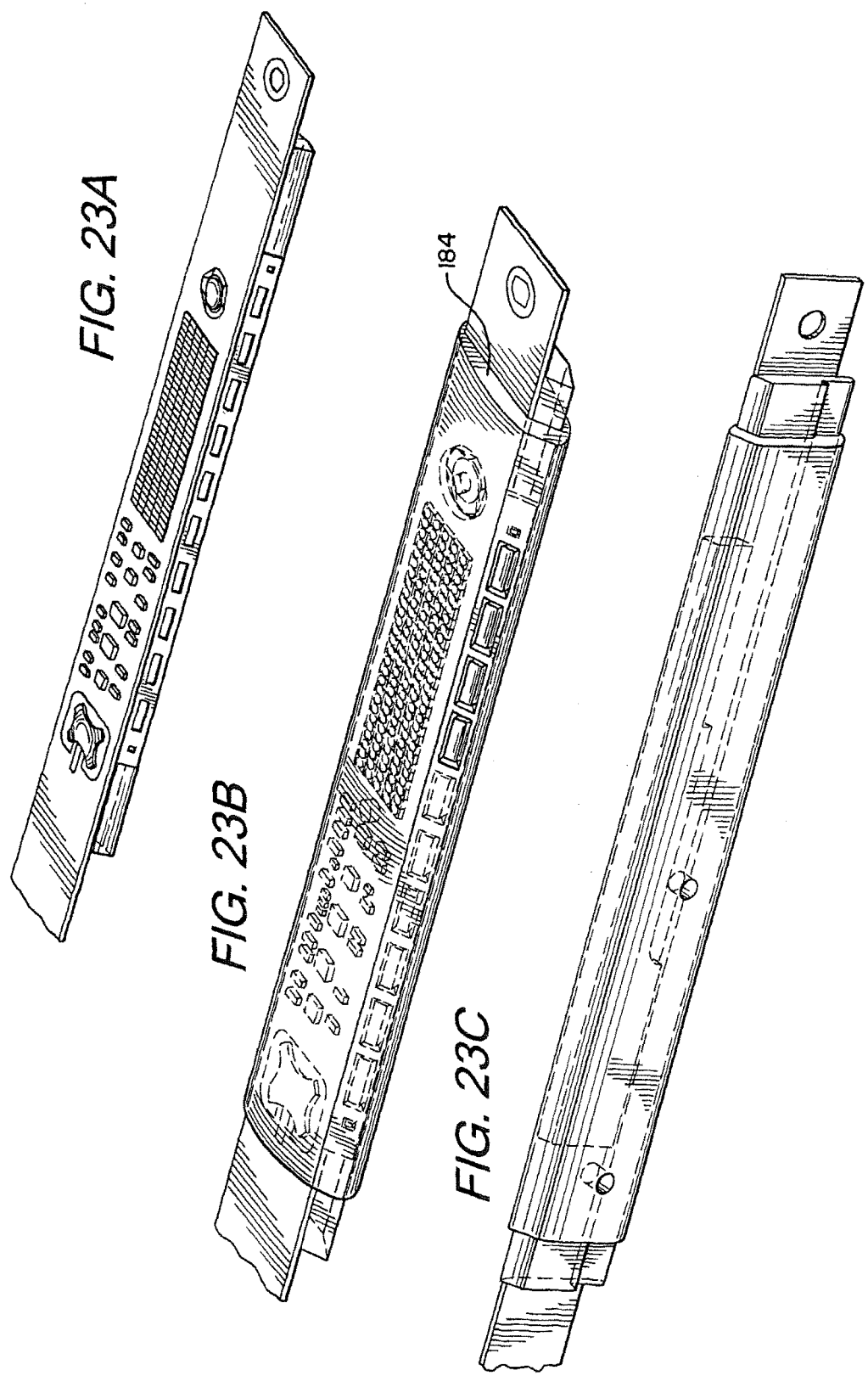
FIGS. 23a-c disclose additional views of controller components and a display and indicator system according to alternative embodiments of the device.

FIGS. 22 and 23 disclose components of a controller according to an alternative embodiment of the invention. Similar components may be referred to with similar reference numerals. The PCB member 140 supports other components of the controller 14. The indicator system 20 may also be provided with separate light member compartments 180 and a cover member 182 positioned over the light members of the indicator system. An additional cover member 184 may be positioned over the PCB member 140 as shown in FIGS. 23*a-c*. It is understood that the controller as shown in FIGS. 23*a-c* can then be wrapped onto a spine member 22 and fixedly attached thereto.

Figure 24:
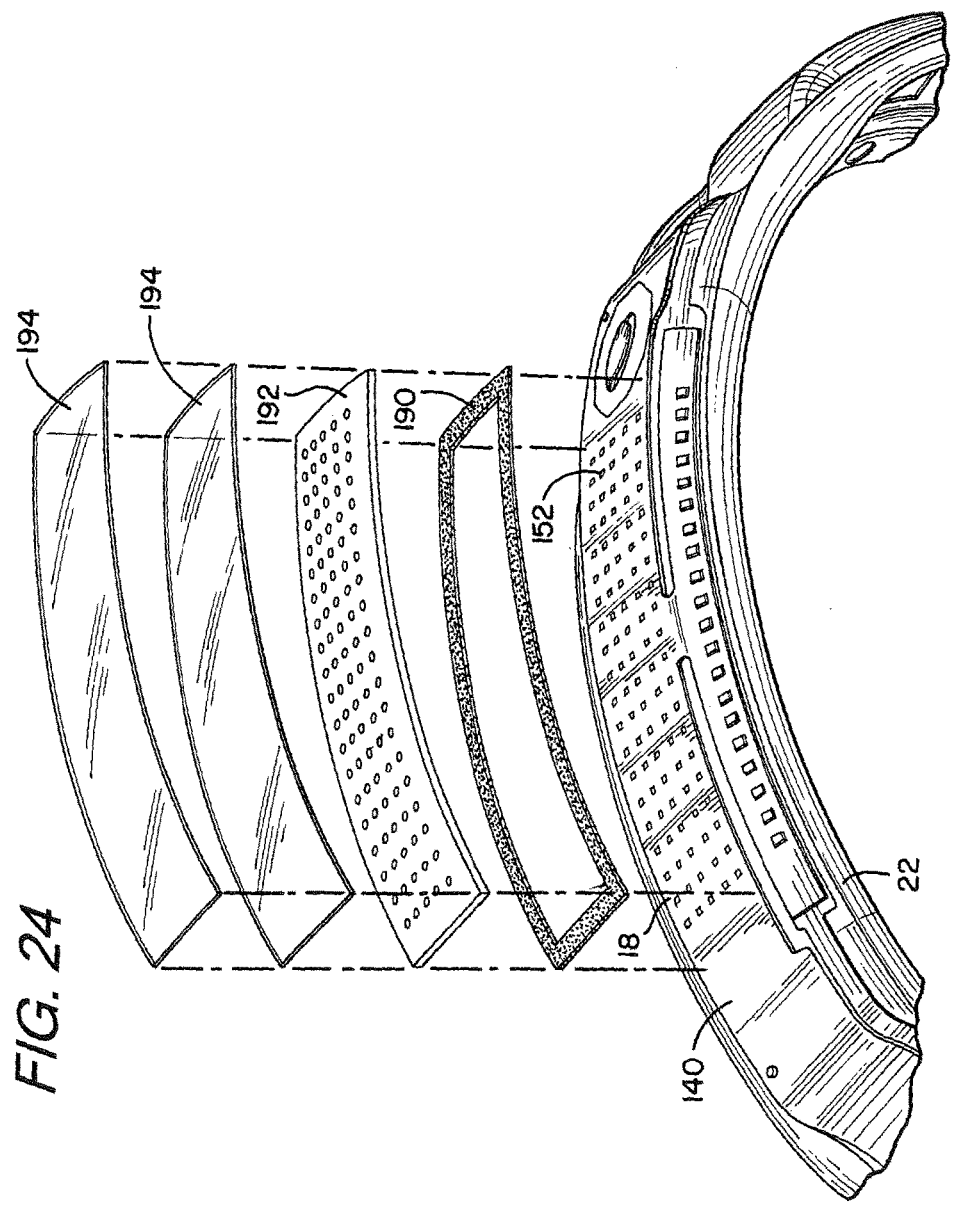
FIG. 24 is a partial exploded perspective view of an alternative embodiment of a display and indicator system associated with the controller of the device.
Figure 25:
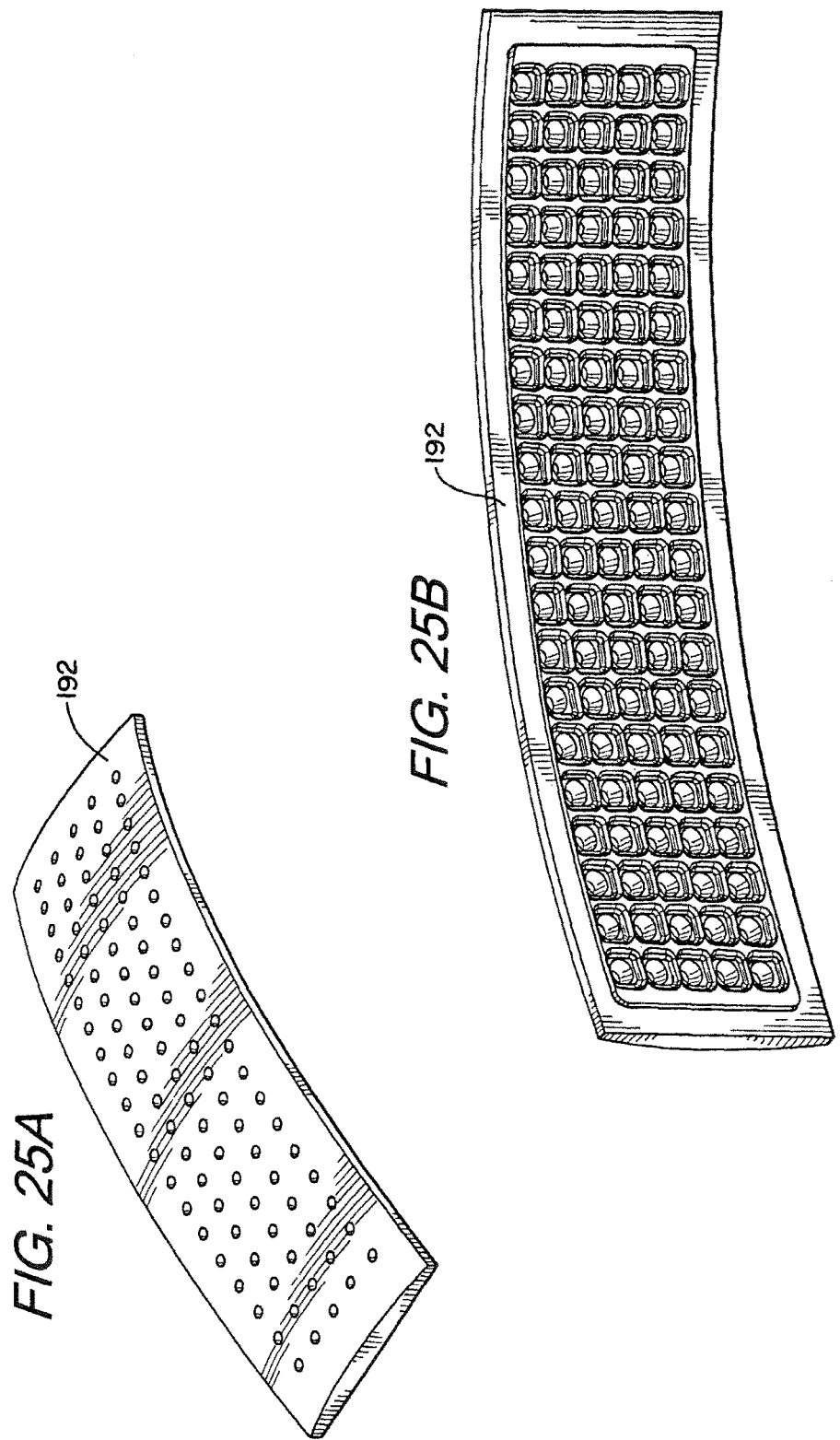
FIG. 25a is a perspective view of a cap member used in the display shown in FIG. 24.
FIG. 25b is an underside view of the cap member shown in FIG. 24.

FIGS. 24-27 disclose display components of an alternative embodiment of the device 10. FIG. 24 discloses an exploded view of components of a display according to an alternative embodiment of the invention. Similar components may be referred to with similar reference numerals. The display 18 in this embodiment has a plurality of light members 152 operably connected to the PCB member 140 of the controller 14 and mounted to the spine member 22. A seal member 190 has an opening therethrough and shaped to be positioned around the peripheral edges of the plurality of light members 152. A first cap member 192 having a plurality of apertures therethrough is positioned over the plurality of light members 152. The apertures are positioned to correspond to respective light members. A pair of additional transparent cover members 194 is positioned over the cap member 192. A single transparent cover member could also be utilized. As can be appreciated from FIG. 24, the seal member 190, cap member 192 and cover members 194 are positioned over the plurality of light members 152 of the display 18. The cap member 192 is sandwiched between the seal member 190 and the cover members 194. When the plurality of light members 152 are illuminated, light can pass through the apertures of the cap member 192 and is viewable through the cover members 194.

Figure 26:
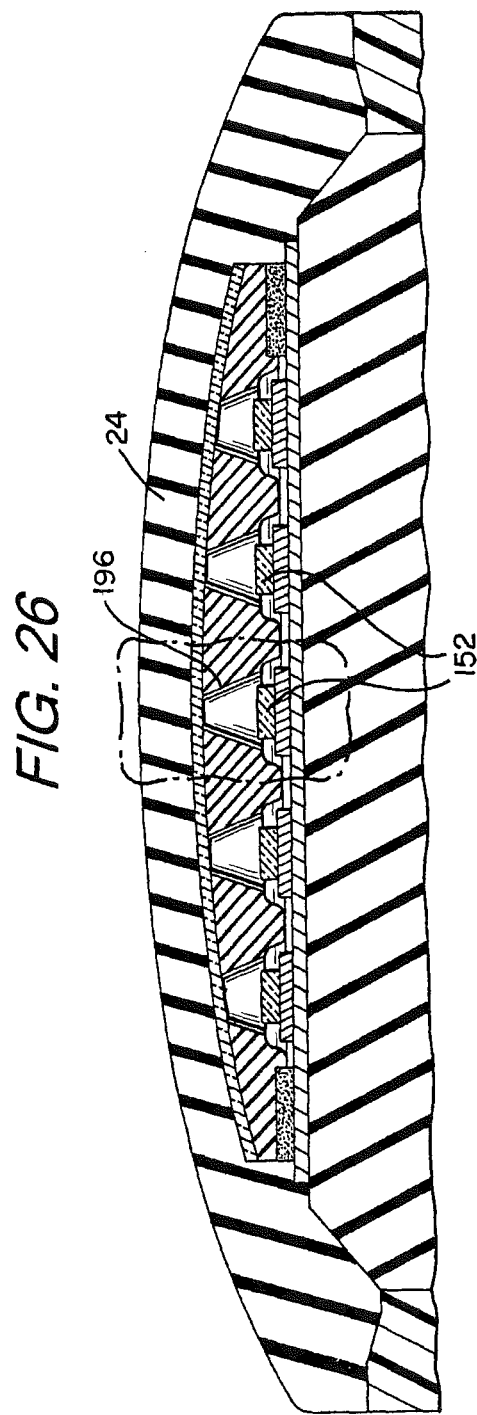
FIG. 26 is a partial cross-sectional view of the display of FIG. 24.
Figure 27:
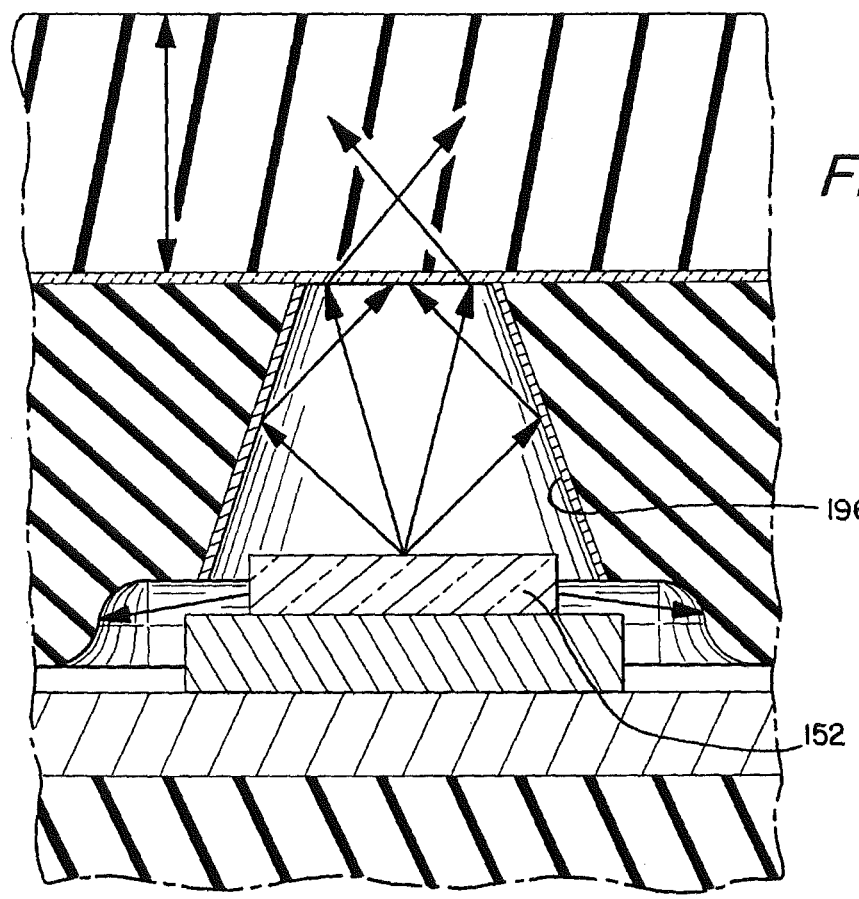
FIG. 27 is a partial enlarged cross-sectional view of a light member and cap member of the display of FIG. 24.

FIGS. 25*a* and 25*b* disclose the cap member 192 in greater detail. The cap member 192 is configured to be positioned over the plurality of light members 152 of the display 18. The cap member 192 has a convex outer surface. FIG. 25*b* discloses an underside view of the cap member 192 shown in FIG. 25*a*. The cap member 192 has the plurality of apertures that generally correspond to the position of the plurality of light members 152 of the display 18. As further shown in FIG. 26, each aperture is in communication with a column 196 extending into the underside of the cap member 192. As shown in FIGS. 26 and 27, each column 196 has a general frusto-conical shape. A bottom portion of the column is dimensioned to completely surround the light member 152 of the display 18. As can be appreciated from FIGS. 26 and 27, the cap member 192 is positioned over the plurality of light members 152 wherein each light member 152 is positioned within a respective column 196 of the cap member 192. The outer encasement member 24 of the device 10 is positioned over the cap member 192 and is structured and dimensioned such that when the light member is illuminated, light is viewable through the outer encasement member 24. As shown in FIG. 27, when the light member is illuminated, the frusto-conical column 196 assists in reflecting light such that the light if directed in a more focused manner through the aperture and outer encasement member 24. It is understood that the outer encasement member in this embodiment could have an opening wherein the clear cover members 194 extends past the opening and wherein the light members are viewable through the opening.

Figure 28:
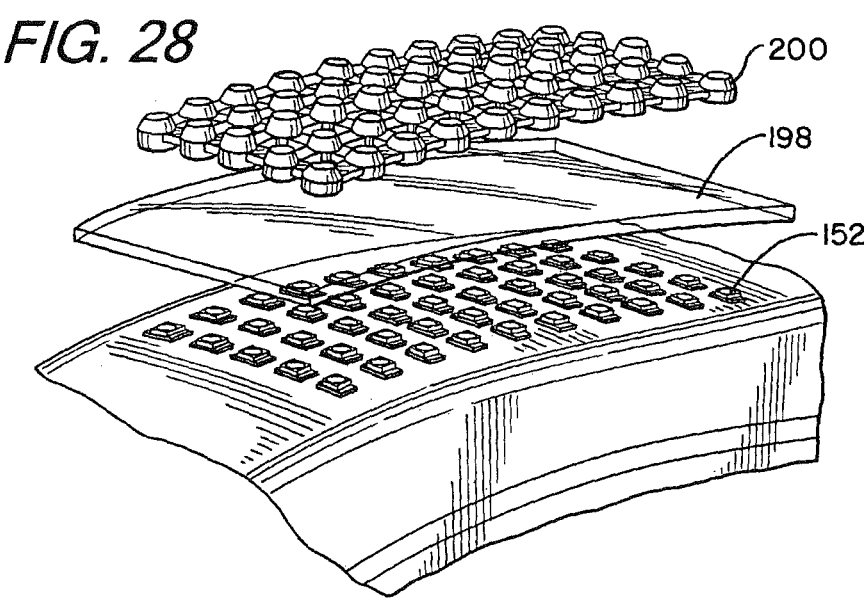
FIG. 28 is a partial exploded perspective view of components of an alternative display of the device.
Figure 29:
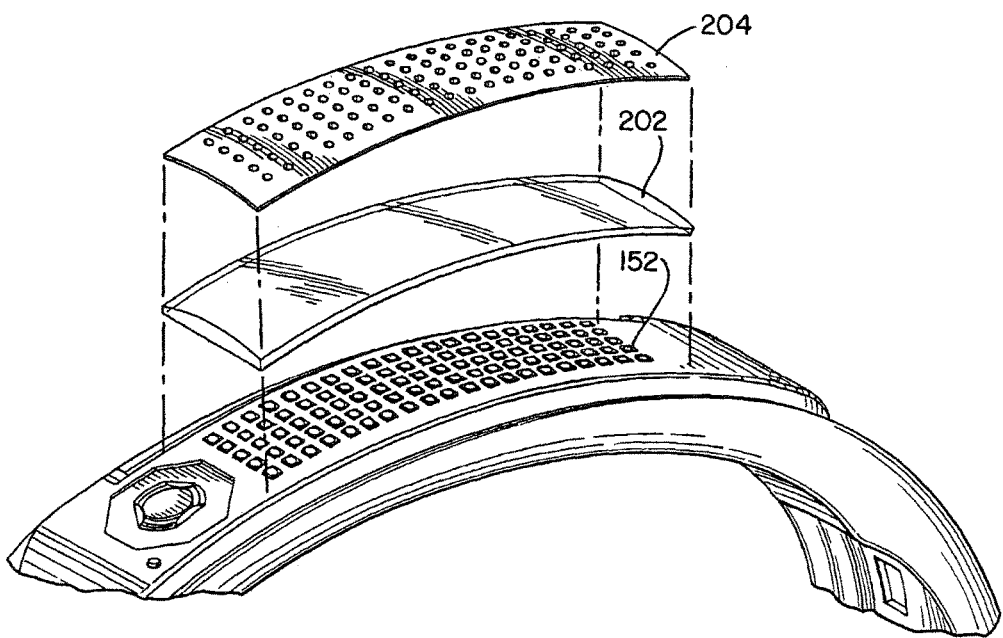
FIG. 29 is a partial exploded view of an alternative embodiment of a display of the device.

FIGS. 28 and 29 show additional alternative embodiments of a display. In FIG. 28, a thin, transparent cover member 198 is positioned over the plurality of light members 152 of the display. A cap member 200 having a plurality of interconnected caps is positioned over the plurality of lights. Each cap is dimensioned to fit over a respective light member. FIG. 29 also shows a display utilizing a transparent cover member 202 over the plurality of light members 152. A cap member 204 having a plurality of apertures is positioned over the cover member 202.

Figure 30:
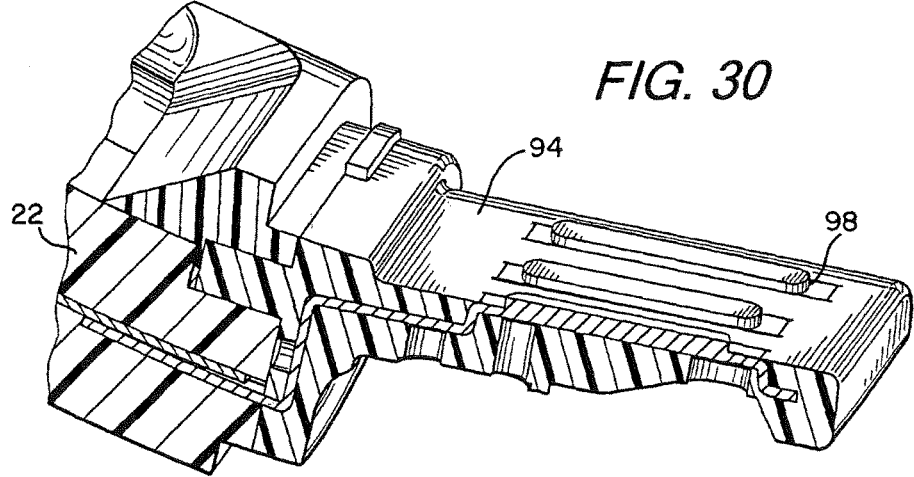
FIG. 30 is a partial cross-sectional view of a component of a latch member incorporating a USB connector.

FIG. 30 shows a partial cross-sectional view of the USB connector 94. The USB connector 94 is connected to a distal end of the spine member 22. The USB connector has the plurality of USB leads 98 and wherein the USB leads 98 include ribs thereon thus having raised configuration. As further shown in FIG. 30, the USB leads are connected to connectors that extend through the spine member 22 and are operably connected to the controller 14.

Figure 31A:
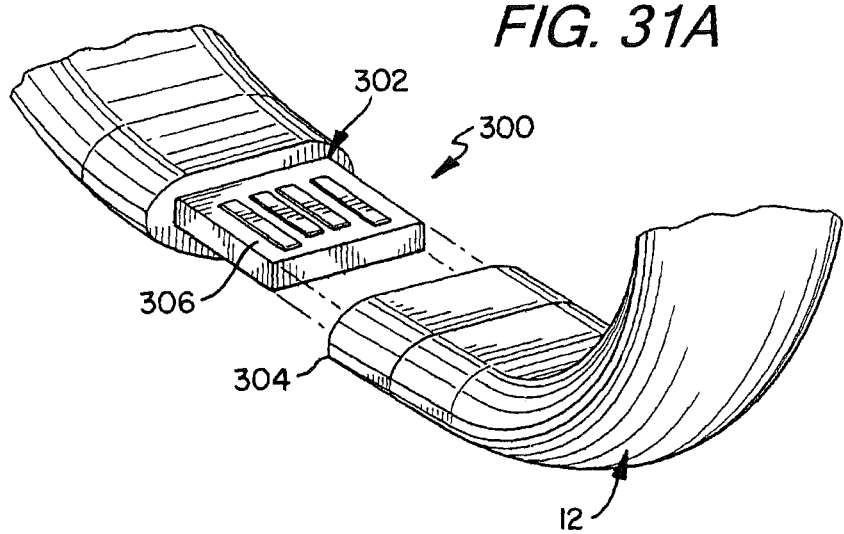
FIGS. 31a-33d are views of a latch mechanism of an alternative embodiment of the device.
Figure 31B:
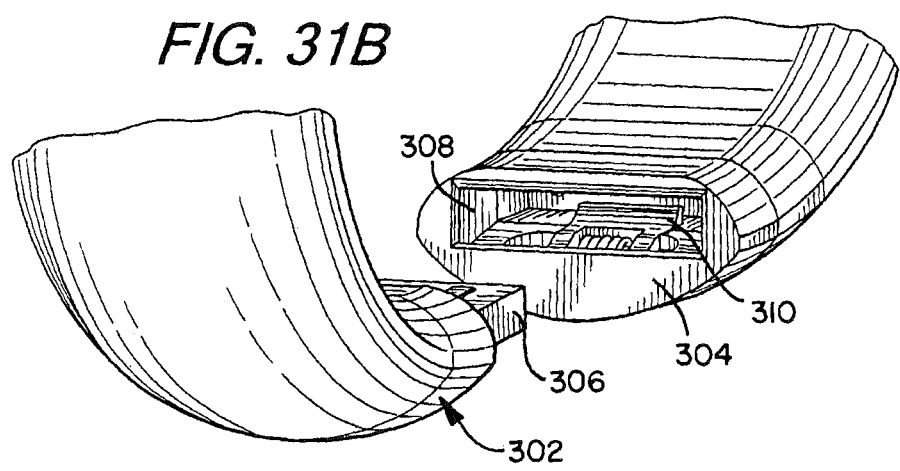

FIGS. 31-33 illustrate an alternative fastening mechanism that can be used in the device 10 of the present invention. The fastening mechanism 300 has cooperating components that can be operably associated with the housing 12 of the device 10. The fastening mechanism 300 generally has a first projection member 302 and a second receiver member 304. Similar to prior embodiments, the fastening mechanism incorporates a USB device that is configured to attach to one end of a housing 12 of the device assembly 10 on one side and to connect to a receiving end on the housing 12 on the other side. For example, as shown in FIGS. 31a and 31b, a USB connector 306 incorporated into the first projection member 302 is insertable into the second receiver member 304. The USB connector is similar in structure as prior embodiments and has a plurality of leads. The receiver member 304 includes an opening 308 or slot having a shape and size corresponding to the size and shape of the USB connector 306. The opening 308 of the receiver member 304 may include a spring-loaded latch 310 that is configured to secure the USB connector 306 to the receiver member 304 upon insertion. The opening 308 or slot may extend through the entire receiver member 304 in a lengthwise direction. The length of the receiver member 304 may be less than the entire length of USB connector 306. In one example, the length of the receiver member 304 may correspond to approximately one-half or one-third of the length of the USB connector 306. The spring-loaded latch 310 may extend out of and past a rear portion of the receiver member 304 to align with one or more portions of the USB connector 306 when the USB connector 306 is fully inserted into receiver member 304.

Figure 32A:
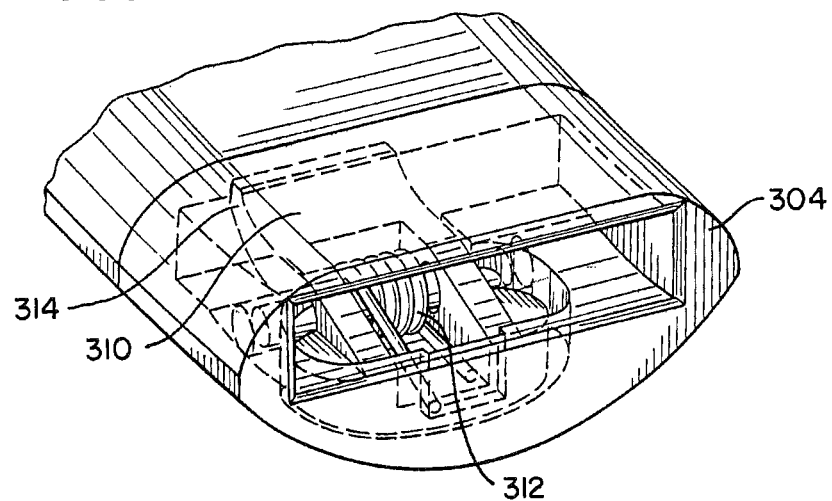

FIG. 32a illustrates an interior view of the receiver member 304. The latch 310 pivots around a spring 312 and biases the latch 310 to a latching position. The latch 310 also has a finger 314 and a button 316 for activating the latch 310. The latch finger 314 pivots in an opposite direction to the button 316. By pressing the button 316, the finger 314 may be dislodged from the USB connector 306 (FIGS. 31a-31b), allowing the USB connector 306 to be removed/detached from receiver member 304.

Figure 32B:
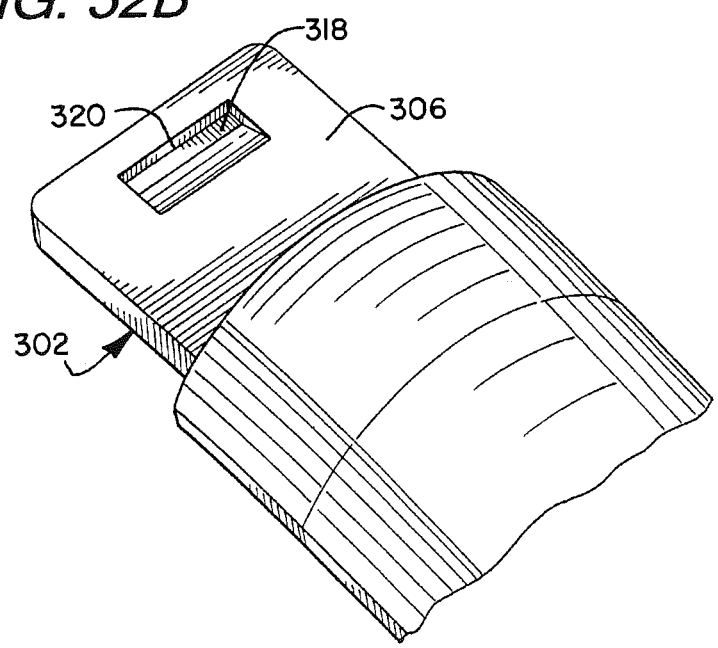

FIG. 32b illustrates a bottom surface of the USB connector 306 configured to engage with the latch 310 of the receiver member 302. The bottom surface of the USB connector 306 has a recess 318 which defines an engagement surface 320, wherein the latch 310 is configured to engage the surface when USB connector 306 is inserted. In the illustrated arrangement, the recess 318 is on a surface of the USB connector 306 opposite the USB connector leads.

Because the receiver member 304 may be shorter than the overall length of the USB connector 306, the end of the housing of the wearable device assembly 10 may include an opening having a length equal to a length of the USB connector 61 that remains exposed after insertion into receiver member 304.

Figure 33A:
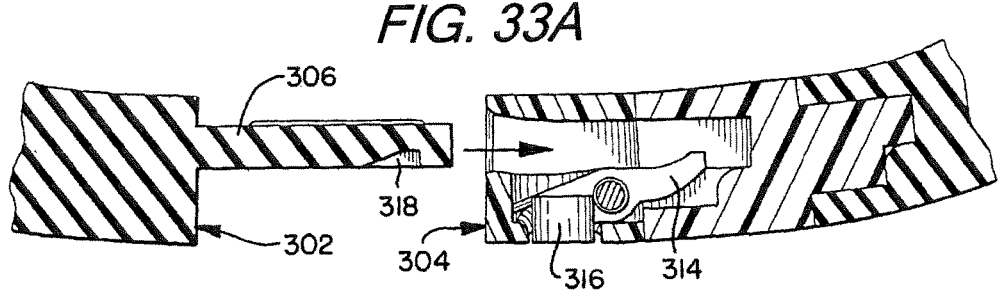
Figure 33B:
Figure 33C:
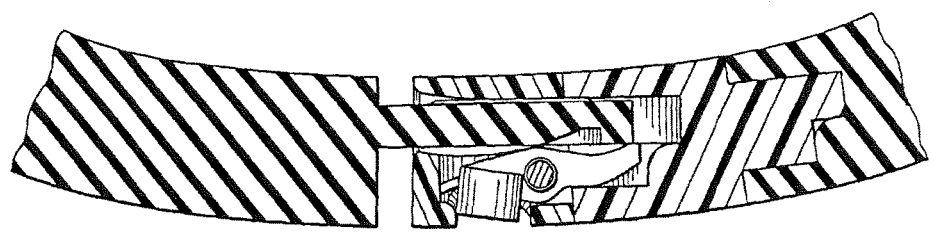
Figure 33D:
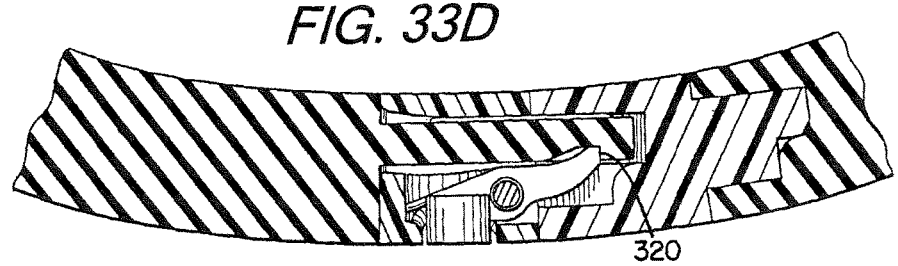

FIGS. 33a-33d illustrate a process by which the USB connector 306 is inserted into the receiver member 304 and a further opening in an end of the housing 12 of the wearable device assembly 10 to which the receiver member 304 is attached. In FIG. 33a, the latch 310 may initially be biased such that finger 314 protrudes into the opening in the housing 12. As the USB connector 306 is inserted into the opening 308 of the receiver member 304 and into the additional opening (as illustrated in FIG. 33b), the finger 314 may be forced downward by the USB connector 306 contacting an inclined surface of the finger 314. Upon the USB connector 306 being inserted into the receiver member 304 and the opening to a point where the recess 318 is aligned with the latch 310, the finger 314 may protrude into the recess 318 and engage the engagement surface 320 due to the spring bias as illustrated in FIG. 33d. This engagement provides a secure connection between the USB connector 306 and the receiver member 304. Accordingly, a fastening mechanism is provided between the ends of the housing of the device 10.

FIGS. 34a and 34b disclose a spacer assembly or expansion element used to increase the size of the wearable device assembly 10, and also can be used with the fastening mechanism 300 shown in FIGS. 31-33. The expansion element may also include an opening 336 into which a portion of a USB connector 306 may be inserted and engaged. FIGS. 34a-34b, for example, illustrates an expansion element 330 having a connector portion 332 configured to mate with and connect to an opening 334 in the housing 12. This connection can take various forms. For example, a shape of the connector portion 332 may match the shape and size of opening 334. To facilitate the use of the expansion elements, the receiver member 304 may be removably detachable from the main body of the wearable device assembly 10. The expansion element 330 may then be inserted between receiver member 304 and the end of the housing 12. Clasps or other types of fastening mechanisms might also be included in the opening 334 and/or connector portion 332 to provide a secure attachment. One end of the expansion element 330 may include an opening 336 that is of similar shape and size to the opening 334 in the end of the housing 12. This allows the USB connector 306 to mate with the opening 336 in the expansion element 330, in the event a user wishes to use one or more expansion elements. FIG. 34b illustrates the overall device assembly upon insertion of the extension element 330 and connection of the USB connector with the receiving portion.

FIGS. 35-37 illustrate another example alternative fastening mechanism in which a micro USB connector may be used instead of a full sized USB connector. In this arrangement, the micro USB connector may be tapered in shape to help simplify the engagement between the micro USB connector and the receiving portion of the other end of the wearable device assembly 10. The fastening mechanism 350 has cooperating components that can be operably associated with the housing 12 of the device. The fastening mechanism 300 generally has a first projection member 352 and a second receiver member 354.

Figure 35A:
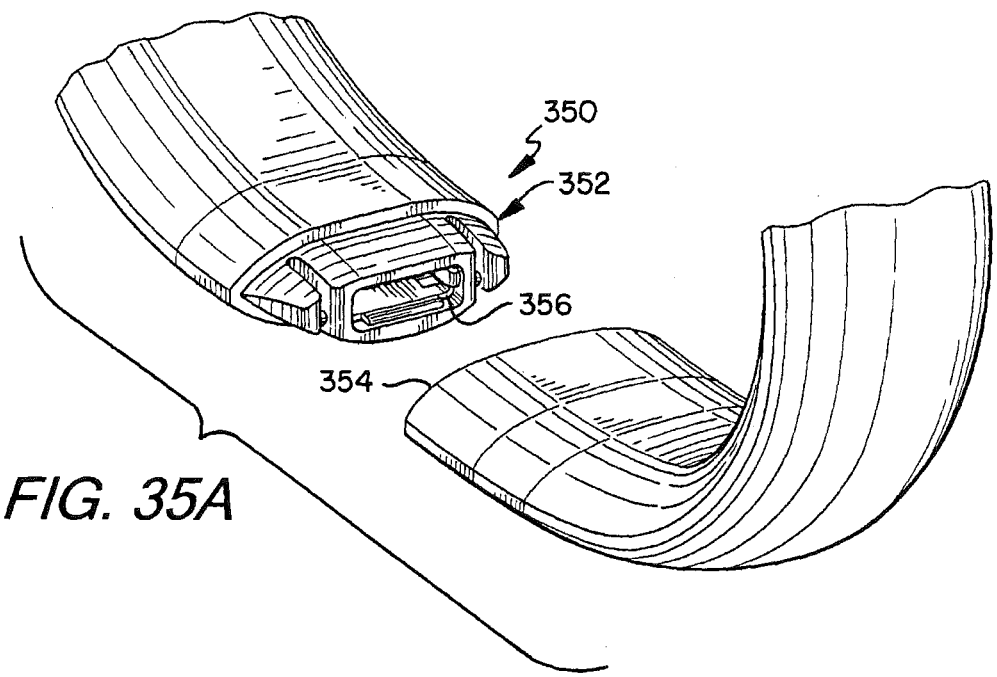
FIGS. 35a-37e are views of another alternative embodiment of a latch mechanism of the device.
Figure 35B:
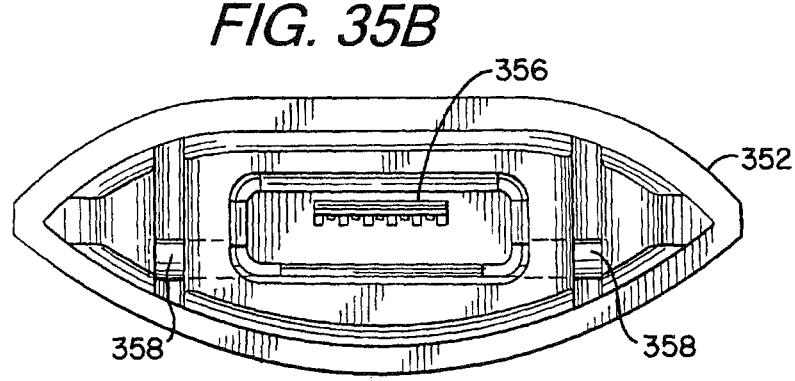
Figure 35C:
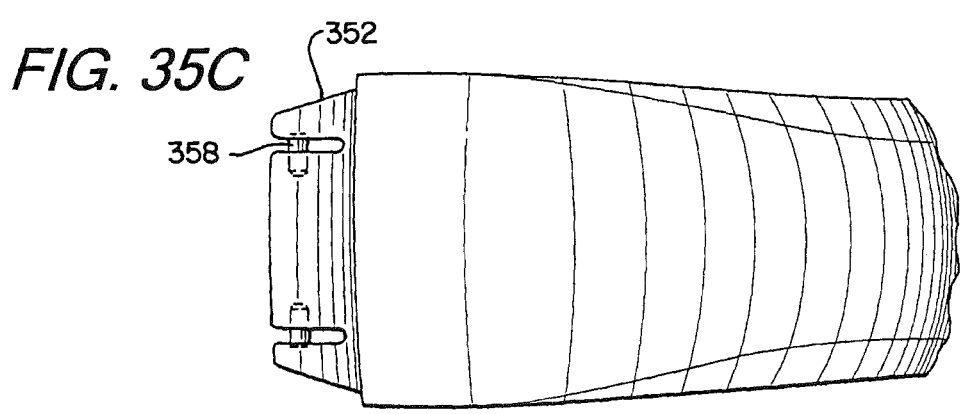

As illustrated in FIGS. 35a-c, the first projection member 352 supports a micro USB connector 356. The micro USB connector 356 may include metal pins 358 that may be used to secure the micro USB connector end 356 to the receiver member 354 of the wearable device assembly 10.

Figure 36A:
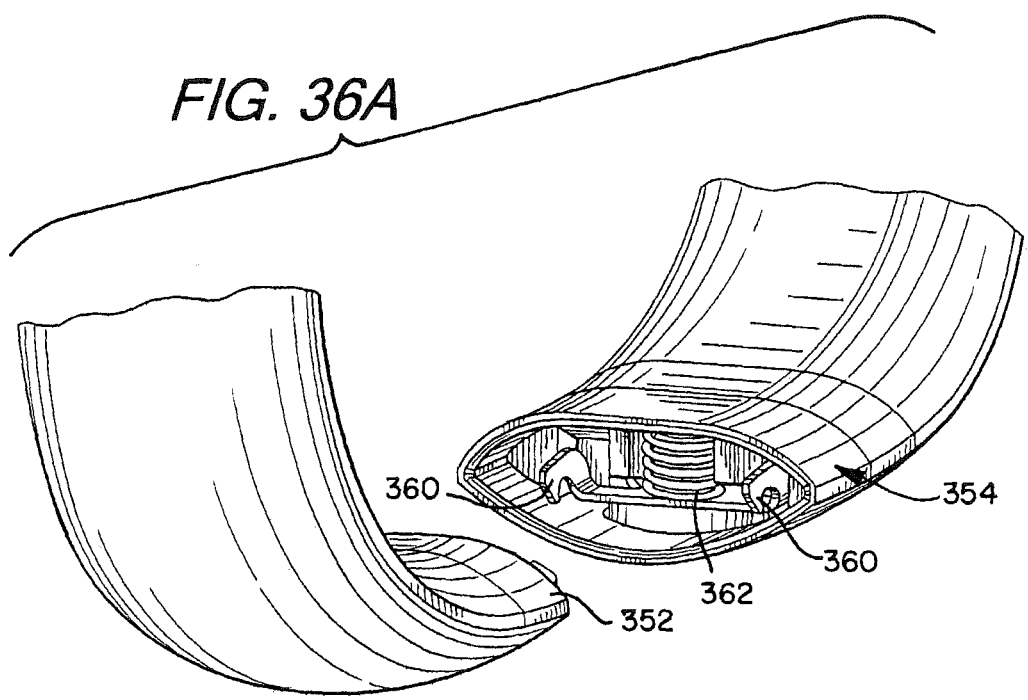
Figure 36B:
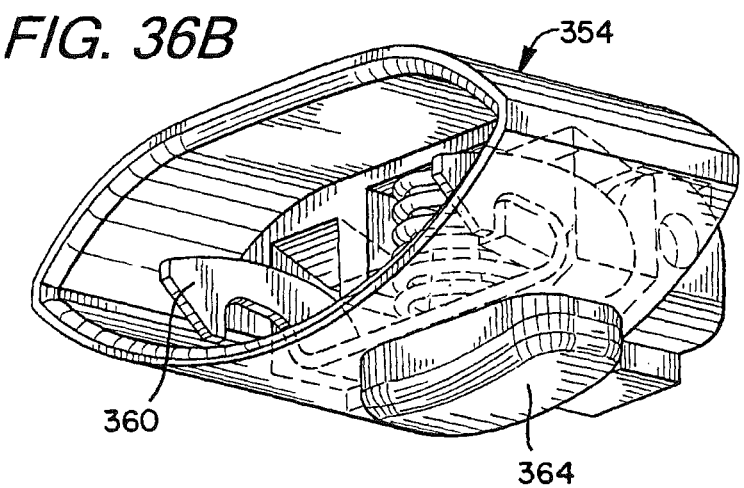
Figure 37A:
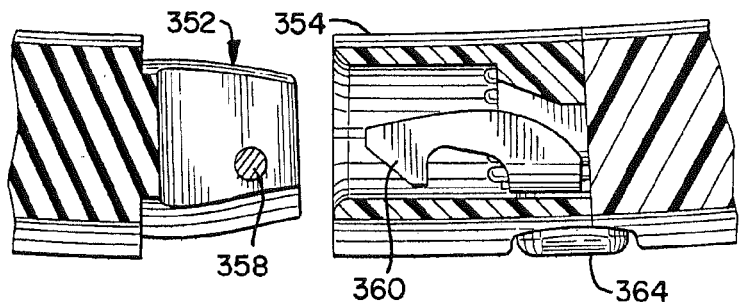
Figure 37B:
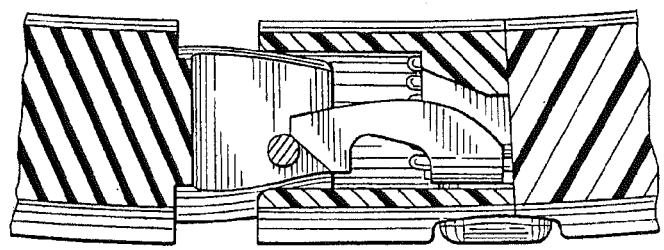
Figure 37C:
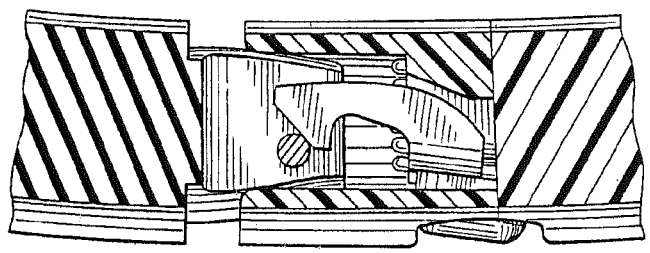
Figure 37D:
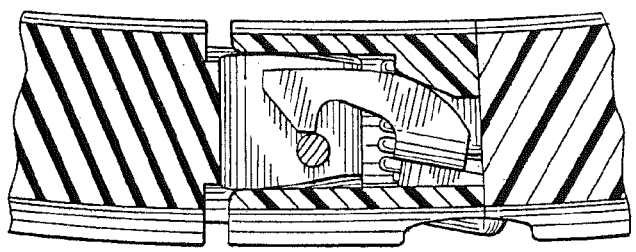
Figure 37E:
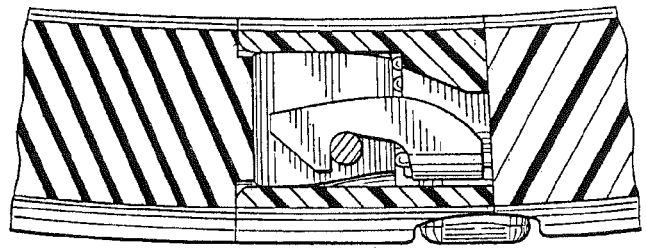

FIGS. 36a and 36b illustrate different perspective views of the receiver member 354. As illustrated, the receiver member 354 has an opening having hook members 360 supported therein for latching onto the metal pins 358 (of FIGS. 35b and 35c). In an exemplary embodiment, the hook members 360 may be biased with a spring member 362 and moveable against the spring bias by a depressible button 364.

FIGS. 37a-e illustrates an example process by which the micro USB connector 356 of the first projection member 352 is connected to the receiver member 354. As the micro USB connector 356 is inserted into the opening of the receiver member 354, inclined surfaces of the hook members 360 engage the metal pins 358 and are forced upwards against the force of the spring 362. Once inserted further into the opening, the hook members 360 pass beyond the metal pins 358 wherein the spring 362 biases the hook downwards wherein the hook members 360 engage against the pins 358 wherein the latch mechanism is in a latched position. The user may depress the button 364 to disengage the members 352,354.

Figures 38A, 38B:
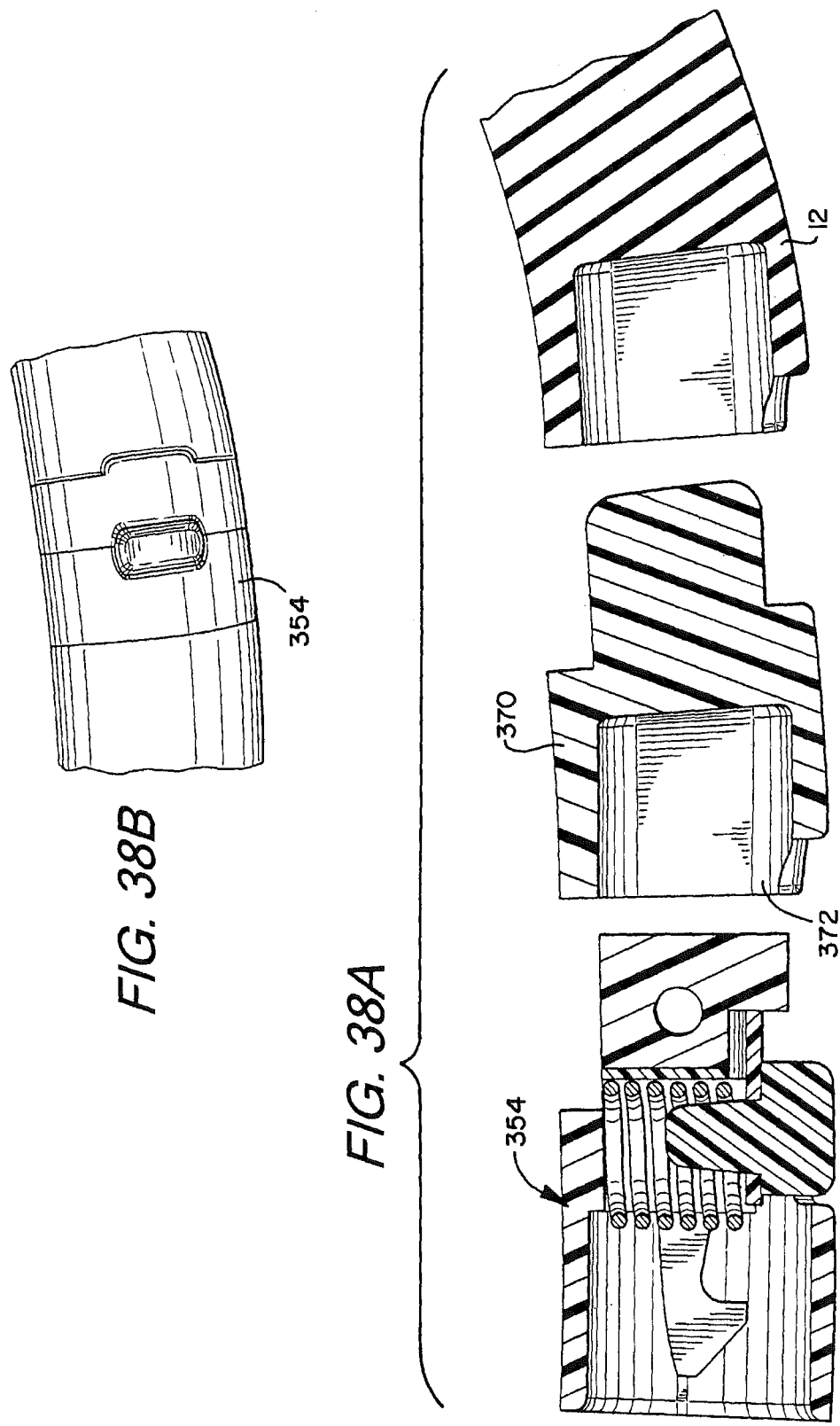
FIGS. 38a-b are views of another alternative embodiment of a spacer assembly of the device.

FIGS. 38a and 38b illustrate views of the fastening mechanism 350 of FIGS. 35-37 using an expansion element 370. In particular, the receiver member 354 may be removably detachable from the housing 12 of the wearable device assembly 10 so that expansion elements such as the expansion element 370 may be inserted between the receiver member 354 and the housing 12 of the wearable device assembly 10. Each expansion element 370 may include an opening 372 into which receiver member 354 may be inserted and secured. FIG. 38b illustrates a wearable device assembly 10 having the micro USB connector 356 and the expansion element 370 or spacer inserted.

It is understood that other alternative fastening mechanisms could be utilized to releasably connect distal ends of the housing 12 of the wearable device assembly. Other structures could include interference fit connections, hook and loop fasteners, or other buckle type configurations. The housing 12 could also have a permanent annular configuration while having an expanded configuration to allow a user to fit the assembly onto the wrist etc.

As discussed and shown herein, the various components of the wearable device assembly 10 are connected and supported by the spine member 22 wherein the elastomer material is formed over the components to place the device 10 in its final form as shown in FIGS. 1 and 2. As can be appreciated from the Figures, the fastening mechanism 26 can be unlatched wherein the device 10 can be positioned around a wrist of the user and the fastening mechanism 26 can be subsequently placed in a latched position. The user can wear the device 10 at all times if desired.

When worn by the user, the device 10 can track activity of the user. It is understood that the controller 14 of the device 10 has certain algorithms associated with the controller and sensor to process and utilize data sensed by the sensor(s). It is understood that the controller can utilize a single algorithm or multiple algorithms as desired. Certain algorithms may be utilized for specific activity engaged in by the user. The controller 10 can also be configured such that certain algorithms are automatically selected based on the data sensed by the sensor. In an exemplary embodiment, an input can be provided to the device 10 for activation wherein the device 10 begins tracking activity of the user. For example, the sensor such as the three-axis accelerometer can sense movement of the user wherein the device 10 records data associated with such movement. Activity tracked can vary including steps taken by the user, energy expended by the user or other metrics or parameters. Certain parameters tracked can also include speed and distance, heart rate, or other parameters. Additional processing may be employed with the sensor, algorithm and sensed data. In one exemplary embodiment, the device 10 may utilize a transfer function/algorithm that translates the data measured by the accelerometer and energy expenditure, wherein acceleration is mapped to approximate oxygen kinetics (calories burned). The display and/or indicator system may display indicia indicative of such activity. The device may also wirelessly interact with a mobile device associated with the user or a remote website such as a site dedicated to fitness or health related subject matter. At some predetermined time, the user may wish to transfer data from the device to another location. As shown in FIG. 44 the user may unlatch the device 10 and plug the USB connector 94 into a computer. In response, data stored on the device 10 may be transferred to the user's computer and/or to a remote site for further processing and display. Data may also be loaded onto the device 10 from the user's computer or remote site. The device 10 and/or computer may be configured such that the user is prompted to commence a data transfer or the data transfer can commence automatically once the device 10 is plugged into the port of the computer. Such data may be configured to trigger operational events on the device 10 such as illuminating the display or indicator system based on time, activity currency or other variables. When the device 10 is plugged into a computer to sync and transfer data, certain light members of the indicator system may be illuminated to indicate a syncing process. The batteries of the device 10 are also charged when the USB connector 94 is plugged into the user's computer. It is understood that the device 10 can also be configured such that data transfer and/or device charging can be done via wireless and/or wired connections. For example, the device 10 may be configured for re-charging batteries via induction charging. The device 10 could also be configured to automatically transfer data wirelessly if the device 10 senses another suitable paired device. Once a syncing process is complete and the device 10 is sufficiently charged, the device 10 can be removed from the computer, and again worn by the user and activated to begin detecting activity. Further user interfaces and user experiences associated with operation of the device will be described below. In some arrangements, the indicator system (e.g., indicator system 20) may be a second display. The indicator system 20 and the display 18 may be controllable independently of one another.

FIG. 43 is an example block diagram of a wearable activity detection and tracking device 4300. The device may include a variety of components including a main controller or host processor 4301 configured to execute instructions and control other components of the device 4300 in accordance with the instructions. The device 4300 may further include memory for storage of data and instructions including volatile and non-volatile memory such as random access memory (RAM) 4303, read-only memory (ROM) 4305 and storage 4307. Additionally, the device 4300 may include a charging component 4309 for charging one or more batteries (not shown) powering the device 4300. The device 4300 may further include various input and output adapters and other components including an ambient light sensor 4311, a display adapter 4313, an accelerometer 4315 and input adapter 4317. Ambient light sensor 4311 may be used to determine a level of brightness for one or more displays for viewability. Light sensor 4311 may also be used to determine a general time of day. Input adapter 4317 may be configured to receive and process various types of input including button presses, touch input, scroll wheel input and the like, depending on the types of input devices included in the device 4300. Accelerometer 4315 may be configured for detecting movement of the wearable device and the user when the device is worn. In some examples, accelerometer 4315 may be a six-axis accelerometer. Other sensors including heart-rate sensors, temperature sensors, humidity sensors and the like may also be included in the device 4300.

Communication by the device 4300 may be performed through wired and wireless connection means. In one example, device 4300 may include a radio component 4319 configured to communicate with other devices wirelessly through radio frequency transmissions. The radio component 4319 may correspond to a BLUETOOTH transceiver, an RFID device, a Wi-LAN transceiver, cellular transceiver and the like and/or combinations thereof, and/or may include a dedicated processor. Display adapter 4313 may be configured to control one or more displays of the device in conveying various activity information, interaction information, alerts, notifications and the like. In one example, display adapter 4313 may be configured to control a first display independently from controlling a second display of the device 4300. The wearable device may further include location determination components such as global positioning system (GPS) component 4321. Location determination may also be performed using other devices including a cellular transceiver (e.g., based on cellular triangulation). Components described herein may be combined into a single device or may be distributed over multiple components. Moreover, additional or alternative components may be used to provide additional or alternative functionalities.

For example, the device 10 may provide a daily progress goal indication. The user may set a goal to the device 10 wherein the user is to complete a certain amount of activity during a day, or 24 hour period or lesser time period. The device 10 detects and records the activity of the user as the user progresses through the day. Based on the activity sensed, the controller illuminates light elements on the indicator system corresponding to the progress towards the goal set on the device 10. For example, a number of light elements on the indicator system based on the amount of progress (e.g., a %) toward the user's goals. Additionally, the color of the illuminated light members indicates how active the user was over the past predetermined amount of time. For example, the indicator system could be illuminated to show how active a user has been for the past hour on a color scale from red to yellow to green with a red color being least active and a green color being most active. When the user engaged in enough activity wherein the goal is reached, all of the light elements of the indicator system will be illuminated. One or more of the light elements (e.g., on a side indicator system or display) may also blink on and off to indicate the goal has been reached. For example, the leftmost light element may blink on and off every 5 seconds until receiving some user interaction (e.g., user input through a particular input device or any input device) or upon the goal being reset (e.g., at midnight for a daily goal or other specified automatic or manual reset time).

Alternatively or additionally, a current progress indication may also be provided by blinking or otherwise illuminating a lighting element of an indicator system (e.g., indicator 20) corresponding to a current amount of progress toward reaching the goal. For example, the current progress indication may be provided whenever a user's progress reaches another level (e.g., another lighting element) on the indicator system. In a particular example, if each segment of indicator system 20 corresponds to a different interval of progress, once the user changes from a current interval of progress (e.g., 10-25% progress towards goal) to another interval of progress (e.g., 26-40% progress), progress indication may be provided. Accordingly, upon reaching the other level of progress, the corresponding area or element of the indicator system may be illuminated, blinked or the like for a specified amount of time (e.g., 5 second cycles for 30 seconds). Current progress indication may also be provided whenever any change or specified threshold amounts of change occur. According to some aspects, the current progress indicator may be provided when the device is in one or more types of sleep or inactive states. The progress indicator may be provided periodically or based on some other defined schedule. Other types of progress indicators may also be used including audible and haptic indicators.

Such a blinking configuration can be triggered even when the device is not being interacted with by the user. An audible alarm could also be provided via a speaker operably associated with the controller and supported by the housing. The device 10 could also have an initial default goal that can be subsequently changed by the user. If a new goal is set, a certain light element of the indicator system can initially blink to indicate to the user where on the indicator system the goal progression will start. Goals and goal tracking are described in further detail herein. Additionally or alternatively, goal and activity information may be reset at a predetermined time each day or at the expiration of the goal time period.

As discussed, the device 10 tracks activity of the user and displays indicia indicative of such activity such as on the indicator system 20. The device 10 is capable of displaying data according to several different features. In one exemplary embodiment, the indicator system 20 has a plurality of twenty light members. Each light member of the indicator system may display a plurality of perceptively different colors including colors such as red, yellow, green, orange, white, blue or other colors as desired. A certain number of light elements can be illuminated to indicate a level of activity (e.g. one illuminated light element for low activity and twenty illuminated light elements for high activity), and a certain color could be used to indicate a level of activity (e.g., red color for low activity, yellow color for medium activity and green color for high activity). Combination of such illuminated light elements can also be employed. In addition, certain illuminated colors or illuminated color schemes could be used for specific designations such as to designate a specific sponsored event, to designate that the user is performing activity in support of a charity, or to designate that the user is interacting with another user. The plurality of light elements of the indicator system can also be designated into separate segments to display indicia according to aspects of the invention as described herein.

According to one or more configurations, a wearable athletic performance device such as wearable device 4300 (FIG. 43) may include multiple modes and functions. In one example, upon the device being activated for the first time, the device may enter an initial start-up mode that displays an icon indicating that the device is to be plugged into a computer or a power source. In this mode, low battery warnings might not be provided and the icon indicating that the device is to be plugged into a power source may be sufficient. Once connected to a computer, the device may enter a setup mode, allowing the user to configure various aspects of the device through a program executing on the computer to which the device is connected. In a particular example, the setup program on the computer may automatically be installed on and launched by the computer upon connection of the device. The setup program, in some instances, may be stored on the device and transferred to and installed on the computer upon connecting the device. Additionally or alternatively, in the setup mode, a battery icon may be displayed on a display (e.g., top display or side display) of the device indicating a currently battery level. The battery indication may remain on the display of the device until the device assembly is unplugged from the computer. In some arrangements, in order to progress from the setup mode (e.g., to a subsequent mode such as an activity tracking mode), the user may be required to complete a setup process through the setup program. If the user unplugs the device prior to completing the setup process, the device may revert to a pre-setup mode (e.g., the initial start-up mode). If the user completes the setup process through the setup program, the device may enter a subsequent mode such as an activity evaluation mode. In some examples, the activity evaluation mode might only be available or activated once the device has reached a certain amount of battery charge (e.g., 20%, 30%, 40%, 50%, 65%, 75%, 100%, etc.). In other examples, the activity evaluation mode may be available or activated regardless of a level of battery charge.

During initial setup (e.g., for a first user), the user might not be able to use the device until the device has a threshold amount of charge such as 90%. For example, the device might not provide any interactivity including functional or information displays, synchronization functions, goal setting options and the like. Additionally or alternatively, activation of the device to begin recording athletic activity may require the user to complete a setup process on the device through the device itself or another computing device (e.g., mobile communication device, desktop computer, laptop computing device, etc.). In one example, if the user does not complete the setup process (e.g., by entering all required information and selecting a "COMPLETE" or "START" button in setup software), and attempts to use the device (e.g., by disconnecting the device from another computing device through which setup is performed), the device may be reset to a pre-setup state such as an initial start-up mode. In one example, all information previously entered in the setup mode may be deleted. In other examples, the information previously entered may be stored and pre-populated when the user repeats the setup process.

The device may wait for a signal indicating completion of the setup process before unlocking activity tracking functionality. As noted, this signal may, in some arrangements, be provided from another computing device if the setup is performed through that other computing device. The signal may correspond to an indication that setup is complete, or the signal may correspond to a determination that all required information such as user profile data, goal information and the like has been entered and synchronized with the device. Moreover, the device may provide a signal such as a haptic, visual and/or audible signal to the user that the device may be used to track athletic activity. For example, a message such as "GO!" may be displayed on the device. Alternatively, if setup is not complete (e.g., not all required data has been inputted), the device may display a message such as "NO GO" or "ERROR."

Figure 45:
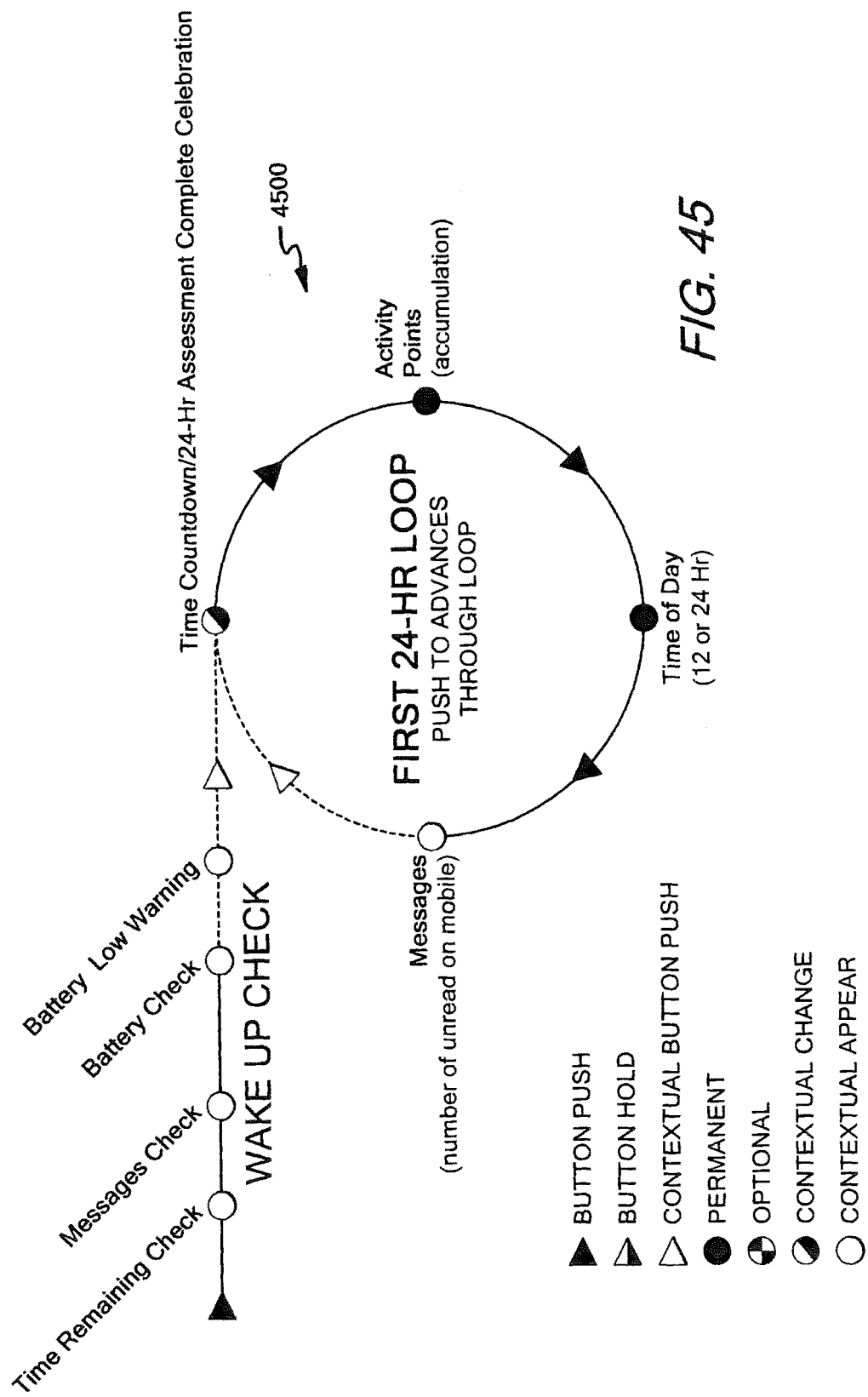
FIG. 45 is an example process flow for an evaluation time period of a wearable device assembly.

The activity evaluation mode may include a specified period of time after initial activation of the device, during which the user's activity level is measured and recorded. The activity evaluation mode may be a required activity prior to full activation of the device (e.g., unlocking all functionalities). Alternatively, the evaluation mode might not be required or included in the device. FIG. 45 illustrates an example flow diagram for an activity evaluation mode of the device. Flow diagram 4500 may represent a function or status flow upon the activity evaluation mode being activated. In a particular example, the period of time during which the user's activity level is measured and recorded may be 1 day (e.g., 24 hours). However, any period of time may be used including 30 minutes, 1 hour, 6 hours, 12 hours, 1 week, 5 days and the like. In some arrangements, the period of time may be used to calibrate the device and/or to establish a baseline activity level for a wearer of the device. Calibration may include determining a conversion factor between a detected athletic performance metric value and an actual performance metric value. For example, if the device detects that the user ran 0.8 miles, but the actual distance run was 1 mile (e.g., based on a user's own measurement or determination), the calibration may set a conversion factor of 1.25 to account for the discrepancy. Baseline measurements, on the other hand, may be used to determine a user's current and/or typical (e.g., average) athletic activity level and may be used to define goals and determine trends in a user's athletic activity.

The process of diagram 4500 might only be executed if the device determines that the initial calibration or baseline activity measurement has not been performed or has not been completed. For example, the device may set a flag upon performing the initial calibration or baseline activity level measurement so that the evaluation mode is not reactivated again. Accordingly, if the flag is not set, the device may undergo the process of diagram 4500. Alternatively, the device may check for calibration or baseline activity measurement data to determine if the initial calibration or baseline measurement was performed. In some examples, a flag might be set if the initial calibration and/or baseline activity level measurement has been completed (e.g., once the initial time period has passed or expired).

The process of diagram 4500 may include a time remaining check to determine whether the evaluation time period has expired, a messages check to determine whether messages have received on the device or on a connected communication device, a battery check to determine a level of charge available and a battery low warning display if the level of charge is below a specified threshold. Additionally or alternatively, a memory check may be performed to determine whether an amount of available memory in the device is low. If so, a warning may be displayed and/or the device might not allow further data tracking and storing. For example, data detected using the accelerometer might not be recorded or stored in the device. Alternatively or additionally, the device may display a "SYNCH" message to encourage the user to synchronize data with one or more other devices so that memory may be freed.

The various checks and warning messages may be performed and displayed, respectively, upon a button on the device being pressed or other interaction with an input component on the device when the device is in a sleep mode. A sleep mode may correspond to a mode in which the display is not activated. For example, the sleep mode may correspond to a mode in which one or more displays are deactivated after a specified amount of time of no user interaction (e.g., no pressing of one or more buttons or other interactions with input mechanisms on the device). In a particular example, a user may press a button to view an amount of calories burned. The display on the device may indicate the amount of calories burned and subsequently turn off if no further user interaction is received. A display may include static displays of information (e.g., text, icons, images, symbols, etc.) as well as animations. In some arrangements, information may also be conveyed audibly or haptically. According to some configurations, a sleep mode may correspond to a deactivated display mode while an inactive or low power mode may correspond to deactivation of one or more additional components after a certain amount of non-active time. A sleep mode need not be based on an amount of inactivity time.

The timeout period for entering a sleep or inactive mode may differ for different functionalities or information displays. For example, a link or pair function may have a longer timeout period since it may take a longer amount of time to establish a link than to enter a tag, for instance. Moreover, the timeout period may differ between different device modes such as between the information display mode or loop and the action mode or loop.

The sleep mode may include a state in which both of the display and indicator system are not illuminated. By depressing the input button, a user can check on activity progress. In response to depressing the input button, the indicator system can illuminate in an animated fashion with individual light members being progressively illuminated until the light members reach a number corresponding to the user's activity level. If a user does not press the button on the device or otherwise interact with the device (e.g., movement of the device, using any input elements of the device, etc.), the device may enter the sleep mode or an inactive state after a predetermined amount of time (e.g., 4 seconds, 30 seconds, 1 minute, 2 minutes, etc.), which may be user-configurable. The device may further provide a time countdown display as part of the process of diagram 4500. The time countdown may indicate an amount of time remaining for the evaluation period. For example, the evaluation time period may start at 24 hours and count down from there. If the evaluation period is over (e.g., the amount of time remaining is 0), the device may display an evaluation completion messages instead of the countdown message. In some examples, the time countdown or evaluation completion message might always be the first information interface to be displayed on a first button press or other user interaction of the day or of an activity time period (e.g., a goal time period). In other examples, the time countdown or evaluation completion message might always be displayed first based on other rules including upon detecting the first button press or user interaction of the hour, minute, 12 hours, morning, afternoon, evening and the like. Yet other triggers may include particular buttons or other specified input mechanisms being pressed and/or types of input including an amount of time a button is pressed, a pattern of button pressing (e.g., 4 short button presses within 5 seconds or 1 short button press followed by a 2 second button press or the like). Such display rules may be used to maximize relevance of displayed information to the user. If the device determines that the evaluation period has been completed, instead of displaying a countdown, the device may display a completion celebration message followed by a plug icon or animation requesting that the user connect the device to the computing device to synchronize the data (e.g., uploading the recorded activity information to the computing device).

Upon receiving further button presses (or user interactions of different types or of the same type), the device display may be scrolled between an accumulated points display (e.g., a measure of athletic activity display), a time of day display, a calories display, a steps display and a messages display. In some examples, the messages display might only be shown if there are messages on the device or on the connected communication device. For example, the device may be wirelessly or wire connected to a communication device such as a mobile phone. Accordingly, the device may be configured to detect (e.g., receive notifications of) messages on the mobile phone. The messages may include voice mail messages, electronic mail messages, text messages, multimedia messages and the like. If no messages are available, the device might not display the messages display (e.g., rather than display 0 messages, the messages display might not be provided). In some arrangements, the device might only provide an indication of a number of new messages or unread/unheard messages. Upon an evaluation mode time period expiring, one or more of the metrics or information displays may be hidden and might no longer be accessible and viewable. For example, the activity points display, the calories display and the steps display may be hidden or not shown, leaving time of day and/or the number of messages as the only viewable or accessible displays once the evaluation mode time period has expired.

According to some configurations, completion of the evaluation mode on the device may be required to enter an activity goal tracking mode. In one example, completion of the evaluation mode may include connecting the device to a computing device and synchronizing the data with the computing device. The device may synchronize wirelessly (or using a wired connection) with a mobile device in some arrangements. The computing device and/or software executing thereon may subsequently transmit a signal to the device activating the activity goal setting mode. In some examples, the synchronization may be uploaded to a remote network site. Accordingly, activation of the activity goal tracking mode may be authorized or otherwise specified by the remote network site upon determining that the evaluation period has been completed and activity data for that period of time has been synchronized. Alternatively or additionally, the wearable device may independently, or jointly with another device or system, determine whether the evaluation time period has been completed and activate the goal tracking mode upon determining that the evaluation time period has been completed.

The activity goal tracking mode may include two user interface sub-modes: an information loop mode and an action loop mode. The information loop may include a first set of interfaces displaying activity and time information to the user while the action loop may include a second set of interfaces providing accessibility to various functions using the device. The information display loop may be activated by a button press of a first duration while the action loop may be activated by a button press of a second duration. In one example, the first duration may be 0.5 seconds or less and the second duration may be more than 2 seconds. Other durations and interaction rules may be defined for activation of the various loops within the activity goal tracking mode. Additionally or alternatively, information or interfaces provided in each of these modes may be presented in different manners to help the user differentiate between the two modes or loops. For example, interfaces of the information display loop may scroll onto the display in a first direction (e.g., horizontally) while interfaces of the action loop may scroll onto the display in a second direction (e.g., vertically). The direction in which the various information display loops and/or specific display items are scrolled onto the display or otherwise appear on the display may be configurable. For example, a user may define a scroll direction on a separate computing device (e.g., mobile communication device, desktop computer, laptop computer, etc.) having software for configuring the athletic activity monitoring device. In another example, the athletic activity monitoring device may have configuration options and receive user configuration input itself. Thus, the information display loop may be configured to not scroll (e.g., the information will be displayed/appear without scrolling) or may be configured to scroll in a similar direction as the action loop.

Additionally or alternatively, scroll directions and display orientations may automatically change based on an orientation of the device. For instance, if the user wears the device on his right wrist, the device may orient characters, numbers and other display information in a first arrangement to facilitate viewing and readability from the right wrist. On the other hand, if the user wears the device on his or her left wrist, the device may automatically change the orientation of the display and/or animation or movement directions to facilitate viewing and readability from the left wrist. The change in orientation of the device may be detected based on one or more sensors or through user input. In one example, the change in orientation of the device may be detected via an accelerometer included therein. In other examples, the direction of scrolling might always be defined as from a button side (e.g., input device side) to a side away from the button or input device. Thus, changing an orientation of the device (e.g., handedness) might not affect the direction of scrolling or animation in some arrangements.

In some arrangements, a worn monitoring device may include a touch sensitive display with selectable options displayed in various sections of the display. Upon selecting an option the user may be presented with a further level of options and so on. Selection of an option may be performed using touch input, physical gestures (e.g., waving the user's wrist in a particular pattern), touch gestures and the like. Physical gestures and movements may be detected using an accelerometer, a gyroscope and/or other sensors. The touch sensitive display may be used instead of or in addition to a button input device or other types of input devices. Accordingly, in some examples, a user may have multiple input devices through which additional types of inputs and combinations of inputs may be entered.

Figure 46:
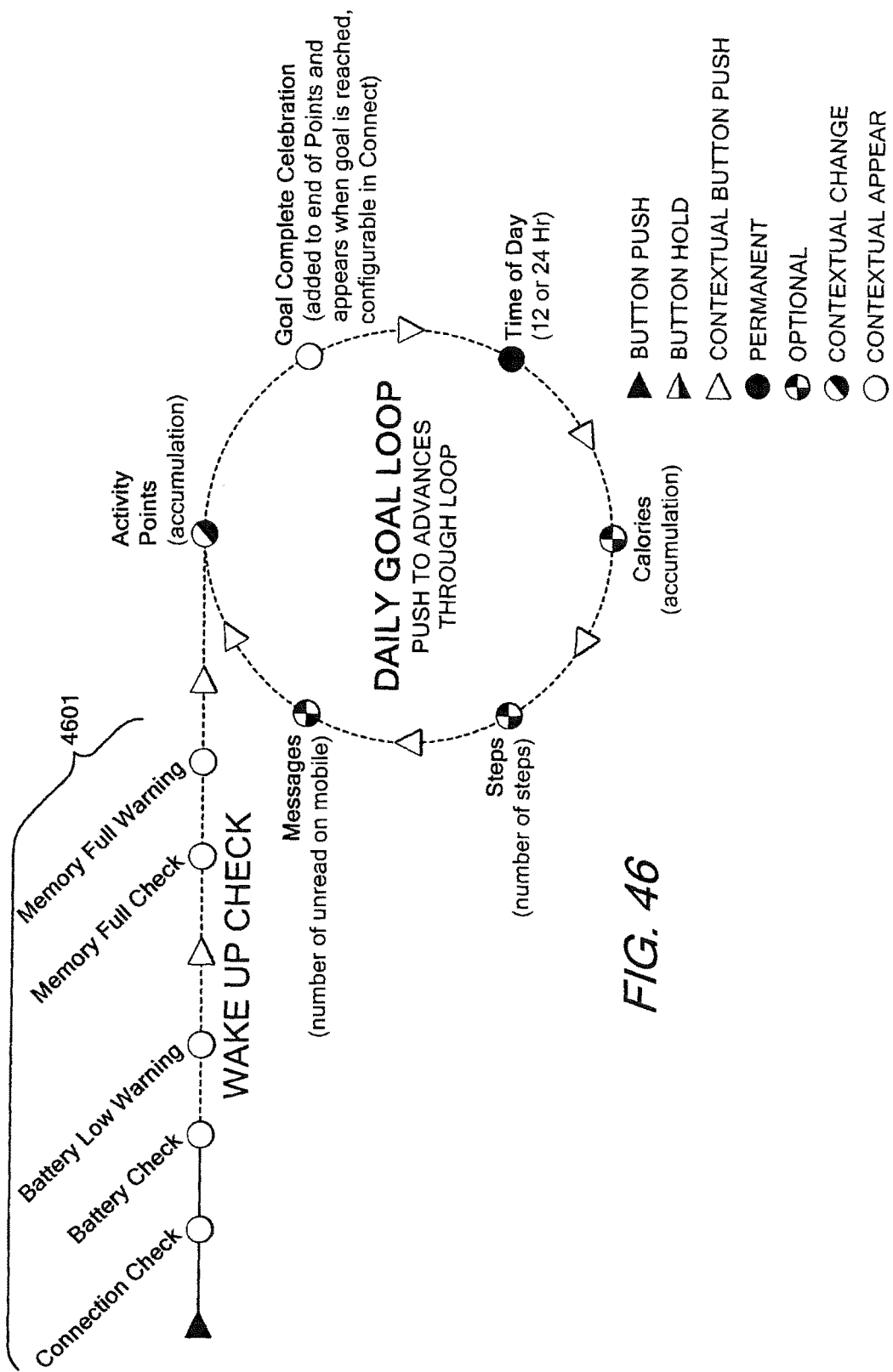
FIGS. 46 and 46a are example process flows for an information display mode of a wearable device assembly.

FIG. 46 illustrates a process flow for an information display loop in the goal tracking mode. The goal tracking mode may include tracking user activity when a goal is set and when a goal is not set. In the information display loop, the device may initially perform a series of checks 4601 upon detecting user interaction or input such as a button press. In some arrangements, the series of checks 4601 might only be performed on a specified schedule (e.g., once an hour, once every 30 minutes, once every 5 minutes, once every 30 seconds and the like). Accordingly, the series of checks is set to be performed only once every minute, the device might only perform the checks 4601 once if the user presses a button more than one time during that 1 minute period.

Warning messages may be automatically scrolled from one to another until a first activity metric (e.g., time, calories, activity points, distance, etc.) is reached without requiring any additional user input. In other examples, a user may be required to provide user input to progress from one warning message to another or from warning messages (which may be scrolling through automatically) to a first activity metric display.

Upon completing checks 4601 and displaying any applicable warning messages, the device may proceed to display a metric or display most recently viewed prior to the device exiting the information display loop by, for instance, entering a sleep mode or inactivity mode. For example, if a user does not interact with the device for a specified amount of time (e.g., 1 second, 3 seconds, 5 seconds, 10 seconds, etc.), the device may time-out from the information display loop by deactivating one or more displays (e.g., to conserve power) and/or other device components. In some arrangements, the number of activity points might always be displayed first upon first button press (or other user interaction) when the device is used or when the device is being used for the first time or when the device has been reset (e.g., instead of displaying the most recently viewed metric). In another example, a time of day might always be displayed as the first information display upon a first button press, reset and the like. Metrics or displays may include activity points, time of day, calories, steps, messages and the like and may be toggled on and off from the information display loop. For example, a user may elect to remove calories and steps from the information loop such that calories and steps are not displayed as a user scrolls through the activity metrics and information.

FIGS. 47A, 47B and 48-52 illustrate example device interface displays that may be provided during the information loop. According to one or more aspects, the activity information included in the information loop may include different activity metrics or types of information than information that is viewable or accessible in the evaluation mode. In one example, the information loop may include at least one metric that is not included in the information interfaces of the evaluation mode.

FIGS. 47A and 47B illustrate activity point displays. In FIG. 47A, for instance, the device may initially display an activity point symbol in top display 4701 along with a display of a current amount of accumulated activity points 4703 and an indicator of a target level of activity points 4705 in side display 4707. The amount of accumulated activity points 4703 may be represented by a number of lights (e.g., LEDs) or illuminable segments that are activated alongside display 4707. If there are 20 lights or illuminable sections, for instance, each light or section may represent 5% of the goal. Accordingly, if a user has completed 50% of the goal, 10 indicator lights or sections may be illuminated. In another example, 99% or 99.99% of the goal amount may be divided evenly or otherwise amongst all but 1 of the illuminable sections. The last section might only be illuminated when the goal is achieved by completing the last 1% or 0.01% of the goal. Accordingly, if there are 20 lights, each of the first 19 lights may represent 99.99%/19 of the goal. The last section or light may represent the last 0.01% of the goal.

In some arrangements, the lights alongside display 4707 may differ in color or be configured to change colors depending on a level of activity achieved. For example, the colors of the lights in display 4707 may transition from red to green going from right to left (or, alternatively, left to right). The lights in display 4707 may change colors such that all activated lights display the same color depending on the level of user activity. For example, if a user has accumulated a low level of activity points, 3 out of 20 lights may be illuminated and the lights may be illuminated in red while if the user has accumulated a moderate level of activity points, 10 out of the 20 lights may be illuminated, all in yellow. In yet another example, the lights may flash or otherwise be animated to reflect an activity level. In a particular example, the lights may flash faster as the user accumulates more activity points. Various other combinations of colors, patterns, animations and the like may be used to convey the activity level.

The display of the indicator and the activity points level may be animated in one or more configurations. For example, the indicator may scroll onto the display 4701. Additionally, the lights or illuminable sections of side display 4707 may be illuminated in sequence (e.g., right to left) at the same rate as the indicator scrolling to a final position on display 4701. The target light or section of side display 4707 may blink a certain number of times to represent the target activity level. Once the points icon or indicator has been displayed for a specified amount of time (e.g., 1 second), the number of activity points may be displayed in top display 4701, replacing the icon or indicator. Displaying the icon or indicator may notify the user of the metric that is about to be displayed. The metric values may be displayed for a specified amount of time such as 2 seconds, 3 seconds, 5 seconds, 10 seconds, etc. The amount of display times described herein may be user-configurable in some arrangements. In some instances, display of the number of activity points may cause the side display 4707 to be cleared (e.g., all lights or illuminable sections deactivated). In other arrangements, the device may maintain side display 4707 with the activity level and target information even after the number of activity points is displayed in top display 4701.

FIG. 47B illustrates an example display in which the number of side display elements 4711 corresponding to a current goal progress are illuminated in a sequenced fashion. In one example, the rate at which the number of side display elements 4711 are illuminated corresponds to a rate at which the amount of activity points accumulated is scrolled on or otherwise displayed on top display 4715.

Figure 50:
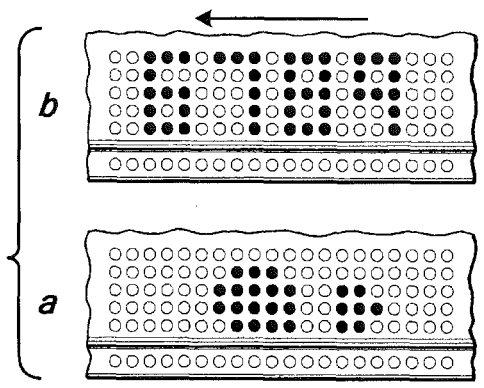

FIGS. 48-50 illustrate additional examples of activity metrics including time (FIG. 48), calories (FIG. 49) and steps (FIG. 50). The display of these additional activity metrics may operate similarly to the display of activity points. Although not illustrated, the side display may also be used to track a goal specific to each of the activity metrics. Accordingly, a user may set different goals for each of the various activity metrics and track the goals separately. The device may, upon receiving user interaction or actuation (e.g., a button press) to display a particular metric, determine whether a goal is set for that metric. If so, the device may activate and display goal information in the side display as well. The device may cycle through the various metrics and information types automatically or upon a user's button press. However, in some configurations, multiple button presses (or other type of user input) within a specified amount of time (e.g., 0.5 seconds, 1 second, 2 seconds, etc.) of each other or during the same display (e.g., a calorie display) might only be registered as a single user input such as a single button press. Other types of inputs may also be used to register the same functionality or results. For example, if another type of input device such as a touch-sensitive display is included in the device, touch-sensitive input may be used to interact with and actuate functions and the like. In yet other examples, input may correspond to physical motions and gestures.

Figure 51:
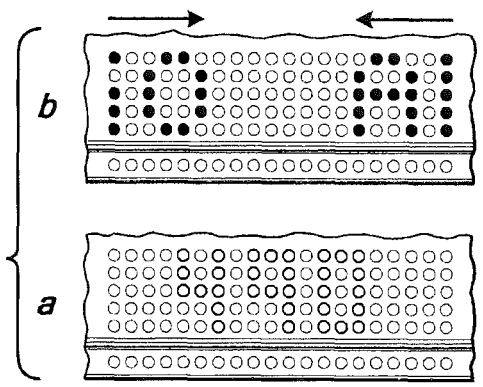
Figure 52:
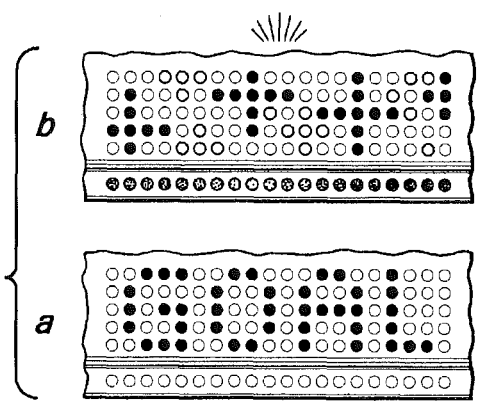

FIGS. 51 and 52 illustrate example interfaces that may be displayed upon a user reaching a target or goal. The goal celebration may be displayed after displaying an activity points total or after displaying any other metric for which the goal is set. Alternatively, the goal celebration may be displayed without displaying the metric value. The goal celebration message may include a user specified or selected graphic or message. Alternatively or additionally, a side display of the device may provide an indicator that the goal has been reached regardless of whether the device is currently displaying the information loop. For example, upon reaching the activity point goal, the side display may illuminate one or more of the lights or illuminable sections in a static manner or in an animated fashion (e.g., blinking or activating the lights in sequence from left to right or the like) to indicate the goal has been reached. In a particular example, a left most illuminable section or light may blink to indicate that the user has reached his or her goal. The device may stop indicating goal completion upon entry into a sleep mode, but reactivate the goal indication upon exiting the sleep mode (e.g., upon an activity sensor detecting movement or activity). The goal completion indicator may also stop flashing or blinking after a goal celebration display is initiated (e.g., pressing a button to display a goal celebration image or icon). Goal celebration messages and goal achievement indicators may be toggled on or off depending on user preferences. In one or more arrangements, the device may also display an amount of activity points still needed to accomplish the goal. In addition to goals, medals or and other achievements may be indicated as well.

Figure 53:
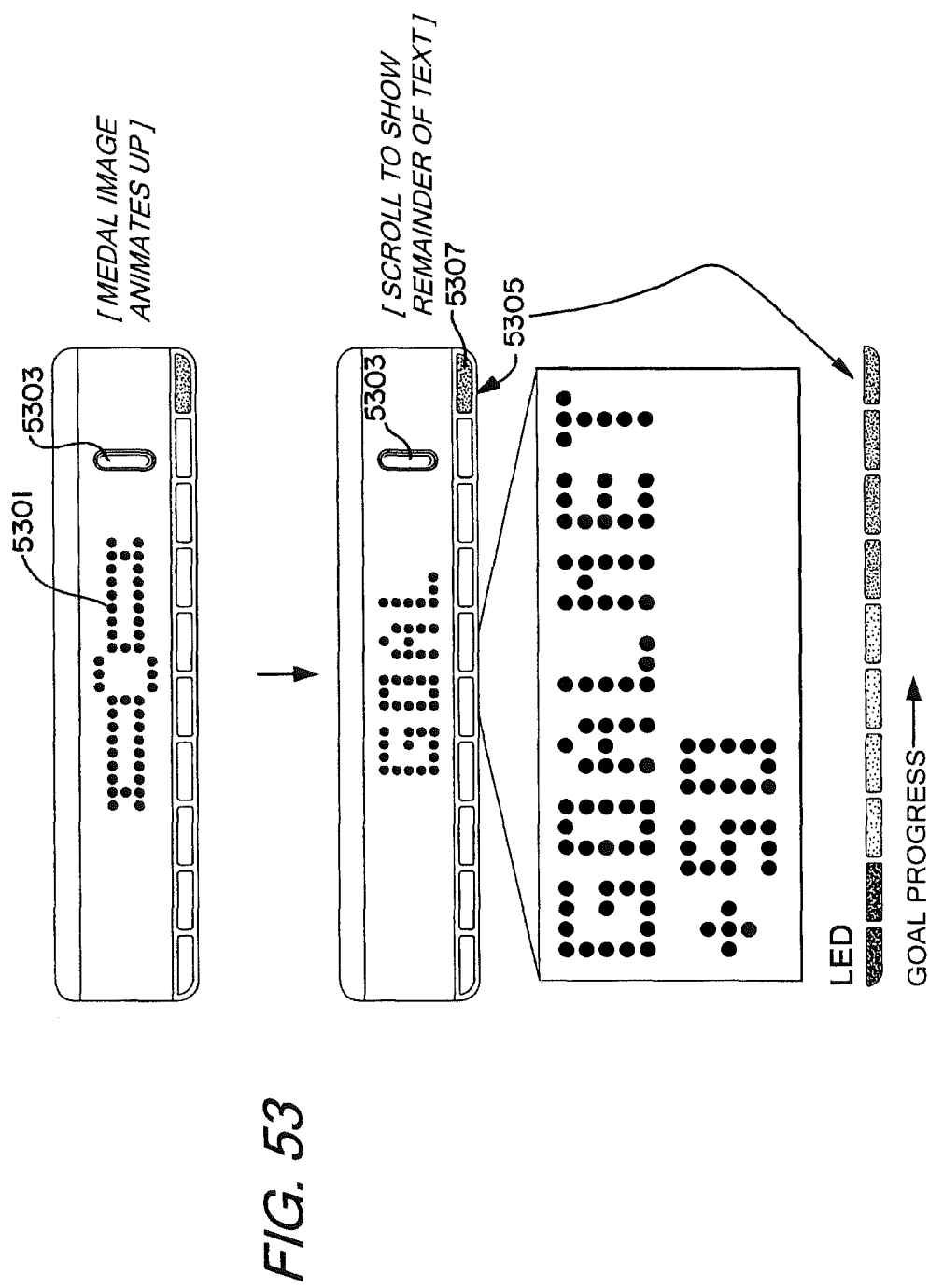

FIG. 53 illustrates another example series of device displays indicating that a user has completed his or her goal. In particular, the wearable device assembly displays a symbol such as a medal 5301 representing goal completion. Goal information may further be displayed automatically (e.g., after displaying medal 5301) or upon a user selecting button 5303. The additional goal information may include a message that indicates a goal was met and, in some cases, if the user exceeded the goal by a certain amount (e.g., 50 calories or 50 minutes or 50 miles). Indicator lights 5305 may also indicate goal completion by illuminating a predefined light such as the right most indicator light 5307 and, in some arrangements, illuminating the light in particular color such as green. The lights may be illuminated from left to right or right to left as the user progresses toward a goal. The side display may also indicate when a goal has been exceeded by a specified amount differently than when a goal has been met (e.g., reaching the goal but not achieving the specified excess amount). For example, the side display may illuminate every other lighting element to indicate that the user exceeded the goal by 10% or an absolute amount of a metric. If the user exceeds the goal by 25%, the side display may alternate illuminate of a left half of the side display and a right half of the side display. Any various patterns, animations, lighting configurations, colors and the like may be used.

Figure 54:
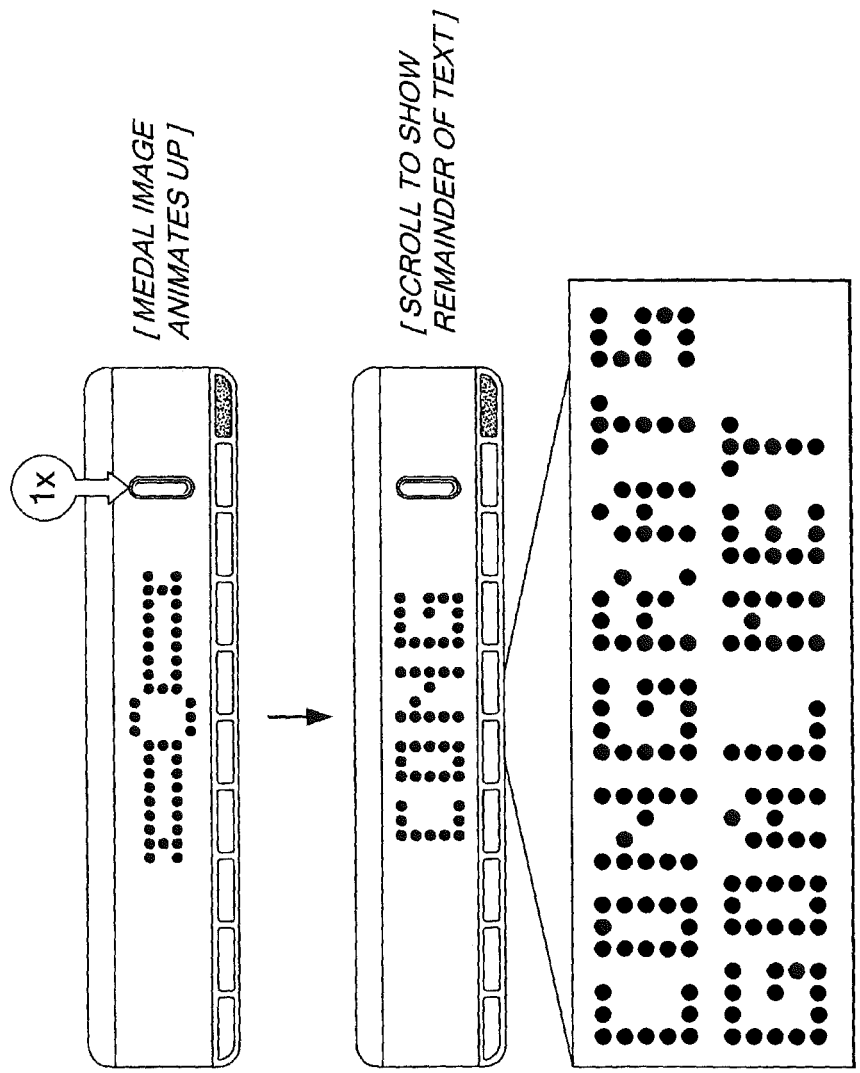

FIG. 54 illustrates an example scrolling message that may be displayed on the wearable device assembly upon user completion of an athletic goal.

FIG. 55 illustrates an example user interface that may be displayed on a wearable device assembly upon setting a new goal. New goals (e.g., upon completion of a previous goal) may be defined by a user or may be adaptively controlled and defined. In one example, the wearable device assembly may automatically define a user's goal by increasing the amount of distance run, calories burned, weight lifted, heart rate reached, time performing athletic activity and/or combinations thereof by a predefined amount or percentage (e.g., 100 calories, 10%, 0.5 miles, etc.) once a previous goal and/or goal time period has been completed. If a user did not complete the previous goal, however, the device might not increase the goal and/or may increase the goal by a lower amount than if the user had completed the goal. In some arrangements, the adaptively defined goal may be defined based on an overall goal specified by the user. For example, if the user has indicated a desire to train for a marathon, the wearable device assembly may define a new goal based on a workout plan to help the user reach a level of endurance that will allow him or her to run 26.2 miles.

Figure 46A:
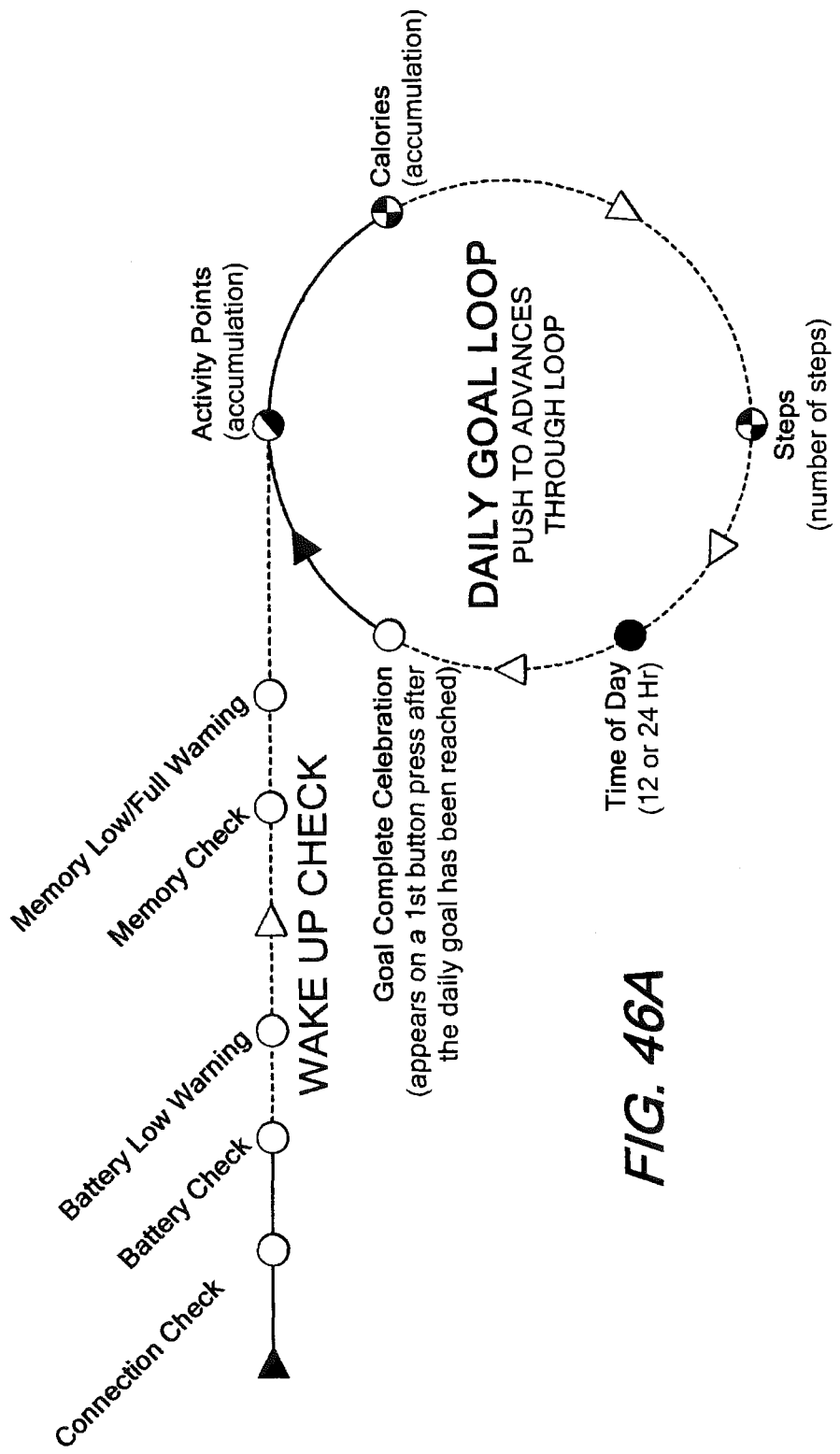

FIG. 46A illustrates another example information loop that may be used instead of or in addition to the example loop of FIG. 46. For example, FIG. 46A illustrates a different order in which metrics such as activity points, calories, steps and time of day and messages or information such as goal celebrations may be displayed. Additionally, information display functionality may also differ. For example, in the loop of FIG. 46A, if the user presses a button or otherwise provides input while the device is in a sleep mode or deactivated state, the device may return to a metric most recently viewed prior to the device entering the sleep mode/deactivated state or leaving the information loop. For some metrics, both a metric name and the metric value may be displayed. For others, only the metric value may be displayed. For example, if the device times out at a time display in the information loop, upon reactivation of the information loop, the device may display the time without the "TIME" label. However, for other metrics such as activity points, calories and the like, the label may be displayed, even when the information loop timed out during display of those metrics.

There may be exceptions to this display configuration including the first time the device is used after setup or a hard reset and when a daily goal is reached. When the device is first used after setup or hard reset, the activity points display may always be displayed first. When a daily goal is reached, the goal celebration message may be displayed first regardless of the metric that was most recently viewed. Once the goal celebration message has been displayed for a specified amount of time, the display loop may progress to the activity point metric, again, regardless of the metric that was most recently viewed. This may provide the user with a logical progression in information displays and alert the user about a completed goal. After the goal completion message is displayed a first time, the goal completion message might not be first displayed in a subsequent activation of the information loop. Instead, a metric most recently viewed in the information loop may be displayed as discussed herein. Additionally, the goal completion message may become a separate display item, independent from the activity point display, after being displayed for a first time, such that the activity point display is no longer displayed automatically after the goal completion message. Multiple types or predefined goal completion messages may be stored in a user's device and one or more of the messages may be randomly or progressively selected for display upon goal completion.

In another example, warning messages, if generated, may always be displayed first upon activating the information loop. Additionally or alternatively, regardless of the metric or message first displayed upon activation of the information loop (e.g., from a sleep mode, deactivated state or other mode), an activity point indicator such as indicator 20 may be illuminated to reflect a current goal progress as described herein while the metric or message is displayed. The goal progress indicator may also be used to display goal progress whenever an activity point metric is displayed regardless of when the activity point metric is displayed. In other arrangements, warning messages may be displayed first without activation/use of the goal progress indicator. Instead, the goal progress indicator may be activated upon completion of displaying warning messages and upon displaying a first metric.

FIG. 56 illustrates an example interfaces for displaying distance information.

Figure 57B:
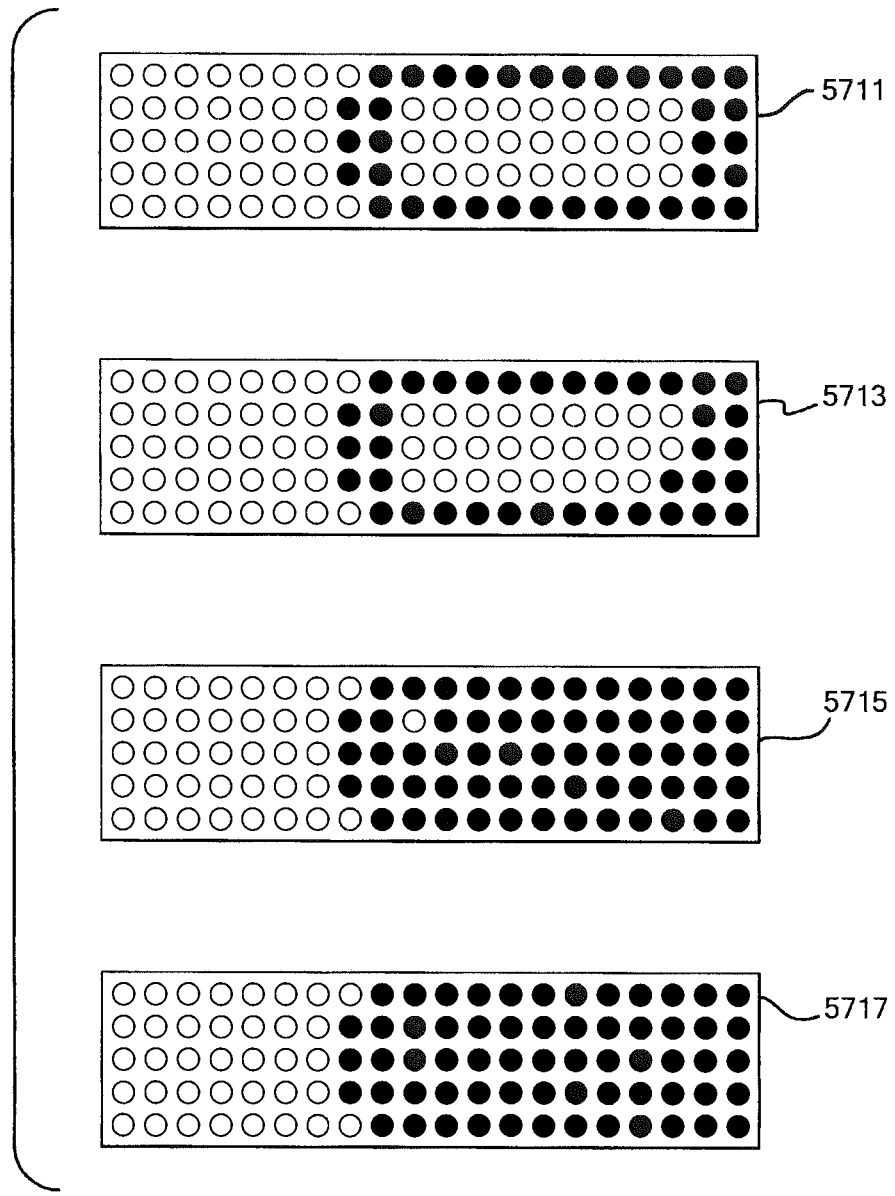

FIGS. 57A and 57B illustrate example battery level indicator displays for a wearable device assembly. In FIG. 57A, for example, the display may include only a battery image or may include a battery image or icon and a number representing an amount of charge (e.g., percentage charged).

In another example, FIG. 57B illustrates interfaces 5711, 5713, 5715 and 5717 displaying a battery icon in various states. Interface 5711 illustrates the battery icon when a low charge is held (e.g., 10%, 15%, 5%, etc.). As the device charges, lighting elements of the display may illuminate from bottom to top and from right to left in that order. Accordingly, as shown in interface 5713, the bottom lighting element (not including the lighting element forming the battery border) to the immediate left of the currently illuminated battery column is illuminated. In some examples, the lighting element corresponding to a current charging level (e.g., 26%, 35%, etc.) may be displayed as a flashing or blinking element to indicate that the device is still charging to that level. Interface 5715 illustrates the battery icon when the device is almost completely charged while interface 5717 illustrates the battery icon when the device is completely charged.

When a device reaches low power (e.g., a specified range of power such as 3-10% or 3-20%), the information loop may inject a "low battery" animation. In this low power range, there might be no change in metric generation and no change in data storage. However, if the battery power reaches another threshold or level such as lower than 3%, the display (e.g., information loop) may stop generating metrics and the device may stop storing data (e.g., accelerometer data samples). Additionally or alternatively, in this further lower power range (lower than 3%), the radio connection may be closed and the network processor may also be shut down. Moreover, various information and displays may no longer be accessible other than one or more predefined images when the lower power range is reached. For example, the display might only show a "plug" animation indicating the need for charging whenever user input is received. If the device is charged above the 3% level, then upon USB or power unplug, the network processor may be reactivated, metric generation may continue, and samples may again be stored. The display may further show the full information loop (with any appropriate warnings). If the battery is completely drained (e.g., 0% power), time may be reset. Upon recharging, the device may require the user to connect again to a setup or configuration software to reinitialize the device. For example, the device might only display a "SYNC" message indicating a need to connect to a configuration program and/or device.

According to some arrangements, the device may further be configured to display reminders to the user. These reminders may include reminders to register the device and/or to synchronize data. The reminders may be triggered by specified rules. For example, the registration reminder may be triggered if the user has not registered the device and the reminder has not been shown for a particular period of time (e.g., last 30 minutes, last hour, last day, last week, etc.) and/or for a particular number of user interactions with or for a particular number of state changes of the device (e.g., last 5 button presses, last 10 transitions from a sleep state, etc.). A registration/synchronization reminder message may include identification of the network address where the user may register and/or synchronize his or her wearable athletic device. If a message (reminder or otherwise) is too wide or too tall to be displayed simultaneously on the device display, the message may be scrolled in a specified direction so that all information is displayed. Text may also be used to convey other metrics, type of metrics and/or units of measurement such as calories burned, steps taken, activity points earned and the like.

FIG. 58 illustrates an example process flow for an action loop that may be activated on a device. In addition to the device checks 5801 that may be performed on the device upon wake up (e.g., transition out of a sleep mode), the device may further perform a battery check, a memory check and a link check. The link check may be used to confirm whether a connection (wired or wireless) exists between the two devices for various purposes including synchronization, message notification and the like. In one example, the device may determine whether a connection is still active with another device to which the device was previously connected. Once the link check has been completed, the device may progress through the action loop. According to one configuration, the device may continue to scroll through the action loop in response to a first type of user interaction such as continuous depression of a button. Releasing the button or a second type of user interaction may stop the loop from advancing and a press and release of the button or a third type of user interaction may activate or cancel/deactivate the currently displayed function or action.

Warning messages may also be provided at this time. For example, upon a user entering input to access the action loop, various checks may be performed and corresponding warning messages displays, if necessary. The user may be required, during the action loop, to continuously provide a type of input such as a continuous button depression through the warning messages to reach the first action option. However, warning messages may still be scrolled to completion (e.g., without reaching the first action option or action loop) regardless of if the user releases the button or if the user provides another button press. In one example, if the user previously viewed the same warnings in an information display loop, those same warning messages might not be displayed again when the action loop is accessed. However, new warnings (e.g., warnings not previously presented to the user) may still be displayed. Alternatively or additionally, a user may be allowed to skip through warning messages by entering a particular type or pattern of input (e.g., two button presses within a short time of each other).

After the initial link check, the device may progress to a tag function that allows a user to tag a current time and/or location as part of the action loop. Depending on whether a link was detected in the link check process, the tag functionality may operate differently. For example, if the tag function is activated, the device may determine and record a time stamp and/or location stamp. The location stamp may be generated based on data received form a location determination system such as GPS in the device or from a separate device (e.g., a mobile communication device). The device may then transfer the tags if the device has a link with the other device. If the link does not exist, the device might not attempt to transfer the tags to the other device. In some arrangements, the location stamp might only be available if the link to the other device is active. For example, if the activity tracking device does not include a location determination mechanism, the activity tracking device may request location stamping by the other device. Accordingly, if a link to the other device does not exist or is not active, the activity tracking device might not provide location stamping functionality.

Figure 58A:
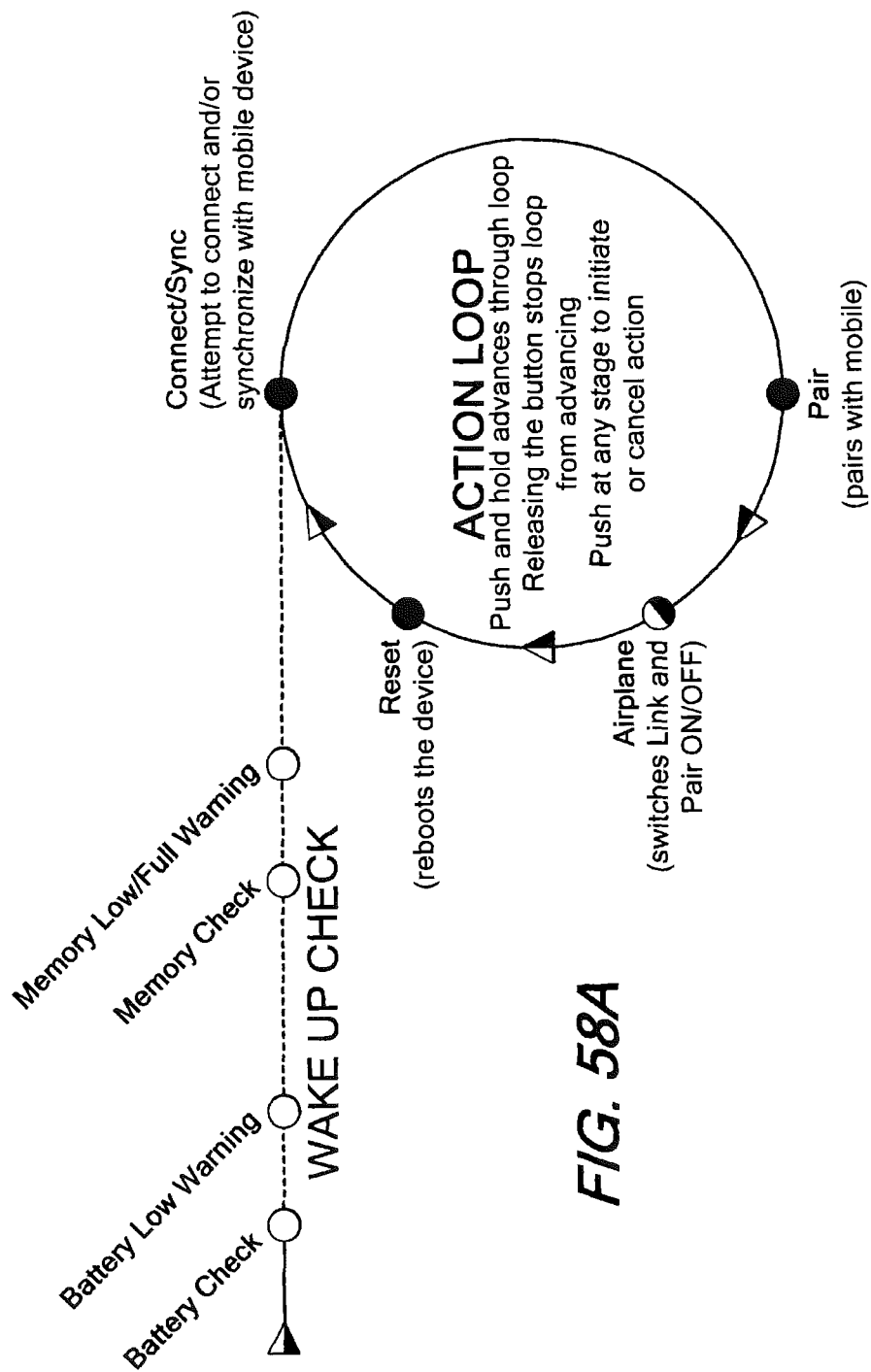

FIG. 58A illustrates another example action loop flow. In this example flow, various action elements may be removed such as tagging and linking depending on the functionalities desired by the user and/or capabilities of the device. For example, a user may wish to remove tagging and linking from the device to reduce battery consumption. Other functions displayed in the action loop may similarly be removed from the action loop using various configuration tools and/or software. Options and displays may also be removed from the various information and action loops or other display states/modes in response to a battery level. For example, if a battery level is below a threshold amount (e.g., 30%), the device may automatically remove some of the options and/or displays. Other threshold amounts may be used. The threshold may also be user-configurable. Additionally, the functions that are removed at different threshold battery levels may also be configured/selected by the user.

FIGS. 59A-59D illustrate example tagging interfaces that may be displayed on an activity tracking device. FIG. 59A illustrates a tag functionality indicator that may be displayed as part of the action loop. In FIG. 59B, the user may select the tag function in interface a. Subsequently, the interface may display the tag icon followed by a check mark to indicate that a time and/or location stamp has been recorded as shown in interface b. If the device is connected to another device, the interface may display an indication of a data transfer process. In one example, the device may blink the tag icon to indicate that a data transfer is being attempted. If the data transfer is successful, the interface may display the tag icon followed by two indicators (e.g., check marks), one indicating the recordation of the time and/or location stamp and the other indicating a successful transfer of the tag as shown in FIG. 59C. If, however, the data transfer is unsuccessful, the interface may display the tag icon followed by a first indicator specifying whether the tag was recorded and a second symbol or indicator (e.g., an "X" symbol) indicating that the data transfer was unsuccessful as shown in FIG. 59D. Other symbols, icons, text, images and the like may be used to indicate successful or unsuccessful tagging and/or transfer.

Referring again to FIG. 58, the action loop may progress from the tag function to an optional link functionality and from the link functionality (or the tag function if the link function is not provided) to a pairing functionality. Both the link function and the pair function may allow a user to connect the activity tracking device to another device such as a mobile phone or a portable music player. The link function may relate to a first type of wireless or wired connection while the pair function may relate to a second type of wireless or wired connection. For example, the first type of connection may include a Wi-Fi connection while the second type of connection may include a BLUETOOTH/BLUETOOTH LOW ENERGY connection. Other types of connections may include infrared-based connections, ZIGBEE, other RF-based connections and the like. The display of the link and pair functions may include a status indicator specifying whether the link or pairing, respectively, is currently active. As noted, in some arrangements, a link function might not be provided in the action loop.

In some examples, the activity monitoring device may further include near-field communication (NFC) components such as RFID systems. For example, NFC components may allow the device to receive or provide information to other devices upon reaching a predefined proximity to the other devices. Such information may include activity information including level of activity, points accumulated, calories burned, activity routes and the like, payment information such as credit card information, bank routing information, check information and the like, contact information sharing and the like and/or combinations thereof. In one example, the user may use his or her monitoring device to make purchases, thus alleviating the use of the need to carry a wallet or other payment items. In another example, a user may use one device to transmit user profile information to another device. Accordingly, if a user purchases another monitoring device, the user may automatically supply user information such as height, weight, name, etc. to the newly purchased device through near field communications. In another example, synchronization of data (or other types of data transfer) may be automatically triggered when the two or more devices are within the predefined proximity as set by the NFC components. In still another example, data may be automatically transmitted to and/or from a gaming console upon the device entering a predefined proximity of the gaming console using NFC. NFC may also be used to open doors to a house or car, access an office, gym, open gym locks, start a vehicle, immobilize a vehicle (e.g., when the device has moved beyond the predefined proximity), log onto a computer and the like.

FIGS. 60A and 60B illustrate example interfaces in which a link function icon is displayed with a status indicator. In FIG. 60A, for example, the status indicator indicates that the link is inactive. In FIG. 60B, on the other hand, the status indicator specifies that the link is active. The link function icon may also change depending on whether the link is active or inactive. For example, the link function icon may display two icons representing two devices. If the link is active, the icons may be displayed and/or displayed with equal illumination/intensity. If the link is inactive, however, one of the icons may be displayed with less illumination or intensity or might not be displayed at all.

Upon activating the link function, the appearance of the link icon or symbol may be modified to reflect an attempt to link the device. In one example, the status indicator may be removed from the interface and the link icon or icons may begin to blink intermittently as shown in FIG. 60C. The link attempt may last for a specified period of time (e.g., 12 seconds). If the link is successful, the interface will display a positive link indicator as shown in interface of FIG. 60D. If the link process is unsuccessful, on the other hand, the interface may display a negative link indicator as shown in interface b of FIG. 60D. If a link is currently active, selecting or activating the link function may cause the link to be broken or deactivated.

The link functionality, in one or more examples, need not be provided as a user-selectable option in the action loop. Instead, the device may automatically attempt to establish a link with one or more devices upon a first button press or other triggering event (e.g., during and/or in conjunction with the link check shown in FIG. 58). In one example, upon the user selecting a button while the device is in a sleep mode, the device may automatically activate a link establishment function (similar to that described above), without requiring the user to manually initiate the link process. Whether the link is automatically established or if the option is shown in the action loop as a user-selectable item may be configurable by the user.

FIG. 61A-61C illustrates example user interfaces for a pairing functionality. For example, the device may include BLUETOOTH communication capabilities (or other short range network capabilities) and thus, may connect with local devices. FIG. 61A illustrates a pairing function icon while FIGS. 61B and 61C illustrate successful and unsuccessful pairing processes, respectively. In one example, upon detecting a particular type of user interaction such as a short button press, the device may initiate a pairing process to detect and attempt to connect to a compatible device. If the device is successful paired to another device, the display may provide a successful pairing indicator such as the checkmark shown in FIG. 61B. If, however, the pairing was unsuccessful, the display may provide an unsuccessful pairing indicator such as an X mark as shown in FIG. 61C.

Alternatively or additionally, the pairing function might only display a status (e.g., success or failure) of the pairing after the pairing function is activated. Accordingly, a pairing status might not be displayed when a user only navigates to the function through the action loop. The device may also be capable of being paired with multiple devices. If a user pairs another device when a maximum number of devices have already been paired, the first device that was paired may be removed from memory (e.g., a first-in-first-out rule).

An airplane mode function might also be included in the action loop. FIGS. 62A and 62B illustrate an example toggling process for turning an airplane mode on or off. Airplane mode may refer to a setting in which all wireless communication capabilities of the device are deactivated so as not to interfere with operations of an airplane. However, airplane mode may be used in any desired circumstance and is not limited to airplane environments. In FIG. 62A, the display may initially provide an indication of the current airplane mode setting (e.g., on or off). Upon activating the function (e.g., via a specified type of user interaction such as a short button press), the airplane mode function may switch to a setting such as on, as shown in FIG. 62B. In the on setting, the device may automatically turn off all wireless communication components including the pairing and link modules of the device. In some arrangements, if airplane mode is activated, the pairing and link functions may also be removed from the action loop, making them unavailable for selection and activation. Upon deactivating airplane mode, the pairing and link functions may be reinserted into the action loop. This automatic removal and insertion may aid the user in determining what actions or functions are allowed during airplane mode. In other arrangements, the activation or deactivation of airplane mode might not affect whether the pairing and link functions are displayed in the action loop. If the user activates the link or pairing function, however, the airplane mode may be automatically toggled to off (e.g., when the mode is set to on). Alternatively or additionally, an airplane mode indicator such as a blinking or static light on either the top display or the side display or both may be illuminated.

Figure 63A:
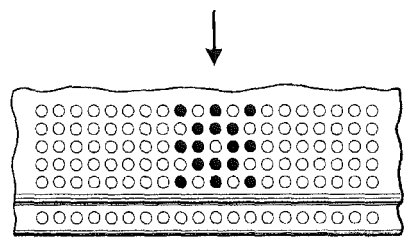
Figure 63B:
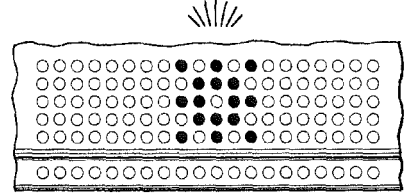

FIG. 63A-63D illustrate an example series of user interfaces that may be displayed for a reset function. The reset function may be used to erase the memory of the device and/or reset all settings on the device (e.g., goals, calibrations, initial activity measurements, etc.). In FIG. 63A, for example, a reset icon, animation, symbol, text or the like may be initially displayed upon the action loop reaching the reset function. Upon activation (e.g., in response to a short press of a button or other type of specified user interaction), the device may display a warning or confirmation that the device is about to initiate a reset function. In a particular example, as illustrated in FIG. 63B, the device may blink the reset icon, animation, symbol or text for a specified amount of time (e.g., 4 seconds, 5 seconds, 10 seconds, 1 second, etc.). During this warning or confirmation time period, the user may be allowed to deactivate or cancel the reset function by providing a specified type of user interaction such as a short button press. Other types of warning or confirmation messages, animations, audio, haptic feedback and the like may be used. If the user does not cancel the reset request, the device may begin the reset process at the end of the warning or confirmation period. Cancelling the reset request may include a user interacting with the device in a specified manner such a short press of a button (e.g., a button press having a duration less than specified threshold duration), a long press of a button (e.g., a button press of at least 2 seconds, 3 seconds, 10 seconds, etc.), movement of the device and the like. In a particular example, cancelling the reset request may correspond to the same type of user interaction as activating the reset function.

Figure 63C:
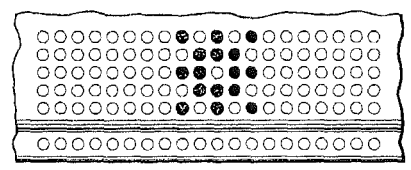
Figure 63D:
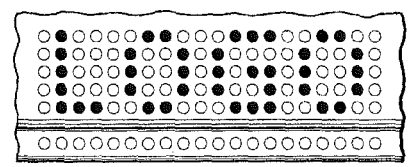

If the reset request is not cancelled within the warning or confirmation period, the device may initiate the reset process. FIG. 63C illustrates an example display that may be used to convey the progress of a resetting process. For example, the reset icon, animation, symbol or text may animate in some fashion such as illuminating clockwise until the reset process is complete. Once the reset process is complete, a completion indicator (e.g., a logo) may be displayed on the device as shown in FIG. 63D. The completion indicator may include a variety of images, symbols, text, icons and the like and may include both static and animated indicators. As noted herein, different types of user input or user interaction may correspond to different commands, functions, actions and the like.

If the action loop is activated or otherwise accessed from the information loop, the action loop may time out to a most recently viewed metric in the information loop. For example, if a user transition from an activity point metric display in the information loop to the action loop and subsequently allows the action loop to time-out (e.g., no user interaction for a specified amount of time), the device may display the activity point metric after exiting the action loop and prior to entering the time-out state (e.g., deactivation of the display).

In one arrangement, a wearable device might only have a single user input device to minimize complexity. The user input device may include a button, a scroll wheel, a touch sensitive input device, a joystick, a trackball and the like. In such cases, different types of interaction with the input device may correspond to different actions such as activating and scrolling through the action loop, activating and scrolling through an information loop, toggling functions on and off, activating various functions and the like. For example, depression of the button for different durations or holding the button down may invoke different actions and functions. In another example, patterns of button depressions may also be used to differentiate between actions and functions. In the example of a touch sensitive input device, different gestures or types of motions may correspond to different actions. In a particular example, a user may contact the touch sensitive input device with a single finger to activate an action loop and two fingers (simultaneously or substantially simultaneously) to activate an information loop.

According to one or more aspects, a user may pair his or her wearable device with another user's wearable device through wireless connections. In one example, the wearable device may both pair with devices and wirelessly link with devices. The pairing function may, in a particular example, specifically relate to BLUETOOTH pairing and connections while linking may refer to Wi-Fi or other types of wired or wireless connections. In other examples, the pairing function may relate to a first type of connection while linking may refer to a second type of connection different from the first type. For example, other connection types may include infrared and RFID.

When a user is within a predefined proximity to another user, the user's wearable device may detect the wearable device of the other user. The first user may then add the second user as a friend by initiating a search process through the first user's wearable device (e.g., BLUETOOTH signal detection). Data such as contact information or identification of the friend may then be transferred from the second user's device to the first user's device (e.g., through wired or wireless connections). The contact information or identification that is transferred between devices may be configurable such that a user may specify the type and content of the contact information or identification that is transmitted to the other device and user. Friend information may be added to the first user's account upon the first user synchronizing his or her wearable device to an athletic performance monitoring service or site. In one or more arrangements, confirmation may be required from the other user or friend before any data transfer is allowed or executed. In some examples, the identification of another device user may correspond to a registered user identifier with a social network or other community site. Accordingly, a user may receive a FACEBOOK username or identifier from another user's device for identification purposes. The device may then store the other user's FACEBOOK username or identifier as a friend in the device and/or in an account of an athletic activity tracking service.

The addition of a friend through pairing of devices may further cause or trigger the establishment of a relationship between the two users on a community site. In the above example in which FACEBOOK usernames are used as identifiers, the device, upon connecting to a network, may trigger generation and transmission of a relationship request to the other user through FACEBOOK. Accordingly, a relationship such as "friends" or "workout partners" may be established on the community site upon the other user accepting the request or upon detecting mutual requests being generated and sent.

Figure 64:
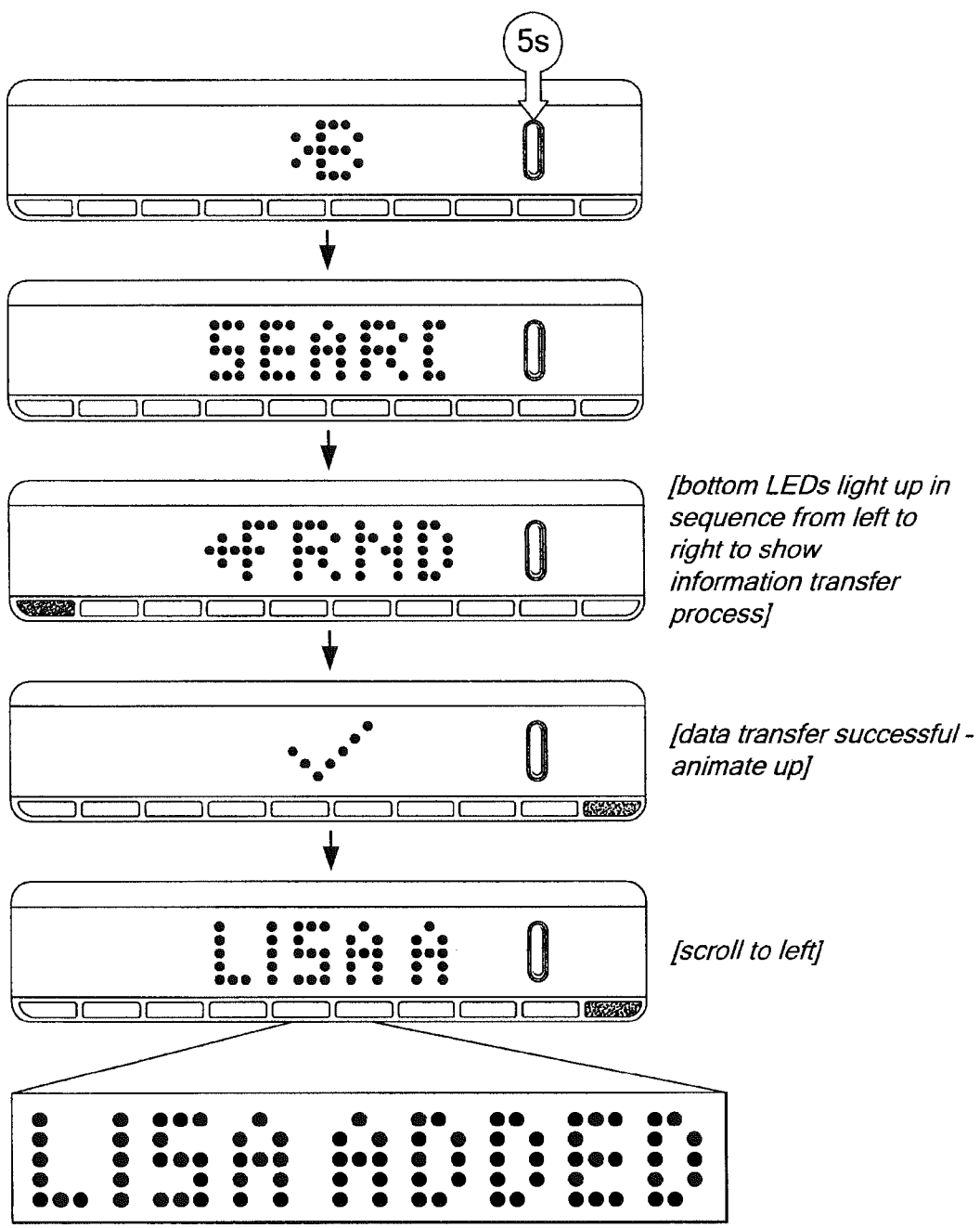

FIG. 64 illustrates example processes and interfaces for adding a friend through a user's wearable device. For example, a user may initially depress an interactive button for a predefined amount of time to activate a friend search function. Upon finding a friend, a "+FRND" message may be displayed and edge indicator lights may be illuminated to indicate a progress of data transfer. As noted above, transferred data may include name, e-mail address, other contact information, user ID and the like. This data may later be used to add the friend to a user's account on an athletic performance monitoring site.

Figure 65:
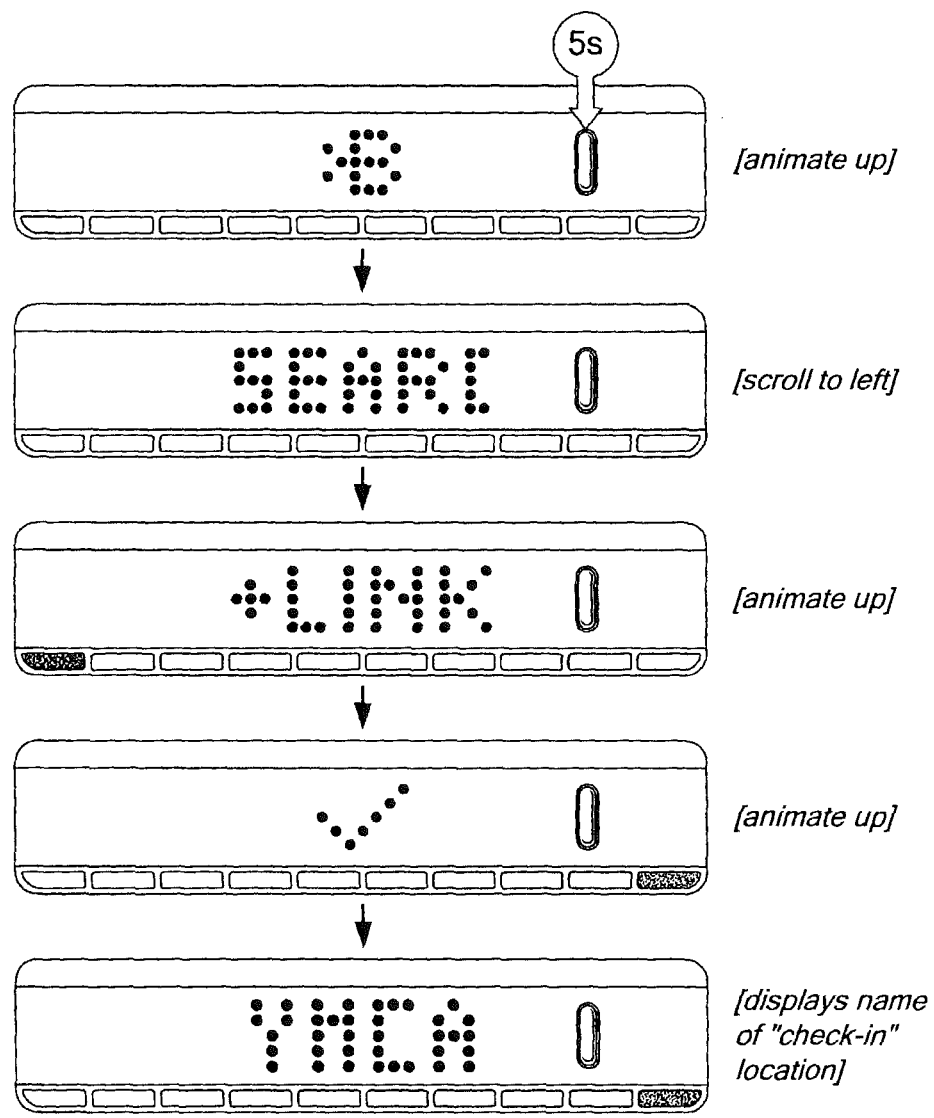

According to another aspect, a user may define and/or store geographic locations in the device. This may allow a wearable device to identify (or assume) a type of activity being performed (e.g., a park location may correspond to a running activity while a ski resort may correspond to a skiing). FIG. 65 illustrates example interfaces which may be provided for determining the user's location if the location has been predefined. For example, upon the user's wearable device detecting the user's location, the wearable device may determine whether this location is known (e.g., stored in the device or another database). Identifying a location may be performed based on latitude and longitude, an area around a set of coordinates, a particular address or area around a particular address and/or combinations thereof. The location information may be determined by the device or based on information received from a connected device such as a mobile communication device or portable music player with location determination components (e.g., GPS, cellular triangulation, etc.). If location information is received from another device, the location information may specify the location of the other device. The location of the other device may then be used to tag the activity or a location of the user or wearable device may be determined based on a known or approximated distance between the wearable device and the other device.

In some examples, a user may manually specify a location (e.g., by entering a zip code, address, etc.) through the device. If a predefined and stored location is found, the corresponding name or label may be displayed for the user's information. The name or label may be defined automatically from a network database or may be manually entered and defined by a user. The network database may comprise information retrieved from search engines, for instance, and/or may include location information defined by friends or other users of the service. In some examples, the wearable device my initially determine whether the location is a known stored location by querying its own storage system. If the location is not a known stored location within the wearable device, the device may query a network database or a database of a connected device to determine whether the location is known.

Figure 66:
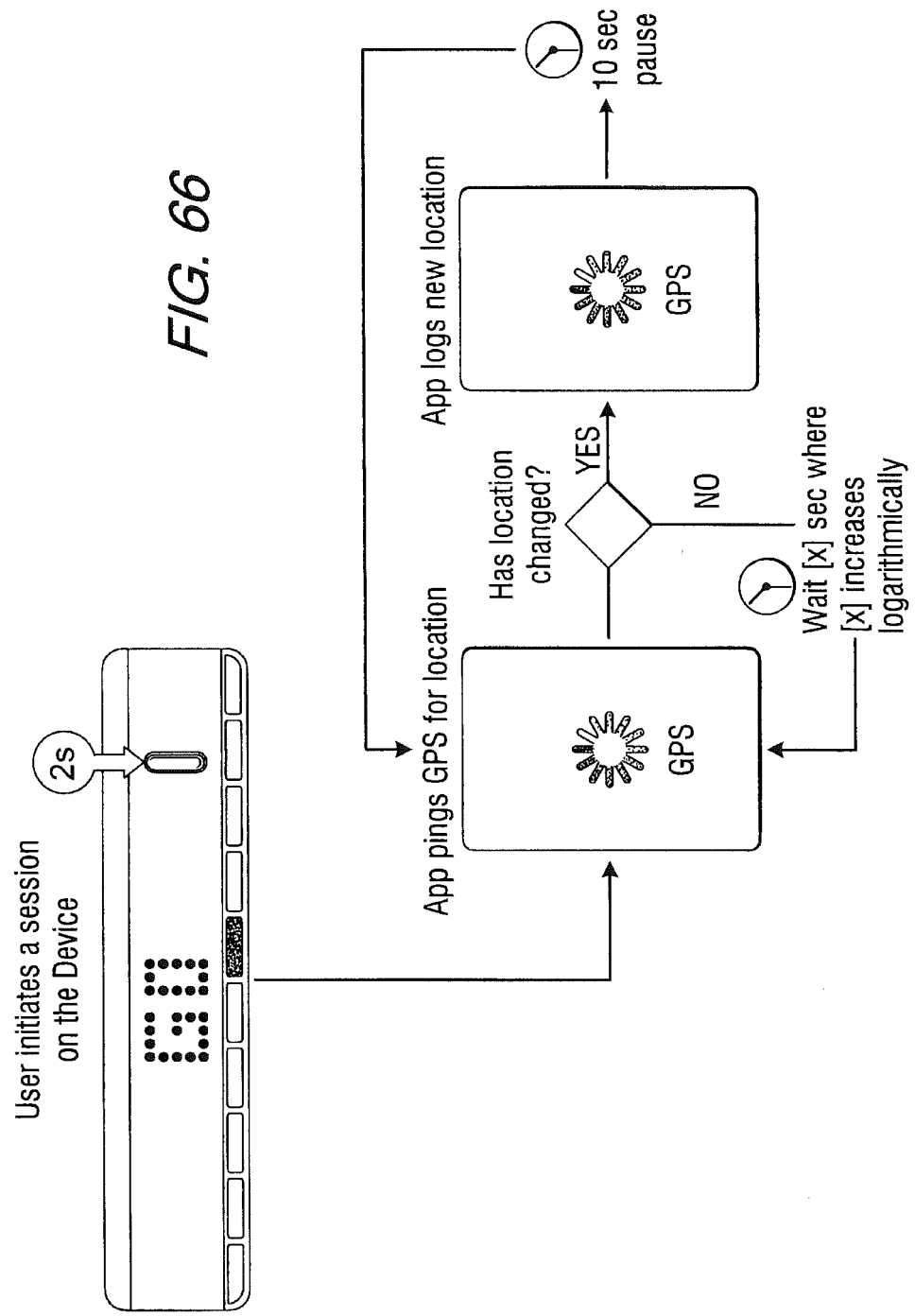
FIG. 66 illustrates an example process by which a location may be detected.

FIG. 66 illustrates a process by which a location determination system may be used to track a user's location. The location information may be stored with the athletic data for a particular athletic activity session. In one example, upon a user initiating a workout or athletic session, a position determination system and function (e.g., using Global Positioning Systems) may be automatically triggered. The position determination system may be provided by the wearable device or on a separate device such as a mobile communication device. In one example, the wearable device may be communicatively linked to the separate location determination device/system. In either case, a location determination application may begin pinging or detecting the device's location. If the user's location has changed, the application may log the new location and wait a predefined amount of time before detecting the device's location again. For example, the application may wait 10 seconds, 15 seconds, 30 seconds, 1 minute, 5 minutes, etc. before requesting the device's location. If, however, the device's location has not changed, the application may wait a predefined amount of time before detecting the device's location again. The wait time may increase logarithmically, incrementally, exponentially or might not increase at all for each successive time the device's location has not changed.

In situations where the location determination is performed on a separate mobile communication device, the application may automatically associate athletic data received from the wearable device with the location information detected by the location determination system. For example, the location data may be stored as metadata or other types of attributes for the athletic data.

To encourage athletic performance, users may compete with one another. For example, a user may compete with another user to see which user can accumulate the most activity points, calories burned, miles run or the like in a day or other predefined time frame. Activity points may be accumulated based on a user's physical movement or activity during the period of time. For example 1 point may be earned for every 20 calories burned. In another example, 1 point may be earned for every 0.25 mile run. Various types of conversion factors may be used. In other arrangements, the competition measure may be the activity metric (e.g., miles, calories, heart rate, etc.). In such cases, other types of activities that are not measured according to the athletic statistic may need to be converted prior to being counted towards the total or might not be counted toward the competition. The competition total/progress may be separate from an overall activity progress and may be stored separately as well.

Figure 67:
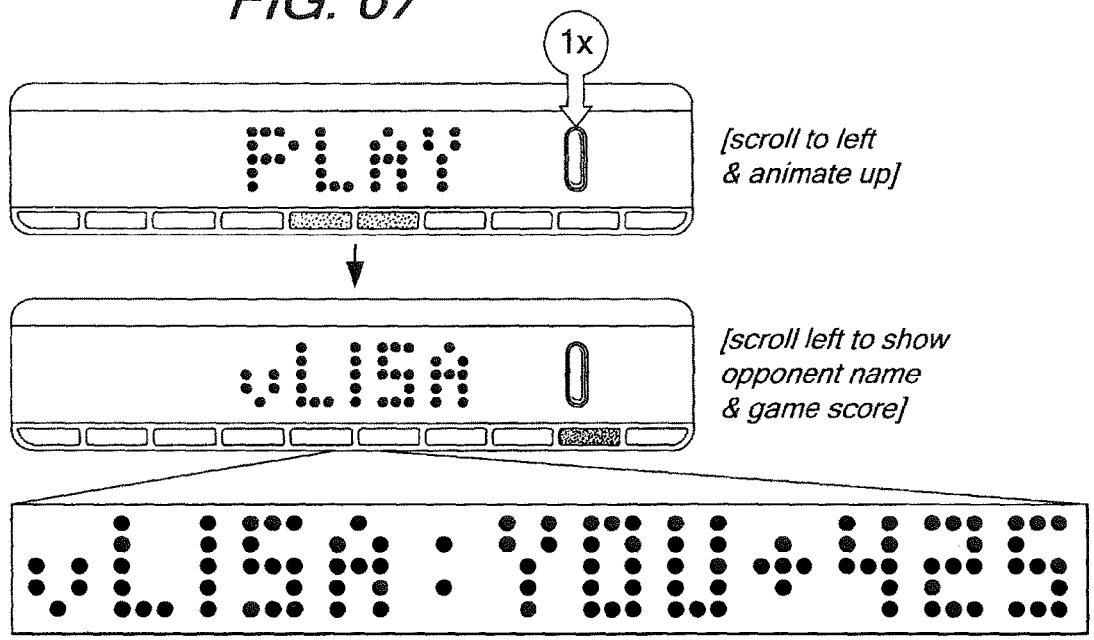
FIGS. 67-71 illustrate additional example user interfaces for a wearable device assembly.

FIG. 67 illustrates an example interface on a wearable device for indicating a current status of a competition between two users. The progress may be conveyed through a message such as "v Lisa: YOU+425," which may indicate that the competition is against another user named Lisa and that the present user is ahead of Lisa by 425 points or calories or other metric. The competitor data (e.g., an amount of calories burned, a number of activity points earned, etc.) may be synchronized through a remote network system and/or directly between the user's wearable devices. In another example, one or more of the user's wearable devices may synchronize data with the other user through a local communication device connected in a wired or wireless manner or other intermediary devices.

Figure 68:
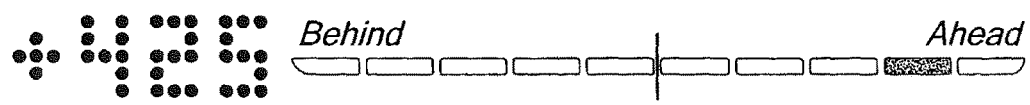
Figure 69:
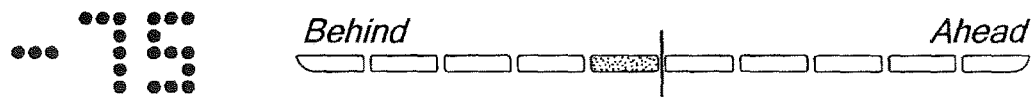

In one or more arrangements, the relative positions of the two users may be indicated on the edge illumination as well. FIGS. 68 and 69 illustrate examples of competition status indication using edge lights (e.g., a side display) of a wearable device. For example, illumination of an edge light toward the right may indicate that the user is behind (as shown in FIG. 68) while illumination of an edge light toward the left may indicate that the user is behind (as shown in FIG. 69). An equilibrium or equal point (e.g., where the users' progress is substantially equal to one another) may be defined anywhere along the side display. In one example, the distance of an illuminated light from a center point of the set of edge lights may represent a degree by which the user is ahead or behind. Other displays or the wearable device may similarly display such information. For example, a top LED matrix display of the wearable device may similarly convey a competition status between two or more individuals.

Figure 70:
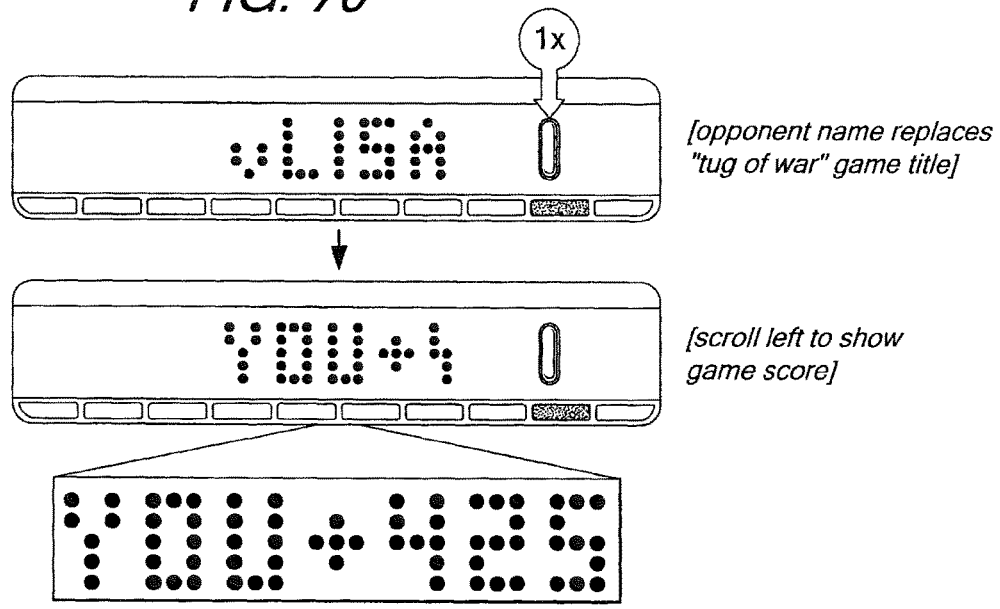

FIG. 70 illustrates another series of example user device interfaces for indicating a game or competition status between the wearer and one or more other users. As with other messages, the competition status message may scroll if it is too large to display at one time on the display interface. Alternatively or additionally, if a message, image or other information is too large to be displayed all at once on a single display, multiple displays may be used. For example, if a message is too tall for a top display of a wearable device, the additional portions may be displayed on the side display of the wearable device.

Figure 71:
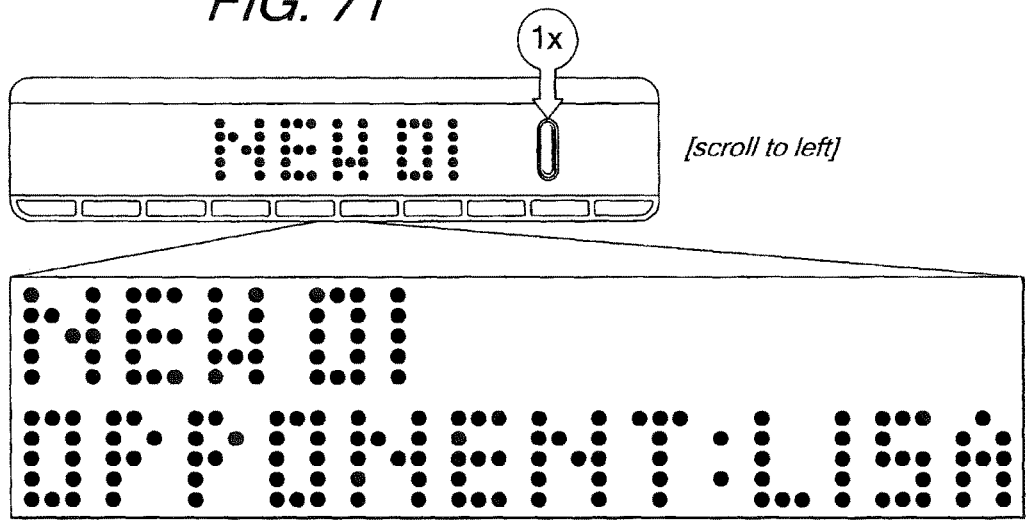

FIG. 71 illustrates an example interface message that may be displayed upon identifying or adding a new opponent. For example, the name of the new opponent may be displayed. A user may be required to confirm that the detected or identified new opponent is the desired opponent by depressing the interactive button for a predefined amount of time.

Figure 72:
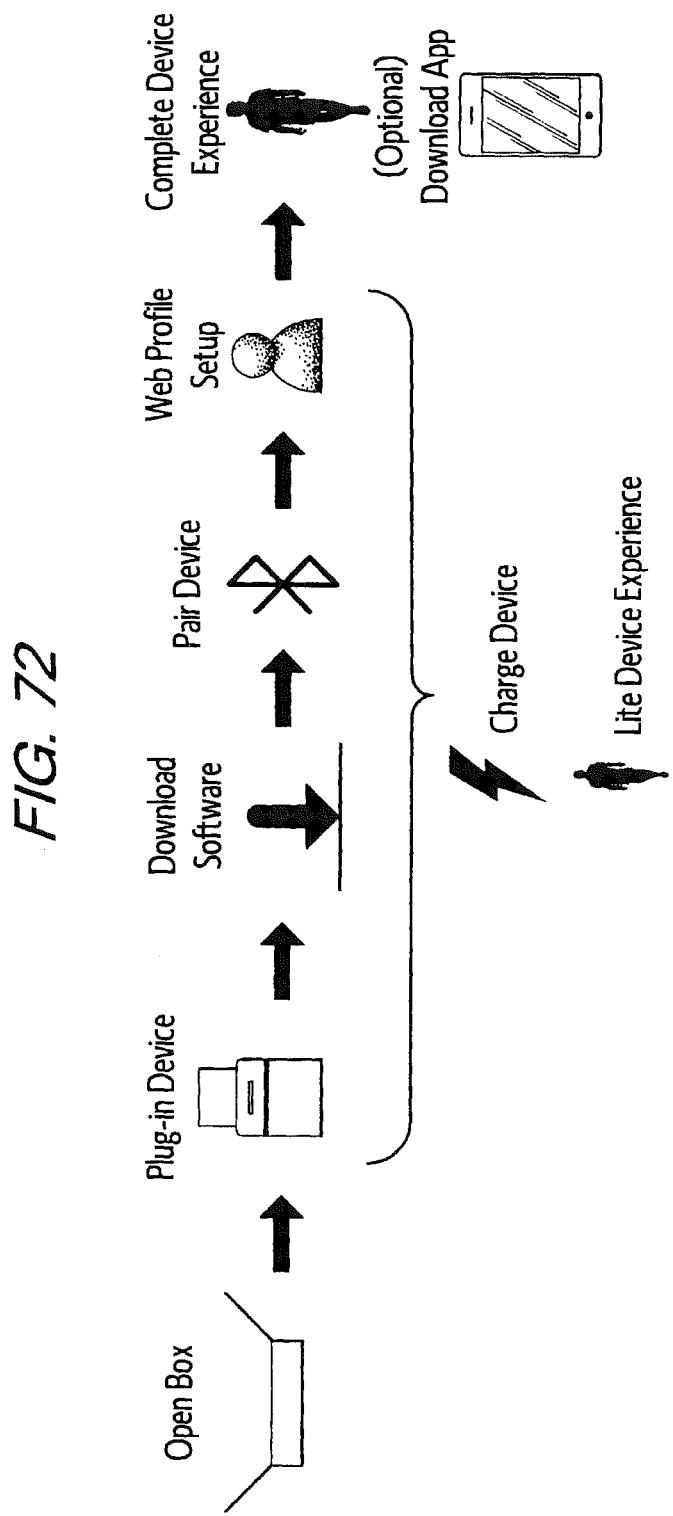
FIG. 72 illustrate an example process for configuring and registering a wearable device assembly.

FIG. 72 illustrates an example registration process flow in which a user may be instructed to initially plug-in the device, download the software and pair the device with the device through which registration will be performed (e.g., a network-connected device). Once connected, the user may then enter registration information to define a service profile for an athletic performance monitoring service. The profile may then be stored at activity monitoring service and provided to the wearable device for storage as well. If a user exits the registration process prior to completion, the device may use default settings.

In some arrangements, an application may be downloaded to one or more computing devices to facilitate and/or enhance the tracking of activity data. For example, the application may enable graphing of activity information and display of such graphs as well as providing recommendations for improvements and setting of goals. The application may further facilitate configuration and updating of the device as well as communication between the device and a remote site such as an activity monitoring service/site. Additionally or alternatively, the wearable device may be locked from use (e.g., all functionality beyond registration disabled, all functionality but normal athletic performance monitoring disabled) prior to registration. Normal activity performance monitoring may include sensing of activity by a user, display of that information on the display interface and/or tracking of goals. However, no data may be stored and no association between the user and the data may be established. In some examples, some data such as activity information may be stored in the device or the application during an initial phase, startup and/or registration.

FIGS. 73A-73G illustrate example registration interfaces that may be used to register a new user and/or device through the Internet or other network.

Figure 74A:
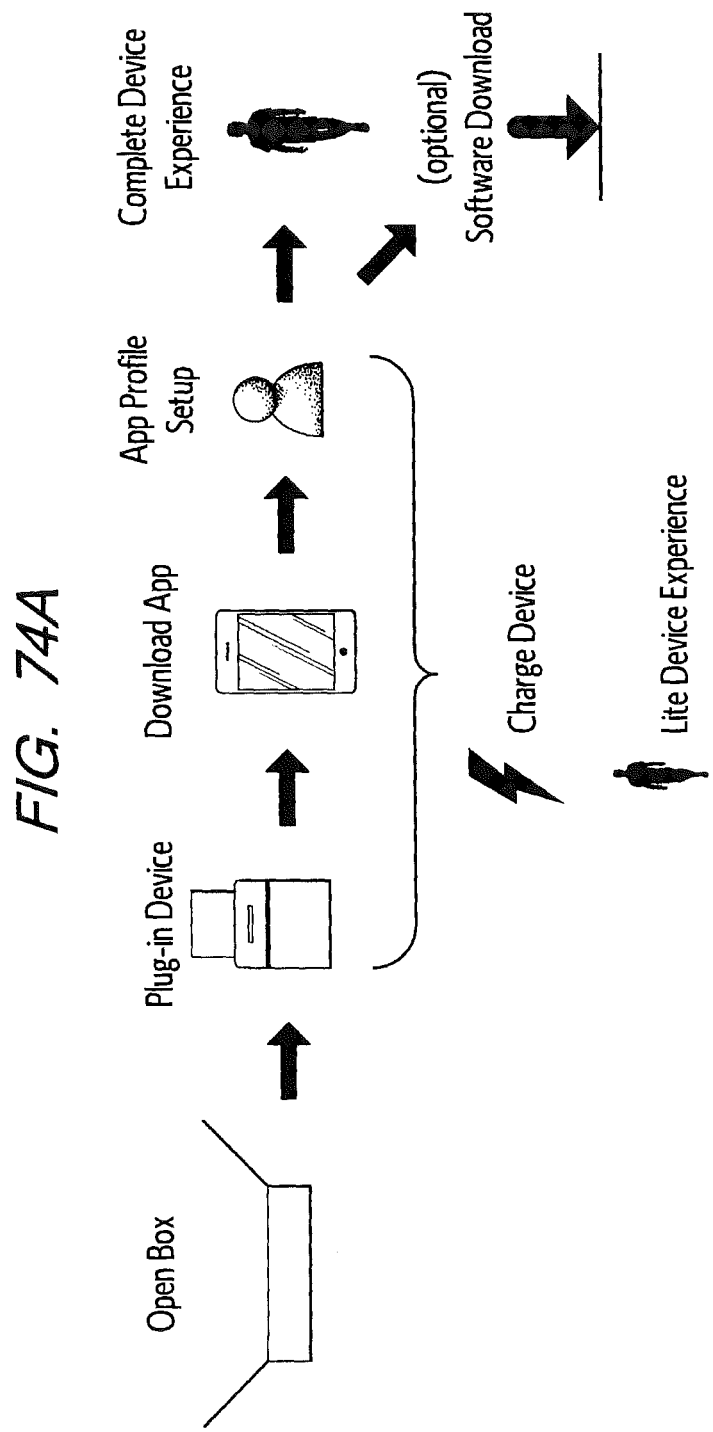
FIG. 74A illustrates another example process for configuring and registering a wearable device assembly.
Figure 74C:
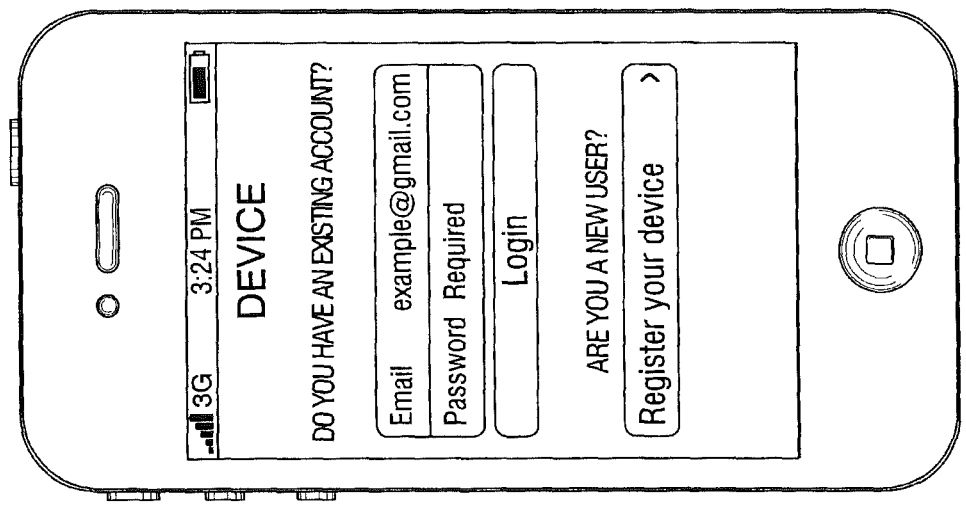
FIGS. 74B-74P illustrate example registration, configuration and setup interfaces.

FIG. 74A illustrates another example registration process flow in which a user may register with the device and the user through a mobile application. In contrast to the process flow of FIG. 72, the registration of FIG. 74A is performed through an application executing on a mobile communication device while in FIG. 72, the registration is performed through a website or other software (e.g., software executing on a desktop or stationary computing device).

Figure 74B:
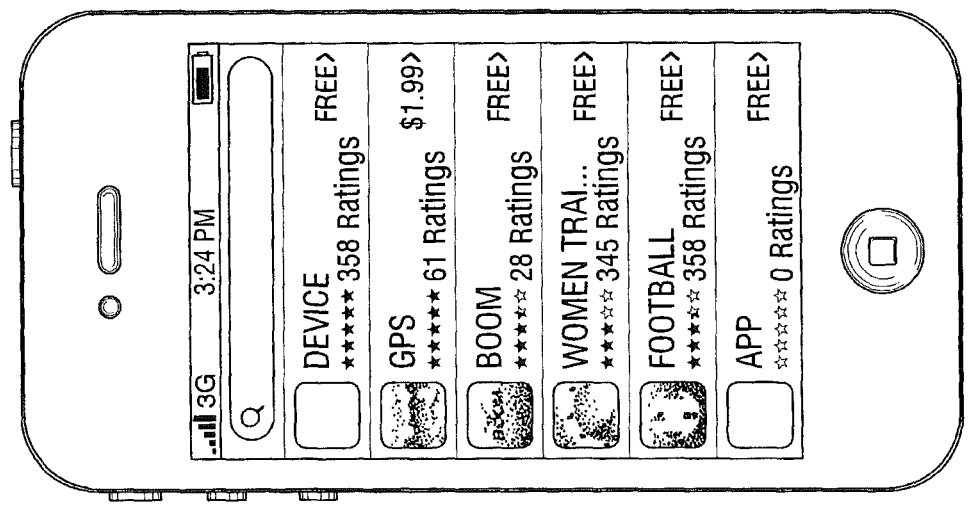
Figure 74F:
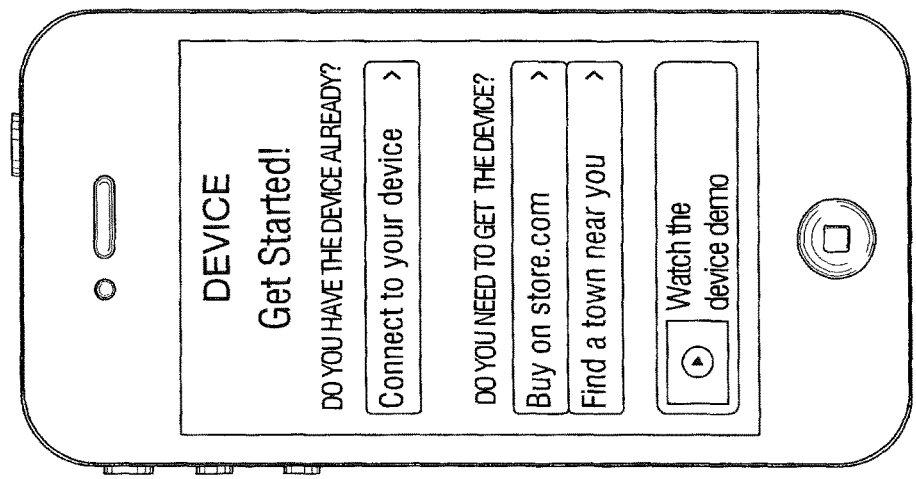
Figure 74E:
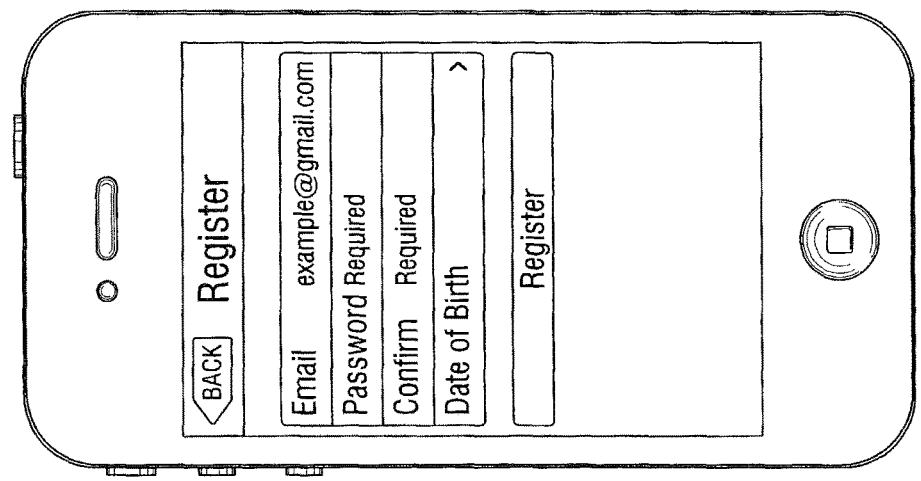
Figure 74D:
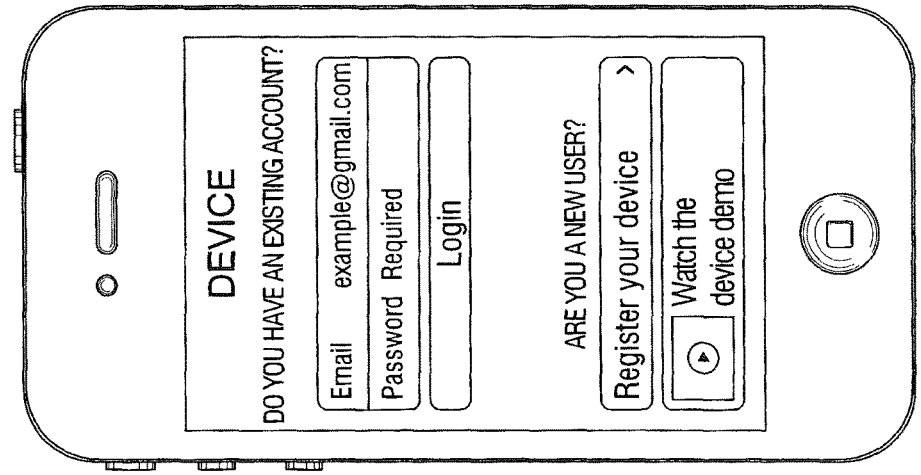
Figure 74H:
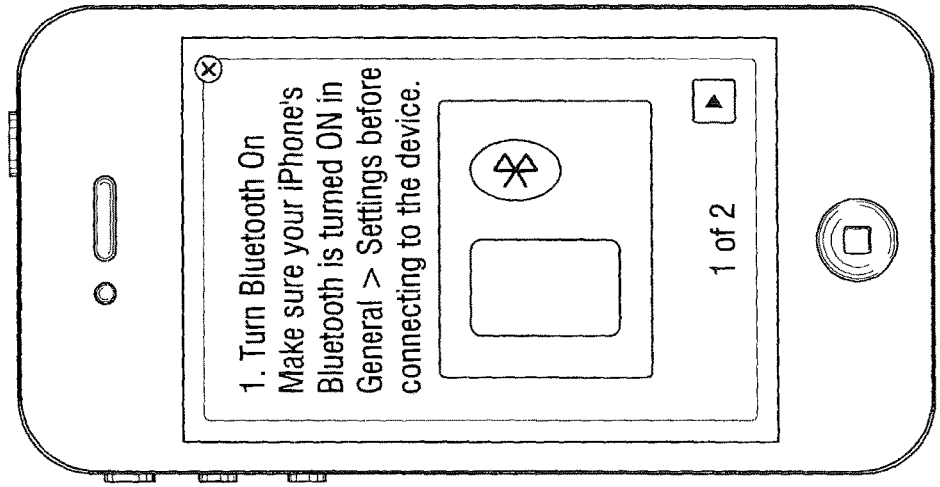
Figure 74G:
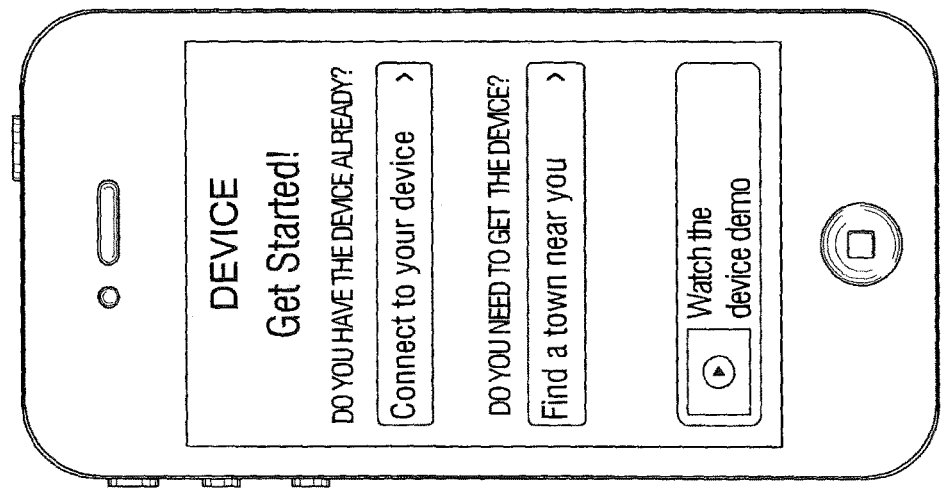
Figure 74J:
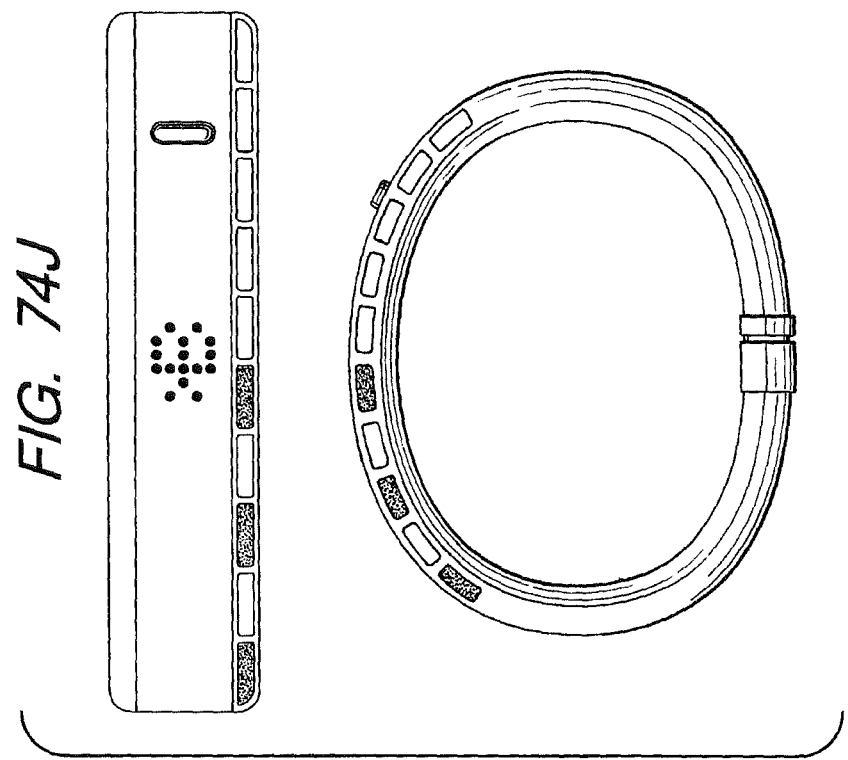
Figure 74I:
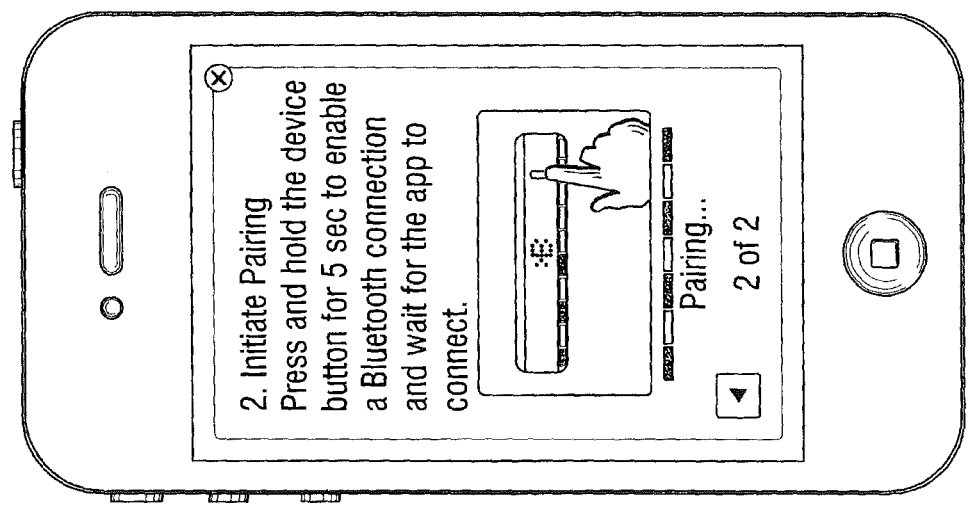
Figure 74K:
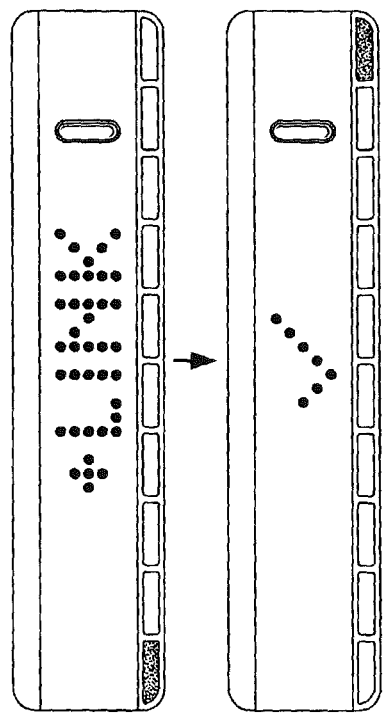
Figure 74L:
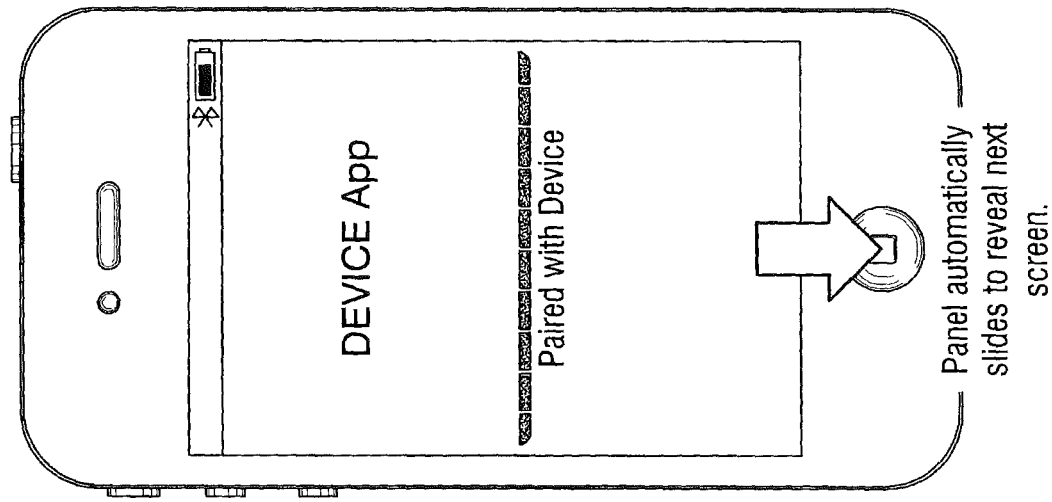
Figure 74P:
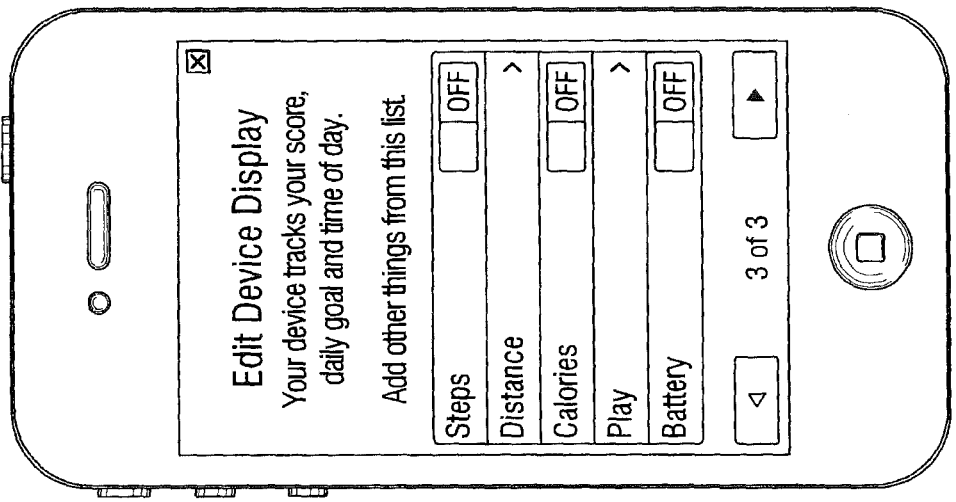
Figure 74O:
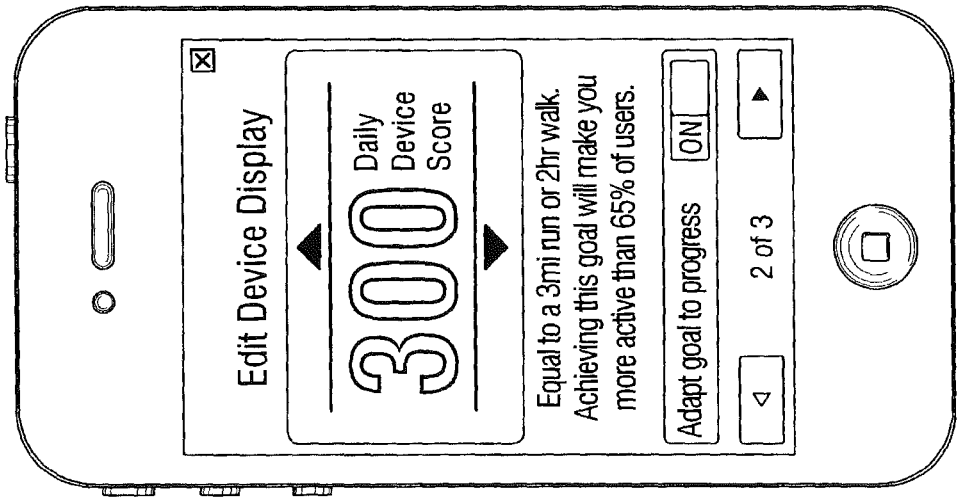

FIGS. 74B-74P illustrate example registration interfaces that may be used to register a new user and/or device through an application on a mobile communication device.

Figure 75:
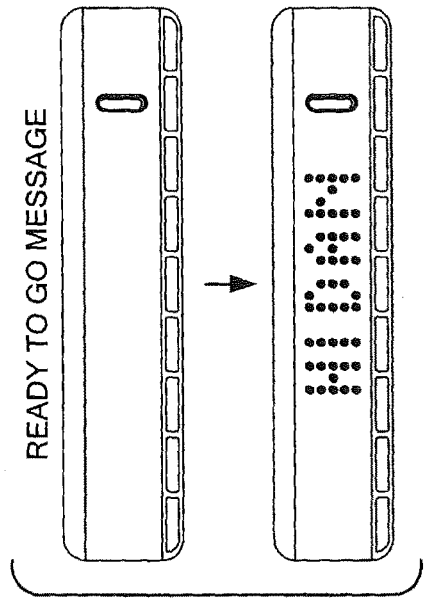
Figure 78A:
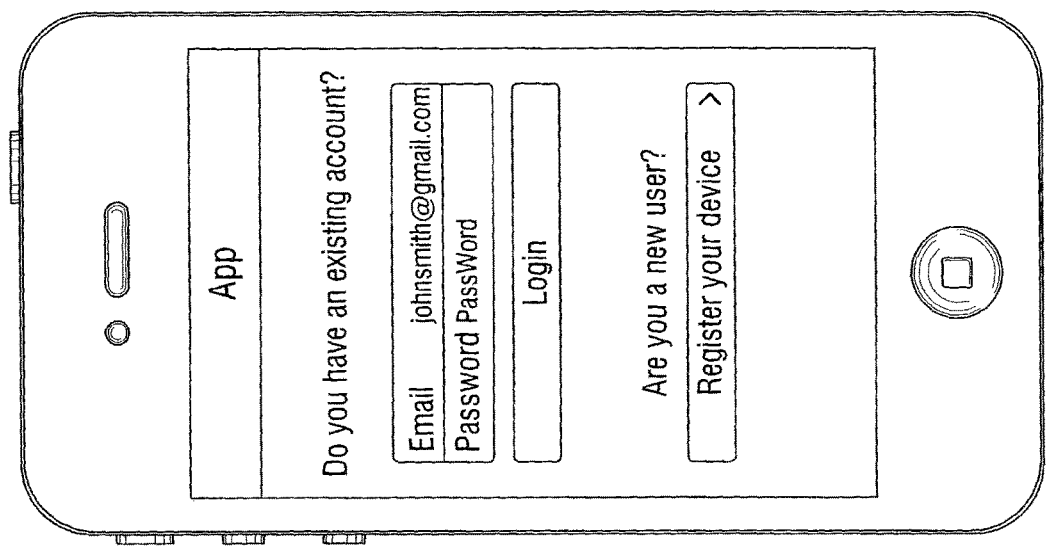
FIGS. 78A-78G illustrate example interfaces for logging into and customizing an activity tracking application.
Figure 78B:
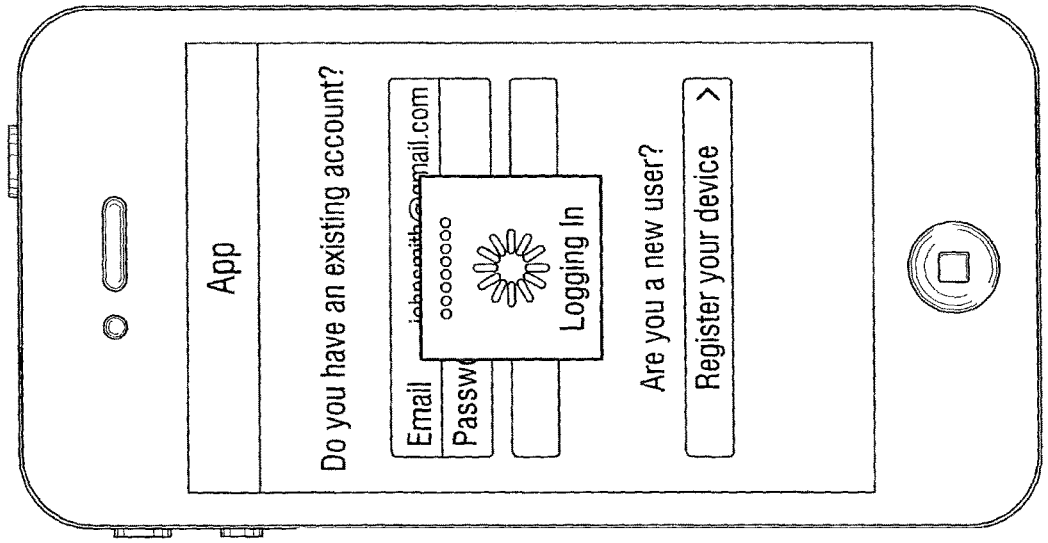
Figure 78D:
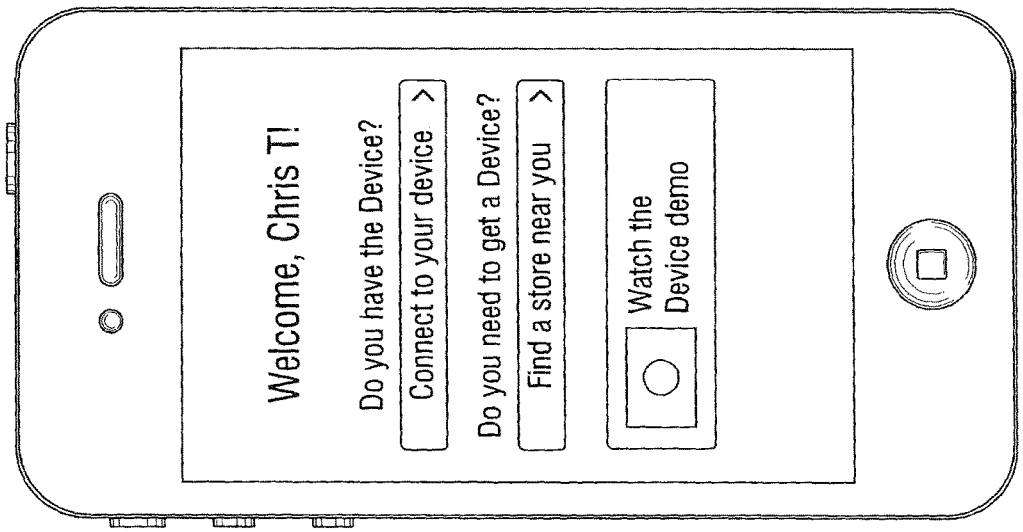
Figure 78C:
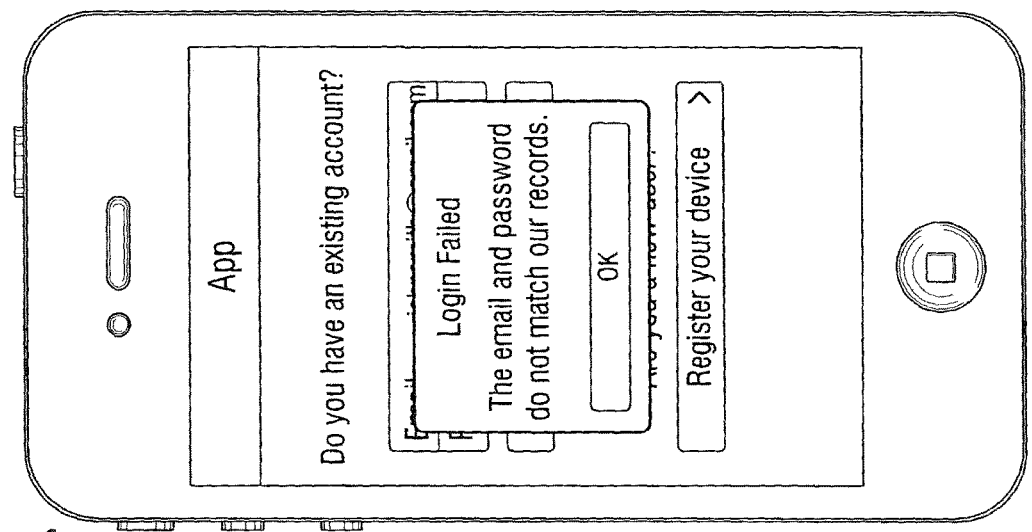
Figure 78G:
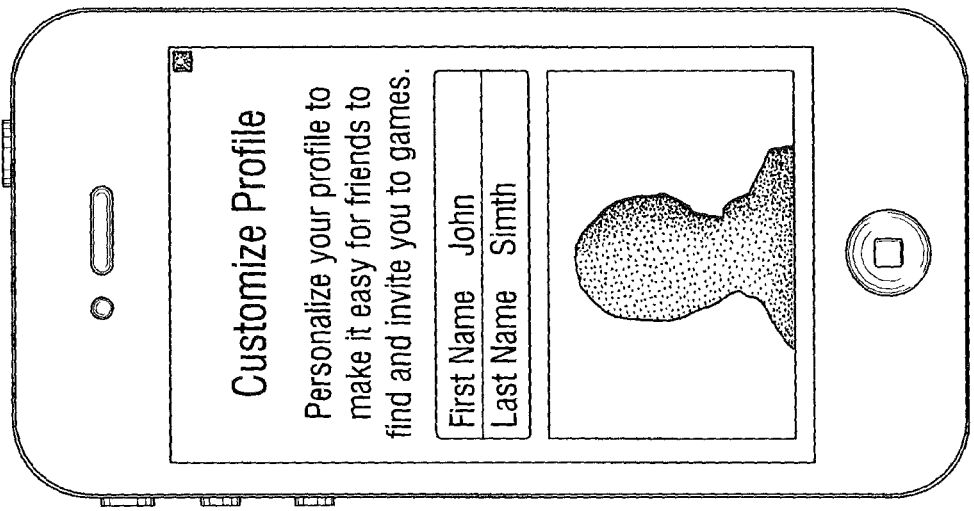
Figure 78F:
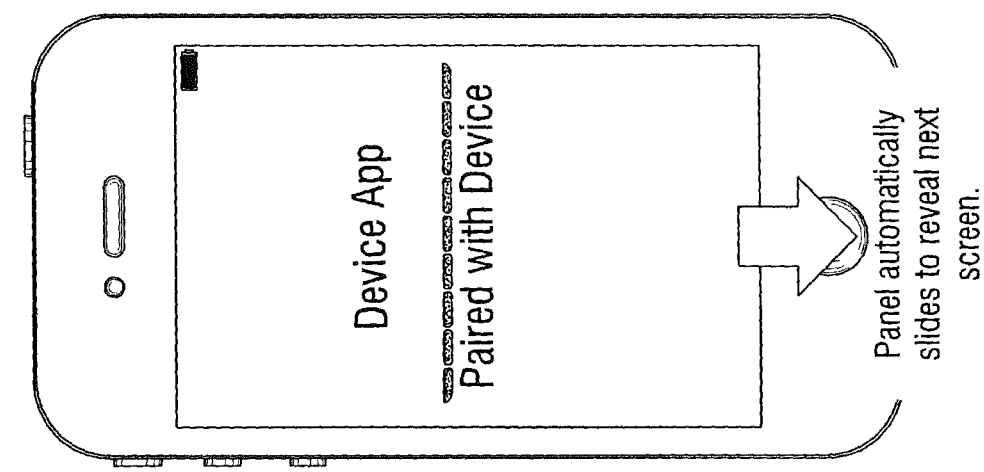
Figure 78E:
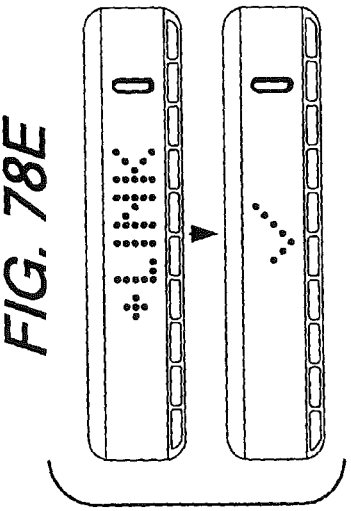

Upon successful registration, the wearable device and the application the mobile communication device may provide indications that the device and application are ready to begin tracking activity. For example, FIG. 75 illustrates an example user interface display on a wearable device including a message greeting the user. The greeting may indicate that the device is ready to begin tracking activity. Other indications may also be used.

Figure 77:
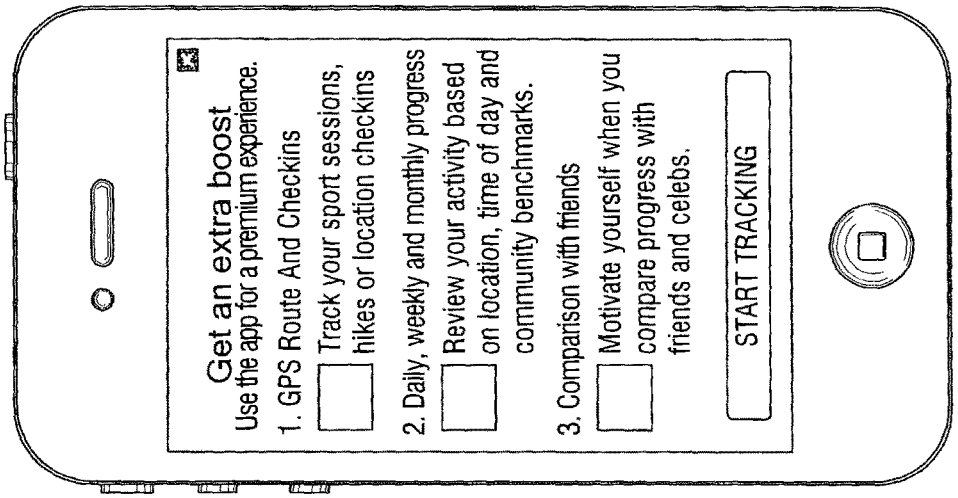
FIG. 77 illustrates an example informational display for using the wearable device assembly.
Figure 76:
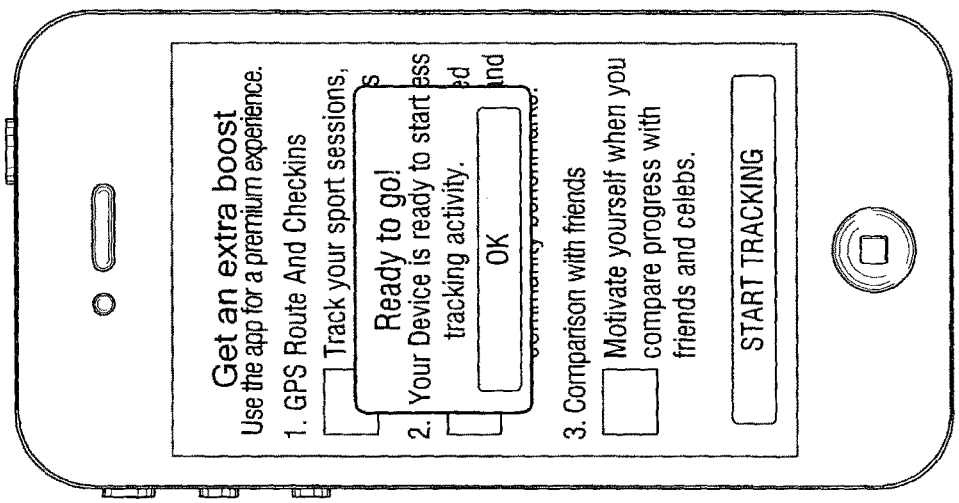
FIGS. 75 and 76 illustrate example messages indicating that the wearable device assembly is ready to be used.

In FIGS. 76 and 77, the application may provide a message that the wearable device is ready for tracking activity and further provide information regarding the capabilities of the application in tracking activity, respectively. For example, while the device may measure and record various metrics including activity points, calories burned, distance run and the like, the application may be configured to process the measured and recorded data to provide additional information including location/route information, progress/trend information and comparison data (e.g., comparing the user's activity with friends or other users).

FIGS. 78A-78G illustrate example user interfaces for registering a new device for an existing user. For example, registration of a new device for an existing user may require the user to enter login credentials. The user may then link the new device upon successful authorization.

Other types of registration processes may also be used including those with more or less options as desired by an activity tracking service and/or the user. In some examples, portions of the registration process may be optional (e.g., setting a daily goal, display setup, etc.).

Figure 79:
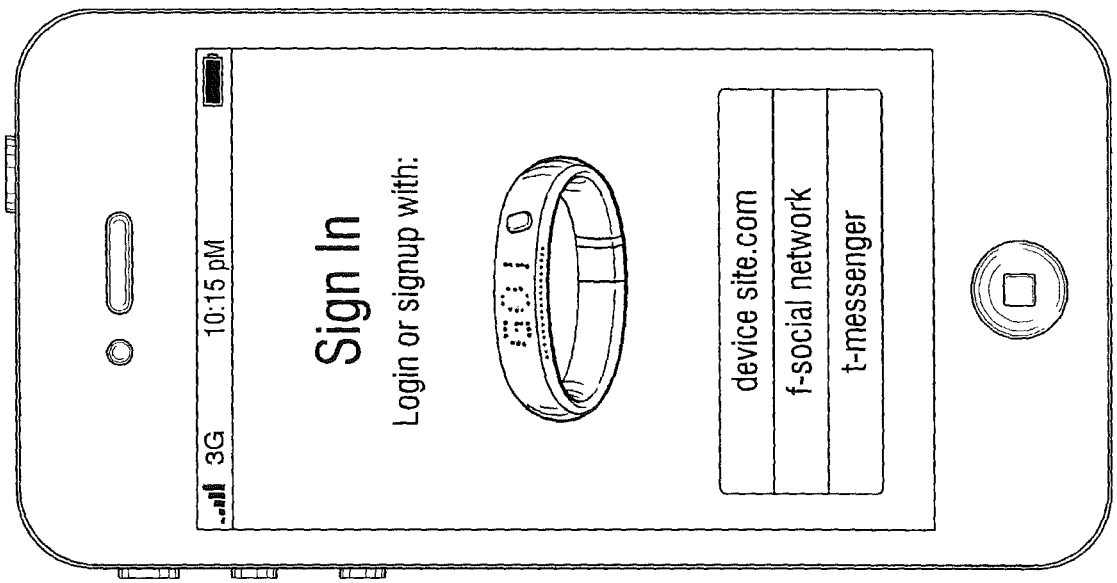

According to one or more aspects, a user may login or sign on to an activity tracking service or application using a variety of different accounts including accounts not provided by the activity tracking service. FIG. 79, for example, illustrates an application display on a mobile device that provides sign in options using different accounts including an activity tracking service account, a FACEBOOK account and a TWITTER account. In one or more examples, the activity tracking service may correspond to a provider of the activity tracking application. To sign in or register with the activity tracking service using external accounts such as a FACEBOOK or TWITTER account, the user may be required to authorize transmission of data and/or other interactions between the activity tracking service and the external system or site.

Figure 80:
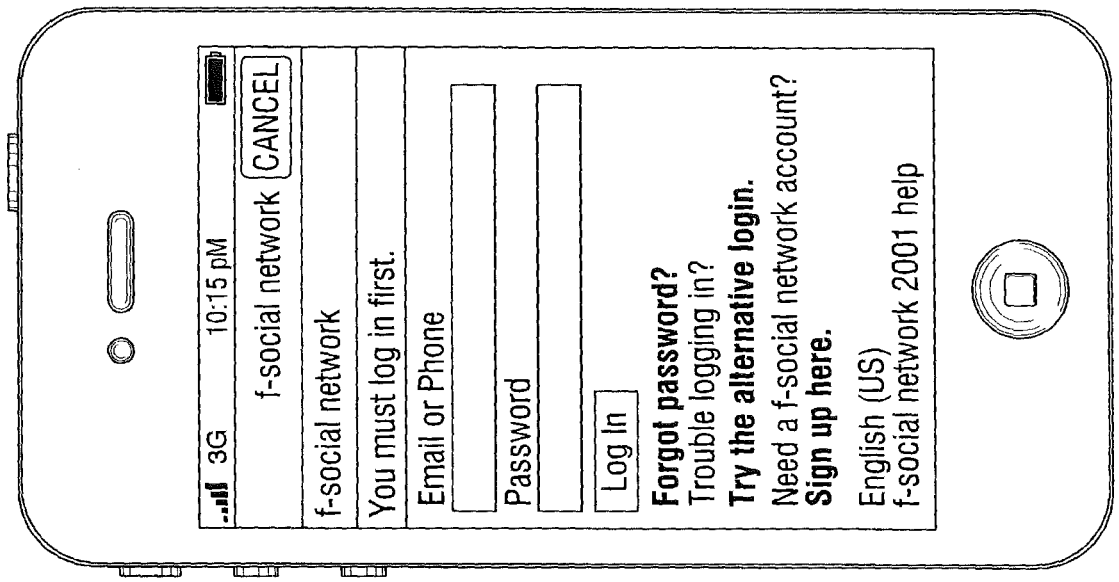
FIGS. 79-81 illustrate example interfaces for associating an activity tracking account with one or more social networking accounts.
Figure 81:

FIGS. 80 and 81 illustrate example user interfaces for providing authorization for the activity tracking site to communicate data with each of the external services.

FIG. 80, for instance, illustrates a FACEBOOK login page requiring the user to enter login information to link the activity tracking service to the user's FACEBOOK account. FIG. 81, on the other hand, illustrates a TWITTER login that may require the user to login to authorize an activity tracking service or application to interact with the user's TWITTER account. As shown in FIG. 81, the user may be advised of the application or service that would be authorized as well as the functions, data, interfaces of the external service that would be made available to the application or service receiving authorization.

Figure 82A:
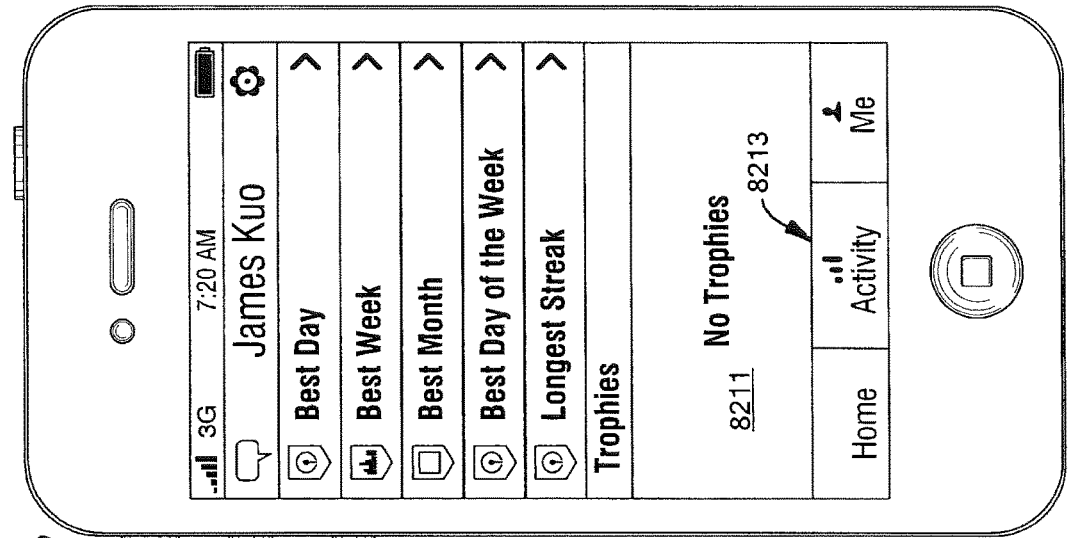
FIGS. 82A and 82B illustrate example user profile interfaces.
Figure 82B:
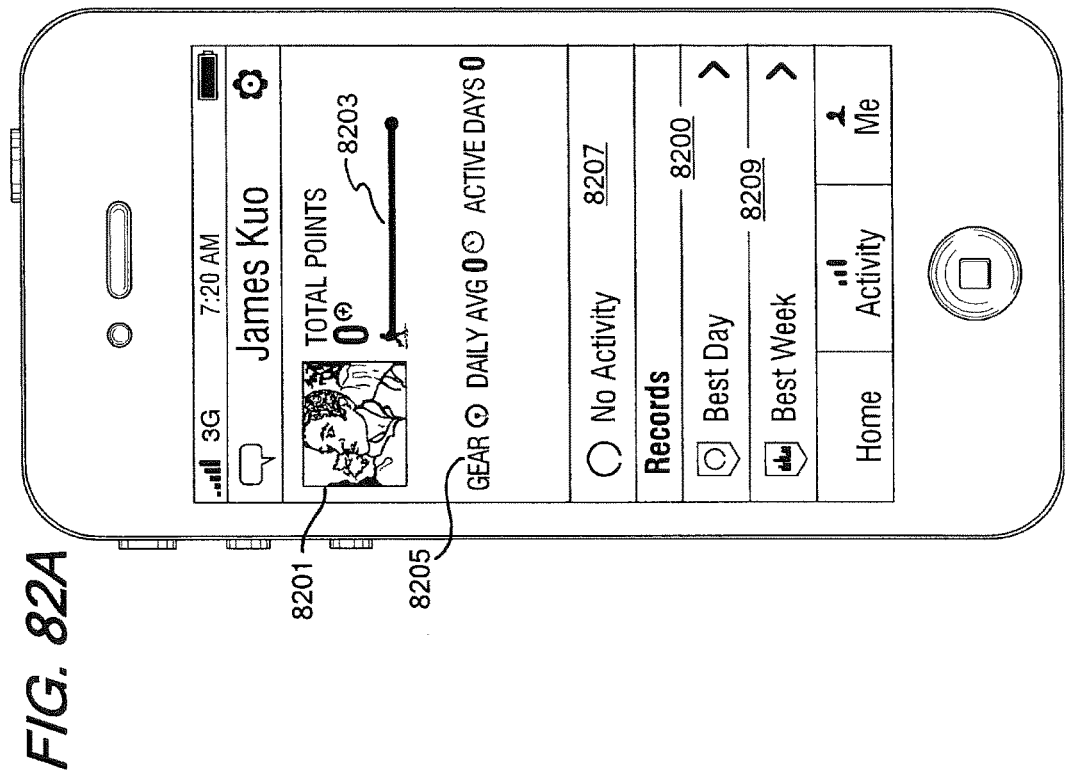

Once a user has logged into the activity tracking service or application, the user may be presented with profile information as illustrated in FIGS. 82A and 82B. The application interface 8200 may include a profile picture 8201, an activity gauge 8203, identification of a device used 8205 and other metrics including a daily activity average and a number of active days. The identification of an activity tracking device used 8205 may correspond to the device used to measure and record activity and may include a listing of multiple devices if the user's activity is tracked using multiple different devices. In some instances, only one of the multiple devices may be identified in interface 8200. For example, the device with which a majority of the user's activity is tracked may be displayed without identifying other devices. In other examples, a user may select a device to be identified in the device identification 8205.

In section 8207, recent activity may be displayed. Activity may be grouped by time periods such as days, weeks, months, hours, two hours, 6 hours, 12 hours and the like. Accordingly, the recent activity section 8207 may display a most recent number of activity periods. In a particular example, section 8207 may display the most recent 3 days of activity, each day being listed as an entry in section 8207. Section 8209 may be used to display records that have been achieved by the user. Records section 8209 may include multiple predefined record categories such as best day, best week, best month, best day of week, longest streak and the like. Selecting one of the categories may cause the application to display the corresponding record for that category. In addition to recent activity and records, the interface 8200 may further include a trophy section 8211 configured to display awards and achievements of the user. For example, various trophies and milestones may be defined such as reaching a certain number of activity points in one day, achieving a streak of days in which the individual has reached an activity point goal, exceeding a goal by a specified amount and the like.

A function bar or toolbar 8213 may be displayed in interface 8200 to allow a user to switch between various top level modes of the application. For example, selecting the "Me" tab in bar 8213 may display the profile information as shown in FIGS. 82A and 82B. Selecting the "Home" tab, on the other hand, may cause a visual display of a current level of activity for a current session or time period to be displayed. In one example, the "Home" tab may cause an activity point tracker to be displayed during an evaluation period. The evaluation period, as described, may, in some instances, correspond to a first 24 hours of using the device.

Figure 82D:
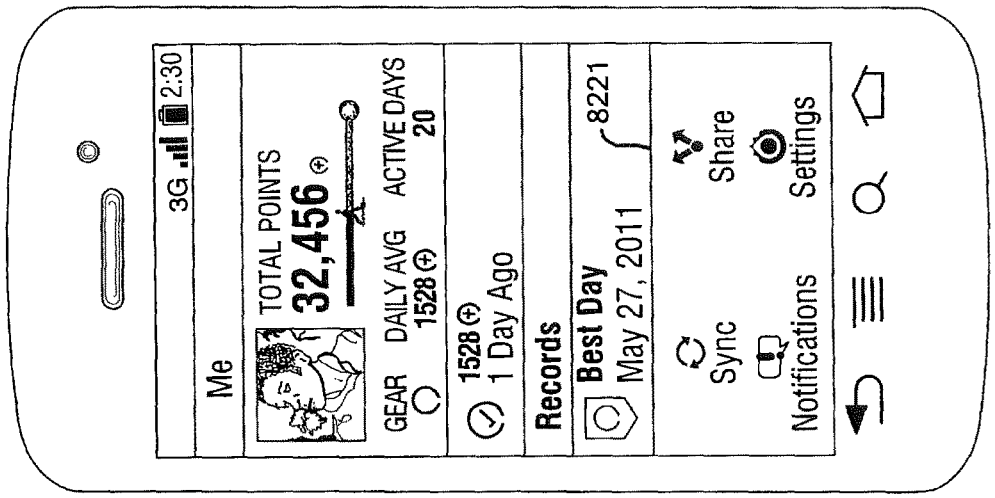
FIG. 82D illustrates another example user profile interface.
Figure 82C:
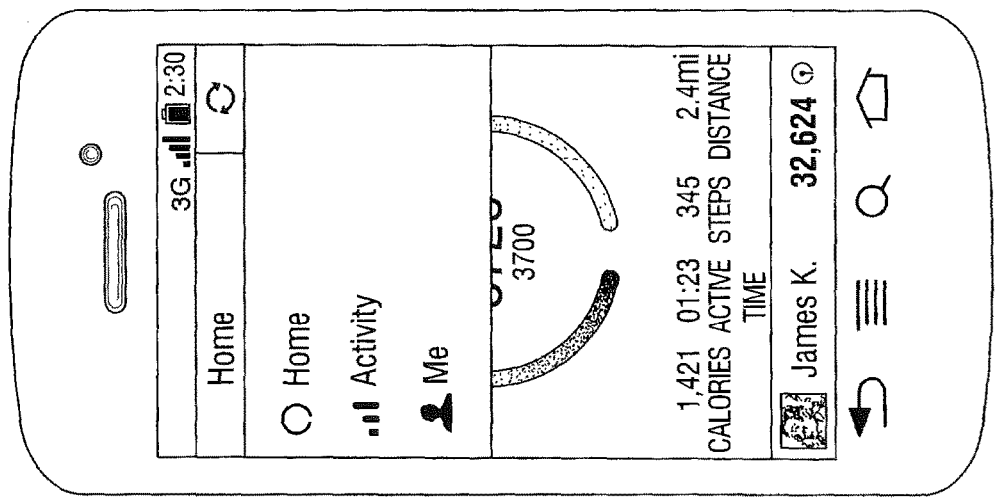
FIG. 82C illustrates an example application mode selection interface.

Alternatively or additionally, the Home, Activity and Me modes or interfaces may be displayed as a drop down menu or other type of menu that is displayed upon user selection of a menu option as illustrated in FIG. 82C. By hiding the Home, Activity and Me mode options, the display may provide more real estate to other visual items. In contrast to the interfaces of FIGS. 82A and 82B, the interface of FIG. 82C may require an additional user input or interaction prior to selecting one of the general sections of the application.

According to another arrangement illustrated in FIG. 82D, a profile interface may further include a menu for additional functions of the application. In one example, menu 8221 may be displayed upon receiving a user interaction different from a user interaction configured to trigger a general mode selection menu as shown in FIG. 82C. In menu 8221, for example, the user may be presented with options such as synchronization (e.g., with a wearable activity tracking device), view notifications, settings and share. The options included in menu 8221 may change depending on the current active interface, information display or mode of the application.

FIGS. 83A-83D illustrate examples interfaces displaying an accumulated amount of activity points during an evaluation period. The activity tracking interface 8300 may include a variety of indicators including an activity point indicator 8301, a graphic evaluation time remaining indicator 8303, a textual evaluation time remaining indicator 8305, and a message portion 8307 that may convey a variety of information including a level of progress. The graphical time remaining indicator 8303 may include a circular track that progressively changes appearance (e.g., fills in in a specified color or appearance) as the evaluation time period counts down. A textual/numerical time indicator 8305 may also be displayed to provide detailed time accounting. Various other graphical indicators may be used to indicate an amount of time completed and/or an amount of time left in the evaluation period. The activity point indicator 8301 may provide the user with information as to a number of activity points that he or she has accumulated. Activity point indicator 8301 may be updated in real-time, substantially in real-time, on-demand, periodically, aperiodically and/or based on other specified schedules or rules. Updating may include synchronizing data with the wearable device. In one or more examples, updating of the activity point count may be triggered by movement of the mobile device or transitioning from a sleep state to an active or idle state. Additionally or alternatively, update indicator 8309 may be used to identify when data is being synchronized or otherwise updated to the mobile application from the wearable device. In some arrangements, an option (not shown) may be provided to request updating or synchronization of the activity point data.

Figure 83B:
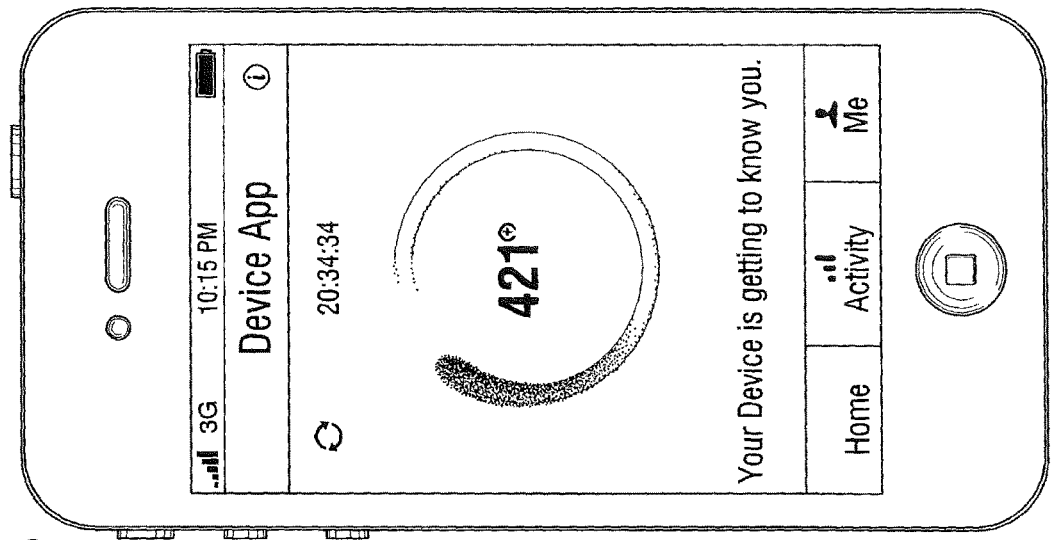
FIGS. 83A-83H illustrate example user interfaces for tracking and visualizing goal achievement progress.
Figure 83A:
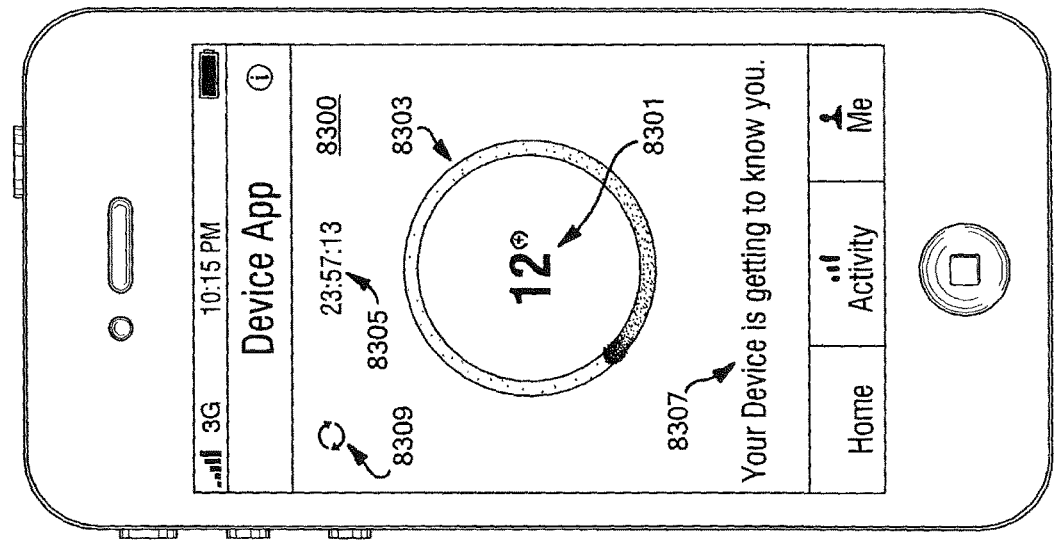
Figure 83D:
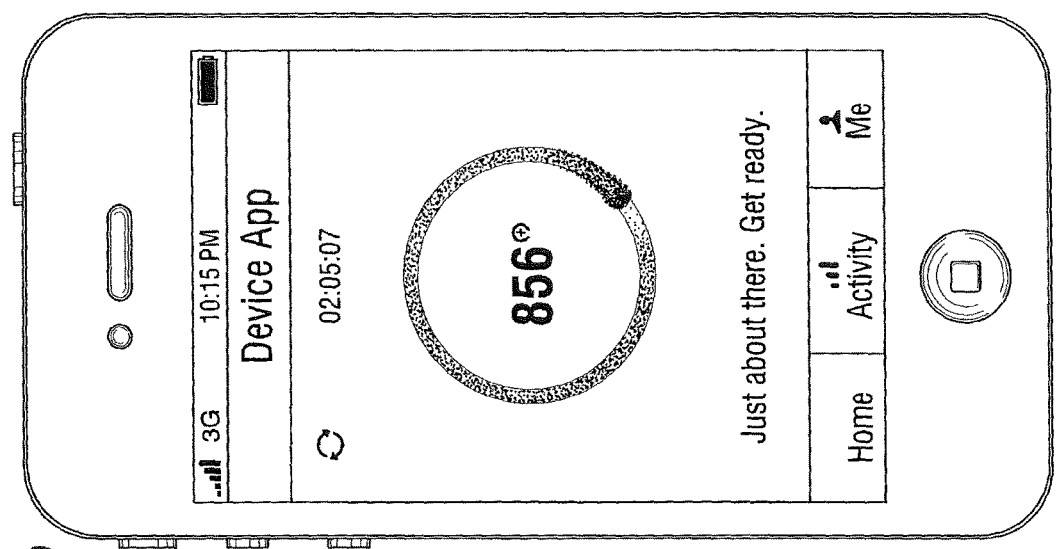
Figure 83C:
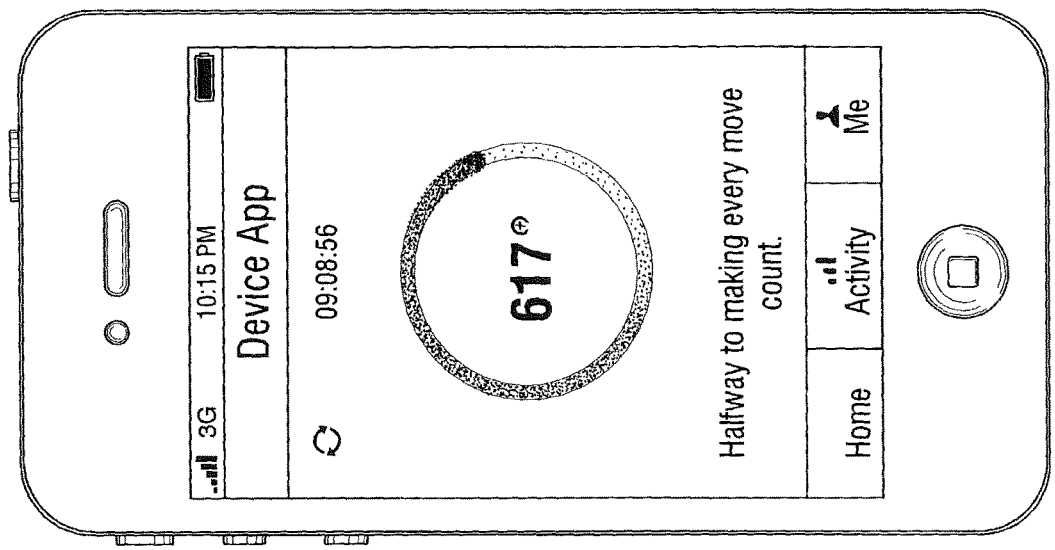
Figure 83F:
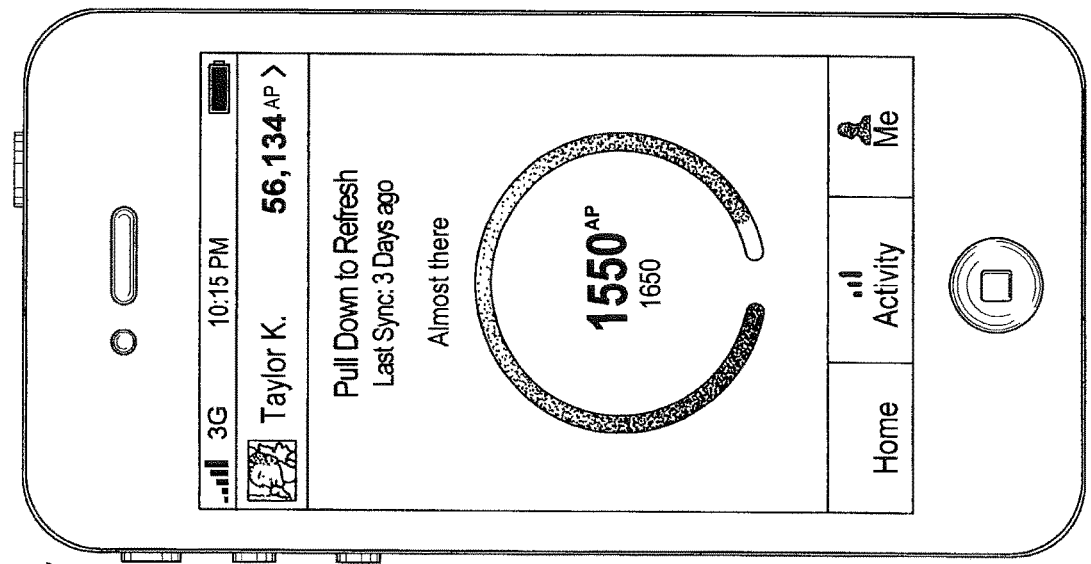
Figure 83E:
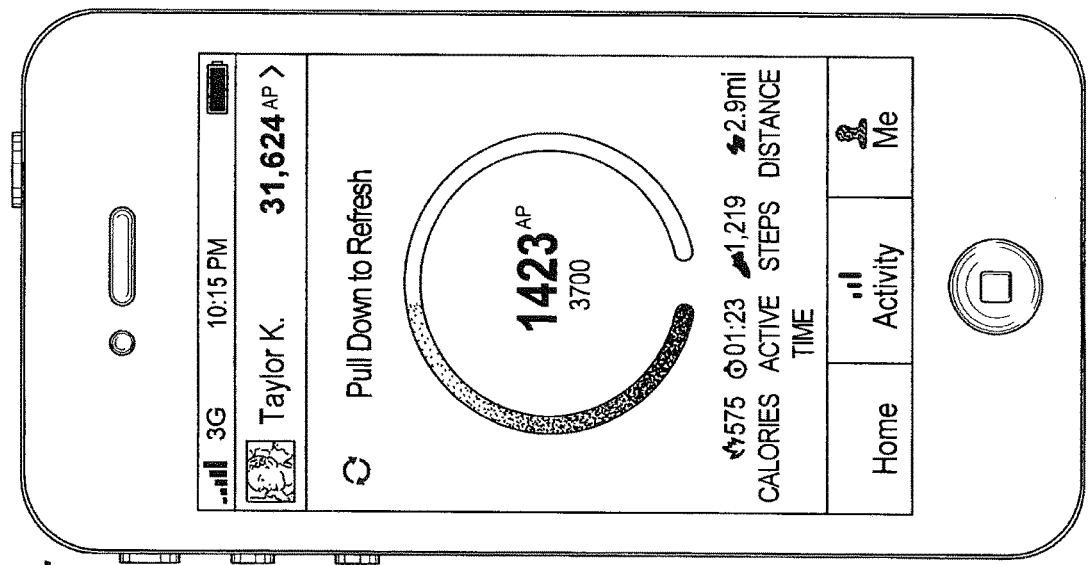
Figure 83H:
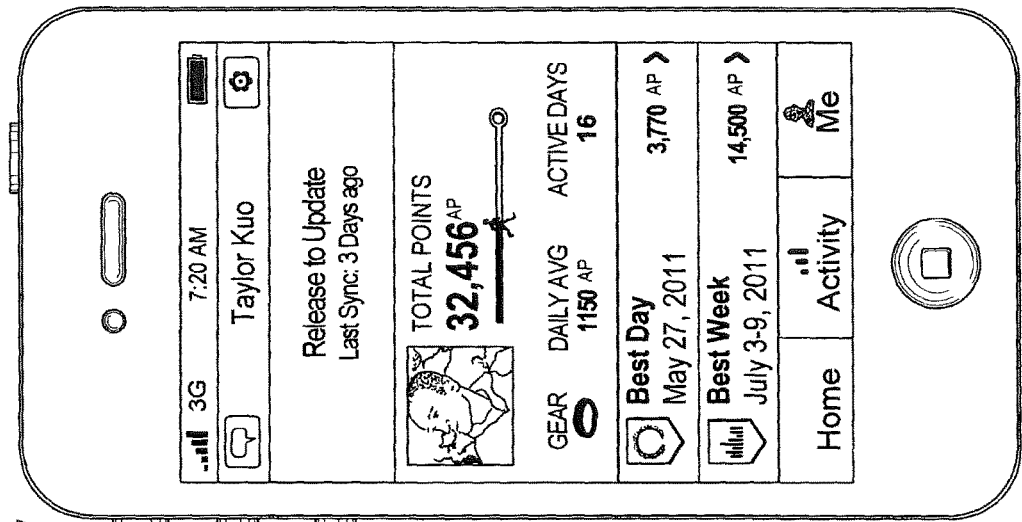
Figure 83G:
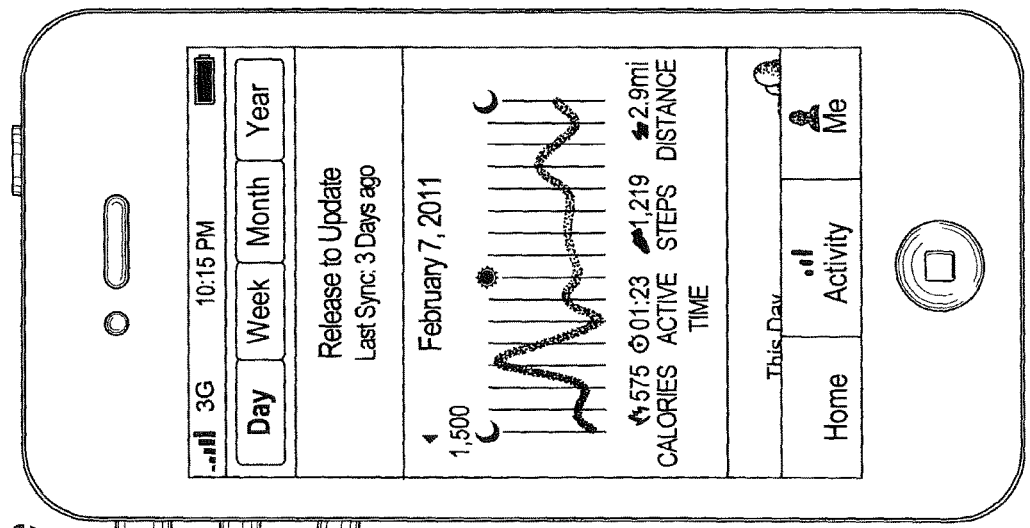

FIGS. 83E-83H illustrate an example synchronization/update functionality that may be activated on the mobile application by performing a predefined gesture in the interface. For example, the user may update or synchronize data from the monitoring device to the mobile communication device by pulling the user interface down using touch input and releasing. Other various types of user inputs and commands may also be defined for activating an update functionality. Accordingly, the activity data may be both updated automatically at predefined times or continuously and/or in response to a manual command from the user. In yet other examples, other triggers may be used to activate updating and synchronization. In one particular example, activation of the mobile communication device display (e.g., from a power save state), activating the activity tracking and monitoring activity, viewing a particular interface in the application and the like and/or combinations thereof may trigger updating. The interfaces shown in FIGS. 83E-83H correspond to non-evaluation modes such as an activity tracking mode, a summary mode and a profile mode, respectively, however, updating activity data may be performed in similar fashion during evaluation modes as well. In some examples, as shown in FIGS. 83F-83H, the interface may also indicate to the user the last time data was updated to the mobile application.

Referring again to FIG. 83A, message portion 8307 may be used to convey contextual information. For example, during the beginning of an evaluation period, the message portion 8307 may indicate that the wearable device is in a preliminary phase of evaluating the user (as shown in FIGS. 83A and 83B). As the evaluation period progresses, the message may change to indicate that the user has completed half of the evaluation period, as illustrated in FIG. 83C. When the user is close to completing the evaluation period (e.g., within 5%, 10%, 15%, 25%, etc.), the message portion 8307 may indicate such a status to the user, as shown in FIG. 83D.

In some instances, the mobile device executing the activity tracking application may enter an idle state (e.g., the display is turned off and a key lock or input lock is initiated). When the device enters the idle state, notifications using the underlying operating system of the mobile device may be generated and displayed. The notifications may indicate a progress toward completion of the evaluation period even when the application is not active or the device is not actively displaying the activity tracking application.

FIGS. 84A-84C illustrate a set of example notification interfaces that may be displayed at various times during the evaluation period. The notifications may, in some arrangements, be displayed on top of a touch input lock screen. Accordingly, the user may still interact with the notification but may be restricted from interacting with any other aspects of the device interface until the input lock is deactivated. Such notifications may also be generated and displayed when the application is executing in a background (e.g., not displayed or executed in a foreground of the operating system). Thus, if the user is checking e-mail or listening to music through other applications, the activity point tracking notifications may still be displayed even when the activity point tracking application is not in the foreground or being actively displayed.

FIGS. 84D-84F illustrate another set of example notification interfaces that may be provided to the user upon detecting various triggering events. The notifications shown in FIGS. 84D-84F may be provided in a drop down menu, where an initial notification indicator is displayed in a header margin of the interface. The activity tracking notifications may be displayed along with notifications from other applications or may be displayed separately from other notifications. The notification system may be provided by the underlying operating system and invoked by the activity tracking application (e.g., running in the background).

Figure 85B:
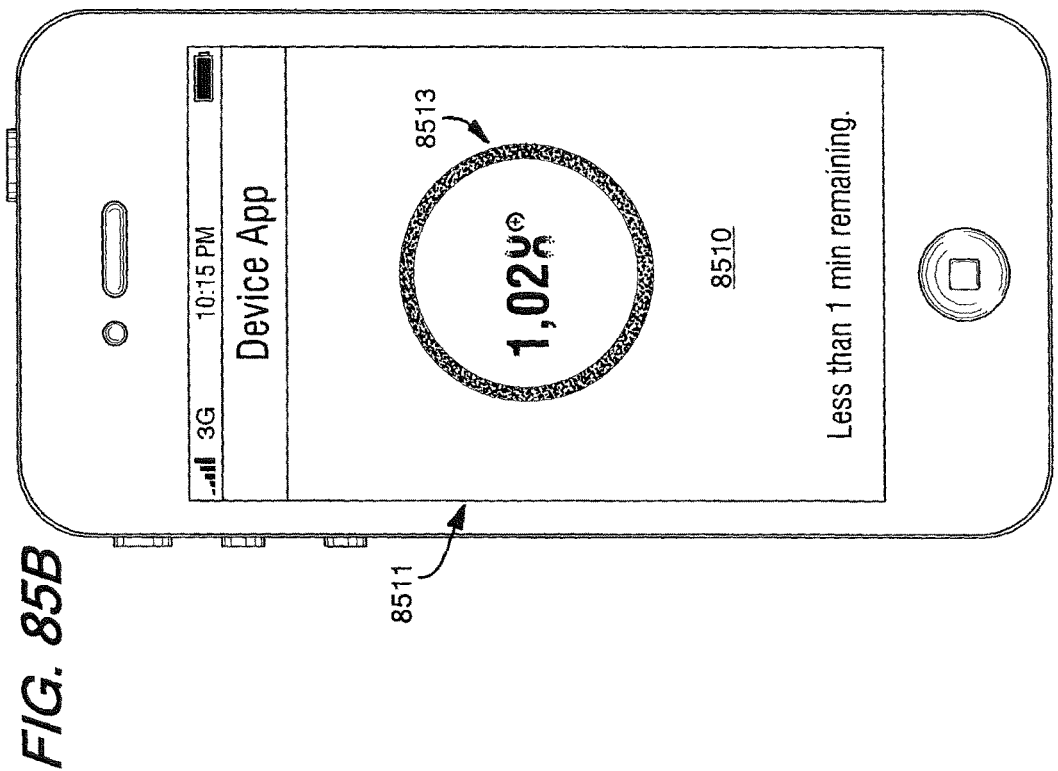
FIGS. 85A, 85B, 86, 87A and 87B illustrate example interfaces and information displays that may be provided upon the user completing an initial evaluation period.
Figure 85A:
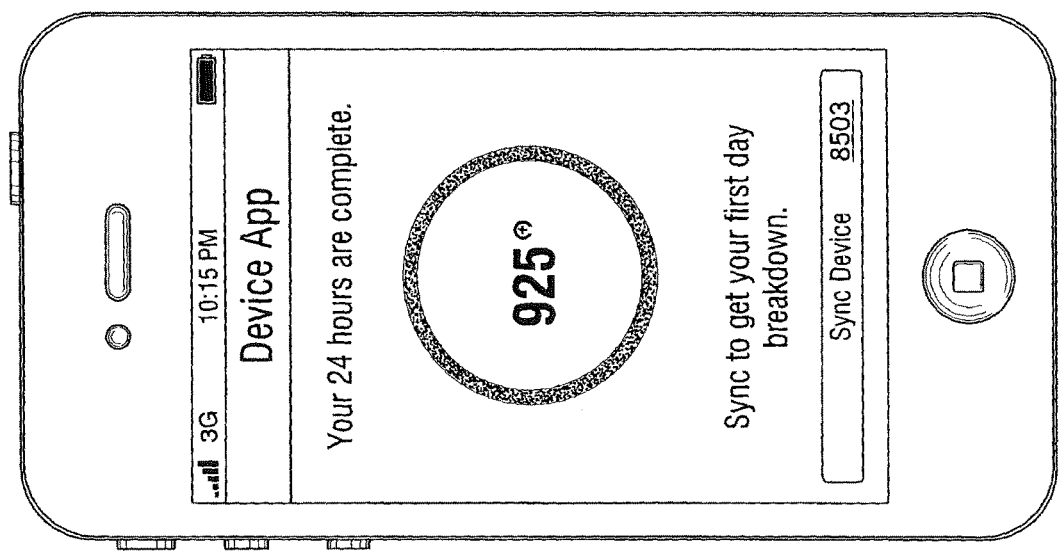

Upon completion of the evaluation period, the application may display a completion message as shown in FIG. 85A. In addition to amount of activity point accumulated during the evaluation period, the application may further display an option to synchronize the activity data from the wearable activity tracking device. In some instances, the activity point amount tracked in the application may be up to date as of the most recent synchronization. Accordingly, the activity data may be up to date if the data is continuously synchronized or synchronized in real-time. In some instances, the activity point amount displayed might not be accurate depending on when the most recent update or synchronization was performed. Accordingly, upon selecting the synchronization option 8503, additional or different data may be received from the wearable device.

The synchronization process may include a synchronization interface 8510 configured to display a progress bar 8511 as shown in FIG. 85B along with a running total of the activity points as the synchronization progresses. For example, the number of activity points display may be animated (e.g., counting up) as additional activity point data is received from the wearable device. The synchronization interface 8510 may further indicate an amount of time remaining in the synchronization process (e.g., via progress bar 8513).

Once the evaluation period has been completed and the evaluation period activity data has been synchronized with the application and mobile device, the application may provide more detailed information regarding the user's activity during the evaluation period. For example, the user's activity may be displayed with more granularity and with additional analysis.

Figure 86:
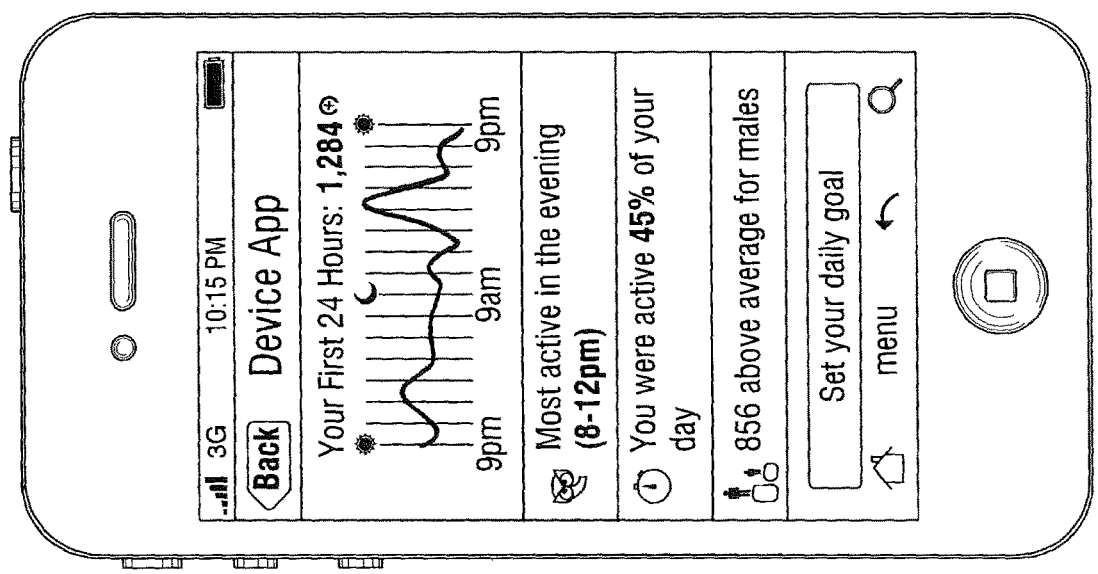

FIG. 86 illustrates an example interface providing a summary of the activity performed during the evaluation time period. For example, the application may determine and identify a period of highest activity as well as a percentage of the time period during which the user was active. The summary may further compare the user's performance with an average for other users. In some arrangements, the average may be an average for users of a particular type. For example, the average may be the average for all males, for all users ages 18-25, for all users living in a particular state, zip code, region, etc., for all users using a particular activity tracking device, for all users of a particular height or weight and/or combinations thereof.

Figure 87B:
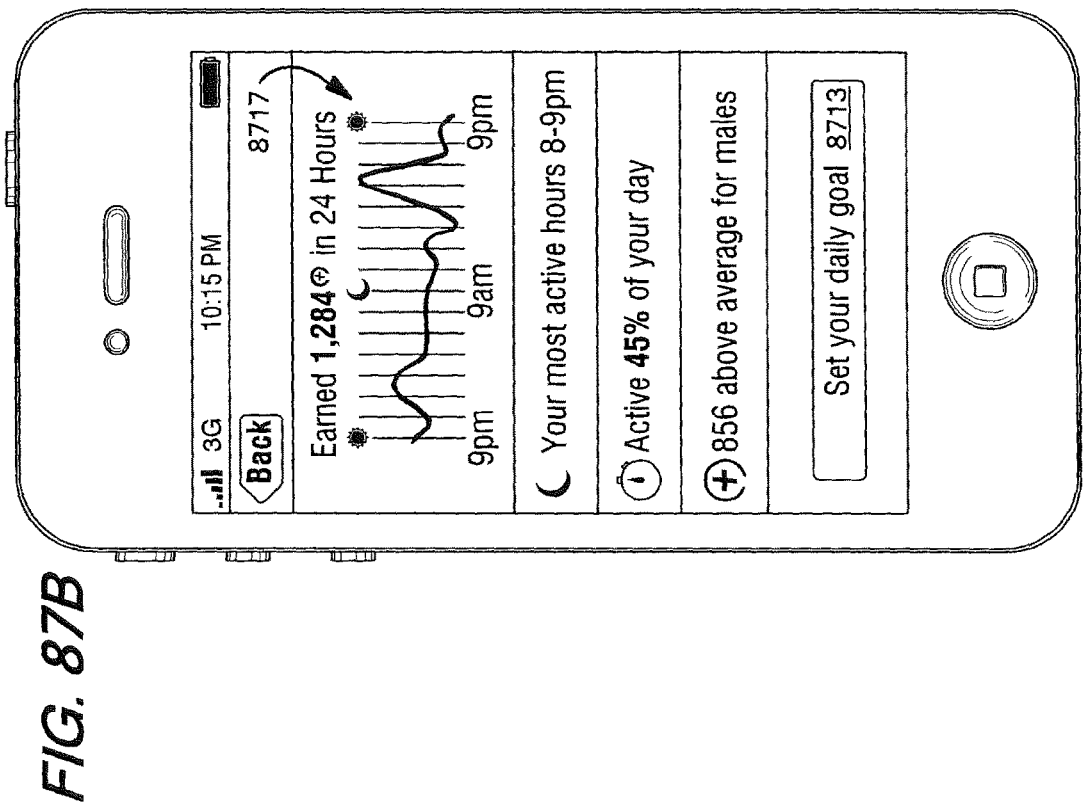
Figure 87A:
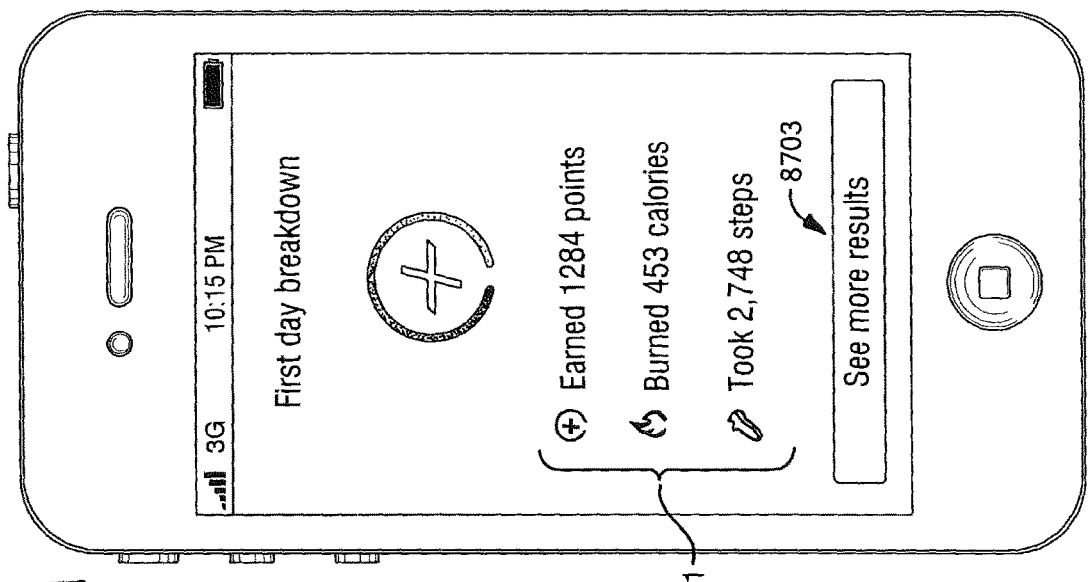

FIGS. 87A and 87B illustrate other example information displays for viewing and analyzing evaluation period activity data. In FIG. 87A, a summary 8701 of the amount of activity points, a number of calories burned and the number of steps taken may be conveyed. Other metrics may also be included as needed or desired and may be configurable by the user, by an activity tracking service or another entity. The display of FIG. 87A may further include an option 8703 to display additional information or details regarding activity performed during the evaluation period.

Upon selection of the additional information option, a more detailed view of the evaluation period activity may be displayed as illustrated in FIG. 87B. For example, a graph 8711 of the user's activity level over time may be displayed to help the user identify particular times of high or low activity. Additionally, analytical information may be displayed including a most active hour, a percentage of the day (or other evaluation time period) that the user was active and a comparison of the user's activity points versus an average user's activity points during the same time period. Being active may be defined as any amount of movement detected and recorded by the wearable device. In other examples, activity or being active may be defined based on a threshold level of movement or activity detected. For example, if activity or movement is detected based on steps, the user may be required to perform at least 2 steps within 5 seconds for those 5 seconds to be registered as active time. In other examples, the movement detected by the wearable device may register as a signal having an amplitude or magnitude. In such cases, the wearable device might only record signals having at least a threshold amplitude or magnitude. Thus, a user might only be considered to be active upon exhibiting movement of a threshold amplitude or magnitude.

From the detailed information display, the user may select a goal setting option 8713. The goal may correspond to a specified amount of time such as a day, an hour, a week, a month or the like. In some arrangements, the goal time period may correspond to the evaluation time period. For example, if the evaluation time period was 1 day, the goal time period may be defined as 1 day. Alternatively, the user may define his or her own goal time period.

Figure 88B:
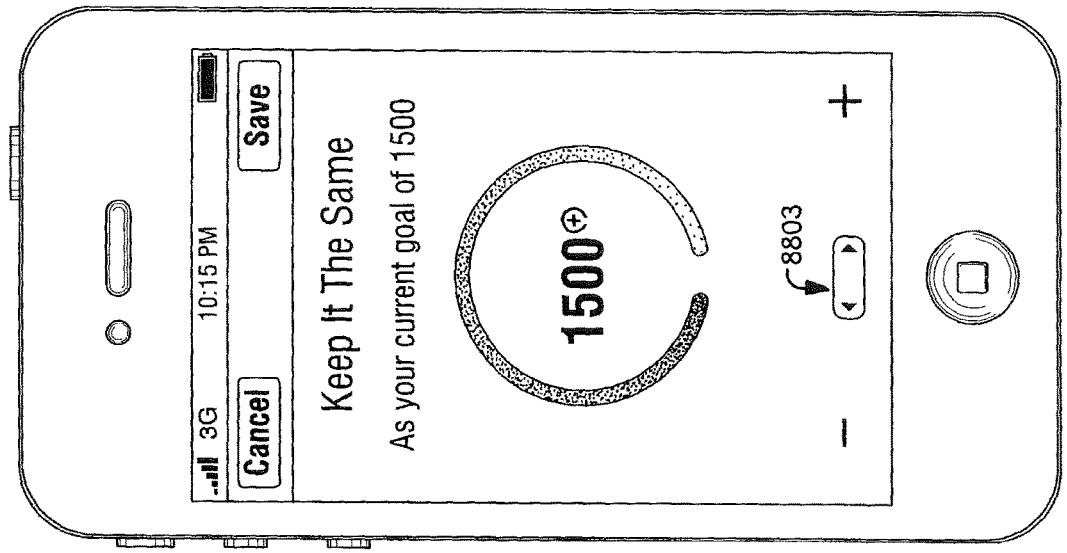
FIGS. 88A and 88B illustrate example interfaces for defining and/or setting an activity goal.
Figure 88A:
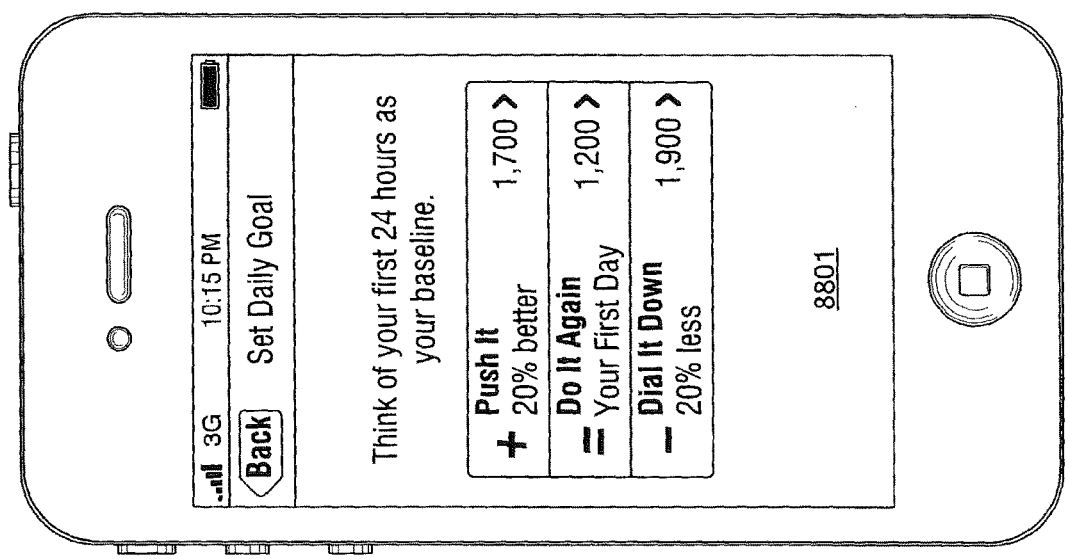

Upon selection of the goal setting option 8713 (FIG. 87B), the application may further display a goal setting menu 8801 as shown in FIG. 88A. In the goal setting menu 8801, the user may be provided with multiple predefined options for setting the goal. The predefined options may be generated based on the activity data recorded during the evaluation time period. For example, the options may include exceeding the activity recorded during the evaluation time period by a specified amount or percentage, setting the goal to be equal to the activity recorded during the evaluation time period, or setting the goal to be a specified amount or percentage less than the activity recorded during the evaluation time period. The goal may be defined by any of the metrics measured and recorded by the wearable device including activity points, calories burned, steps performed and the like. In some arrangements, different goals may be specified for each of the different metrics. For example, a user may specify that he or she wishes to reach 1200 activity points and burn 700 calories. In another example, a user may set goals to achieve 1500 activity points and perform 15000 steps.

After the user has selected one of the predefined goals, the user may have the option to fine tune the goal. FIG. 88B illustrates an example goal tuning interface that may be displayed upon a user selecting a goal from the goal menu 8801 (FIG. 88A). In FIG. 88B, the user may slider bar 8803 to adjust the predefined goal. The slider bar 8803 might only allow the user to decrease or increase the predefined goal by a specified amount or percentage. In other arrangements, the user's ability to decrease or increase the predefined goal may be unrestricted. Once finalized, the user may then save the goal by selection option 8805. The goal may then be set for the goal time period. The goal time period may start immediately or may start at a future time (e.g., the next day, a time selected by the user, upon detecting a triggering event and the like). A triggering event may include a user selecting a button on the wearable device to start the goal time period, detection of sustained activity for greater than a specified amount of time (e.g., 5 minutes, 30 seconds, 1 minute, 1 hour, 30 minutes, 10 minutes, etc.), and the like and/or combinations thereof.

Activity may be tracked based on a specified goal or independently of a goal. In instances where activity is tracked based on a goal, the user may view his or her current progress in a variety of ways. As discussed herein, the activity tracking application may include a profile interface, an activity view interface and a home interface. Each of these interfaces may provide information relating to the user's current progress toward a goal and an amount of activity performed. The different interfaces may provide different levels of detail, different metrics, different activity data analyses, different types of additional information displayed with the current progress information and the like.

FIG. 142 illustrates a notification message that may be generated and provided to the user upon detection that a first full goal period has started. For example, if a goal period corresponds to a day (24 hours), the application may generate a notification message when the first full day (e.g., after application installation, device registration, etc.) has begun. The start of a day or a goal period may be defined by the user or set by default. In one example, the start of a day or 24 hour period may be defined as 8 AM or in other instances, may be defined as midnight. Accordingly, upon reaching the start time, the user may be notified. In some examples, the interface of FIG. 142 may be provided when an evaluation period is not used or required. Thus, instead of initiating an evaluation period, the user may begin a goal tracking session once the user has downloaded the application and completed any required setup.

Figure 89B:
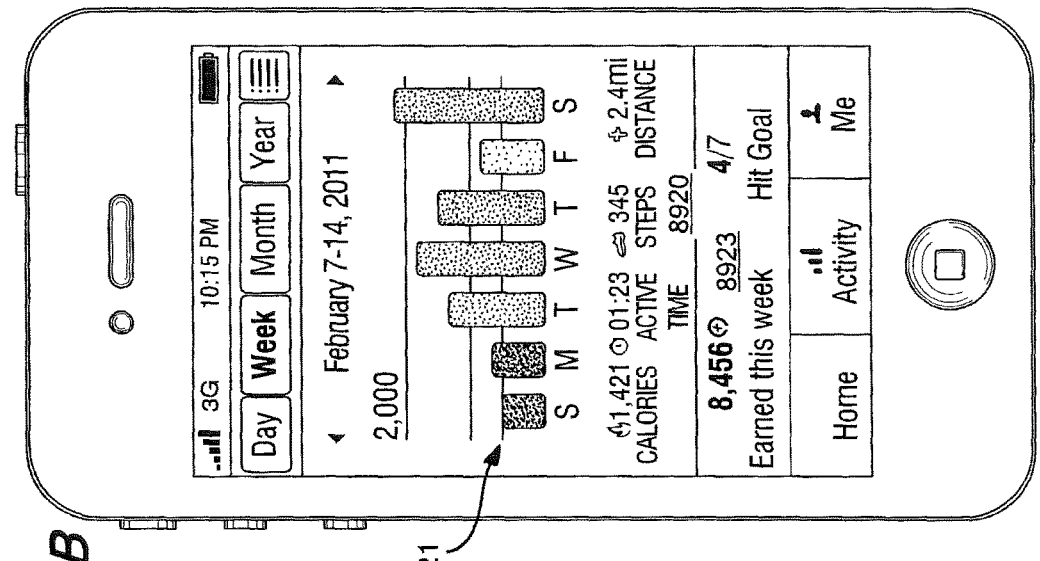
FIGS. 89A-89D illustrate example interfaces for viewing current goal information and activity summaries.
Figure 89A:
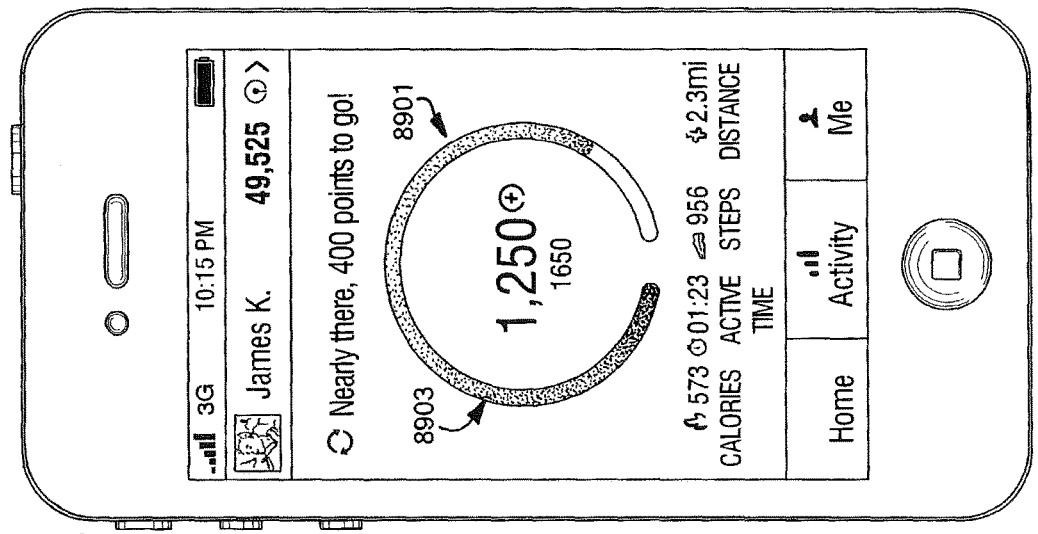

FIG. 89A illustrates an example home interface in which an accumulated (e.g., earned or detected) amount of activity points is tracked in relation to a goal. In a particular example, the goal may be a daily activity point goal. The goal may be visualized as a shape or object 8901 having a transparent or semi-transparent appearance. As the user accumulates activity points, the shape or object 8901 may begin to change appearance. For example, one or more portions of the shape may be modified to display colors. In some instances, the portions of the object that are modified may correspond to a progress bar or indicator such as indicator 8903. The amount of the shape that is modified may correspond to an amount or percentage of the goal that has been completed. Accordingly, if the user has completed 25% of the goal, the goal shape may be 25% colored in and 75% transparent. Other visual effects or visual indicators may be used to differentiate between an amount of a goal still to be achieved and an amount of the goal already completed.

The visual indication of the goal amount completed such as progress bar/indicator 8903 may also include patterns, colors or other visual effects that represent a distance from the goal. For example, red may represent minimal progress towards the goal (e.g., 0-10% progress), while yellow may represent moderate progress (e.g., 40-60% progress). Green may represent significant progress (e.g., 80%+ progress). Other colors may be used to represent the other progress levels (e.g., percentages). In the examples illustrated in FIG. 89A, the goal progress spectrum may be represented by a color spectrum (e.g., range of colors from red to green). In some arrangements, the progress bar may be displayed in a single color, where the color may depend on the amount of the goal achieved (e.g., green when the user has achieved at least 75% of the goal, red if the user has achieved less than 15% of the goal, etc.). In other arrangements, as in FIG. 89A, the progress bar or indicator 8903 may be displayed in multiple colors, where each of the colors represents a level of progress associated to a corresponding section of the shape 8901 and progress indicator 8903.

Additionally, various other metrics and progress information may be displayed in the interface including calories burned, amount of time the individual has been active, a number of steps taken and/or a distance traveled. The application may also provide various messages to the user including motivational messages, instructional messages (to improve activity level), information messages (e.g., a number of activity points needed to complete the goal), trivia information and the like. The metrics may be determined (e.g., calculated) by the application or device on which the application is executing and/or by the wearable activity monitoring device. Similarly, messages may be generated or selected by the application or by the wearable activity monitoring device.

FIG. 89B illustrates an example activity interface that may display other and/or additional types of activity information. Instead of or in additional to display goal information, interface 8920 may display activity summary information that reports user activity for a day, a week, a month, a year, and/or other predefined or customized time periods. In the summary interface 8920, the user's activity may be divided into predefined time periods such as days, hours, weeks, months, years, etc. In one example, the predefined time periods may depend on the view that is selected. In a particular example, if a day view is selected, the user's activity may be divided into hours while if the week view is selected (as shown in interface 8920), the user's activity may be broken down by day.

The user's activity level may be visualized in a variety of manners including using graphs such as bar graph 8921. Each day of the week may be represented by an activity bar in graph 8921 and each bar may be color-coded to represent a level of goal completion. For example, if a user completed a daily goal on one or more days, the bars corresponding to those one or more days may be displayed in a first color such as green. However, if a user failed to reach a first threshold amount of the goal (e.g., 25%), the corresponding bar may be displayed in another color such as red. If a user reached the first threshold but failed to reach a second threshold, the corresponding bar may be displayed in yet another color such as yellow. Any number of thresholds may be defined and any number of colors may be used. In a particular example, thresholds for exceeding the goal may also be defined and may be represented by a color or pattern or visual effect. For example, if a user exceeds a goal by a specified amount (e.g., 10%), the activity bar may be displayed with flames or in black. If the user exceeds the goal by an even greater amount (e.g., 25%), the activity bar may be displayed as an ice block, for instance. Other visual, textual or image-based indicators may be used to indicate a level of completion of a corresponding goal, including icons, animations, patterns, levels of transparency and the like and/or combinations thereof.

Summary section 8923 may further display a total amount of activity points earned by the user for the time period displayed (e.g., a week). Additionally, the interface 8920 may indicate a number of goals that were reached. In the illustrated example, the user completed 4 of 7 daily goals. Interface 8920 may further provide a user with the ability to select one or more of the activity bars to view more detailed information about that day including a number of activity points earned on that day, the goal set for the day and the like. Additionally or alternatively, interface 8920 may also display various metrics for the time period displayed.

Figure 89C:
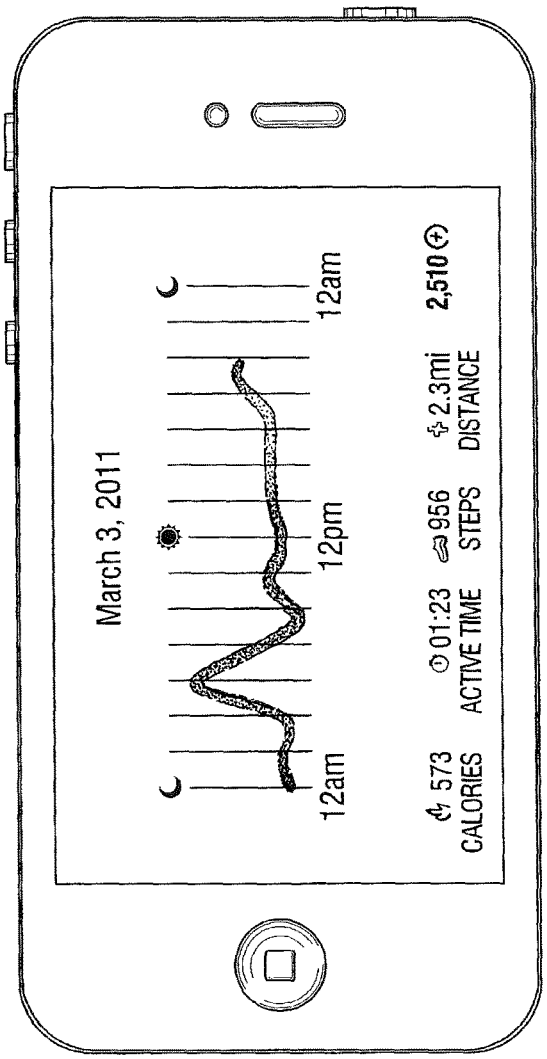

FIG. 89C illustrates another example interface in which activity point information may be displayed. In particular, interface 8930 may include a display of a user's profile including a total amount of activity accumulated (e.g., for all time), averages, a number of activity timer periods (e.g., days, weeks, months, hours, etc.) as well as indications of recent activity and records as described herein. The user may select any of these information items to view additional details. For example, selecting the best day record may display a graph of the user's activity level on that day on an hourly basis. The details may further include a goal that was defined for the day and statistics or metrics (e.g., calories burned, distance moved, steps taken, average pace, etc.) of the activity performed on that day.

Figure 89D:
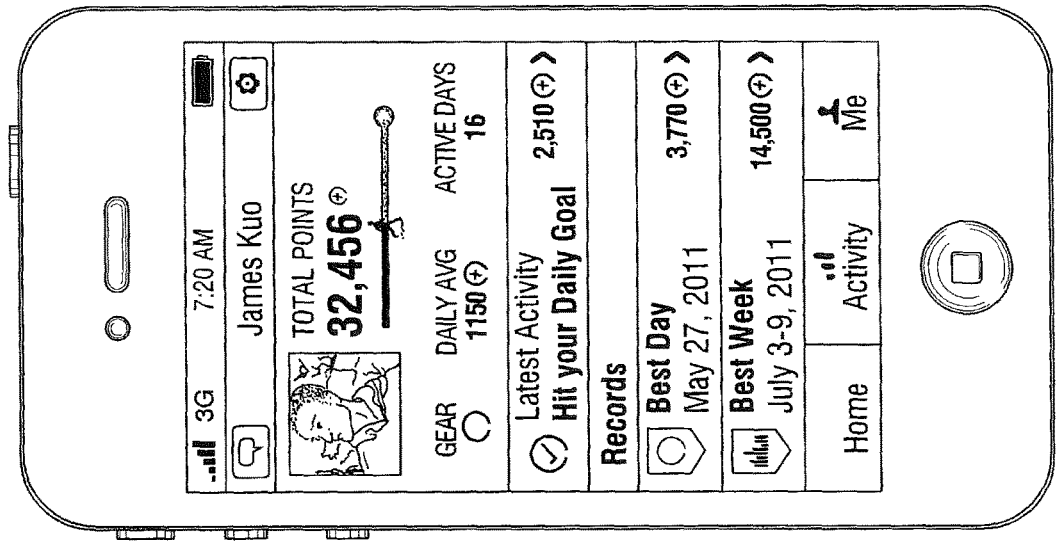

According to one or more aspects, the activity tracking visualization and interface may automatically change depending on an orientation of the displaying device. For example, if the displaying device is held in a profile orientation, the interface may appear as shown in FIG. 89A. However, in some instances, if the displaying device is switched to a landscape orientation, the interface may change to appear as shown in FIG. 89D. In FIG. 89D, the interface may provide a graph of activity earned over a specified unit of time such as per hour, per minute, per second, etc. Accordingly, the landscape view may provide a further level of detail regarding the activity point accumulation of the day or other activity tracking time period. The type of data or interface that is generated and displayed may depend on the dimensions of the display including width and height in the current orientation. For example, a graph that is of a particular width might not be selected or displayed when the display is in an orientation having a width less than the width of the graph. Additionally or alternatively, the view shown in FIG. 89D may be selectable in profile orientation as well. For example, the user may select an option to view the hourly or minute-by-minute breakdown of the activity points earned regardless of the orientation of the display or display device.

As described herein, a user may define a goal to which the user's activity is compared. Once a goal is set, in some arrangements, the user may modify the goal or set another goal for the same time period or another time period (e.g., the next day, a next week, the weekend, etc.). For example, during the course of a day or other time period, the user may realize that he or she is on track to exceed the currently set goal. Accordingly, the user may wish to modify the goal to a more challenging setting. In another example, if a user realizes that he or she is unlikely to complete a currently set goal, the user may modify the goal to be less challenging. The user may also be allowed to set additional goals without having to wait for a current goal or goal time period to expire. For example, while resting during a first day of activity, the user may set a goal for the next day or an upcoming week or the like.

Figure 90B:
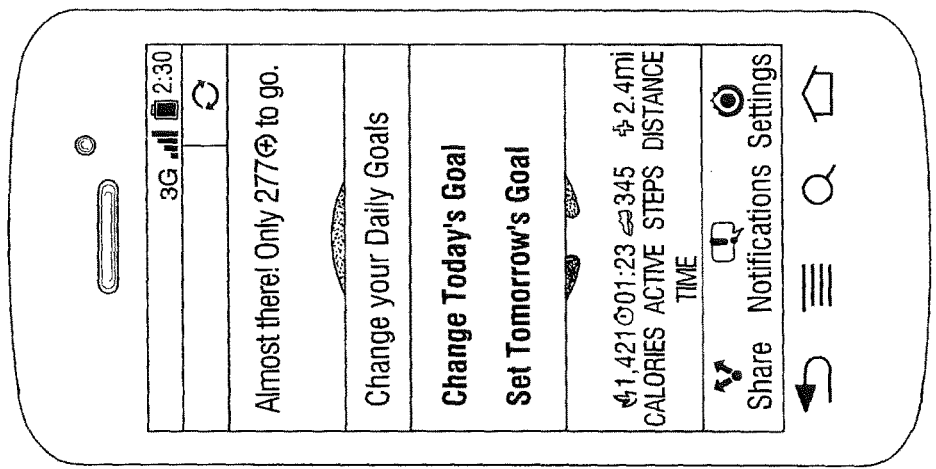
FIGS. 90A-90C, 91-93, and 94A-94D illustrate additional example goal setting interfaces.
Figure 90A:
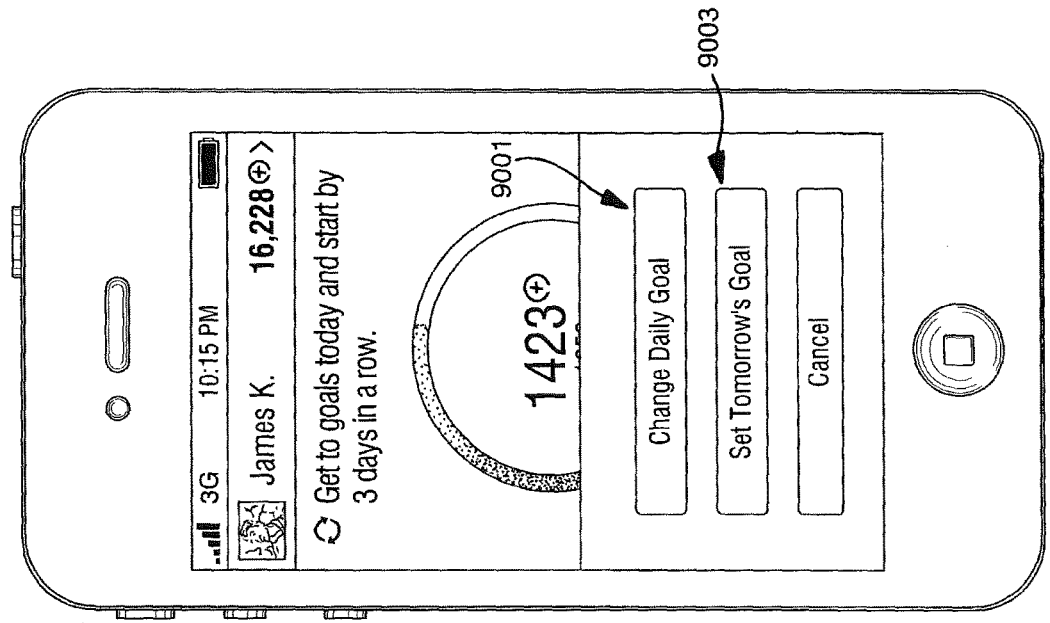

FIG. 90A illustrates an example interface by which a user may activate a goal modification or setting function. The user may activate goal option menu 9001 by selecting a displayed option and/or by interacting with the display device in a specified manner. For example, the user may be required to depress a button for a predefined amount of time to activate the goal option menu 9001. In another example, the user may activate the goal option menu 9001 by entering a gesture on a touch sensitive display device. The goal option menu 9001 may include an option for modifying a current goal or for setting a future goal. The device may automatically select a time period for the future goal based on a first time period for which a goal has not been defined. For example, if a goal has been defined for each of the next 2 days, the device and/or application may define the future goal option 9003 as being directed to the third day. In some arrangements, activity monitoring and tracking may be suspended while the goal modification menu 9001 is active. In other arrangements, activity monitoring and tracking may continue even while the goal modification menu 9001 is active.

Goals may also be modified to reflect different metrics. For example, if a current goal is defined based on activity points, a user may modify the goal to correspond to a number of calories burned or a number of steps taken. Additionally or alternatively, goal progress (e.g., detected or accumulated activity data) may be reset upon setting of a new current goal. In other arrangements, if a user switches metrics for a current goal, the existing goal progress may be converted into the new metric based on a specified conversion factor. In some configurations, activity may be detected and tracked (e.g., by the wearable device and/or by the mobile application device) using multiple metrics. Accordingly, the device may retrieve a different set of metrics if the metric for the goal is modified.

Goal modification and setting functionality on the mobile application, the activity tracking wearable device and/or an activity tracking service might only be made available to users who have completed an initial evaluation period. This requirement may allow the wearable device, the activity monitoring application and/or an activity monitoring site to better tailor goal suggestions, products, coaching tips, and the like to the user prior to the user embarking on a goal. Additionally or alternatively, the evaluation period may allow the wearable device to provide more accurate measurements and tracking by calibrating its sensors and algorithms for activity detection and measurement.

Upon selecting a goal modification or setting function, the user may be provided with an interface for defining a goal. In one example, the interface may appear similar to the goal setting/modification interface as shown in FIG. 88B. Other types of goal modification/setting interfaces, interactive elements, goal representations and the like may be used.

FIG. 90B illustrates another example of a goal setting menu that may be invoked when viewing a goal tracking interface.

Figure 90C:
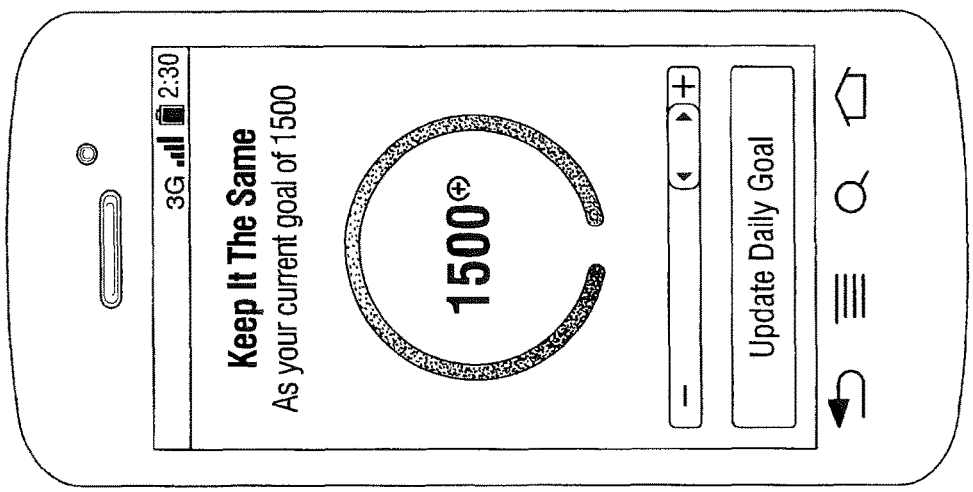

FIG. 90C illustrates another example goal modification interface that may include an update goal option button.

In some instances, the user may be restricted to a certain range of potential goals. For example, the goal setting/modification function might only allow a user to set a goal equal to or above a minimum threshold and below or equal to a maximum threshold. The thresholds may be defined as a percentage of a current goal, a percentage of a baseline activity level (e.g., as determined during an evaluation period), an absolute amount, a percentage of a maximum activity level (e.g., a maximum amount of activity points ever earned or recorded) and the like.

Figure 91:
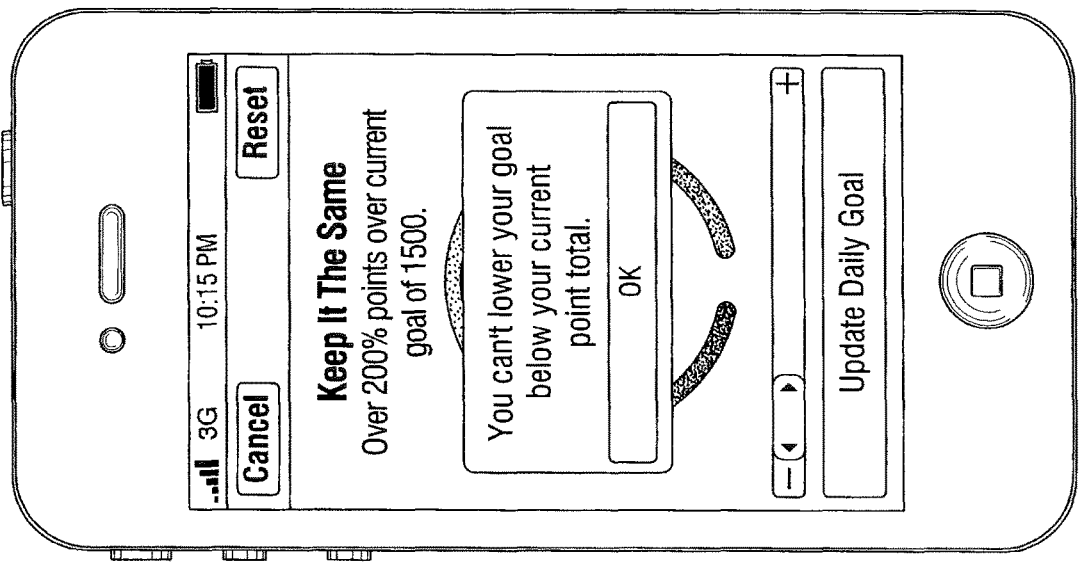

FIG. 91 illustrates an example notification that may be displayed to the user upon the user attempting to set a goal below the minimum threshold.

Figure 92:
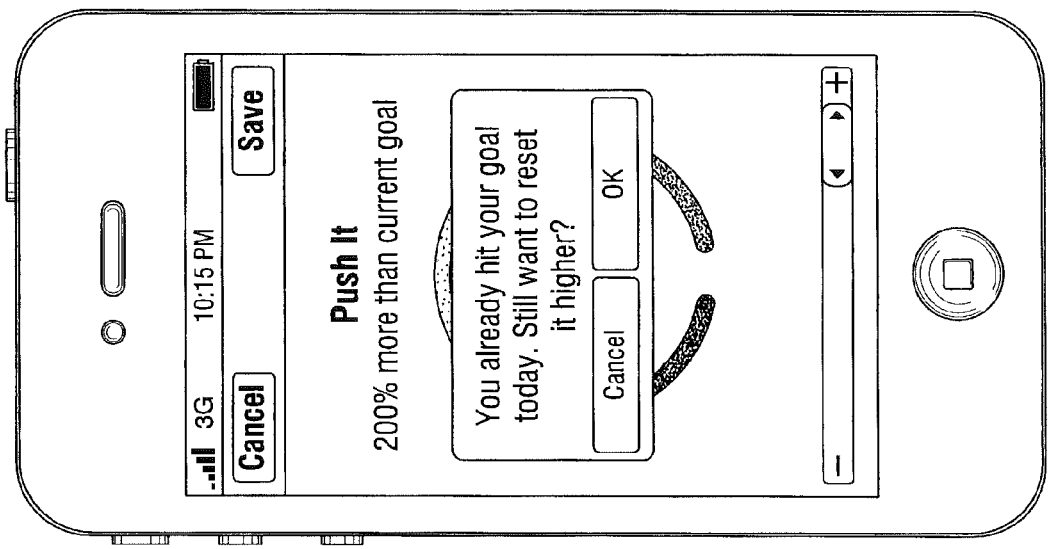

FIG. 92 illustrates an example notification that may be displayed to the user in response to the user attempting to set a goal above a maximum threshold. In some instances, the notifications of FIGS. 91 and 92 may be displayed upon the goal being set to the minimum or maximum threshold, respectively.

Goals may further be modified even after the user has completed a currently set goal. The goal increase may be manually triggered (e.g., by user selection) or may be automatically suggested or recommended to the user by the mobile application upon the user reaching the currently set goal. Allowing the user to increase a current goal (even upon completion) may allow the user to further challenge himself or herself, rather than permitting the user to register little to no activity after completing a goal. In one example, modifying the currently completed goal may be limited to increases to the goal and may be restricted to a certain percentage (e.g., of the current goal or a baseline activity level) or an absolute amount. In other arrangements, goal setting/modification may be unrestricted.

Figure 93:
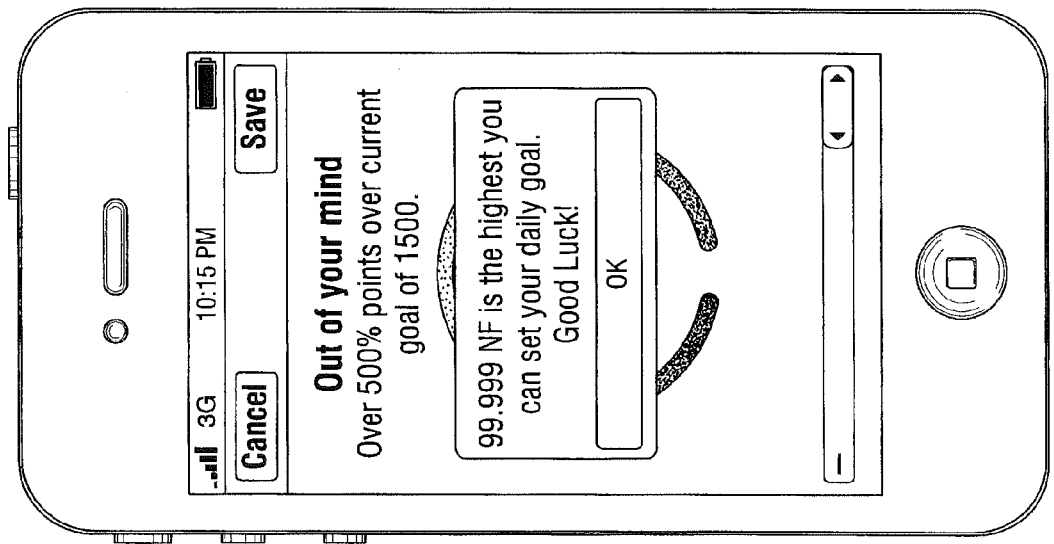

FIG. 93 illustrates an example prompt or notification that may be provided to invite the user to further challenge themselves by increasing his or her completed goal. The prompt shown in FIG. 93 may also be provided to confirm the user's increase in the completed goal after the user has selected a desired revised goal.

Figure 94B:
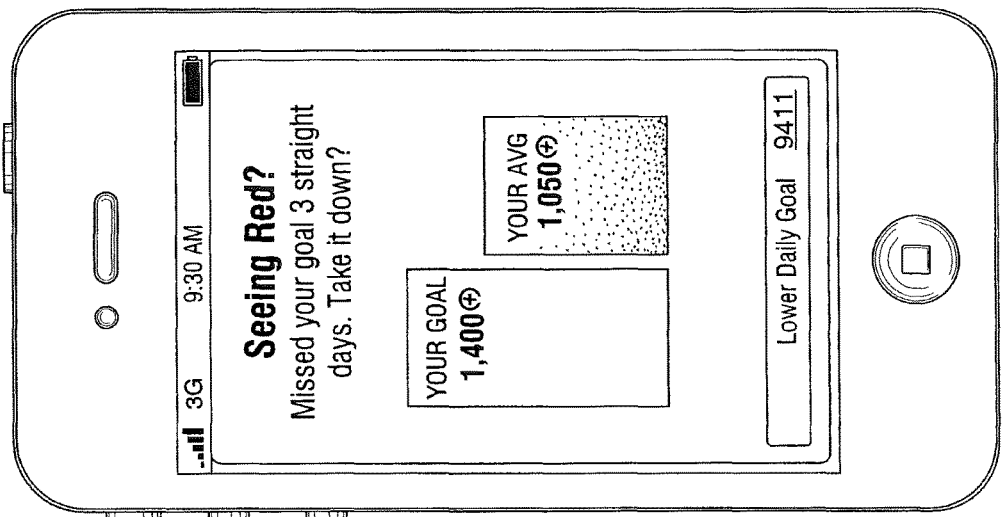
Figure 94A:
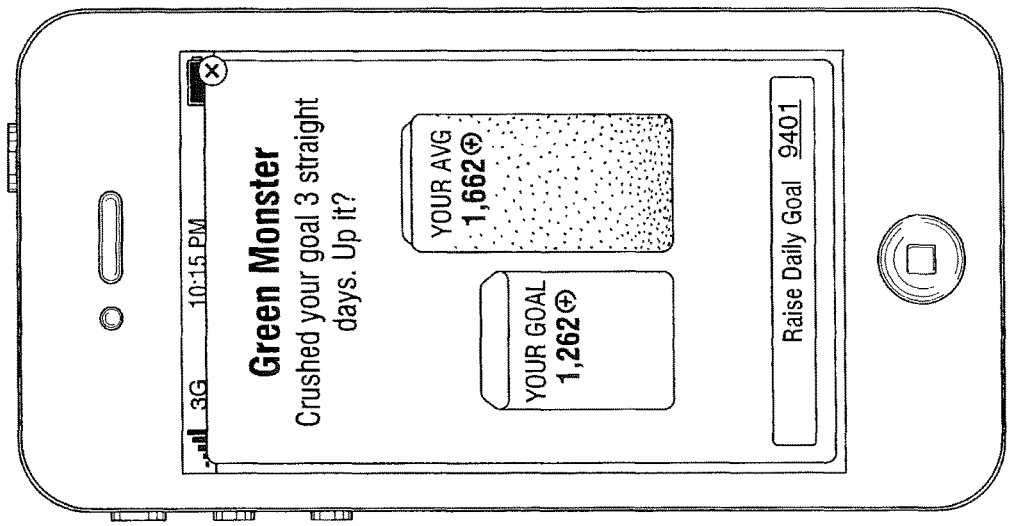

FIGS. 94A and 94B illustrate additional examples interfaces and functions through which a user may modify goals. In some instances, goal modification options may be generated and provided to the user in the mobile application upon reviewing a user's performance over a period of time. For example, in FIG. 94A, an average of the user's last 3 days of activity may be compared to an average goal set for those 3 days. If the user's average actual activity over that time period was above the average goal set or above the average goal by a specified amount, the application may suggest or provide an option 9401 for raising the user's daily goal. Option 9401 might only be provided under certain conditions. For example, option 9401 may be triggered for the user upon determining that the user met the goal for each of the last X goal time periods, that the user exceeded the average goal set by a specified amount (e.g., 10%, 20%, 25%, 50%, etc.), that the user met at least one of the goals over the last X goal time periods, that the average amount by which the user exceeded each of the goals met or exceeded a specified threshold and the like and/or combinations thereof.

On the other hand, if the user may be prompted or provided with an option 9411 to lower his or her goals, as shown in FIG. 94B, if the user's average activity level of the past X goal time periods was below the average goal level or was below the average goal level by a specified amount. As with option 9401 (FIG. 94A), various rules (including ones similar to those described above) may be defined for determining when option 9411 is to be generated by the application and offered to the user.

Figure 94D:
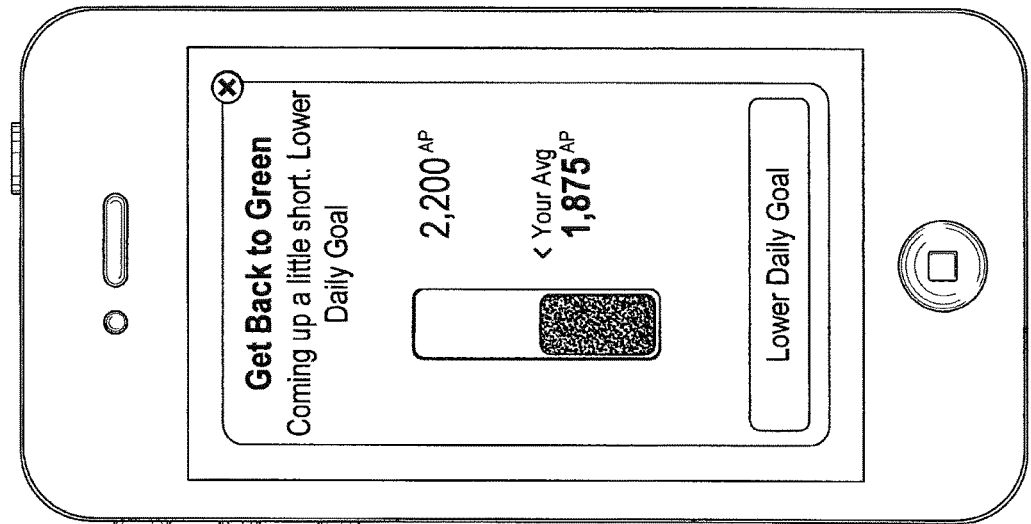
Figure 94C:
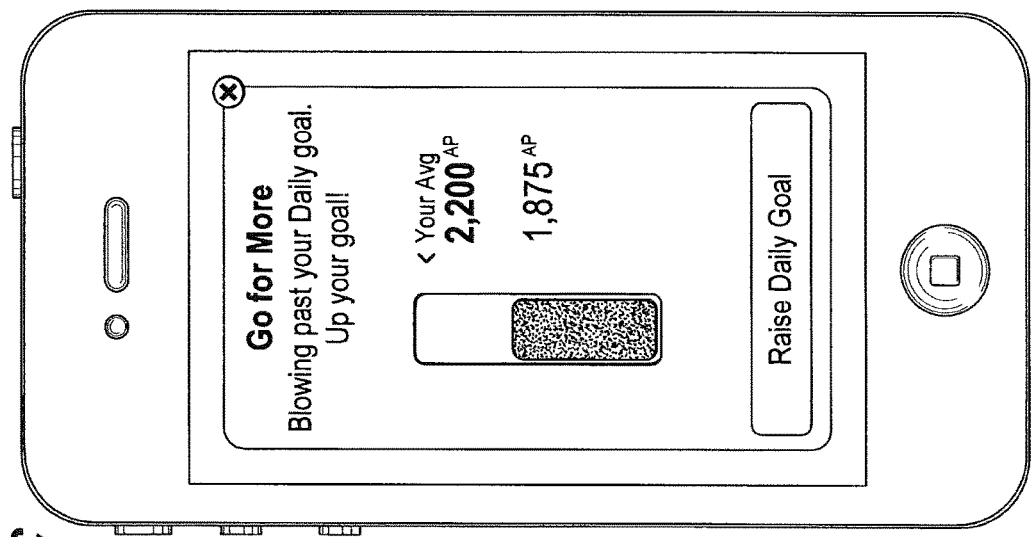

FIGS. 94C and 94D illustrate other example interfaces for modifying or setting a daily goal while viewing a user's average performance versus a set goal.

A user may further review his or her performance during a goal time period in a variety of ways and the information collected during the goal time period may be conveyed to provide additional context. FIGS. 95A-95C, 96A-96C and 97A-97C illustrate various animations for displaying an amount of activity accumulated over a goal time period. For example, in FIGS. 95A-95C, the modification in appearance of a goal object may be animated in nature to increase the user's anticipation as to the final activity total and to provide the user with an increased sense of accomplishment. The animation or activity summary for the goal time period may be conveyed to the user at various times including upon completion of the goal time period, during synchronization of activity data from an activity tracking device, upon the user selecting an option to review his or her activity level for a particular goal time period, in response to the user completing a goal (e.g., the animation or review might not be displayed if the user does not complete the goal for the goal time period), in response to the user reaching a milestone or achievement other than the goal itself.

Figure 95A:
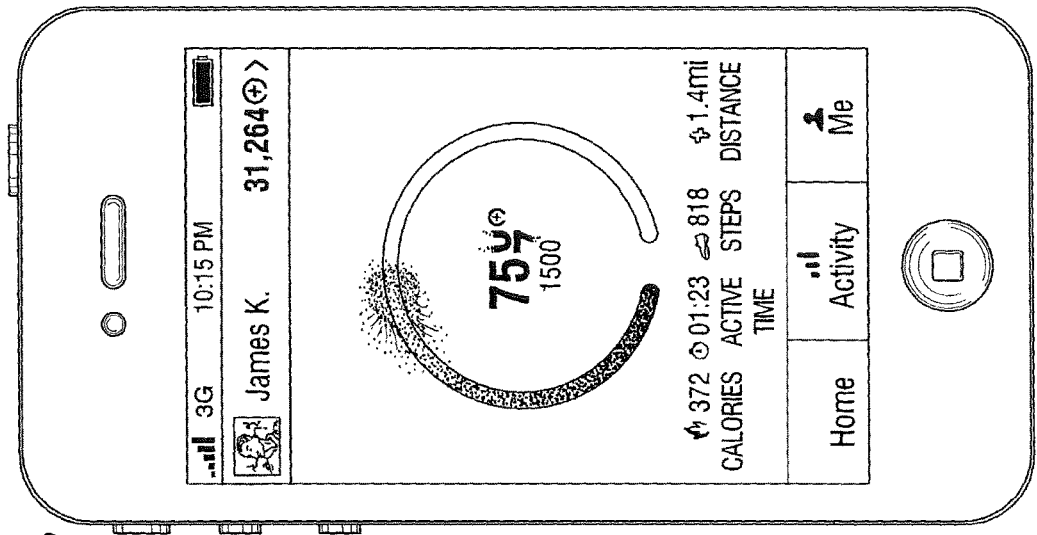
FIGS. 95A-95C, 96A-96C, 97A-97C illustrate example progress tracking interfaces including a progress bar.
Figure 95B:
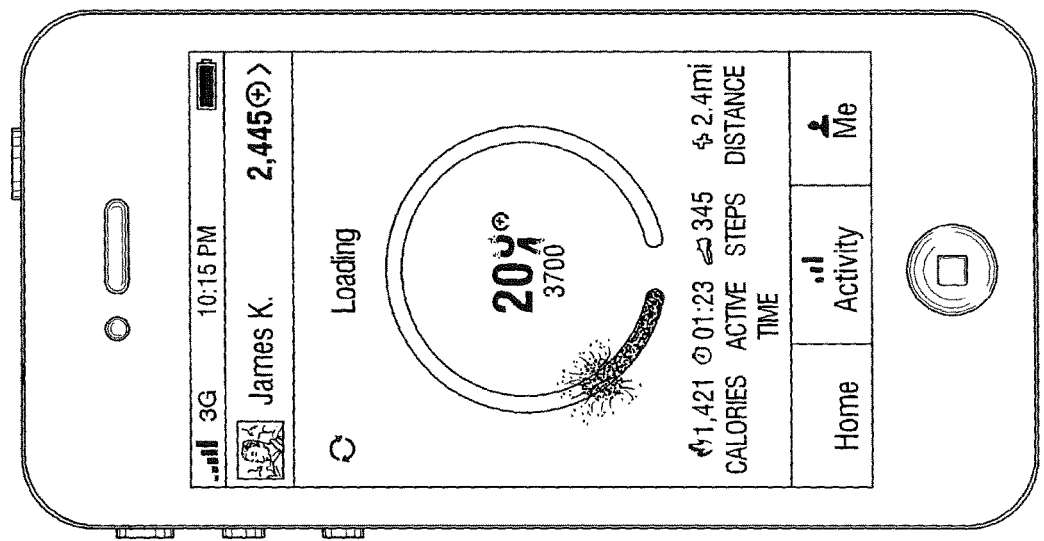
Figure 95C:
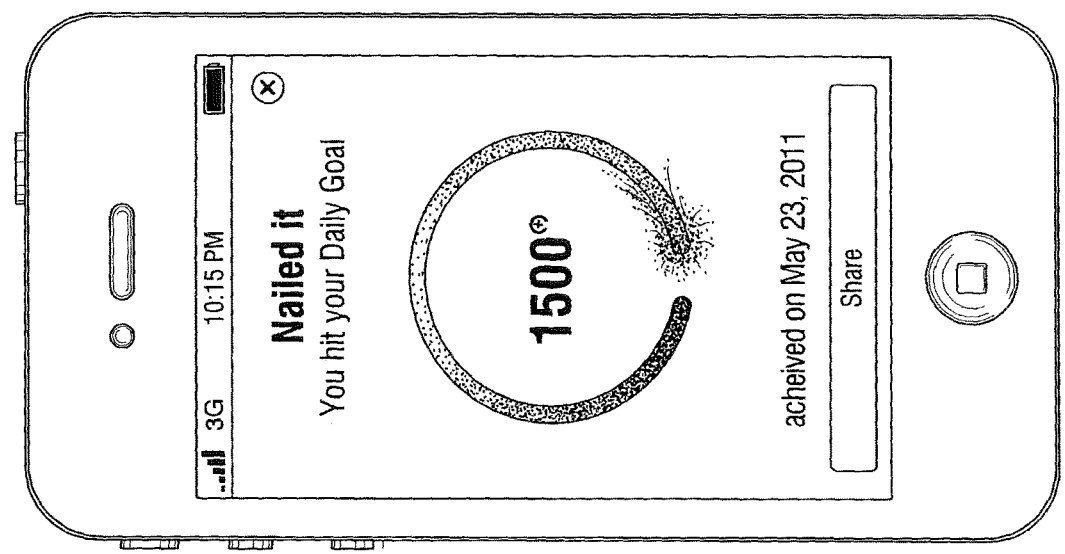

FIG. 95C illustrates an interface in which the activity review for the goal time period (or an animation thereof) is complete. The interface may display a message indicating whether the goal was met, not met, exceeded, and/or an amount by which the goal was exceeded. The interface may also include an option to share the activity recorded for that time period, as will be described in additional detail herein.

Figure 96B:
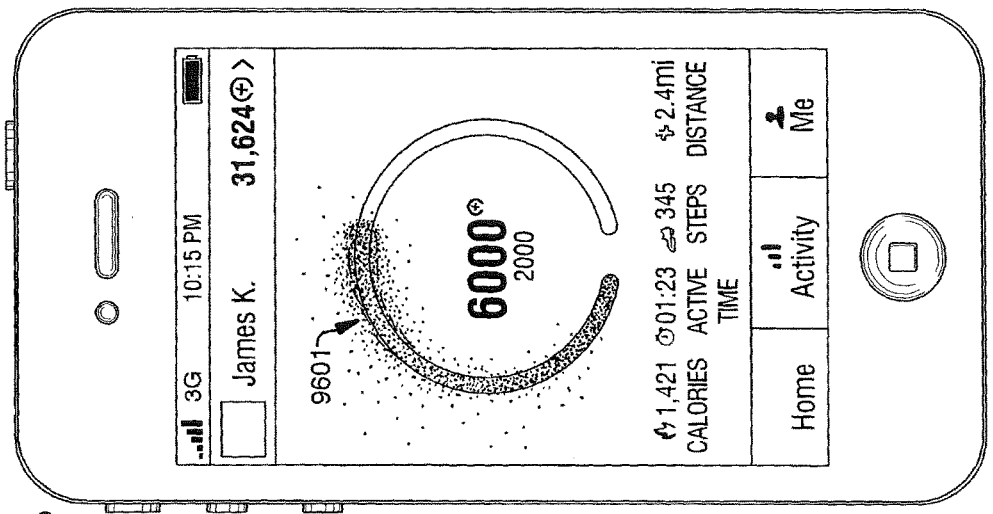
Figure 96A:
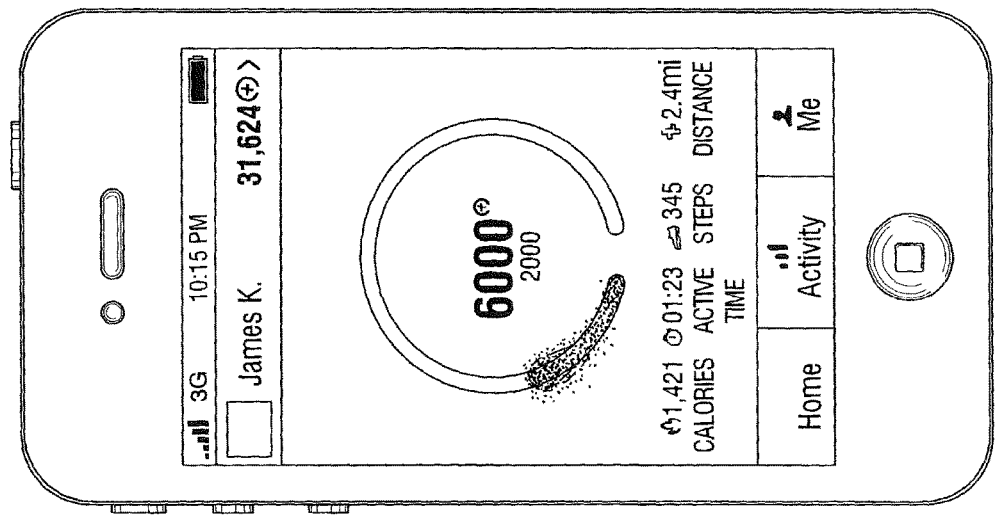
Figure 96C:
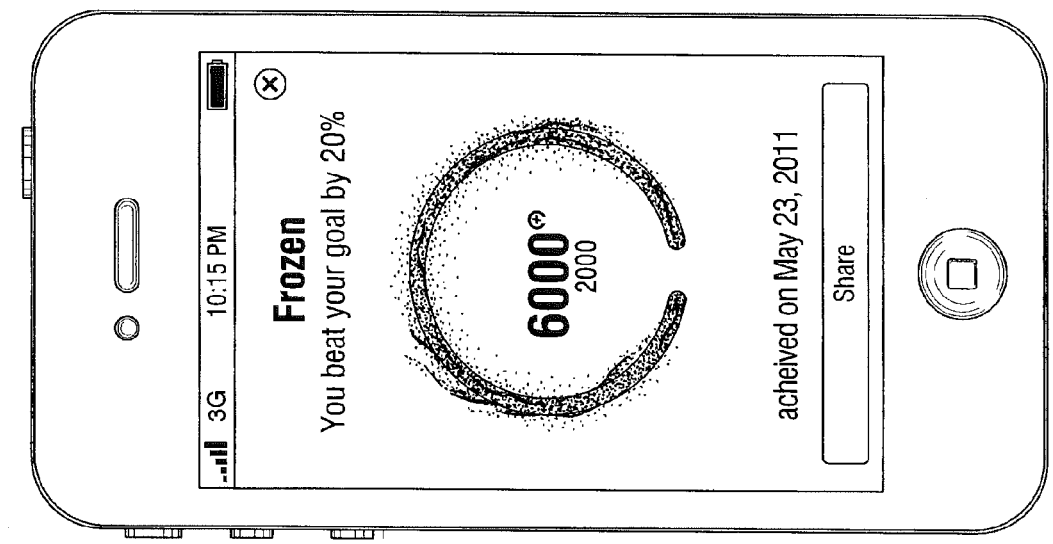

FIGS. 96A-96C and 97A-97C illustrate other example animations and activity review interfaces that may be displayed in various situations. For instance, the animation of the progress bar and/or the appearance of the progress bar may differ if the user exceeded the goal by various amounts, if the user did not meet the goal and/or if the user met the goal, but did not exceed the goal by specified amounts. In FIGS. 96A-96C, for example, the progress bar 9601 may be displayed with an icy appearance to represent that the user exceeded the goal for the time period by 20%. Other attributes of the animation may also differ including a rate at which the progress bar 9601 grows, background colors, patterns, animations or schemes, additional animations ancillary to the growing of the progress bar 9601 (e.g., ice chips or pieces falling away from the progress bar 9601) and the like.

Figure 97B:
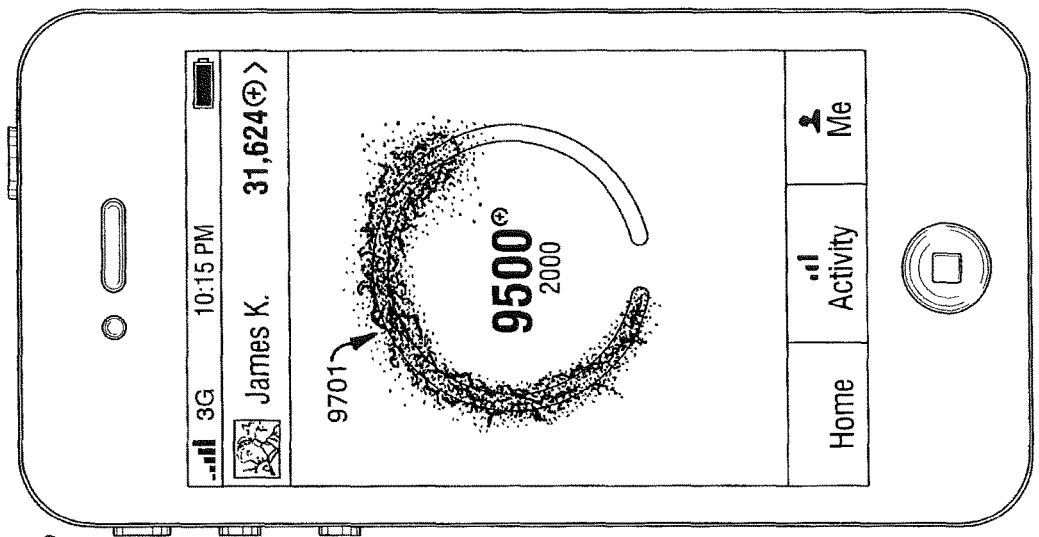
Figure 97A:
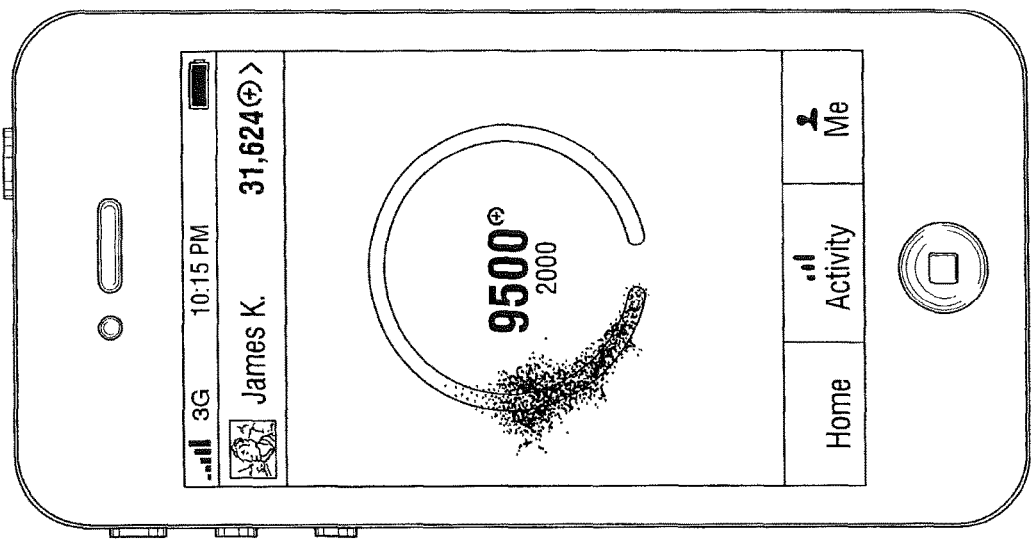
Figure 97C:
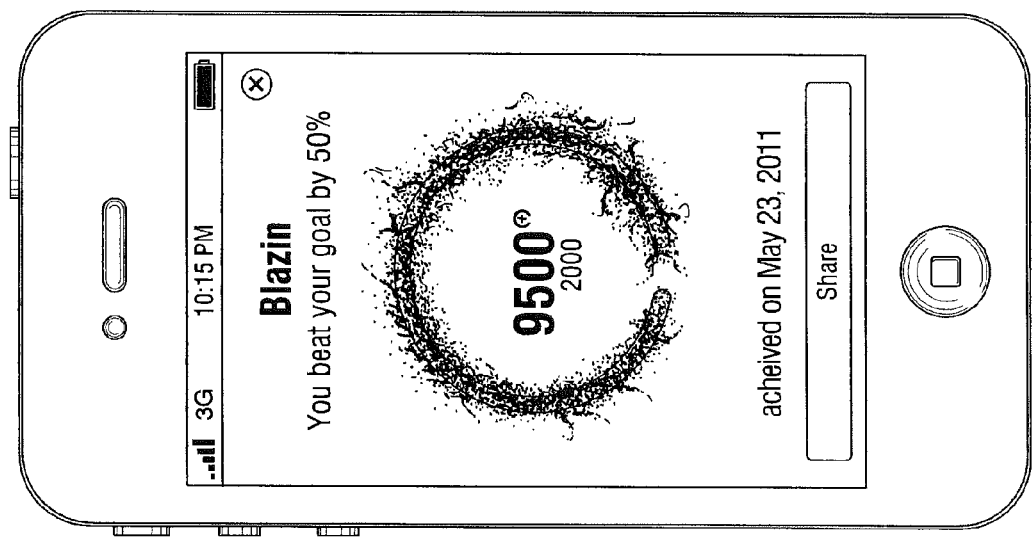

In FIGS. 97A-97C, the progress bar 9701 may be displayed with a fiery appearance upon determining that the goal for that time period was exceeded by 50%.

While the activity tracking application is configured to track individual goal time periods and completion (or non-completion) of goals for those individual time periods, the activity tracking application may further provide feedback and review information relating to multiple goal time periods. In one example, the activity tracking application may track and monitor activity streaks. Streaks may include the completion of multiple goals corresponding to multiple consecutive goal time periods. Streaks might only be recognized when the user has completed goals for X number of consecutive goal time periods, where X may be any number greater than 1 (e.g., greater than or equal to 2). The tracking and recognition of streaks may provide a further motivating factor for the user to maintaining and/or elevating his or her activity level and to meet all goals. Streaks also encourage consistency which may lead to the adoption of a healthier or more active lifestyle. The user may be awarded with rewards or types of recognition including coupons, free products, virtual items including virtual apparel, icons, images etc., services, event tickets and the like. In some examples, a reward may include unlocking a new color or image to be used on a activity tracking device or in the mobile application. Additionally or alternatively, when a user has achieved a streak, an indication of the streak and/or reward may be transmitted to a wearable device through which activity is being tracked.

Figure 98B:
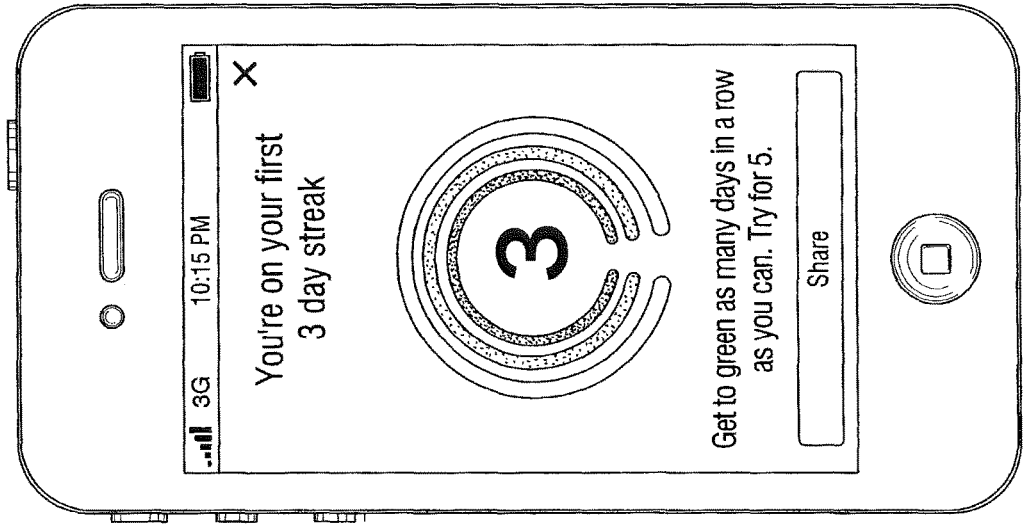
FIGS. 98A-98C and 99 illustrate example streak tracking interfaces.
Figure 98A:
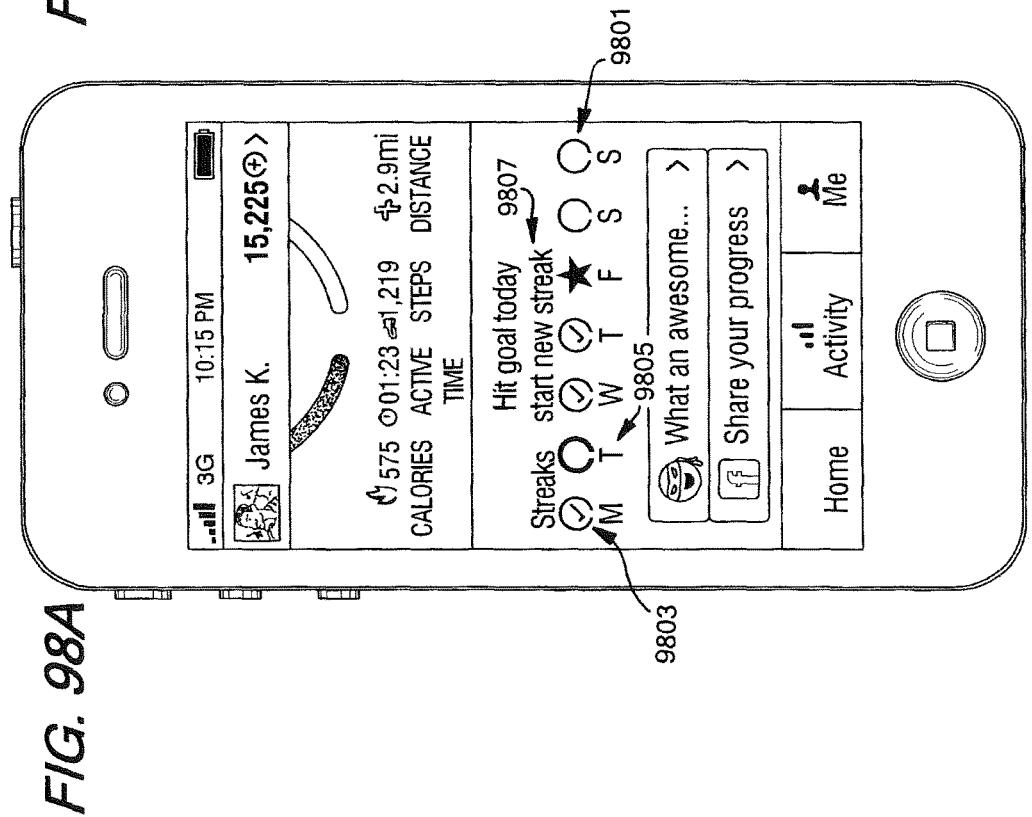

FIG. 98A illustrates an example activity tracking interface portion in which a goal completion status for each of a number of goal time periods 9801 is displayed. The completion status may be represented by an indicator or icon such as icons 9803 and 9805. Icon 9803 may indicate that the goal was met for that goal time period while icon 9805 may indicate that the goal was not met. Streaks indication portion 9807 may further convey to the user whether the user is on a streak, starting a streak, just ended a streak or the like. In some examples, portion 9807 may provide motivating messages to begin or continue a streak. Goal time periods that have yet to occur may be displayed in yet another visual manner. In one example, a current goal time period may be displayed differently from completed goal time periods and goal time periods that have yet to occur. In one example, the beginning of a streak may correspond to an instance where a user's currently completed activity goal is the second of two consecutive goal completion time periods and the number of consecutive goal completion time periods of which the currently completed activity goal is a part) is equal to 2. Breaking a streak, on the other hand, may correspond to a first goal time period in which the user did not complete a goal occurring consecutively after at least two consecutive goal time periods where the activity goal was completed.

Figure 98C:
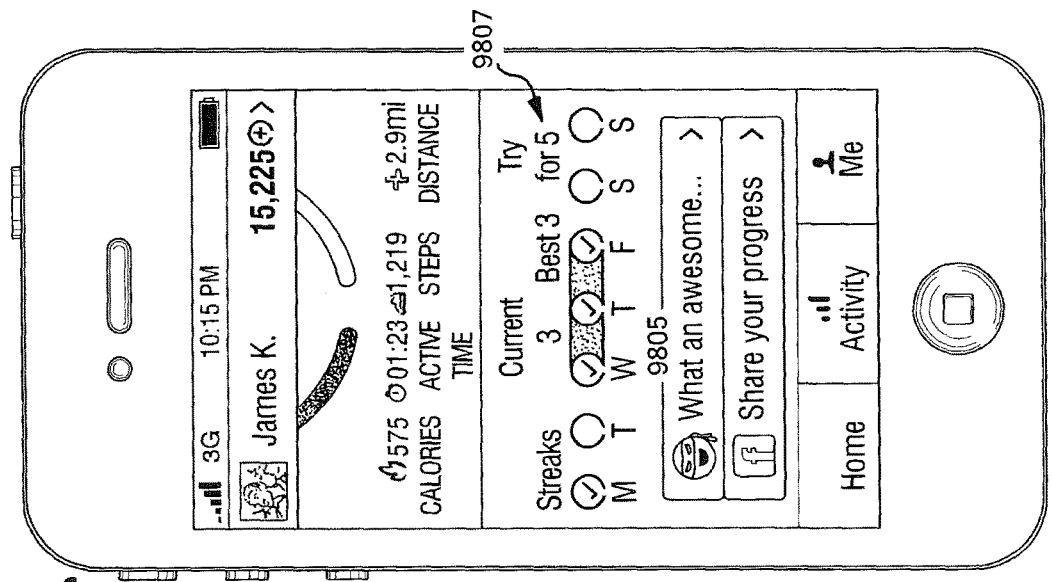

When the user achieves a particular streak (e.g., of 3 days) for the first time, the application may provide a celebration or recognition as shown in FIG. 98B. The celebration of this milestone or achievement may further motivate the user to continue the streak to achieve even greater recognition for longer streaks. The streak achievement may be provided as a reward or a trophy and the recognition may further be shared in a variety of ways including through e-mail, social networking messaging, text message and the like and/or combinations thereof. FIG. 98C illustrates streak indication portion 9807 upon the user completing the goal for the current goal time period and achieving the 3 day streak. Sharing and tagging options may also be provided in the activity tracking interface, as is described in further detail herein.

Figure 99:
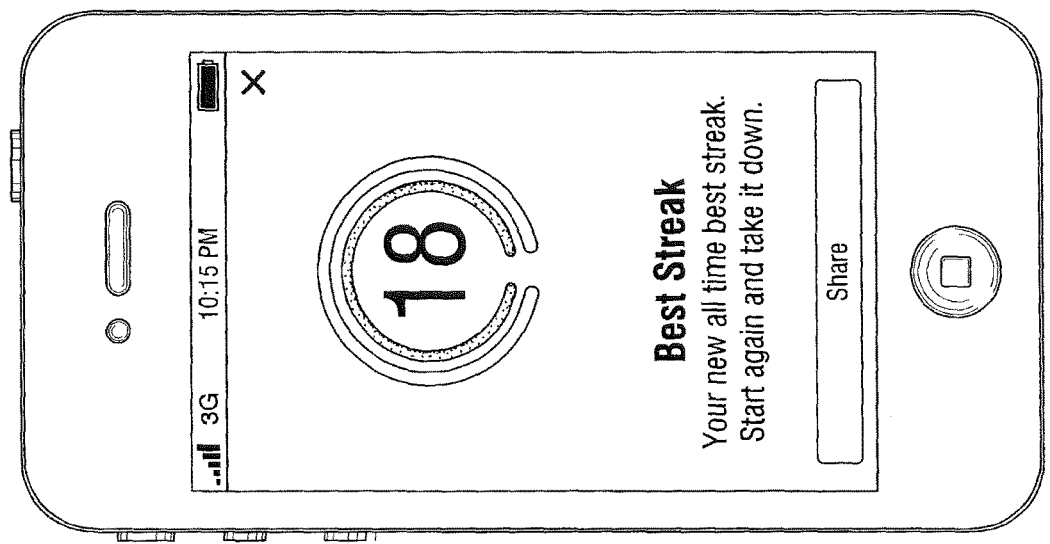

FIG. 99 illustrates another example streak achievement for which a user may be recognized. In particular, beating the user's existing best (e.g., longest) streak may be provided as an achievement, and the new best (e.g., longest) streak may be recognized. A streak may be evaluated for being the best streak each time the streak is extended or upon the user breaking the streak. Various other streak evaluation rules may be defined as desired by an activity monitoring service, the user and/or other entities.

As noted above, a user may tag his or her activity with various information. Tagging may provide a way in which a user associates various emotions, location information, equipment information, weather information, terrain information, activity partner information and the like with a particular activity time period. The tagging information may be specified by the user, automatically detected by the mobile device, automatically detected by the wearable activity tracking device and/or retrieved from other devices. In one example, the wearable device and/or the mobile device may include a location determination component such as a GPS device or cellular triangulation modules. In such an example, the wearable device and/or the mobile device may automatically populate location information if the user wishes to tag recorded activity. In another example, weather information for a location may be automatically retrieved from a weather database.

Figure 100B:
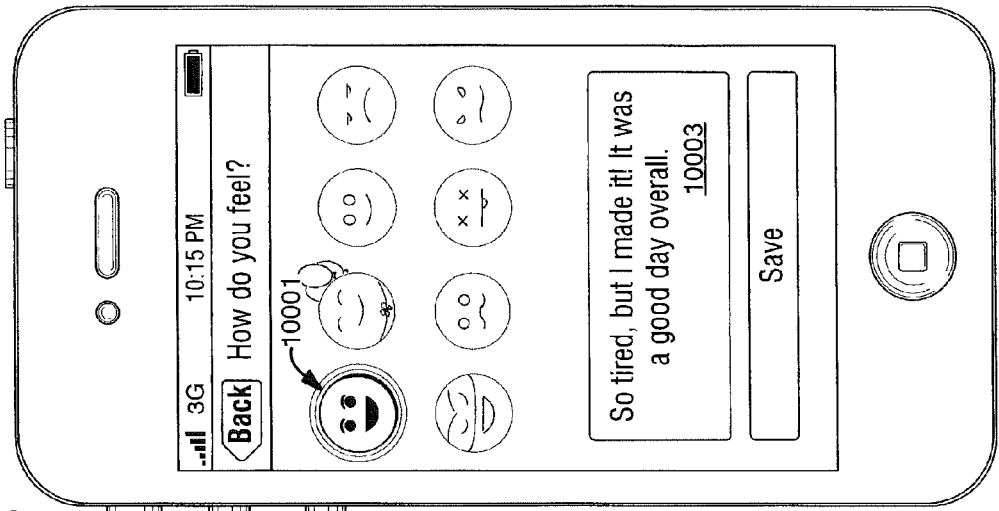
FIGS. 100A-100C illustrate example tagging interfaces for associating information with recorded activity.
Figure 100A:
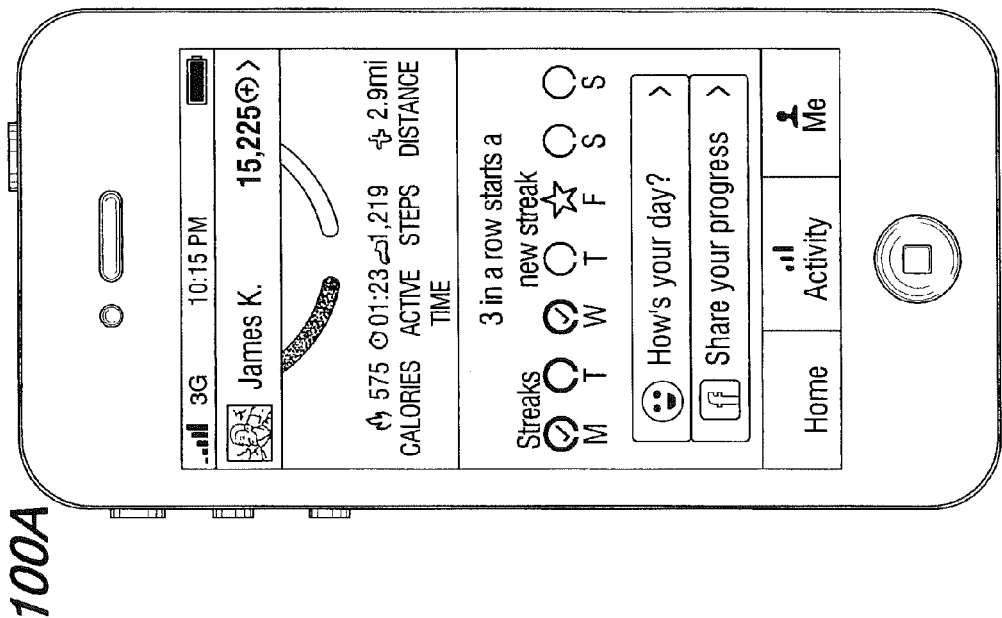

FIG. 100A illustrates an interface through which a user may tag an activity session with the user's mood, attitude or subjective perception of the activity session and/or type of activity performed. The mood or attitude may be specific to the activity performed during the activity session or may relate to the time period in general.

Figure 100C:
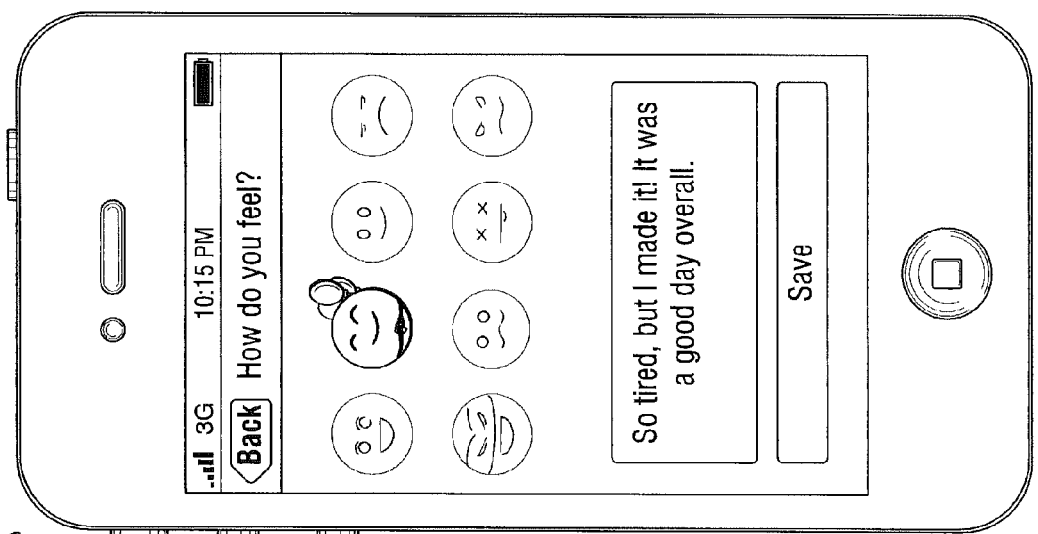

FIGS. 100B and 100C illustrate various emotion, mood or attitude selection menus in which various icons or images 10001 may represent different emotions, moods or attitudes. In some examples, selecting one of the icons or images 10001 may cause pre-defined text to be entered into text entry field 10003. The user may be allowed to edit the text in entry field 10003 or the text may be non-editable. In other examples, the selection of one of the icons or images 10001 might not include automatic population of pre-defined text. Instead, text entry field 10003 may remain blank and editable. Text entry field 10003 may enable the user to record additional thoughts or feelings regarding the activity time period and/or the activity performed during the time period. Once the user elects to save the information (e.g., selected representative image, entered text, etc.), the tag information may be stored in association with the activity time period and activity data recorded for the time period. In association with or separately from the subjective feeling tag such as mood, emotion or attitude, the user may tag the activity with a photograph. The photograph may convey additional subjective or objective information about the activity including a location, weather, the user's mood at that particular day or time and the like. Tags may be specific to an overall goal time period, a specific time, a particular activity session, a particular range of times and the like.

Figure 101:
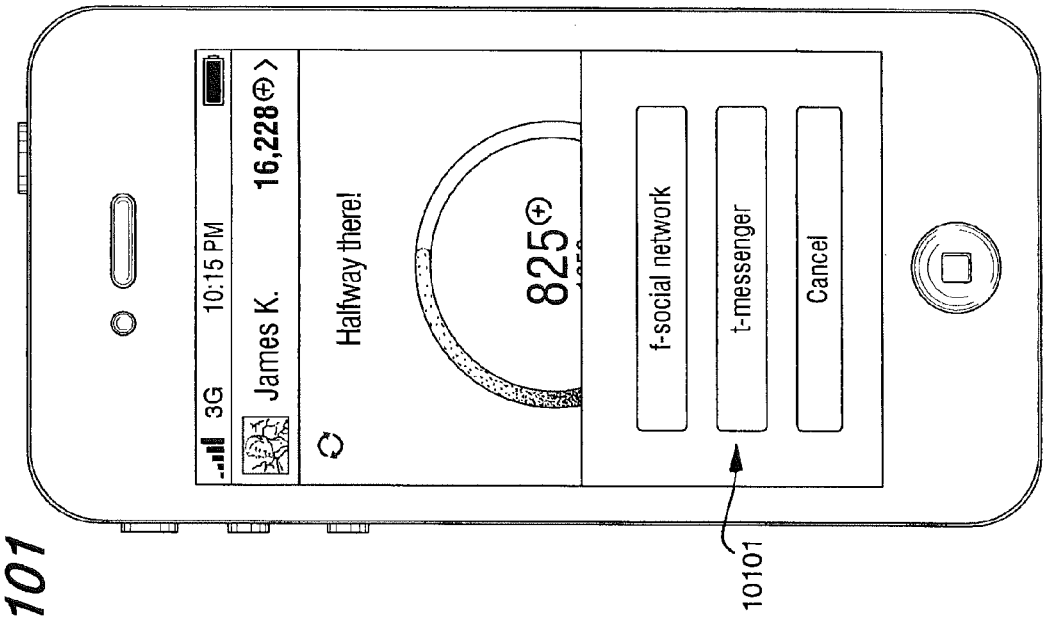
FIGS. 101, 102A, 102B, 103A and 103B illustrate example sharing interfaces through which users may share activity information.

In addition to tagging, the user may share activity information with others through various channels. In one example, the activity information may be posted to a user's profile or account on an activity tracking service site. In other examples, the activity information may be posted through an internal or external social networking system. FIG. 101 illustrates an example sharing menu 10101 providing multiple channels through which activity information may be shared with other users.

Figure 102A:
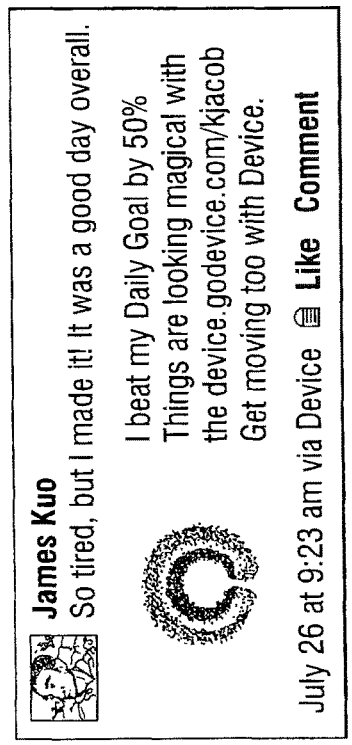

In one example, posting to a FACEBOOK account may include the application automatically generating a template or standard post, as shown in FIG. 102A. The post may include predefined language and images 10201 along with user-specific activity data including goal information, whether the user completed the goal and/or a level a completion (e.g., exceeded the goal by 50%). The post may further include identification of equipment used to track the activity. This may help encourage other users to increase their activity level and identify help products and services for doing so. The user may further enter comments or other information in field 10203 and submit the post via option 10205.

Figure 102B:
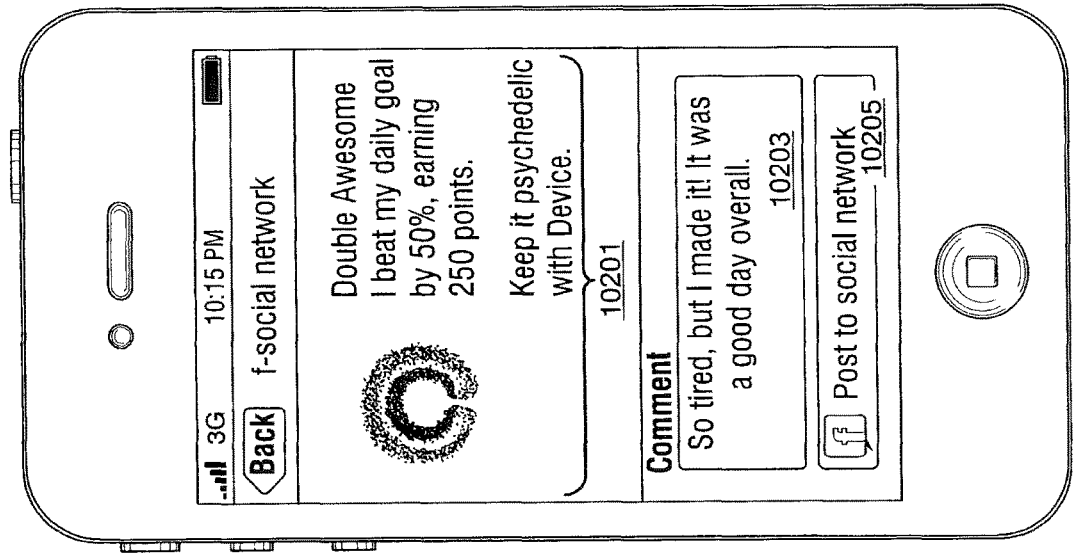

FIG. 102B illustrates an example post that may appear on the user's FACEBOOK page upon submitting the post shown in FIG. 102A to FACEBOOK. In some arrangements, the message posted to the user's FACEBOOK account may include a link to the user's profile on an activity tracking service site and/or to activity tracking product and service information pages.

Figure 103A:
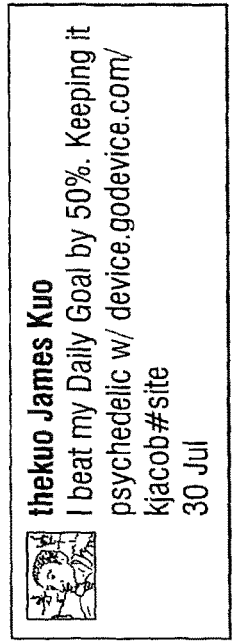
Figure 103B:
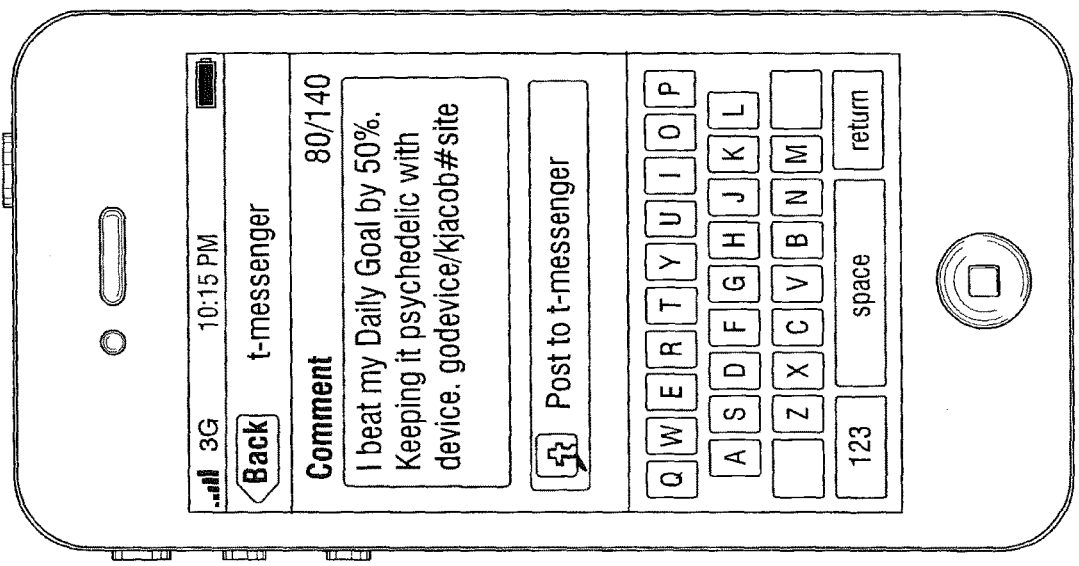

FIGS. 103A and 103B illustrate an example TWITTER posting interface and resulting TWITTER post, respectively.

Figure 104B:
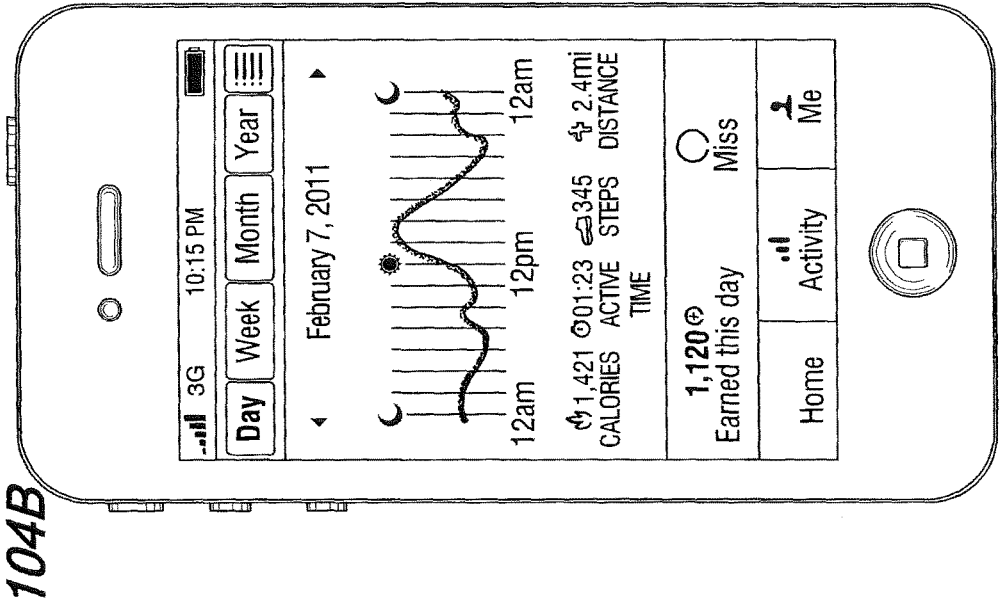
Figure 104A:
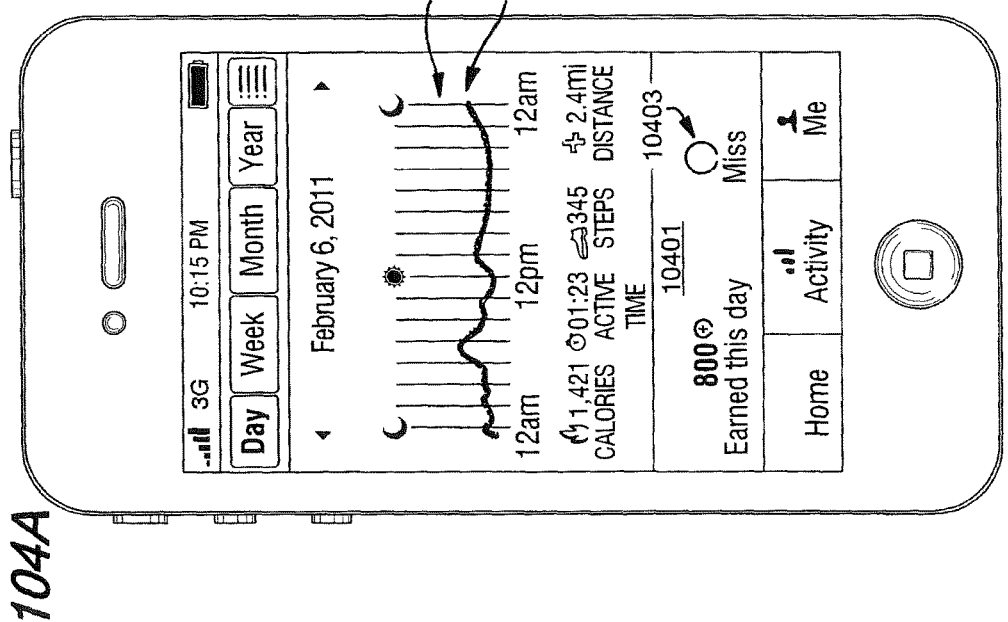
Figures 104C, 104D:
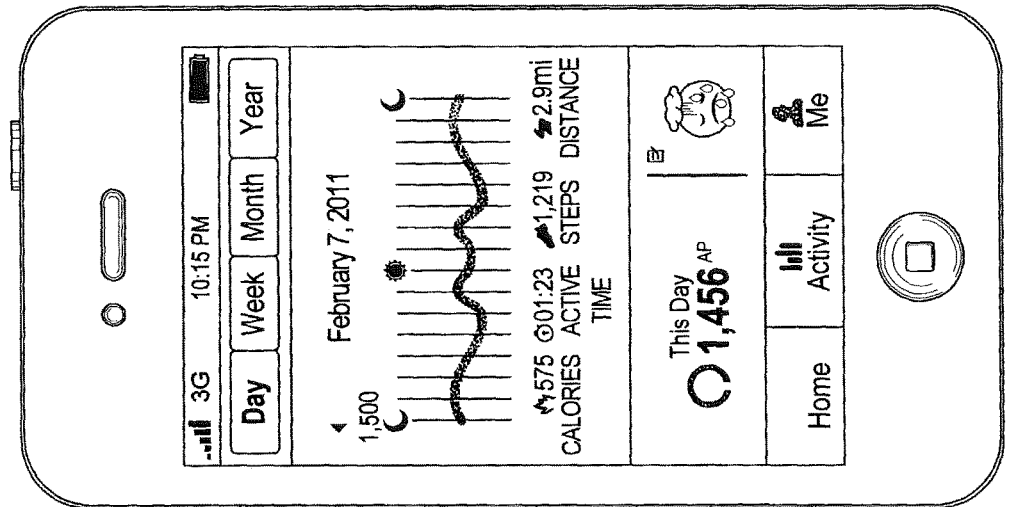

Visual appearance of a user's activity level may help convey various types of information and messages about the activity level to the user. As described herein, different colors may be used to represent different levels of goal completion or non-completion. FIGS. 104A-104C illustrate example interfaces displaying activity level graphs for a goal time period. In addition to the graph of activity level over time, the interface may further include summary portion 10401 in which the amount of activity point earned is displayed as well as an indicator 10403 showing whether the user completed the goal. The color of indicator 10403 may convey an additional detail. In particular, the color of indicator 10403 may represent an amount by which the goal was missed. For example, indicator 10403 appearing in red may indicate that the user only achieved 25% or less of the goal while if the indicator 10403 appears in yellow, the user may recognize that they achieved over 25% of the goal but less than 100%. The appearance of line 10405 in graph 10407 may adopt similar color schemes and visual indications. Other visual characteristics, animations, audio indicators may also be used to convey additional activity data including patterns, transparency levels, highlighting, brightness, size of indicators or graph elements, speed of animation, type of animation, audio messages and the like.

Figure 104E:
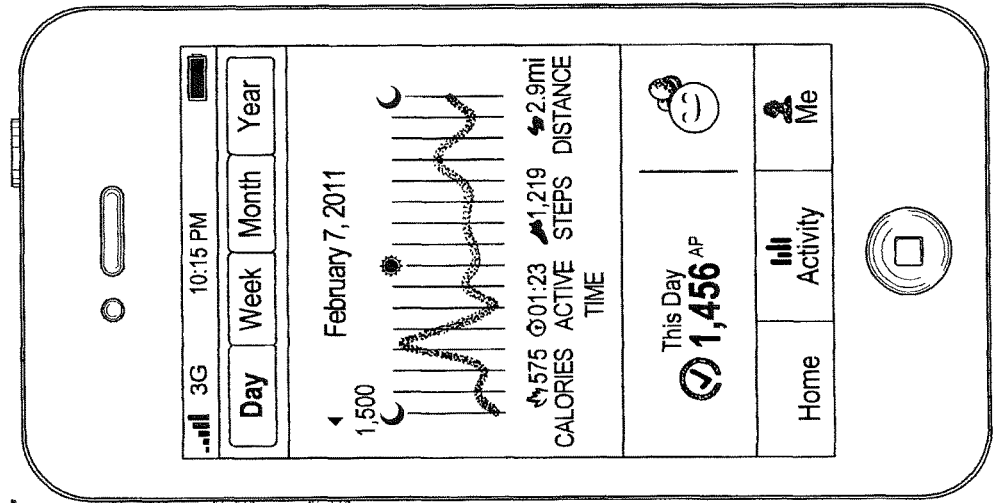
Figure 104F:
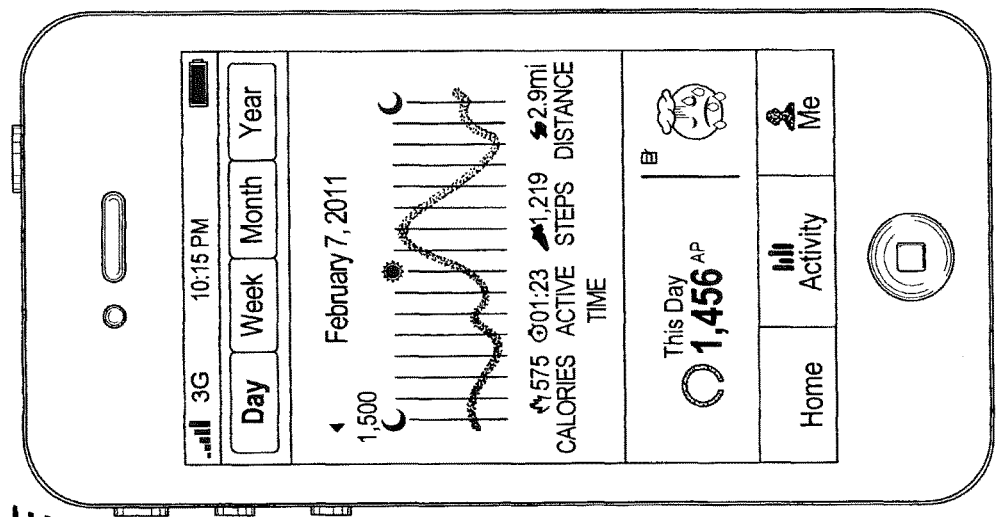

FIGS. 104D-104F illustrate other example interfaces displaying activity level graphs for a goal time period such as a day. In addition or alternatively to the information shown in FIGS. 104A-104C, the interfaces of FIGS. 104D-104F may include a mood indicator representing the user's current subjective feeling about the goal time period, an activity, an activity session and the like. The user may be able to modify the mood indicator throughout the goal time period and during activity sessions performed therein. Alternatively or additionally, the mood indicator may be automatically set by the application based on a level of activity performed and predefined rules correlating the level of activity to a mood and mood indicator. For example, if the user has exhibited a high level of activity (above a first threshold), the mood may be set as happy or excited. In another example, if the user exhibits a low level of activity (e.g., below a second threshold), the mood may be set as sad or disappointed or the like. One or more other thresholds may be set as desired by the user or as defined by the system or an activity tracking service.

FIG. 105 illustrates an example activity summary for multiple activity time periods. In addition to the bars representing each activity time period, the summary 10500 may further include an indicator 10501 identifying the goal. Indicator 10501 may be used to convey an amount by which a goal was exceeded or an amount by which a user underachieved.

Figure 105C:
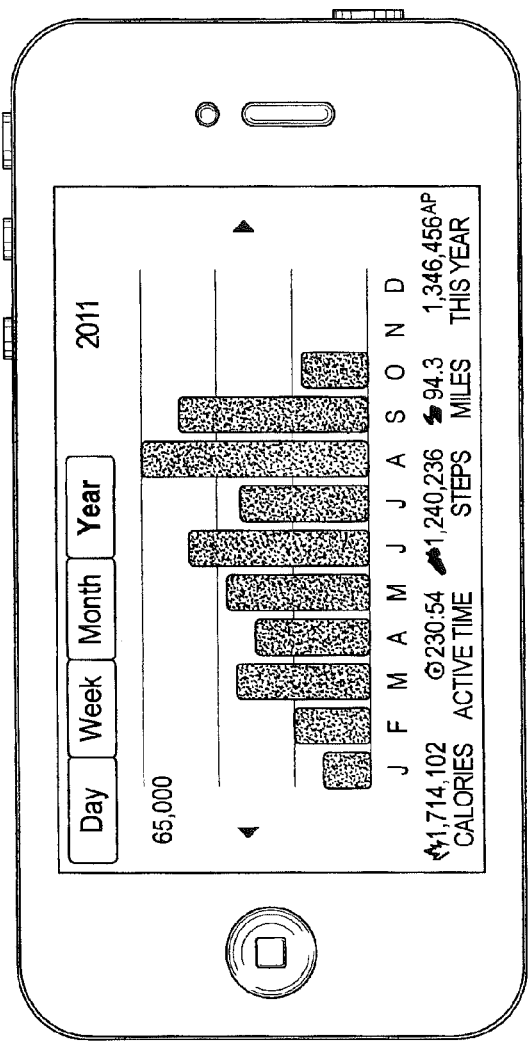

FIGS. 105A-105D illustrate other example activity summaries for multiple activity periods. For example, FIGS. 105A and 105B illustrate example monthly summaries for daily goal periods. The summary may include a counter indicating a number of goal periods in which the goal was reached and a number of total goal periods during the month. A total amount of activity points for the month may also be displayed. As noted above, each goal period may be represented by a bar or other type of graph to indicate a performance during that period. Different colors or other types of visual characteristics may be used to represent whether a user completed the goal and if not, a level of progress made toward the goal. For example, green may represent goal completion, while yellow represents completion up to a certain threshold (e.g., 50%-99%) and red represents completion below a specified threshold (e.g., below 50%). Degree of completion may be conveyed in various other manners as well.

Figure 105D:
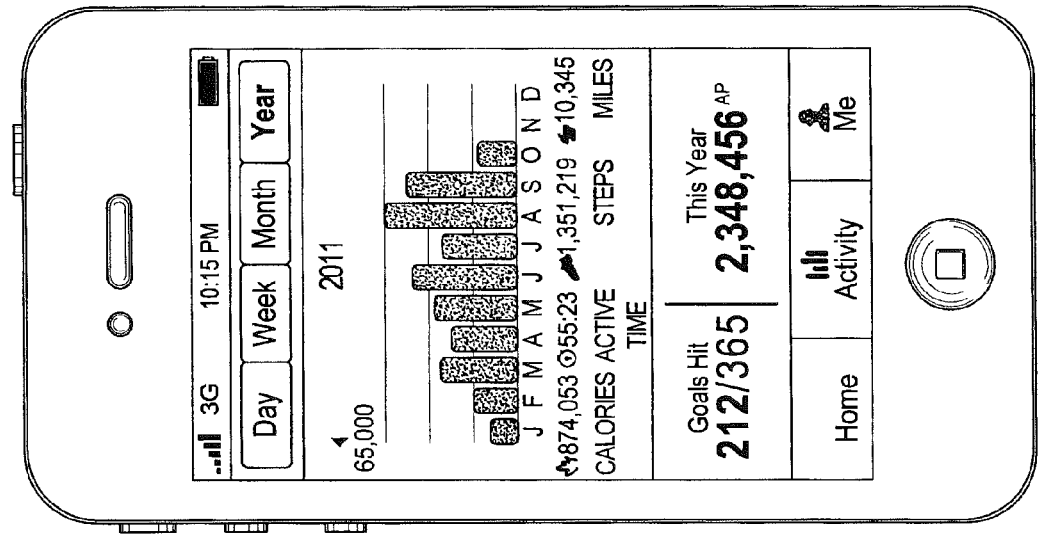

FIGS. 105C and 105D illustrate an example activity summary for a year. Similar statistics and information may be provided in a yearly summary as was discussed with respect to the daily and monthly summary views. Summaries based on a time period may correspond to a rolling time period and thus, may show data from a past month, past week or past year ending with a current time. In the examples illustrated, the summaries of the time periods begin and end at calendar weeks, months and years. As such, some of the data may be empty if certain dates and times are in the future.

Figure 106A:
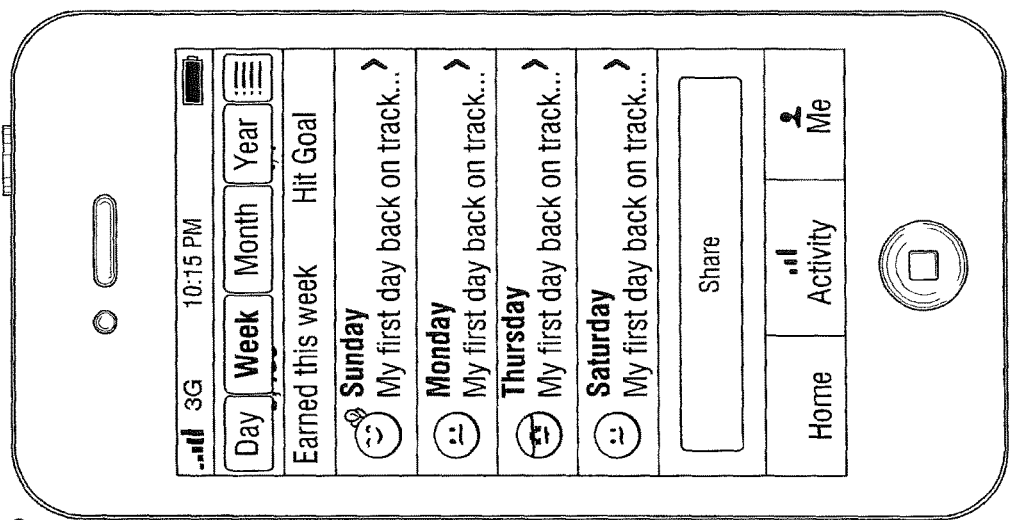
FIGS. 106A, 106B, 107A-107E, 108A, 108B, 109A and 109B illustrate example records, trophies and milestone interfaces.
Figure 106B:
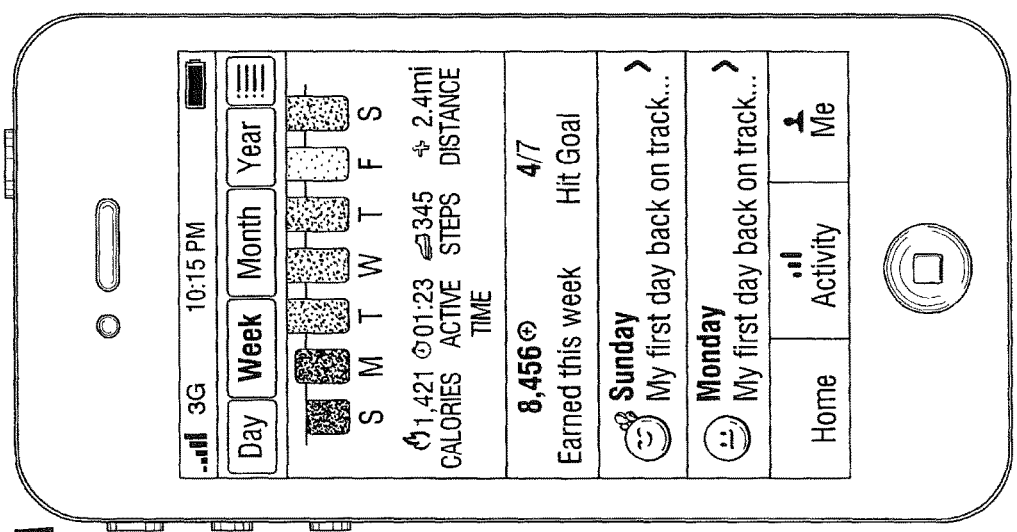

FIGS. 106A and 106B illustrate example interfaces in which tags and, in particular, subjective perception tags may be displayed for multiple activity time periods. These subjective perceptions (e.g., moods, attitudes, other subjective feelings) may further be shared.

Figure 107B:
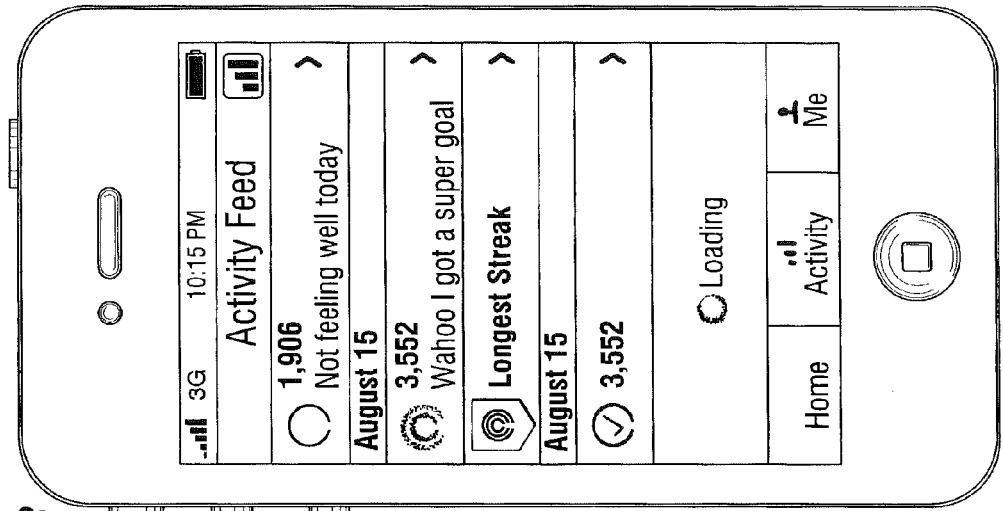
Figure 107A:
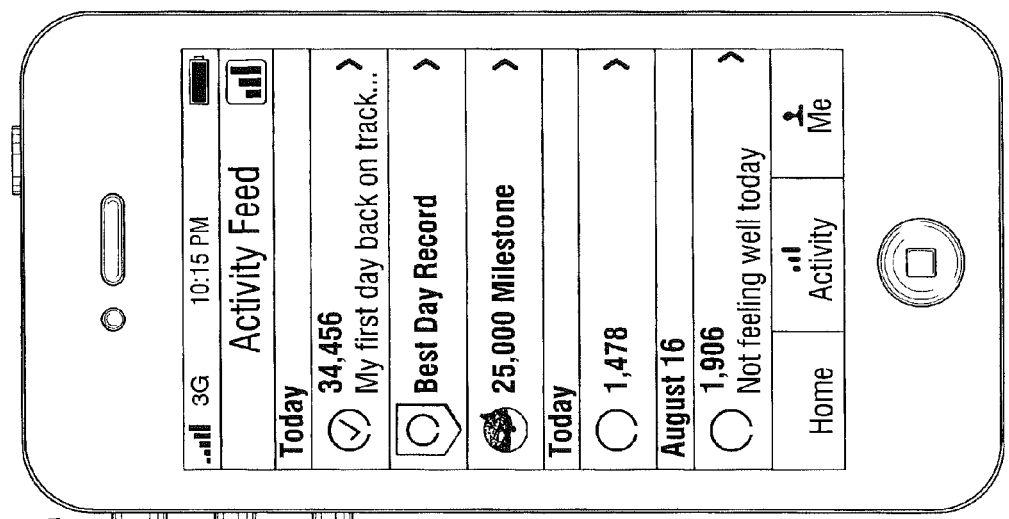

FIGS. 107A and 107B illustrate example interfaces through which activity information and events may be conveyed and viewed. For example, FIGS. 107A and 107B illustrate portions of an activity feed that displays activity levels and other data such as achievements (e.g., whether the goal was completed or missed, streaks, milestones, records, etc.), tags and the like in a list format organized according to activity time period (e.g., day). The activity feed may provide a way for a user to digest activity information for multiple activity time periods through a single interface or display. In some arrangements, the user may configure the types of information that are included in the activity feed based on their specific interests.

Figure 107C:
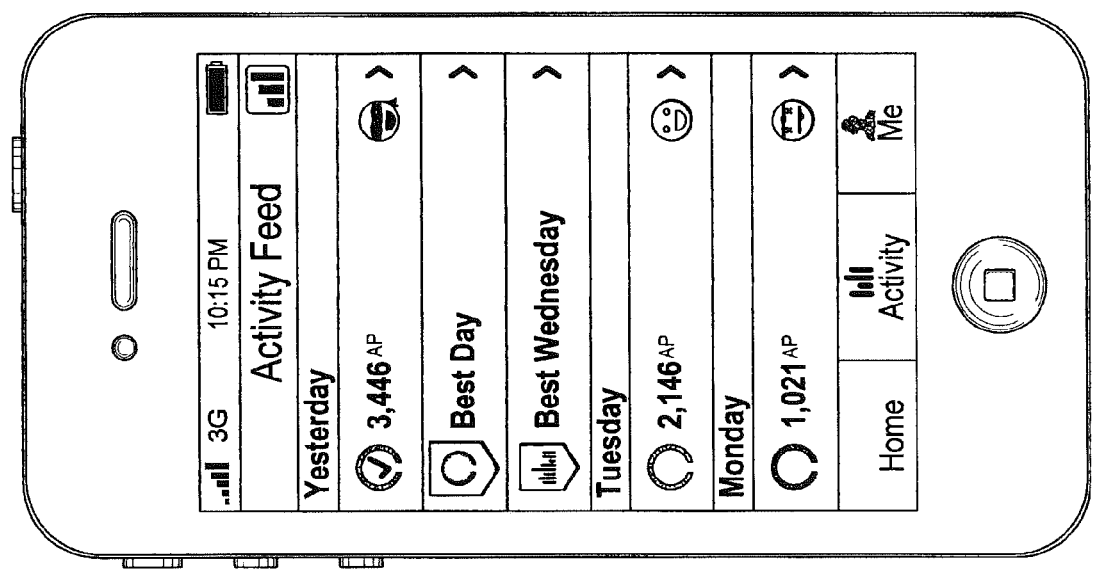
Figure 107D:
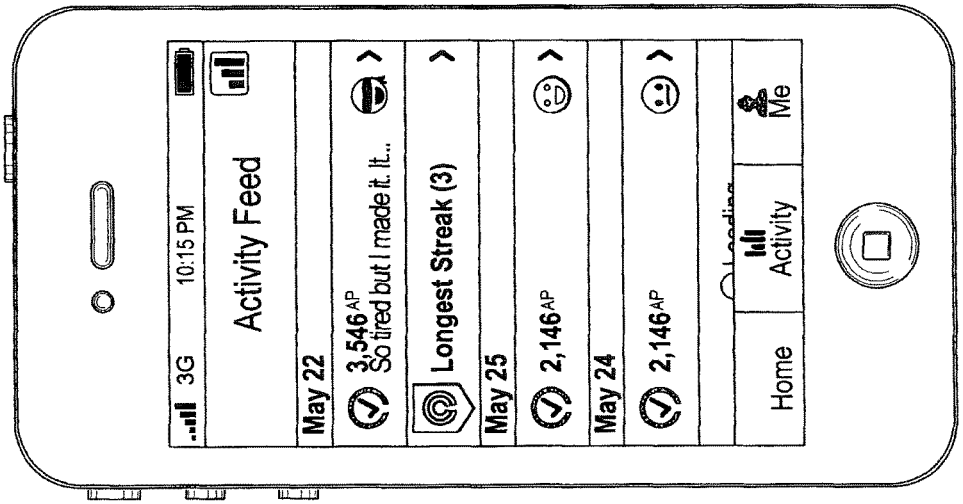
Figure 107E:
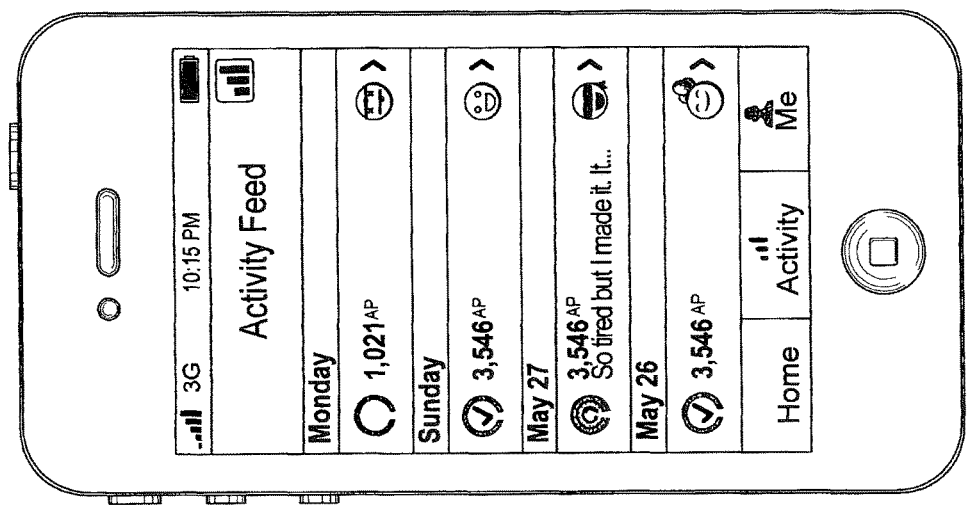

FIGS. 107C-107E illustrate other example interfaces through which activity information and events may be conveyed. In FIGS. 107C-107E, a user's tagged mood or subjective feeling about the goal time period or activity session may also be indicated in the feed/listing. Selecting one of the entries in the feed may provide the user with further information about the goal time period or activity session.

Figure 108B:
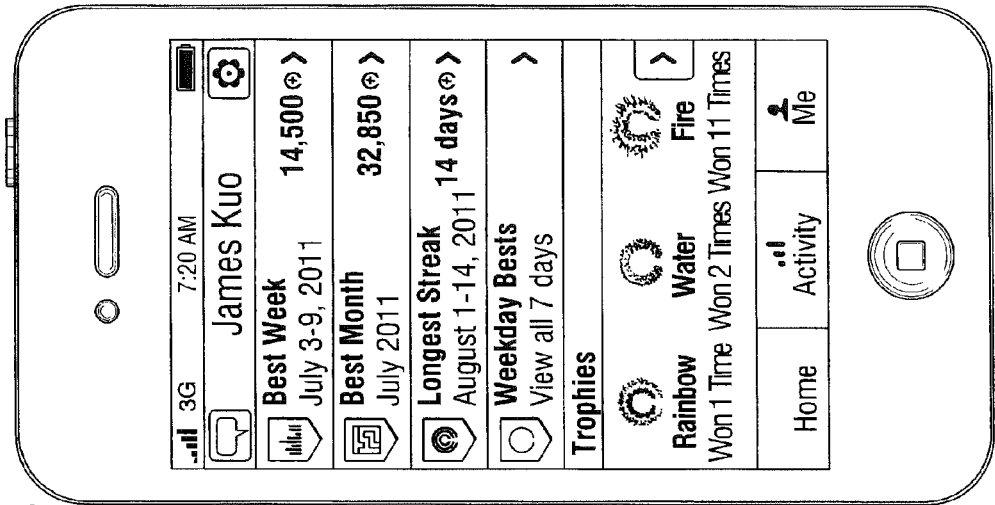
Figure 108A:
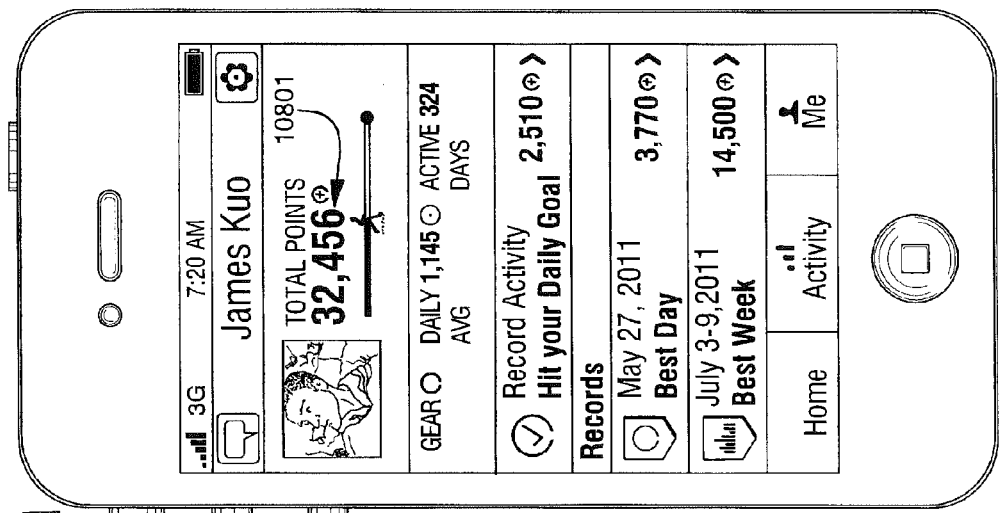

FIGS. 108A and 108B illustrate example user profile or account interfaces through which the user's activity information may be conveyed. In one or more arrangements, the user profile may include a milestone or achievement tracker 10801 (as shown in FIG. 108A). The milestone tracker 10801 may be used to track a goal or achievement that spans multiple time periods or is unrestricted in time (e.g., no specified end date for the goal). For example, users may receive milestone awards or recognition upon reaching various lifetime activity point totals. Accordingly, tracker 10801 may be used to identify a user's progress toward such achievements or milestones. In some examples, the milestone or achievement tracker 10801 may also be displayed in other interfaces including a home interface in which a daily activity level and goal are tracked, an activity review interface in which activity recorded for a single or multiple time periods may be reviewed and the like.

FIG. 108B illustrates another portion of the user profile interface in which records and trophies may be displayed. Trophies may include images, icons, virtual items and the like representing a particular achievement or milestone. In some examples, the trophies may also be displayed with a number of times won or achieved to provide incentive for users to reach the same milestone multiple times.

Figure 109B:
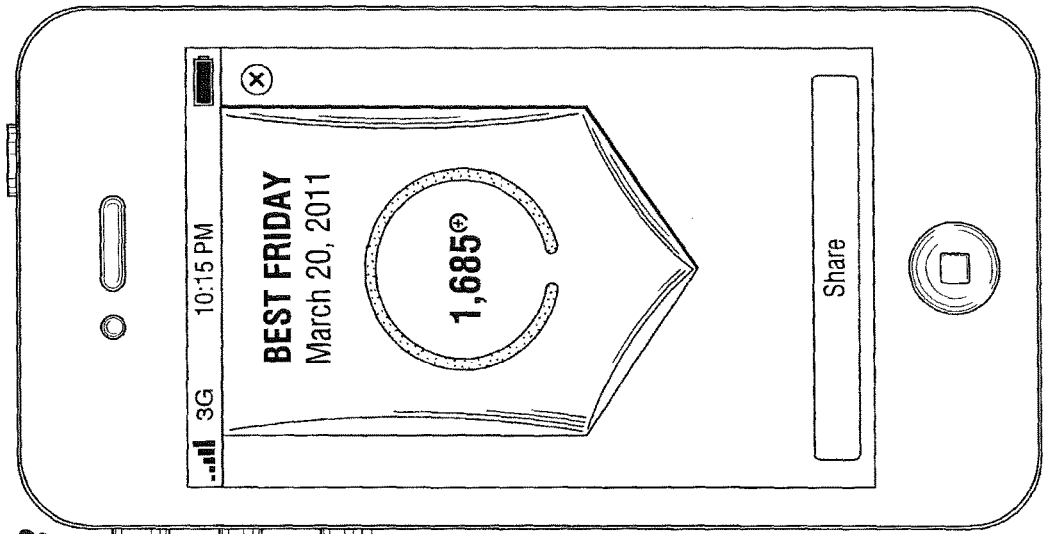
Figure 109A:
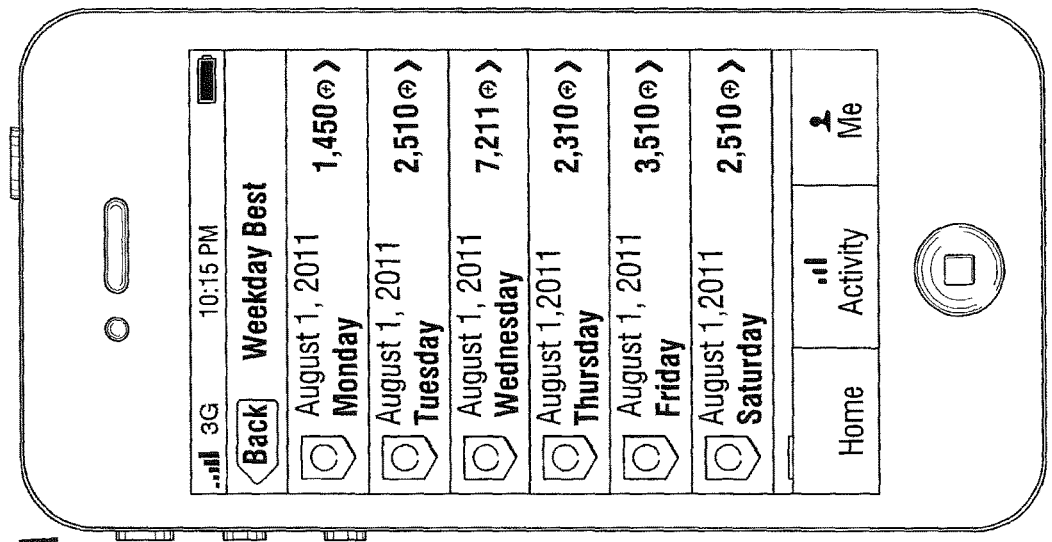

The mobile application may be configured to track still additional types of activity data including a best activity time period for a category of time periods. In the example illustrated in FIGS. 109A and 109B, each activity time period may correspond to a single day. Accordingly, activity time periods may be grouped into days of the week and analyzed to determine a best activity time period for each of the days of the week. This information may then be conveyed to the user and may aid in determining days for which activity needs to be improved. Categorization or grouping of activity time periods may also correspond to months, years, times of day (e.g., afternoon, evening, morning), user-defined groups (e.g., the user may manually assign activity time periods to different predefined or user created groups), type of device used to detect or record the activity, location of activity, type of activity, instructor (e.g., for athletic activity classes), activity partners, times of year (fall, spring, winter, summer) and the like. The best activity time period may be defined in multiple ways including highest activity point total, most activity points accumulated within a particular sub-time period (e.g., between the hours of 8 AM and 8 PM), greatest improvement over a previous activity time period (e.g., an immediately preceding time period), largest amount by which the activity recorded exceeded a goal (e.g., when the goal differs from time period to time period).

Additionally or alternatively, other category-specific statistics may be generated for each of the groups or categories including activity averages, highest and lowest activity levels, most active sub time-periods for the category and the like. Sub-groups or categories may also be defined within each category or group. For example, activity time periods may initially be grouped by day of week. Each day of week category may further be categorized by time of day or time of year and/or the like. Accordingly, not only might category-specific statistics and information be determined, sub-category-specific statistics and data may also be generated. Further levels of sub-categories may be defined or used as desired.

Figure 110B:
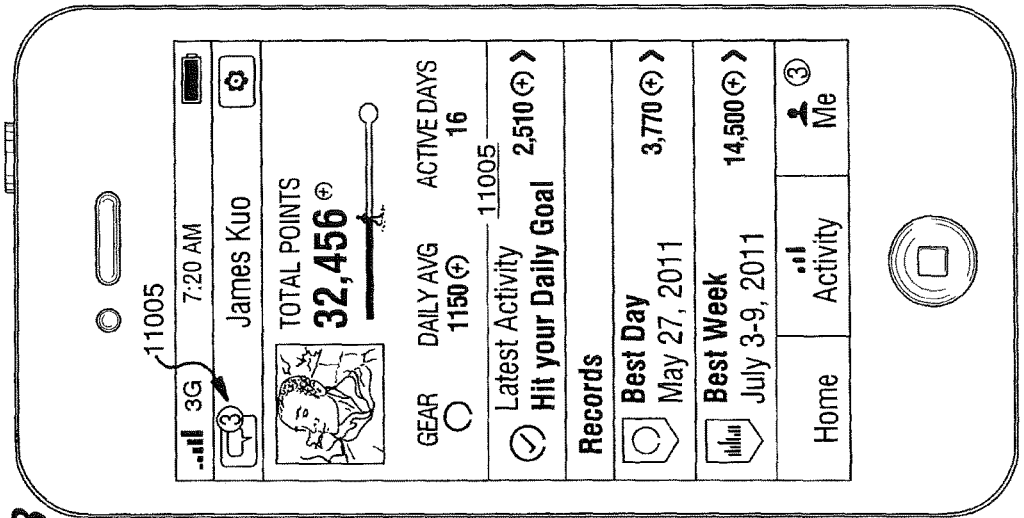
FIGS. 110A and 110B illustrate example notification indicators.
Figure 110A:
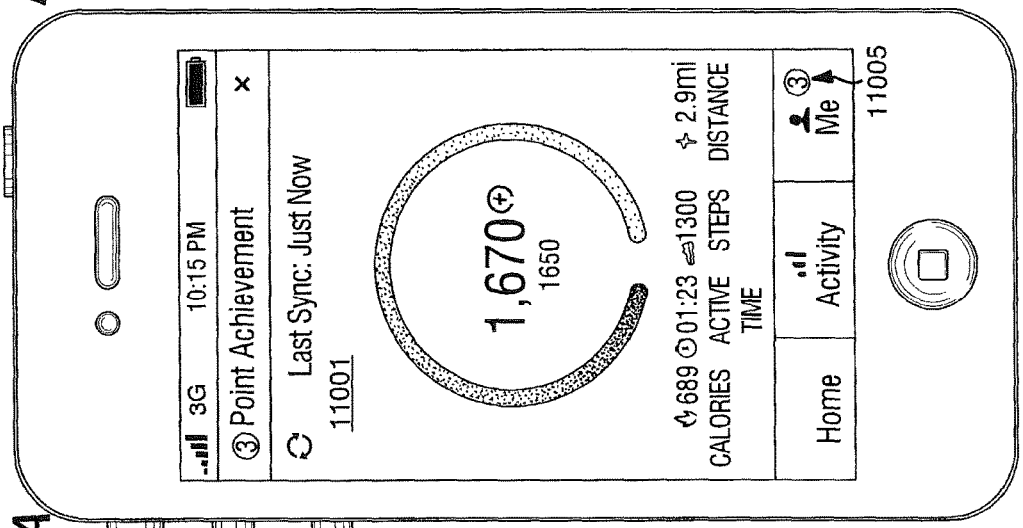

Moreover, various triggering events may cause the mobile application to generate notification messages to the user. The messages may be immediately displayed to the user without user request or prompting or may be stored for user retrieval. For example, in FIGS. 110A and 110B, the home interface 11001 and the profile interface 11003 may both display indicators 11005 that identify available notifications and a number of notifications. The indicators 11005 may be overlaid on elements of the interfaces 11001 and 11003 with which the user must interact in order to view or otherwise retrieve the notification messages.

Figure 111:
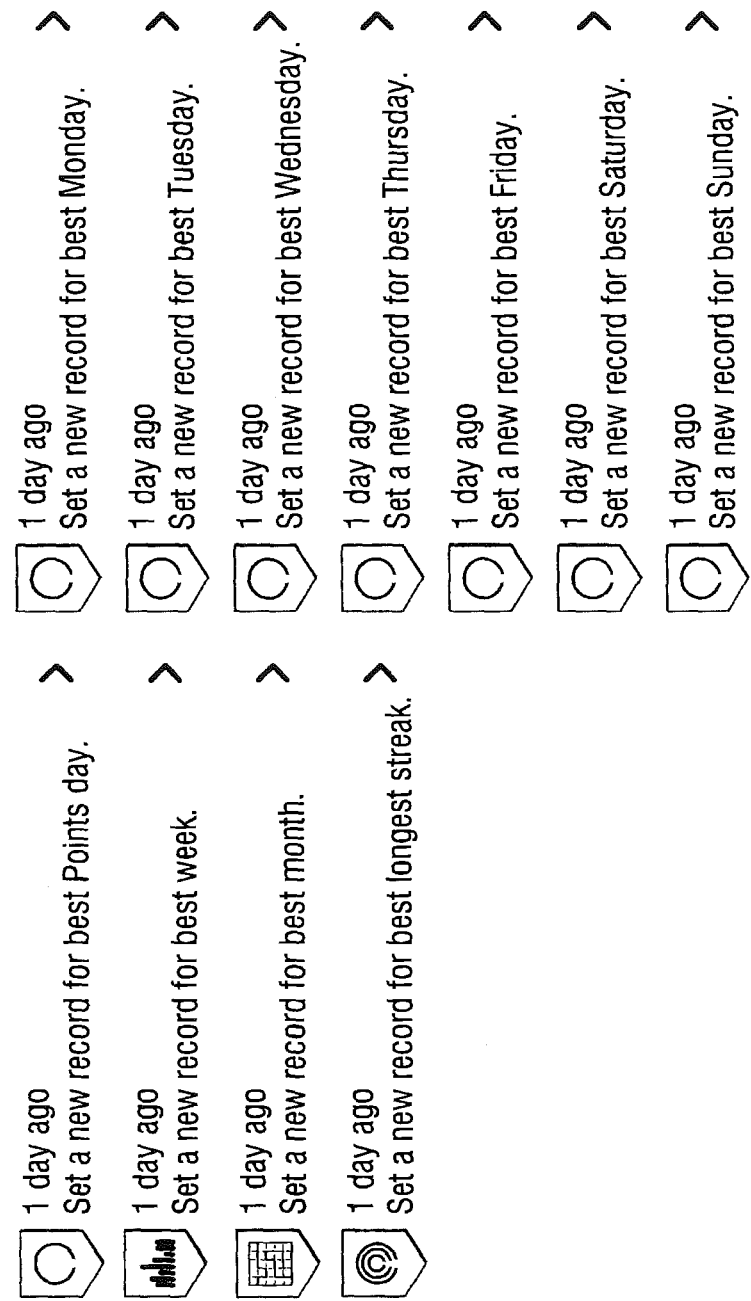
FIG. 111 illustrate example activity notifications.

FIG. 111 illustrate examples notification messages that may be provided to the user.

Figure 112B:
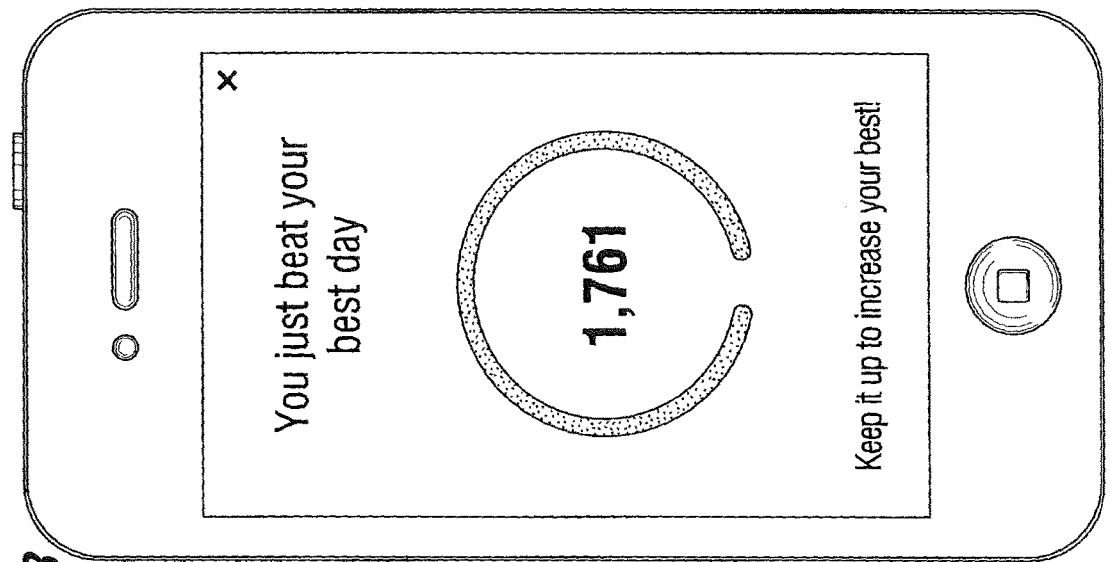
FIGS. 112A-112C, 113A-113C, 114A, 114B, 115 and 116 illustrate example achievements and accomplishment tracking interfaces.
Figure 112A:
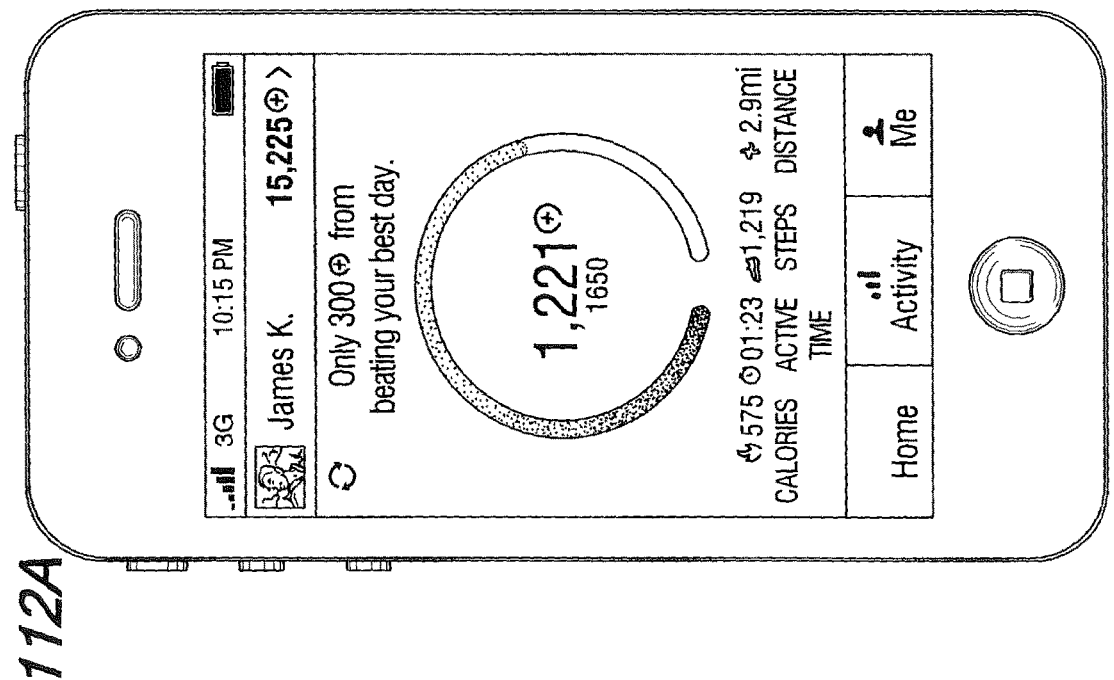
Figure 112C:
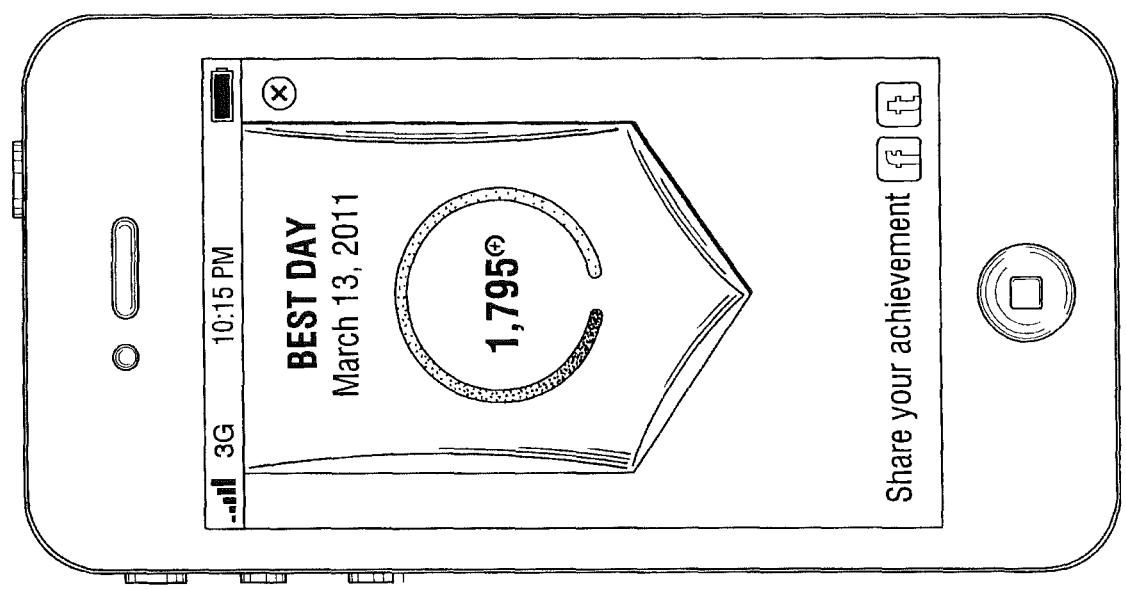
Figure 113B:
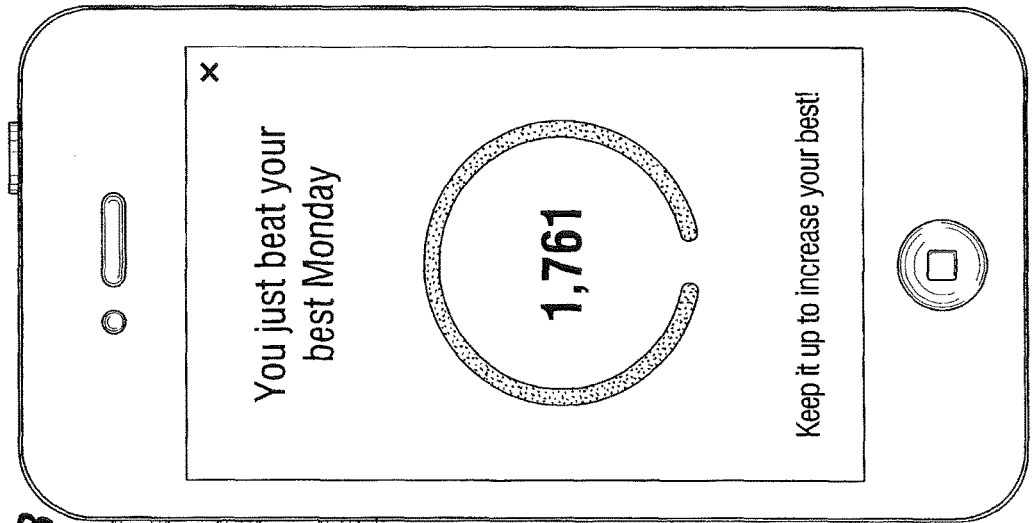
Figure 113A:
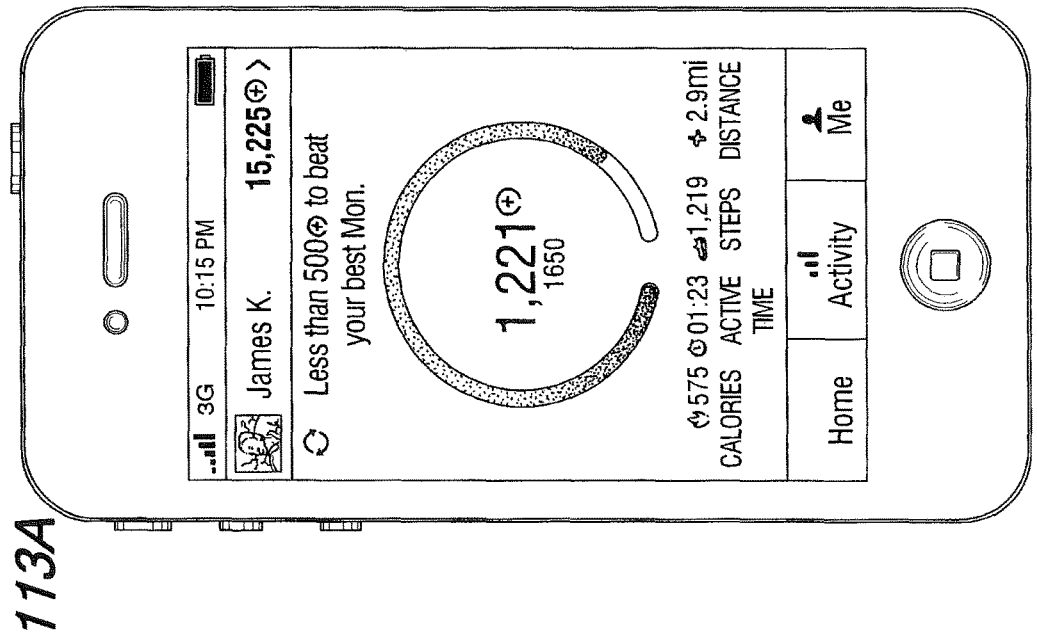
Figure 113C:
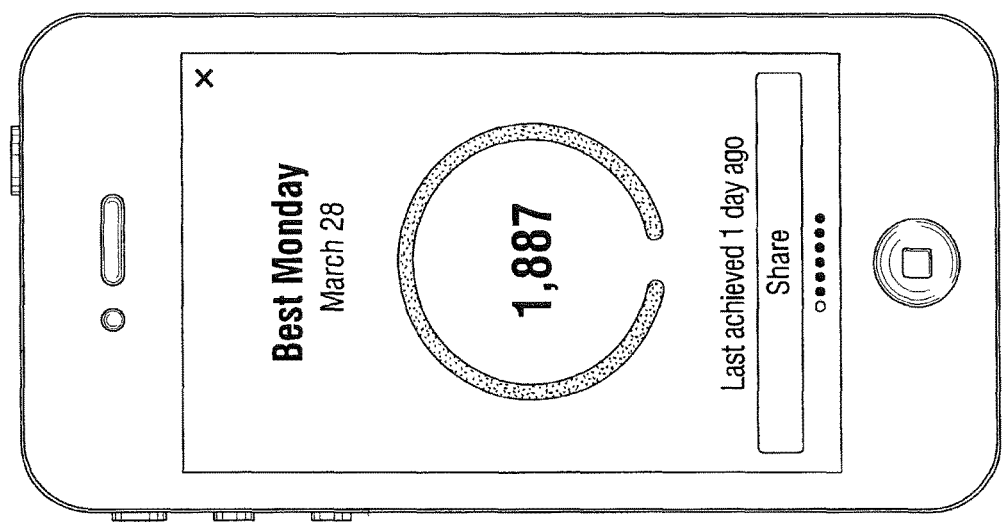
Figure 114B:
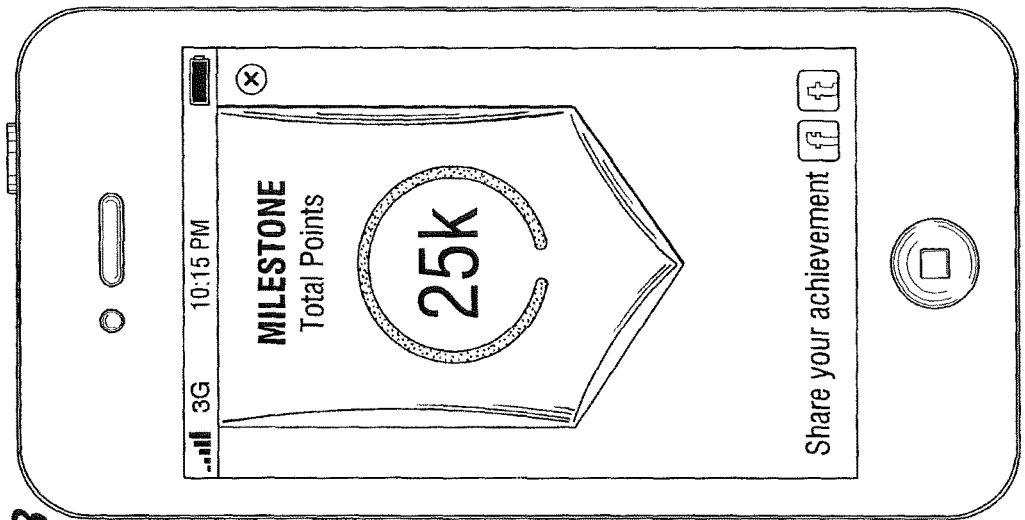
Figure 114A:
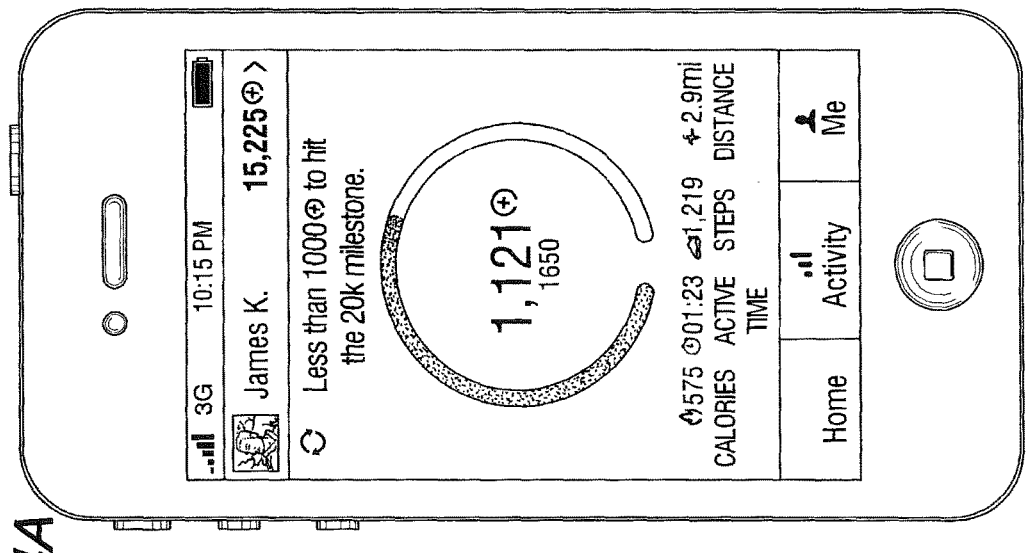
Figure 115:
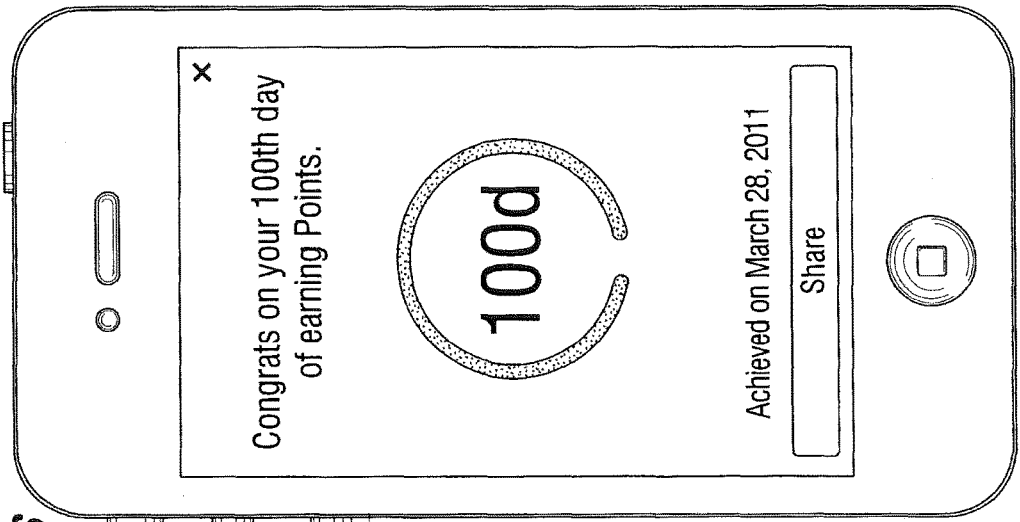
Figure 116:
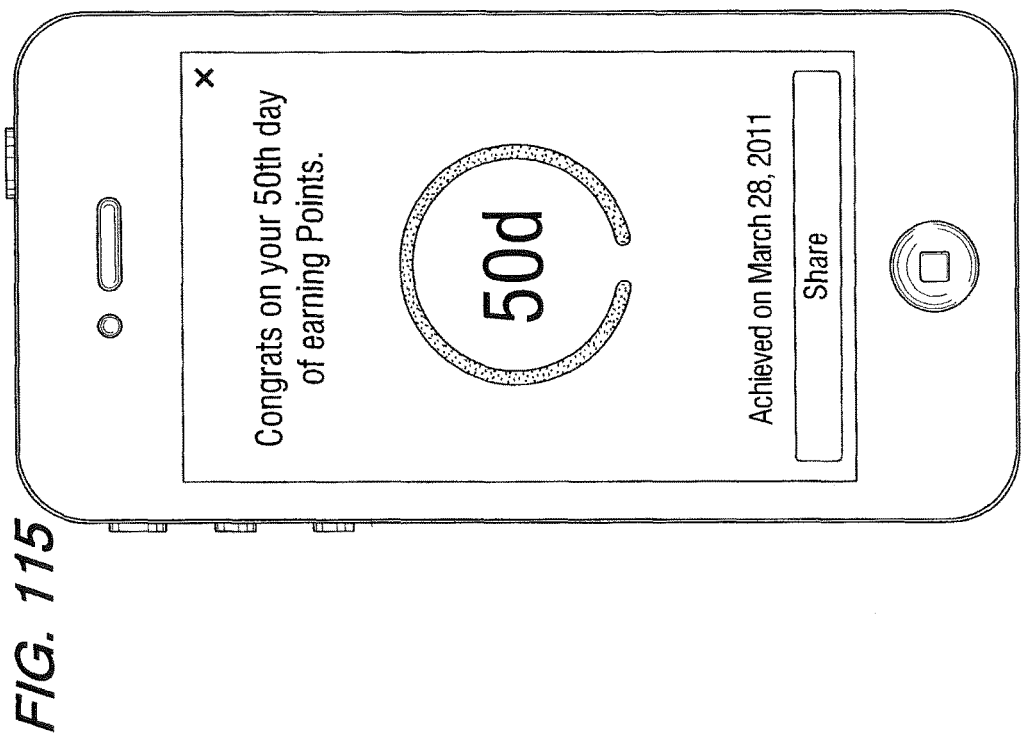

FIGS. 112A-112C, 113A-113C, 114A, 114B, 115A and 115B illustrate other example interfaces that may be generated and displayed for conveying various milestones, achievements and/or other accolades. For example, FIGS. 112A-112C illustrate interfaces for reaching a best day mark while FIGS. 113A-113C illustrate interfaces for exceeding a best day of week. FIGS. 114A and 114B illustrate example interfaces for reaching a lifetime activity point mark (e.g., 25000). FIGS. 115 and 116 illustrate example interfaces indicating that the user has earned activity points for a particular number of days or time periods. These achievements, awards and accolades may be shared as described herein.

Figure 117:
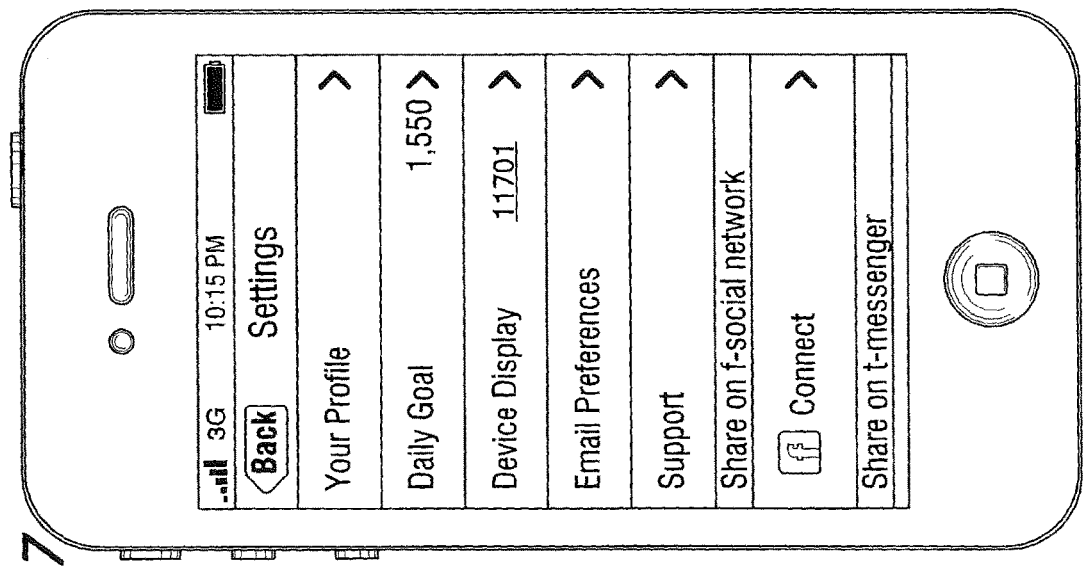
FIG. 117 illustrates an example activity application setting menu.

The activity tracking application may include various settings for customizing the applications functions. FIG. 117 illustrates an example settings menu 11701 that may be used to modify a user's profile, daily goal, display features, communication preferences and sharing options. In one example, a user may login to or otherwise specify authorization information for one or more sharing sites or services such as FACEBOOK and TWITTER. The application may then use the authorization information or login to interact with the user's account on those services.

Figure 118A:
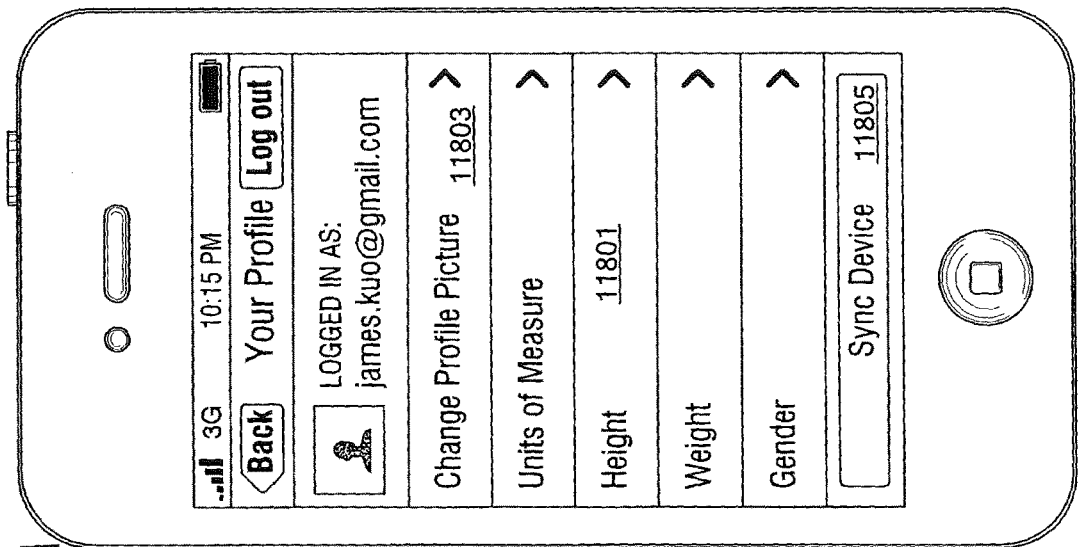
FIGS. 118A-118C illustrate example activity application setting interfaces.
Figure 118B:
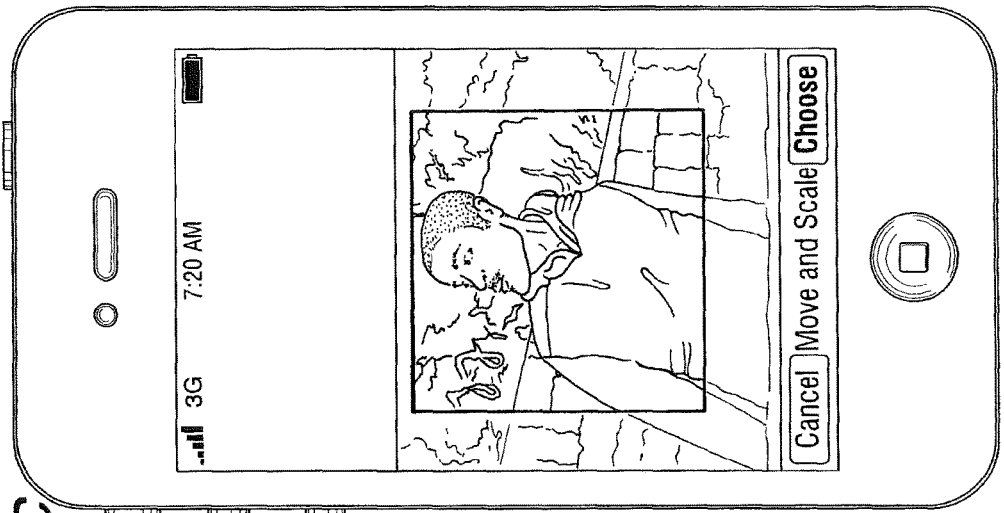
Figure 118C:
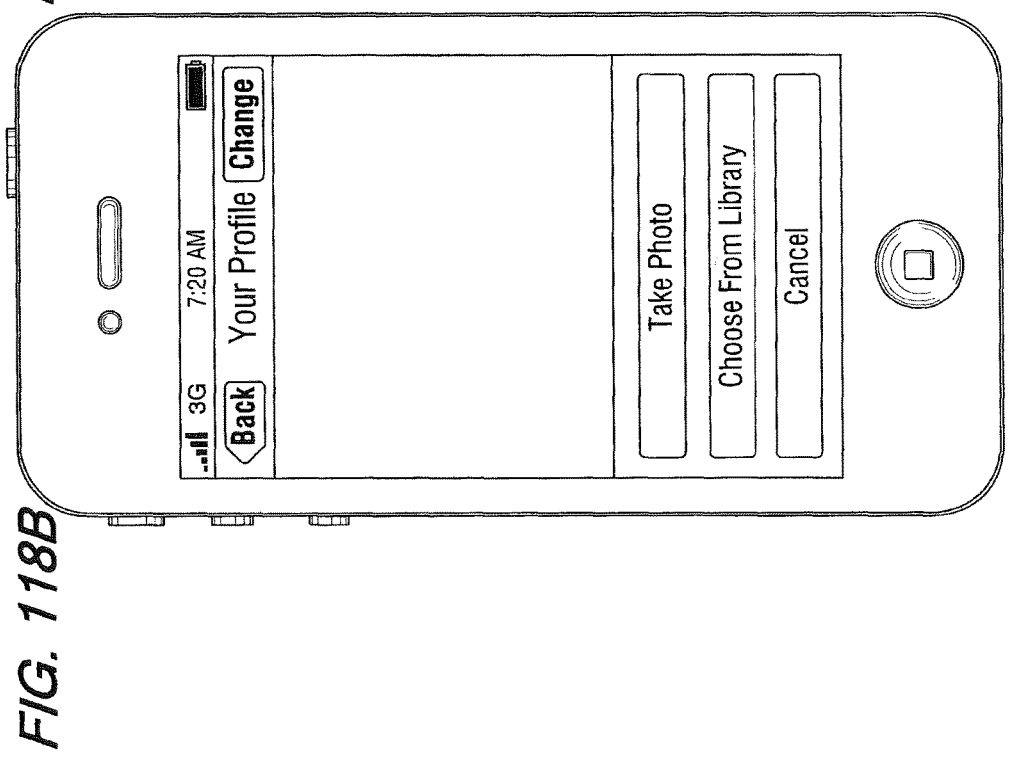

FIGS. 118A-118C illustrate example profile setting interfaces. In addition to the desired units of measure and the user's height, weight and gender, profile setting interface 11801 (FIG. 118A) may further include a profile picture option 11803 and an option 11805 to synchronize data from a wearable activity tracking device. Selecting the profile picture option 11803 may provide multiple picture setting options such as those shown in FIG. 118B. For example, the user may select a picture or image from a library to take a picture using a camera of the mobile device. In some examples, profile pictures or images may also be retrieved from a remote site through a network such as the Internet. In a particular example, the user may retrieve images from his or her social networking account. In still another example, a profile image on a user's social networking account may be automatically populated as the user's profile image in the activity tracking application and/or the user's account on a corresponding activity tracking service and site. Upon selecting or capturing an image for the user's profile, the user may be provided with an image editing interface as shown in FIG. 118C. The user may have the option to crop, resize, rotate, scale and perform other image editing on the image before setting the image as his or her profile picture. Additionally or alternatively, the profile settings entered through the application may be synchronized and uploaded a user's account with a corresponding activity tracking service and site. Accordingly, any changes made the user's profile on the mobile application may be reflected automatically (or in an on-demand fashion) to a user's account on a remote network site.

FIGS. 142 and 143 illustrate other example setting interfaces. For example, FIG. 142 illustrates an example settings menu in which various options are provided to the user including account settings, device settings specific to a user's monitoring device and social network settings. The monitoring device-specific settings may include a daily goal setting, device display settings, help and support information. Different devices may include different types of settings and thus the device-specific settings portion of the menu may differ from device to device (e.g., depending on what devices are connected). Daily goal settings may be defined as described herein. For example, users may manually enter a goal value or specify that they wish to increase or decrease a previous goal by a certain amount. In another example, a user may specify that they wish to set their goal based on an amount of activity points accumulated in a previous goal period. The user may indicate, for instance, that they wish to exceed the number of activity points accumulated in a previous goal period by 10%, 15%, 20%, 50%, 100% and the like. The goal may also be set to be lower than the number of points accumulated in the previous goal period.

FIG. 144 illustrates an example device display settings interface. Through this interface, a user may control various parameters of a device's display or displays. For instance, the user may indicate what metrics are to be displayed including steps, calories and the like. Upon turning off one or more of these metrics, the metrics may be removed from an information display loop of the monitoring device such that the user may no longer view the metric through the device. The user may further indicate a wrist or hand on which the device is worn to help configure an orientation of text or other information that is displayed on the display(s) of the device. Other wear locations may also be provided in the list of options. For example, users may wear devices around their neck, on a belt around their waist, on a shoe, in a shoe, around their head, around the user's knee or elbow, ankle and the like. Depending on the wear locations various display and device characteristics may be set. For example, if the user is wearing the device at a location that is not easily visible while performing activity, the device may be automatically configured to use haptic output or audio output and/or to deactivate one or more displays. In another example, if the user is wearing the device in a visible location, one or more displays may be activated. In still other examples, haptic or audio output may be configured in terms of level of sensation or force and/or volume based on the location at which the device is worn. For example, the farther away from the user's ear the device is worn, the louder the volume may be set. Haptic feedback levels may be set at a higher level (e.g., amount of force) when the device is worn in a less sensitive area and set to a lower level when worn in a more sensitive area. These configurations may be automatically determined and set by the device and/or configuration system based on predefined rules. In some examples, the user may configure multiple displays of a device if the device includes multiple displays. For example, different setting options and values may be defined for each of displays 18 and 20 of device 10. Other settings of the display may be controlled including colors used, font sizes, font styles, types of animations, language, images and the like. Additionally or alternatively, the algorithms for identifying and/or measuring activity may also be automatically selected by the device and/or configuration computing system based on the wear location or other configuration options.

Figure 119A:
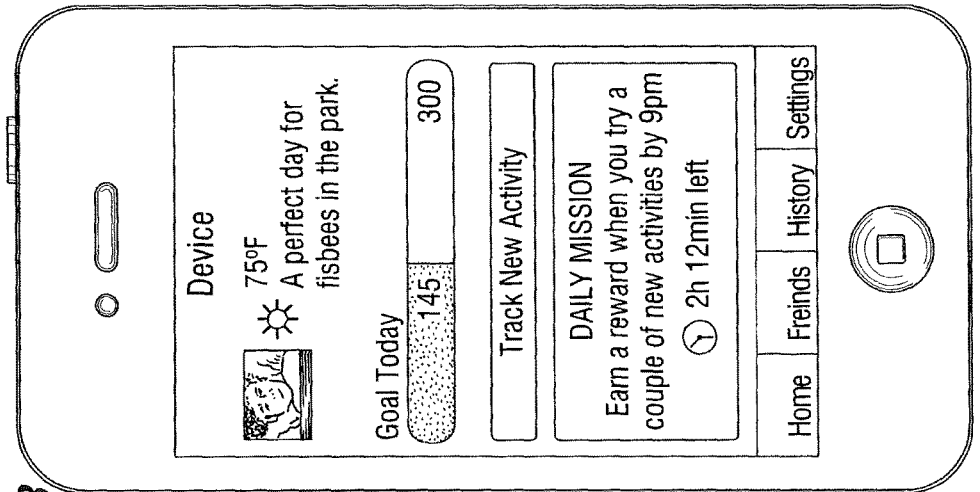
FIGS. 119A, 119B, 120A-120C, 121A-121C, 122A-122C, 123A, and 123B illustrate example activity tracking interfaces that include activity type tracking features.
Figure 119B:
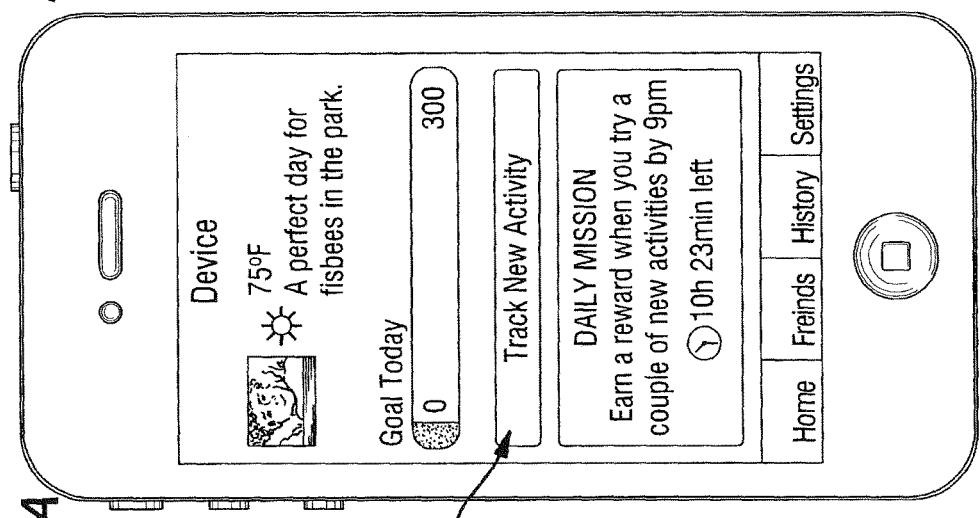

In some arrangements, activity may be detected and activity points may be accumulated regardless of a type of activity that was performed. In other arrangements, activity may be tracked along with the type of activity that was performed. FIGS. 119A and 119B illustrate example activity tracking interfaces that are configured to track a total amount of activity performed by the user as well as a type of activity. For example, option 11901 may be used to select a type of activity. Additionally or alternatively, option 11901 may be used to group activity detected into discrete sessions. The sessions may be smaller than, greater than or equal to a goal time period or other general predefined activity period. For example, the user may tag a portion of activity performed during the day as "Gym time" or "After work." In another example, a user may specify that a week of activity corresponds to a vacation time period. Other activity or time period designations may be used as desired or needed.

Figure 120C:
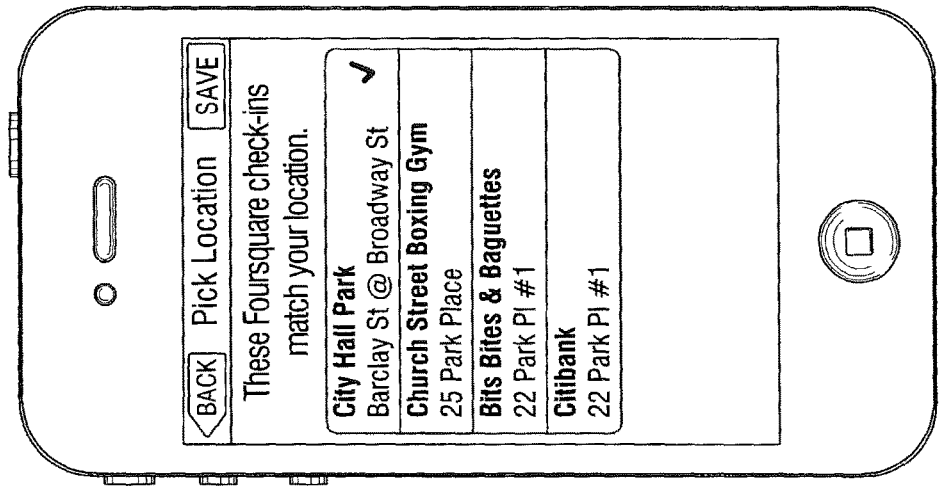
Figure 120B:
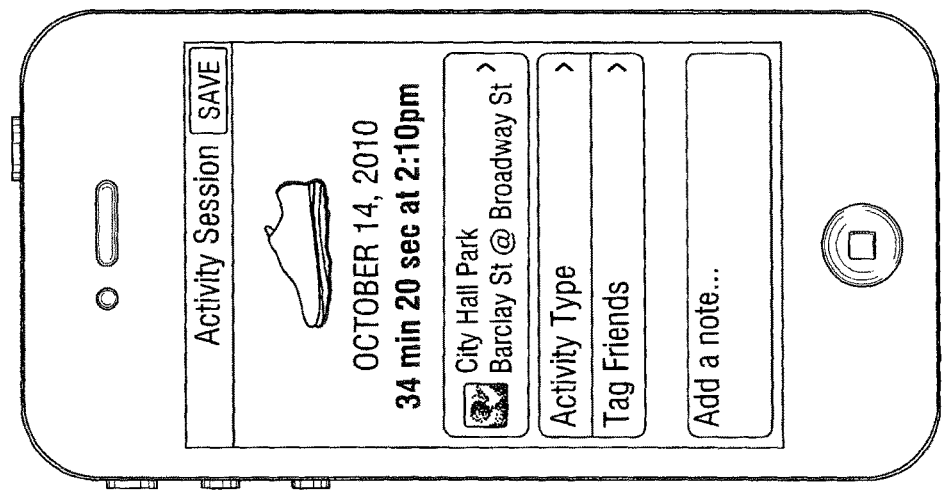
Figure 120A:
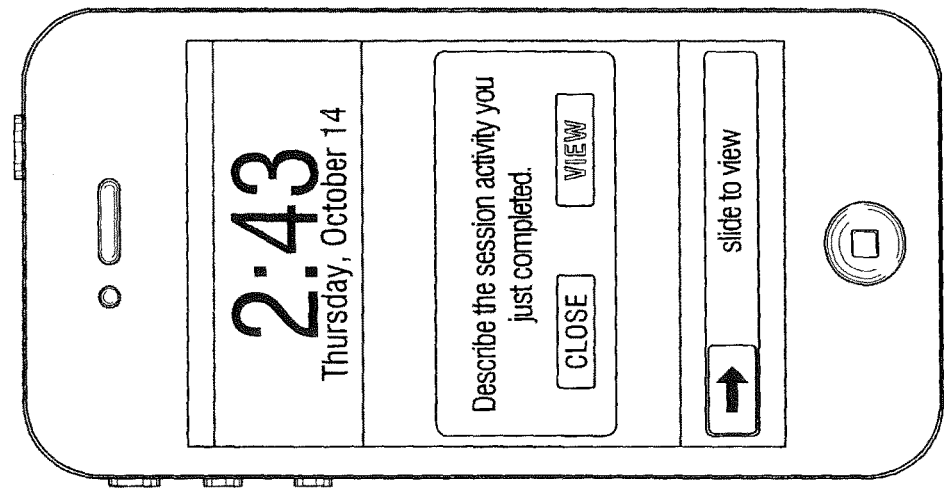

FIGS. 120A-120C illustrate example location marking interfaces that may be used by a user to identify a workout location upon completion of the activity session. For example, in FIG. 120B, a location may be automatically defined by the system based on the detected coordinate information and a database of buildings or places corresponding to those coordinates. A user may be able to edit the specified location, for example as shown in FIG. 120C, by selecting a different suggested or matched building or place. A building or place may be identified by a name, street name, address or other designation other than latitudinal and longitudinal coordinates.

Figure 121A:
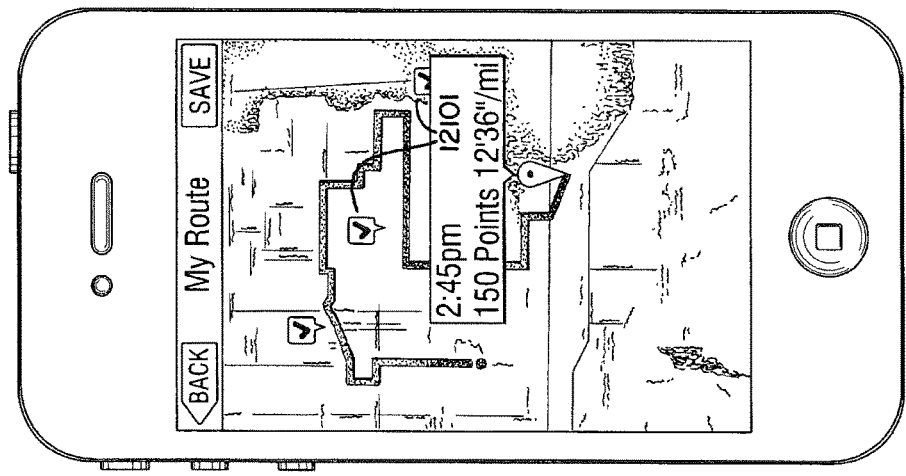
Figure 121B:
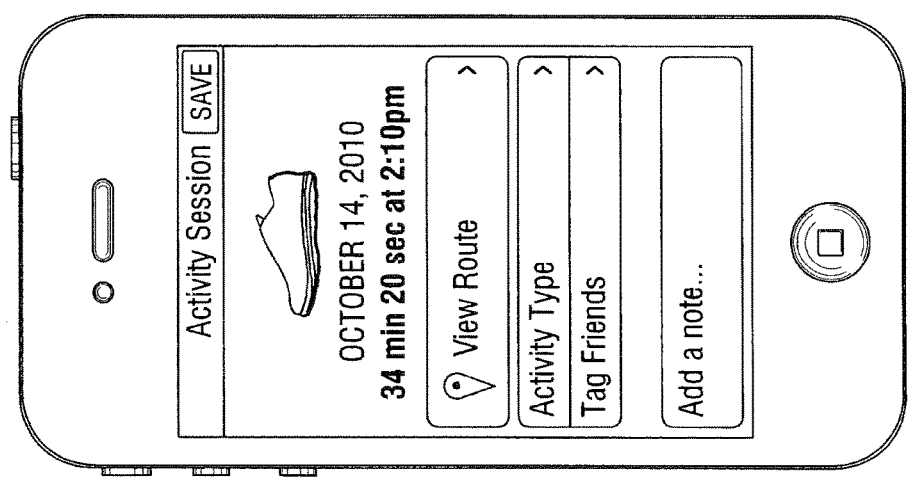
Figure 121C:
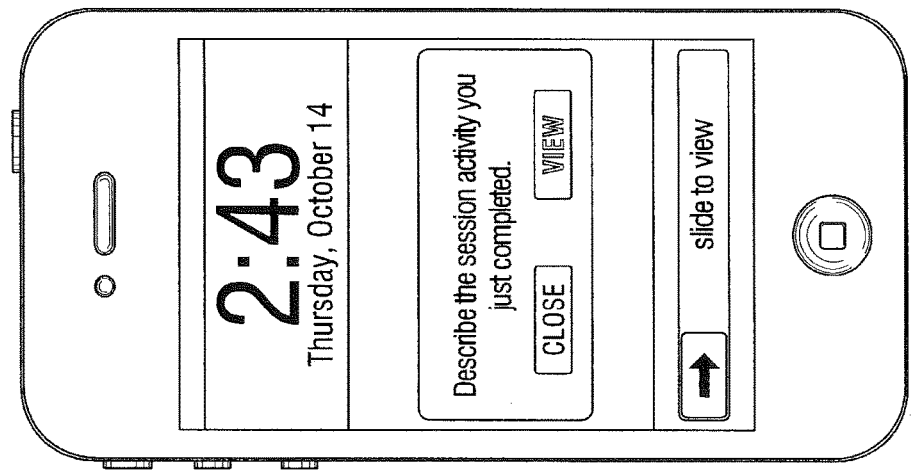

FIGS. 121A-121C illustrate the ability for a performance tracking application to record a route taken by a user. The route may be displayed on a map and various indicators may be displayed on the route. For example, indicators 12101 as shown in FIG. 121C may indicate particular known places that are near or along the user's route. Color of the route may also specify a number of calories burned, speed, pace, user's mood, terrain type (e.g., cobblestone, gravel, asphalt, incline, decline, flat, etc.) and/or combinations thereof. Hovering over any of the indicators or portions of the route may provide further information such as a name of a place, an amount of athletic activity performed at that point, terrain type, user's mood, speed and the like.

Upon completion of, during or prior to an athletic workout, a user may designate a type of activity that was performed, is being performed or will be performed. This may allow the application to better calibrate sensor data and algorithms to measure performance. For example, accelerometer signals may appear differently depending on the type of activity (e.g., cycling versus squash). Accordingly, different data processing algorithms may be used to more closely align the data with the user's actual amount of activity (e.g., steps taken, calories burned, miles run or moved).

Figure 122C:
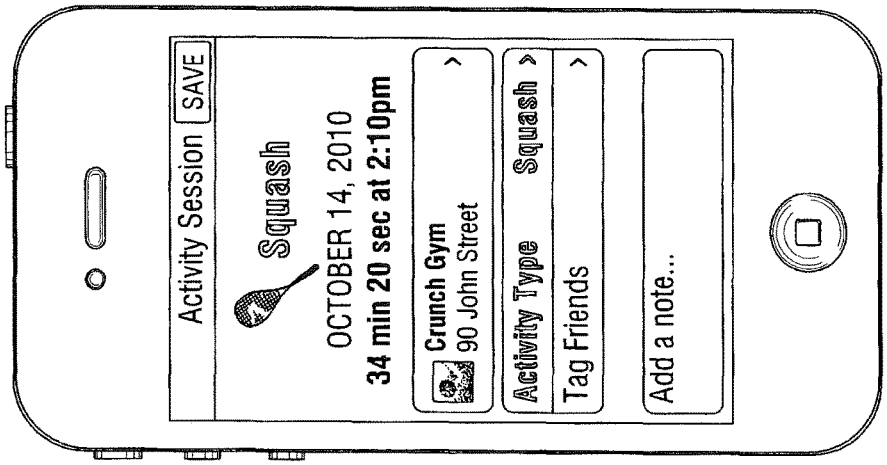
Figure 122B:
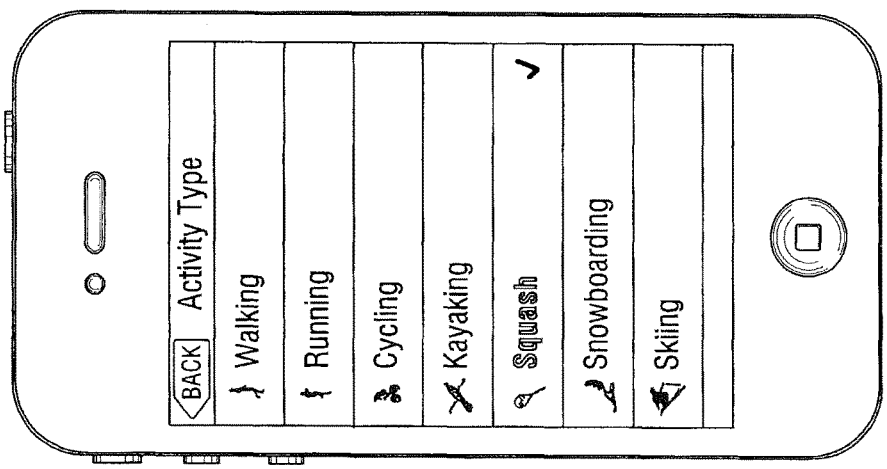
Figure 122A:
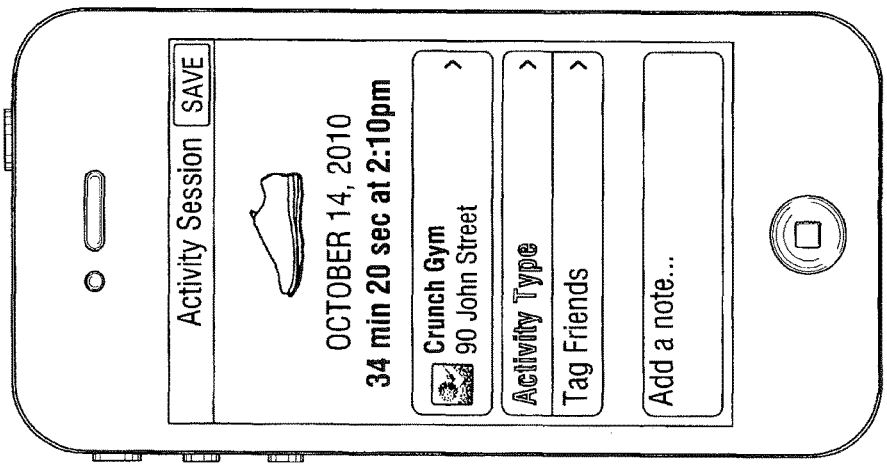

FIGS. 122A-122C illustrate example user interfaces through which a user may select the activity type. Upon selection of the activity type, the application may automatically identify and use a corresponding algorithm to process sensor data. The identified activity type may further be stored in association with the activity data collected during the performance of the activity. The beginning and end of the activity performance may be marked or identified by the user or may be automatically marked or identified based on detecting periods of inactivity reaching a specified threshold.

Figure 123B:
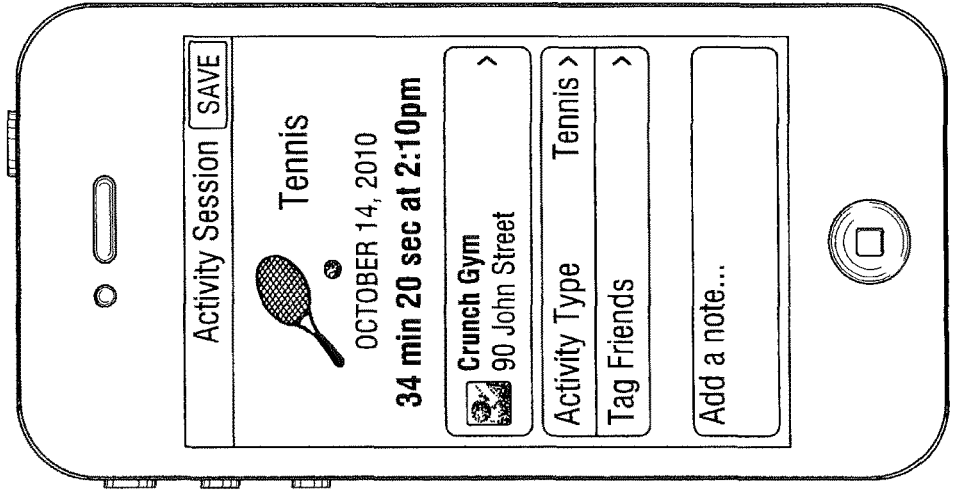
Figure 123A:
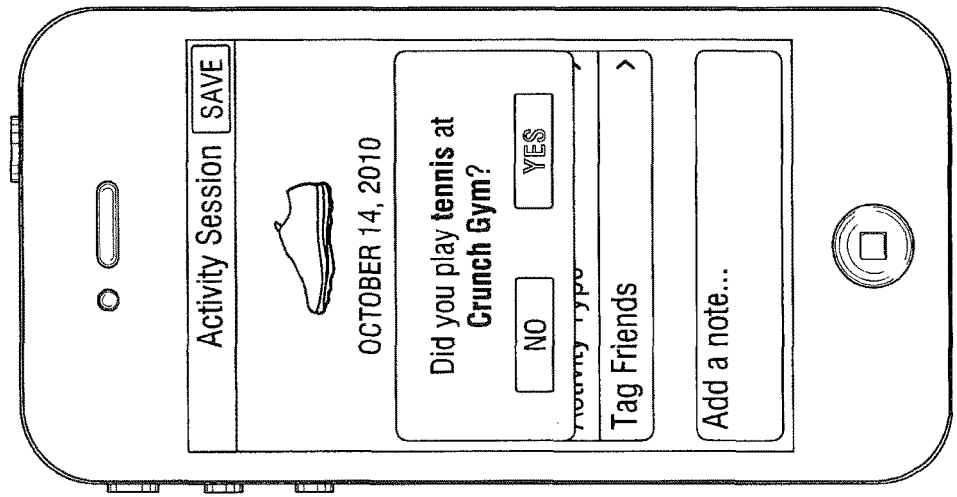

Additionally or alternatively, the activity monitoring application may automatically suggest a location and/or activity type. FIGS. 123A and 123B illustrate an application interface through which a suggested location and activity type are determined. The location may be determined based on a database of previous activity locations or workout locations used by other users or a general database of locations and places defined by coordinates. The activity type, on the other hand, may be determined based on matching the sensor signal with signals of known activities. If there is a substantial similarity between the signal in question and a signal for a predefined activity, the application may suggest or define the user's activity as the predefined activity. In other examples, activity type may be automatically suggested or determined by associating an activity type with a location. The location may have been previously stored by the user and a type of activity may have been previously associated with the location (e.g., by the user). For example, the user may have identified that he or she was running at a high school. Accordingly, the application may automatically suggest a running activity type if the user's location is determined to be the high school. In other examples, the application may identify a type of business or location through on-line directories or network databases such as on-line business listings and the like. The application may then infer, based on the type of business or location, a type of activity that the user is performing. For example, if the user is located at an address corresponding to a yoga studio, the application may suggest that the activity type corresponds to yoga. Other methods and techniques for determining an activity type may also be used.

Figure 124A:
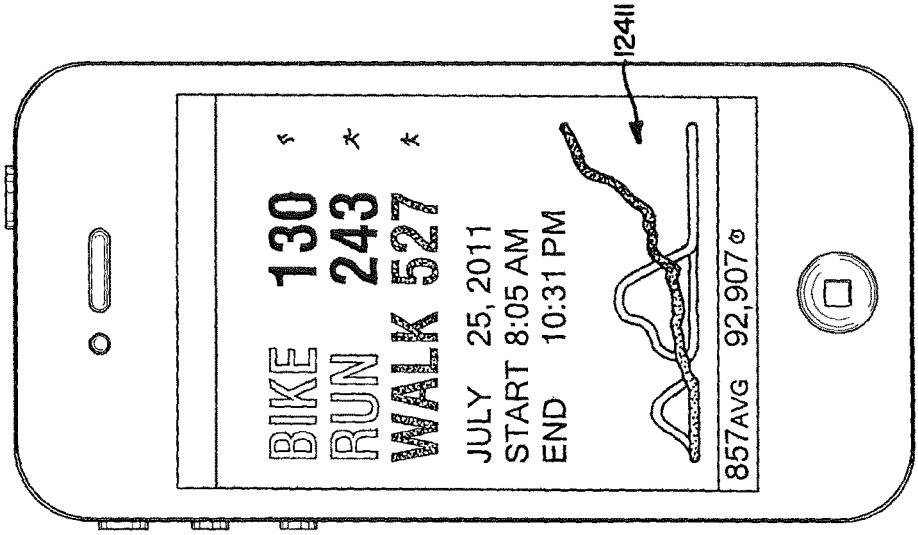
Figure 124B:
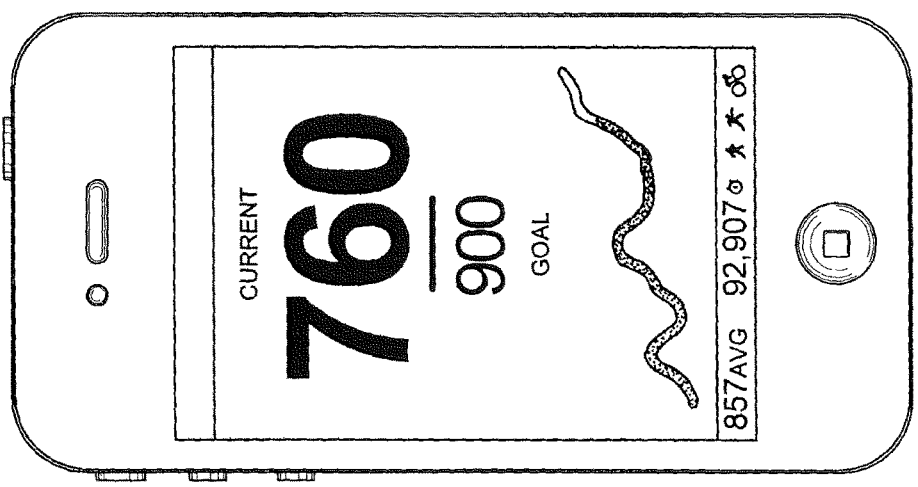
Figure 124C:
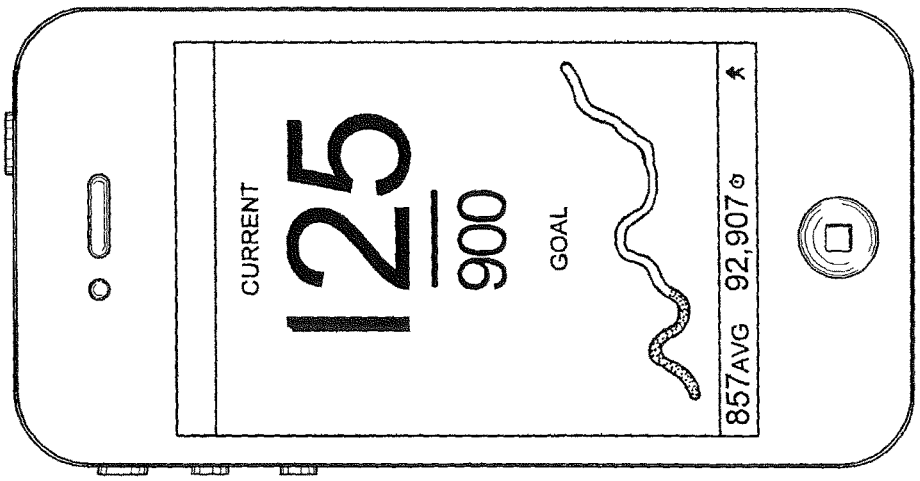
Figure 125C:
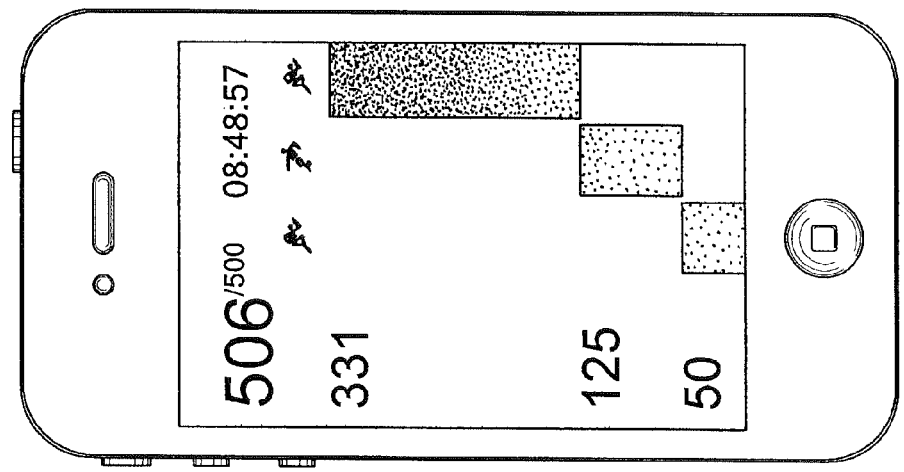
Figure 125B:
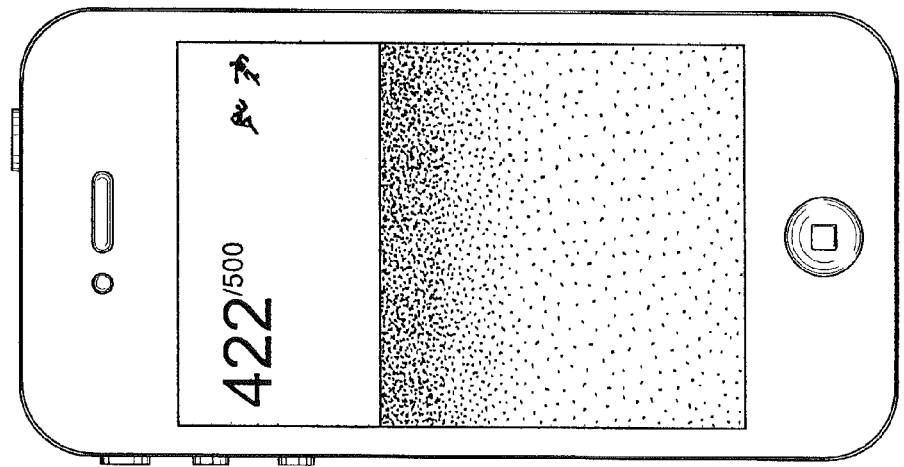
Figure 125A:
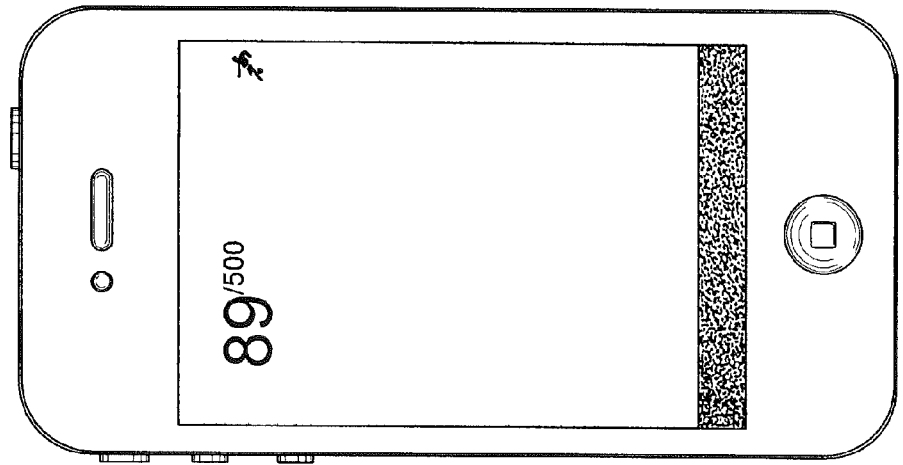

FIG. 124A-124C illustrate example activity tracking interfaces in which an activity type is identified. In FIG. 124A, for example, the type of activity contributing to the activity total is indicated in portion 12401 using images or icons 12403. Icon 12403 may represent the type of activity such as running, aerobics, biking, weight lifting and the like. FIG. 124B illustrates an interface with multiple activity types indicated.

FIG. 124C illustrates an example breakdown view in which the detected/recorded activity is divided into contributing activity type. For example, each of a biking, walking and running activity type is displayed along with a corresponding amount of activity of that activity type performed. Graph 12411 may display an amount of activity by type versus time. The amount of activity corresponding to each of the activity types may be distinguished in various manners including using different colors, patterns, shapes, sizes, transparencies, color or grayscale gradients and the like and/or combinations thereof.

Figure 126A:
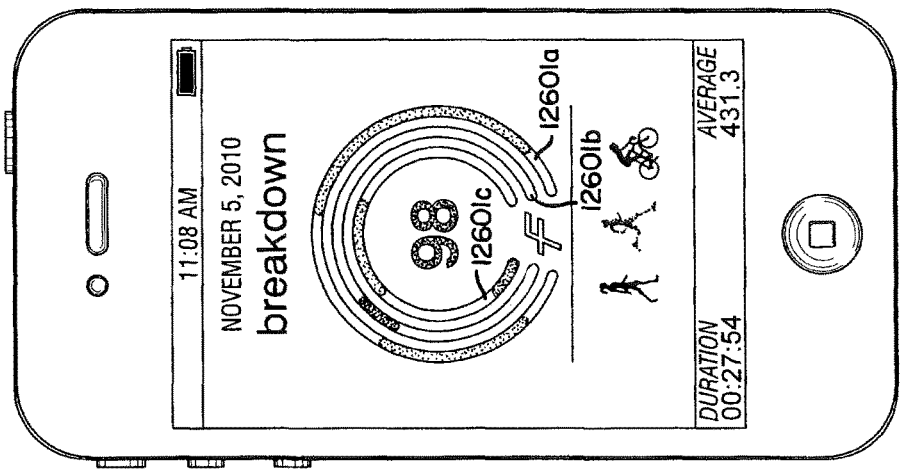
Figure 126B:
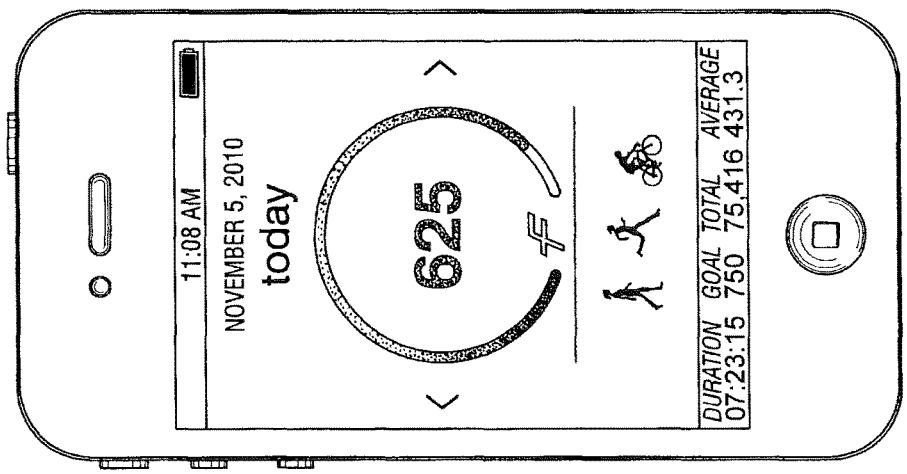
Figure 126C:
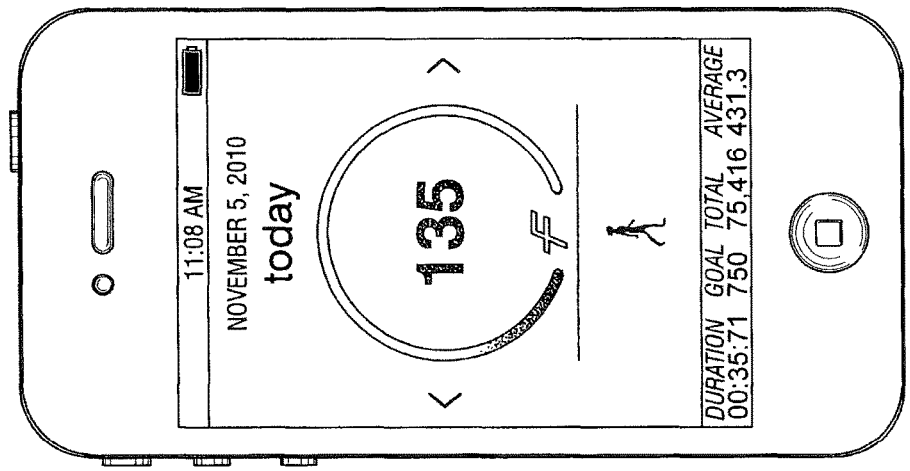
Figure 127A:
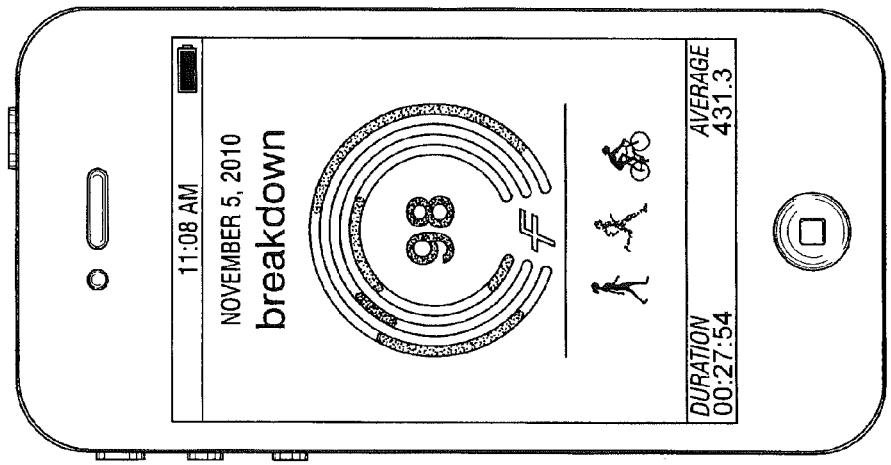
Figure 127B:
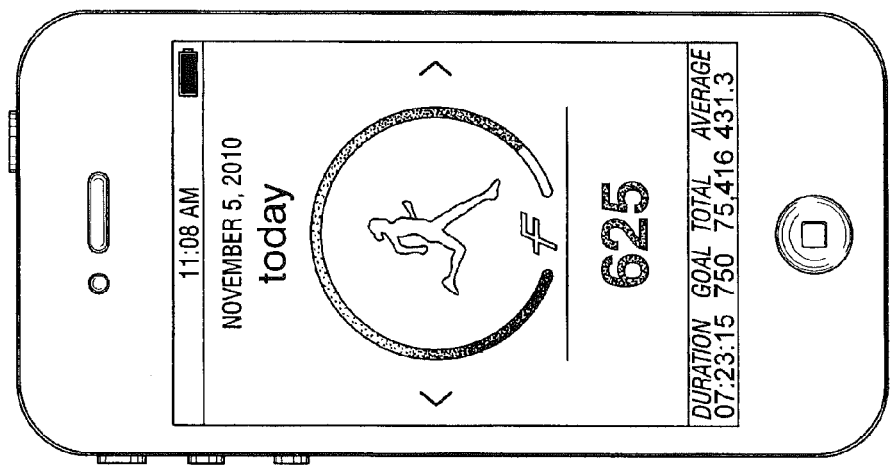
Figure 127C:
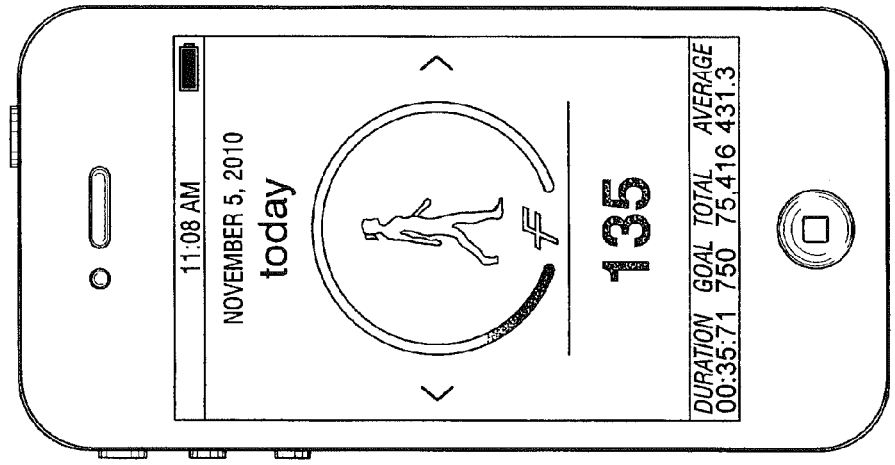
Figure 128C:
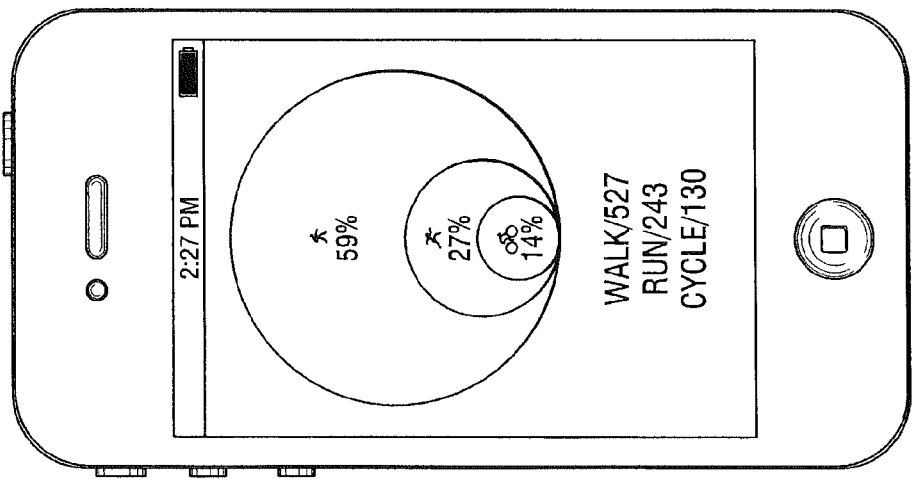
Figure 128B:
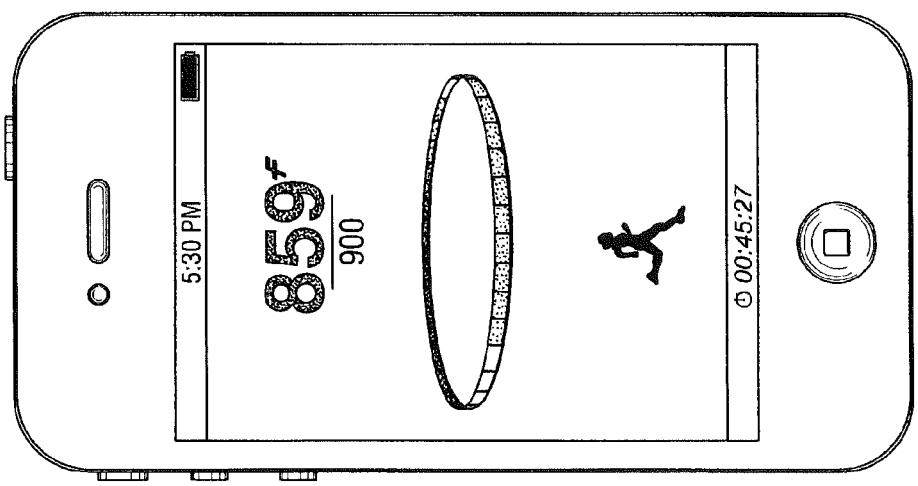
Figure 128A:
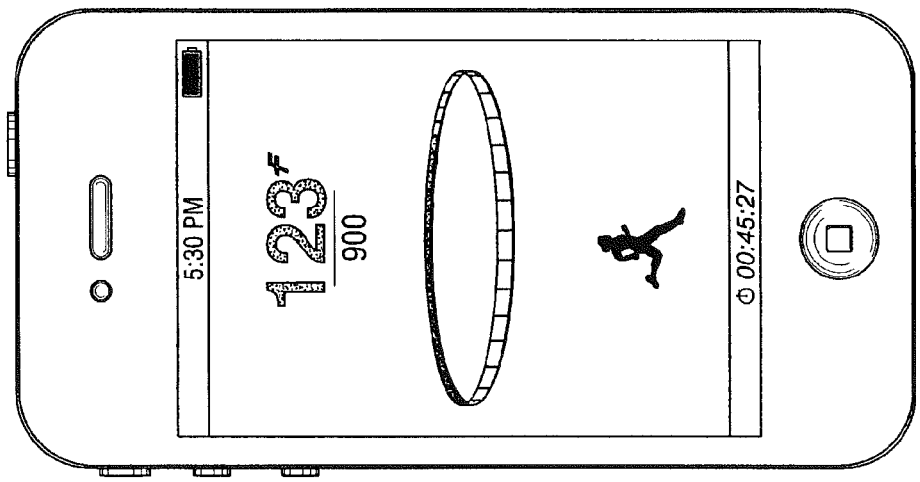
Figure 129C:
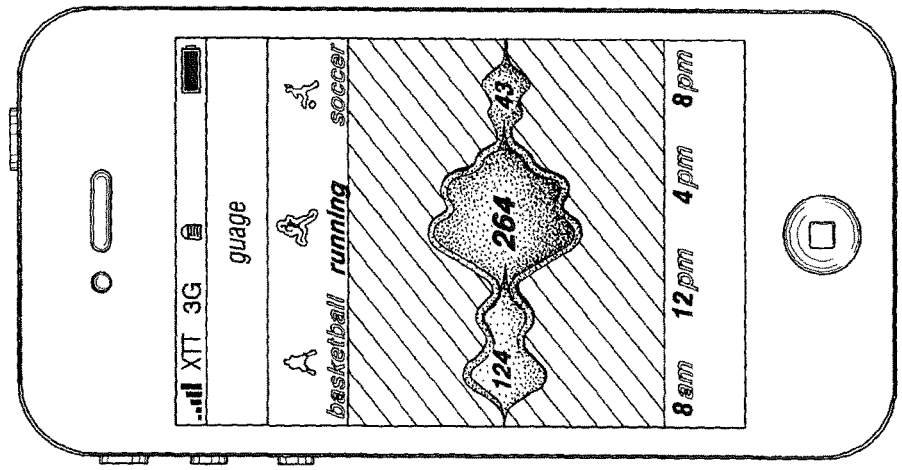
Figure 129B:
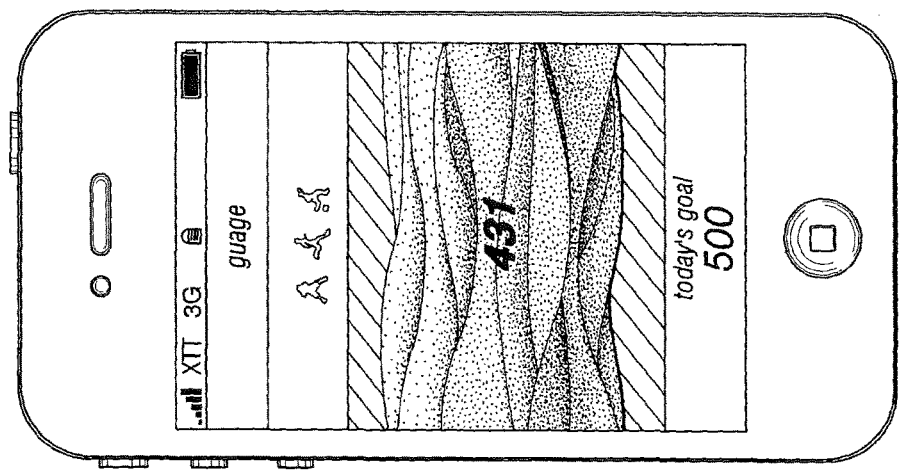
Figure 129A:
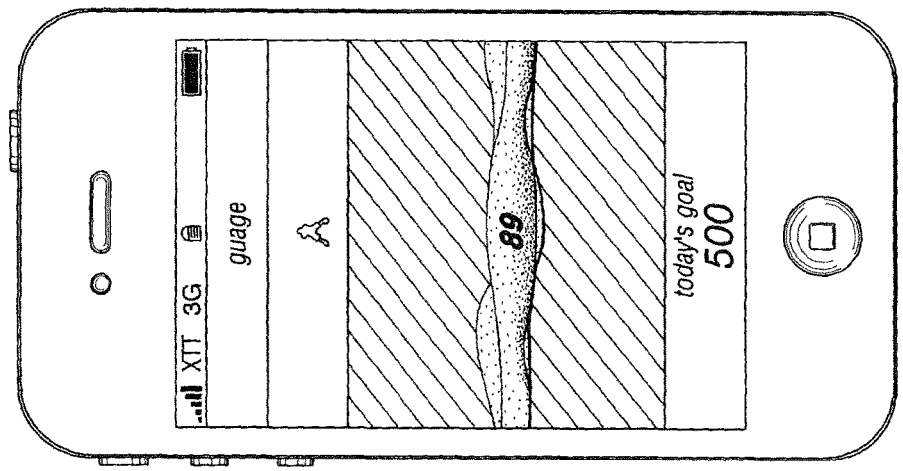
Figure 130C:
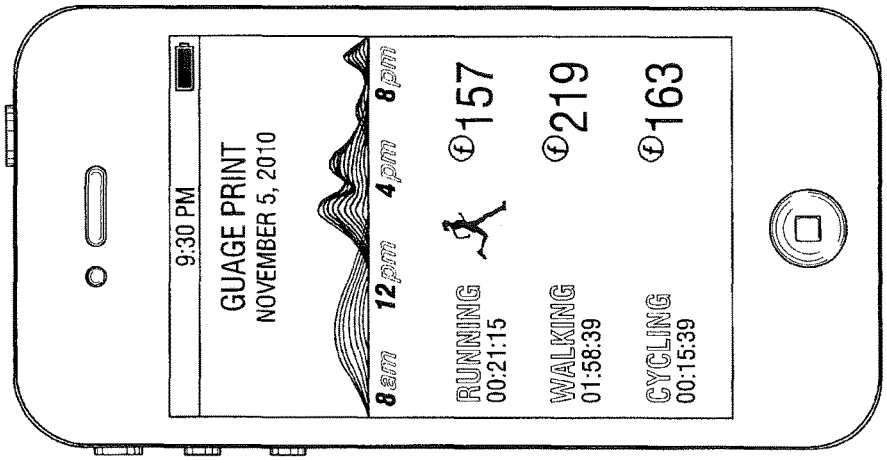
Figure 130B:
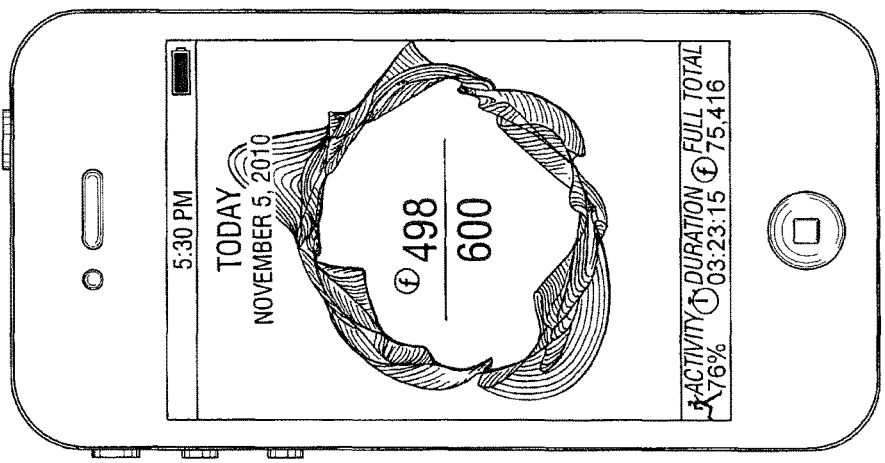
Figure 130A:
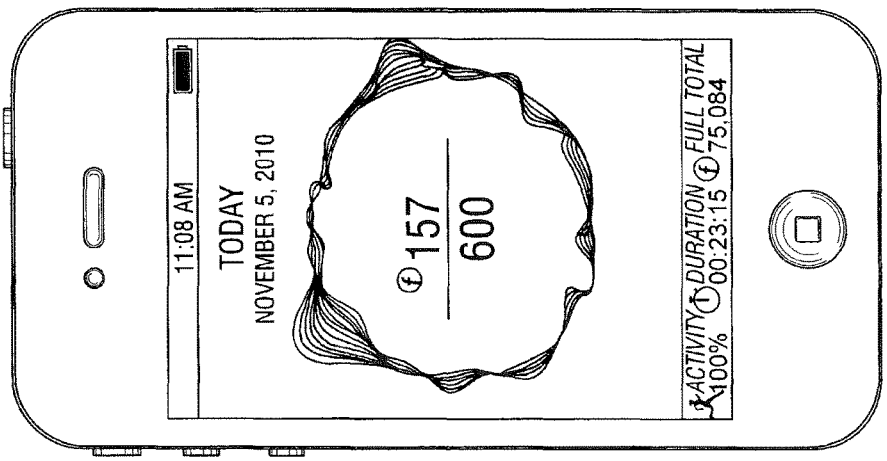
Figure 132A:
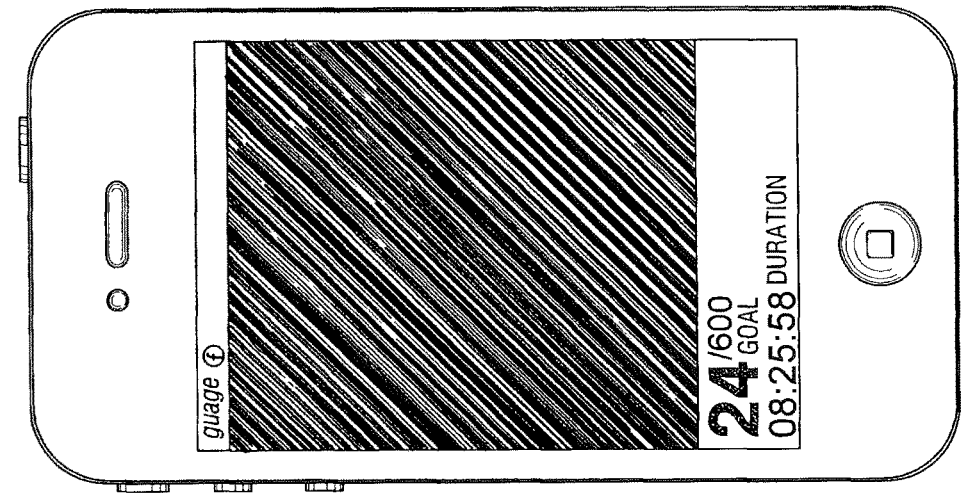
Figure 132B:
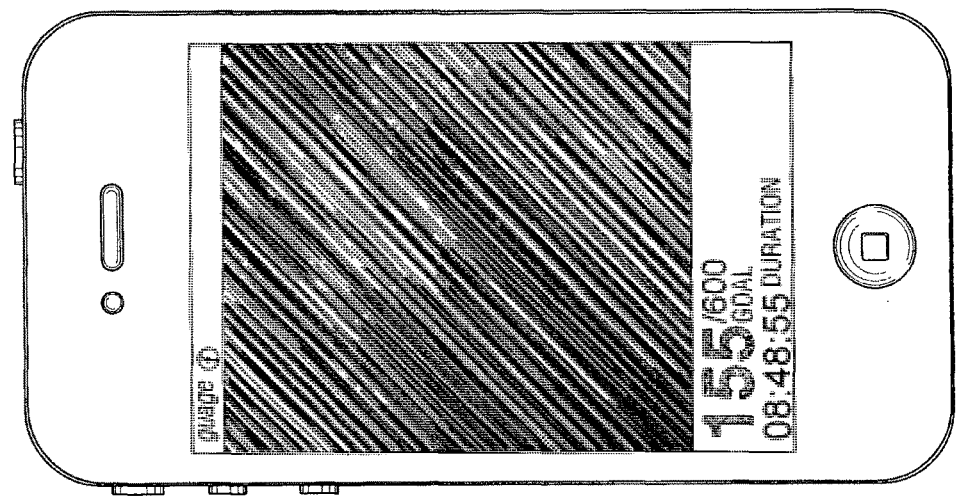
Figure 132C:
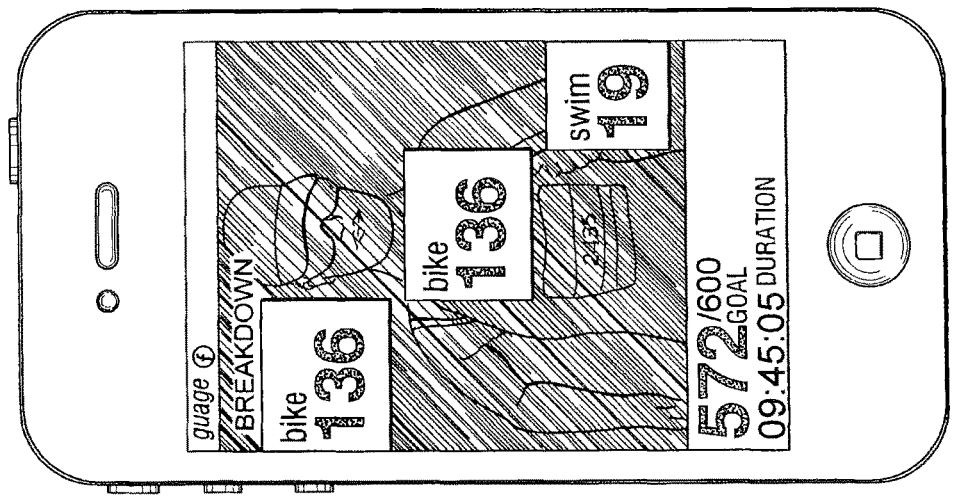
Figure 133A:
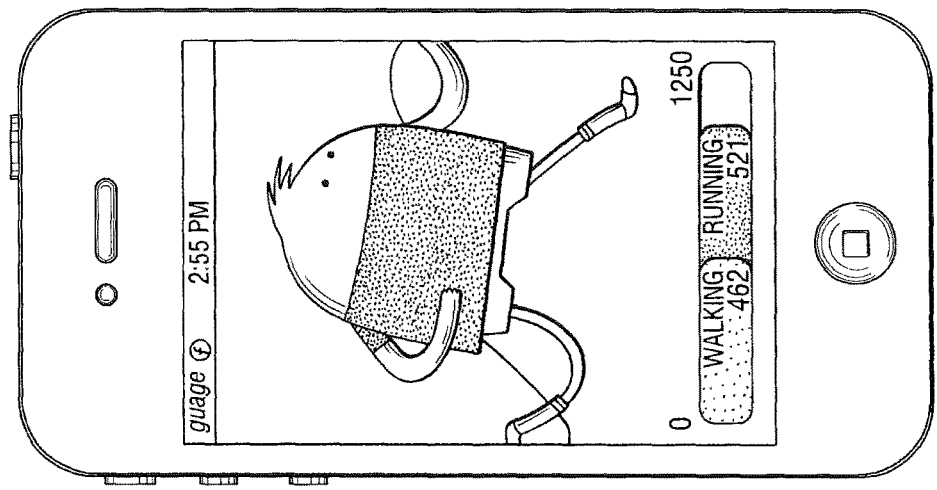
Figure 133B:
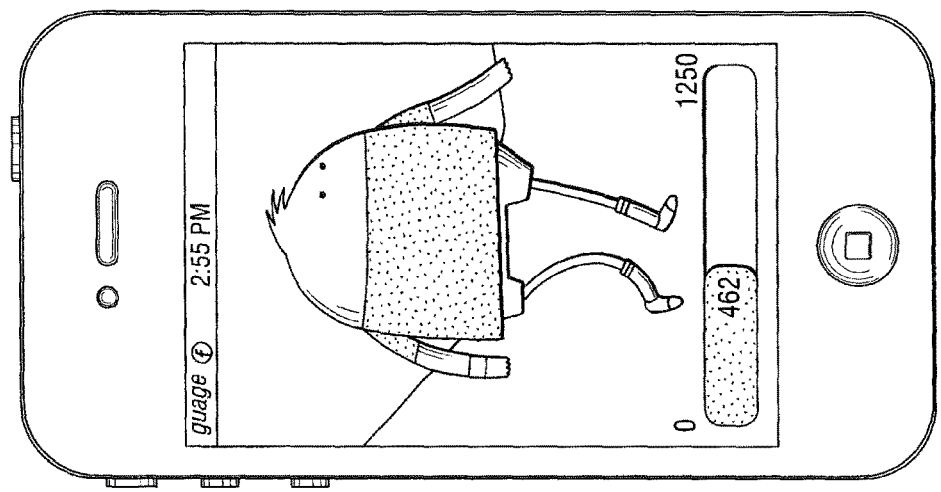
Figure 133C:
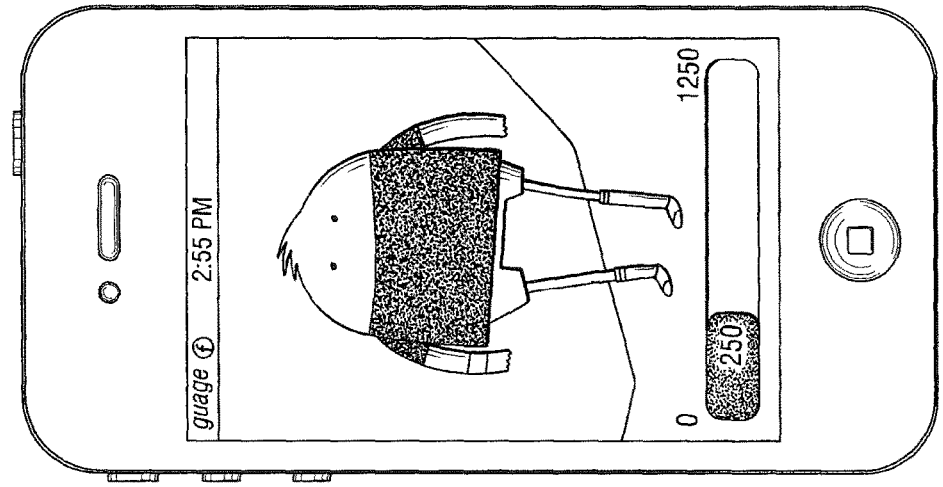

FIGS. 125A-125C, 126A-126C, 127A-127C, 128A-128C, 129A-129C, 130A-130C, 131A-131C, 132A-132C, 133A-133C and 134A-134C illustrate additional examples of activity tracking interfaces in which activity type may be used to categorize or divide the performed activity. In FIG. 126C, for example, each arcuate portion 12601*a*, 12601*b* and 12601*c* may correspond to a different activity. The portion filled in in each of arcuate portions 12601*a*, 12601*b* and 12601*c* may correspond to a time of day at which the activity was performed.

Figure 134C:
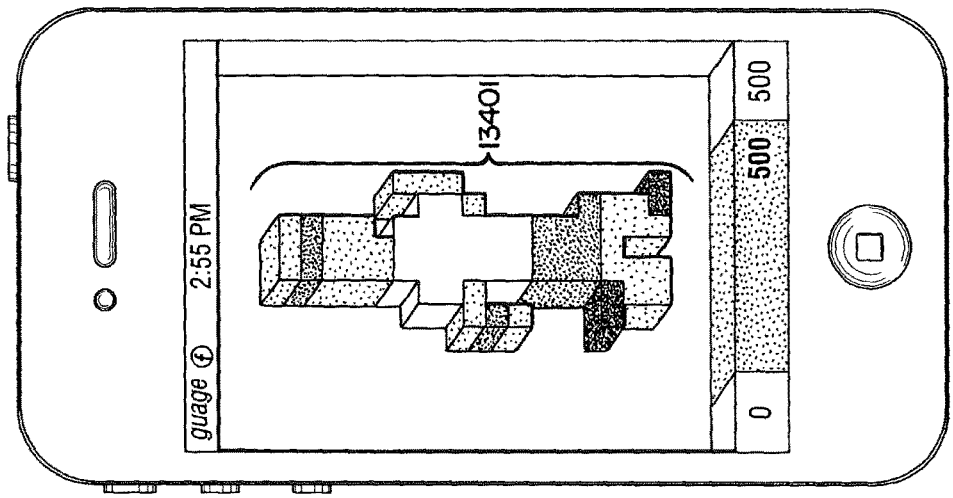
Figure 134B:
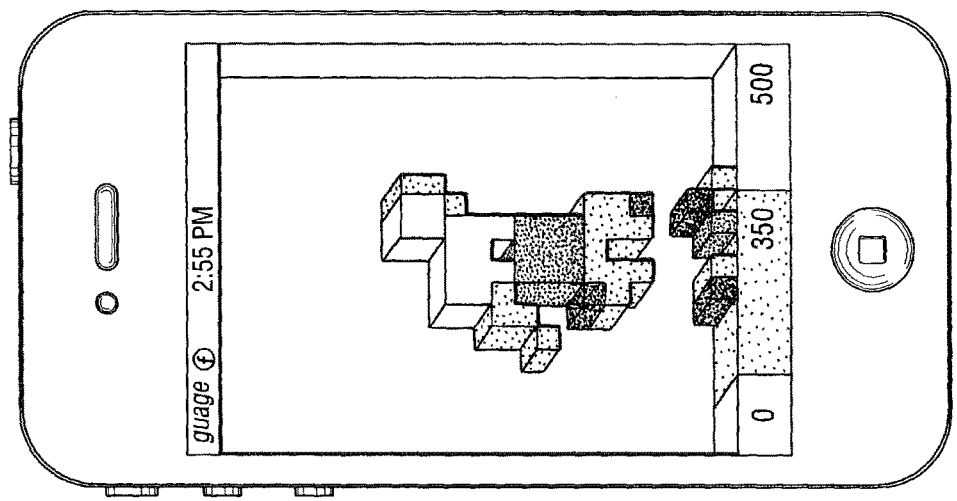
Figure 134A:
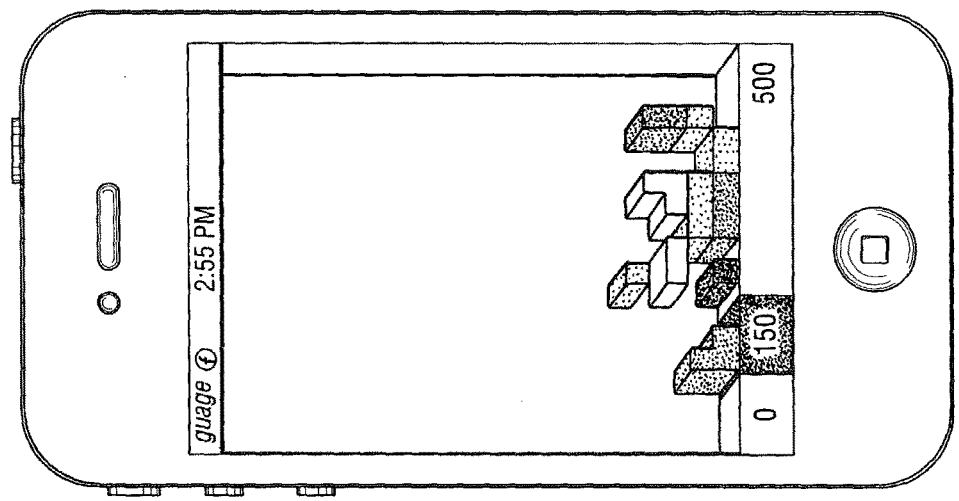
Figure 135B:
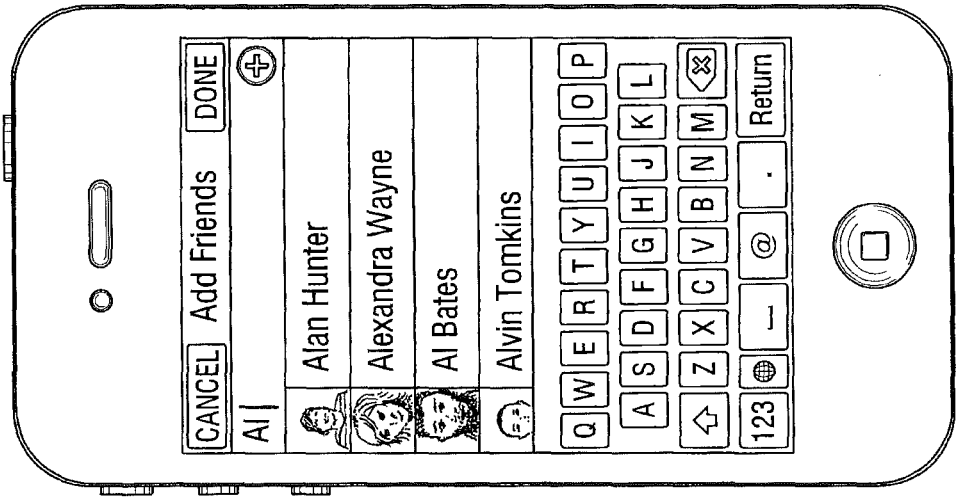
Figure 135A:
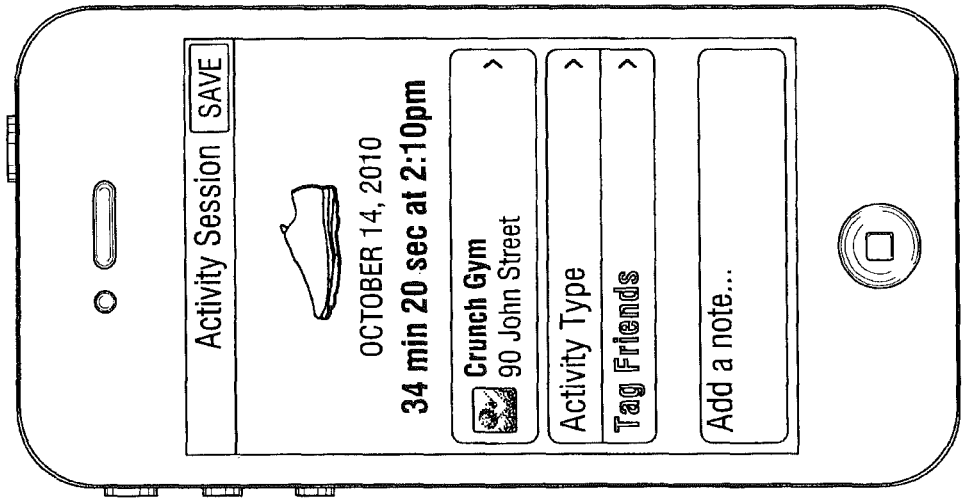

In another examples, FIG. 134C may illustrate a user's activity in the form of interlocking shapes or blocks 13401. The different shapes of the blocks or color of the blocks may correspond to the activity type. Additionally or alternatively, the size of the shapes may correspond to the amount of activity of that type that was performed. Other variations of visual or graphical representations may be used to represent activity type, amount of activity of that activity type and/or a time at which the activity of the activity type was performed in the same image or using different images. Activity may be summarized according to alternate or additional categorizations and divisions as desired and such categorizations may also be reflected and conveyed visually.

FIGS. 135A-135D illustrate a series of interfaces through which a user may tag activity session with friend information. For example, a user may add friends to a activity session by searching through a list of friends or by defining a new friend. This information may then be stored in association with that particular session. More than one friend may be added to the activity session, if appropriate or desired.

Figure 136C:
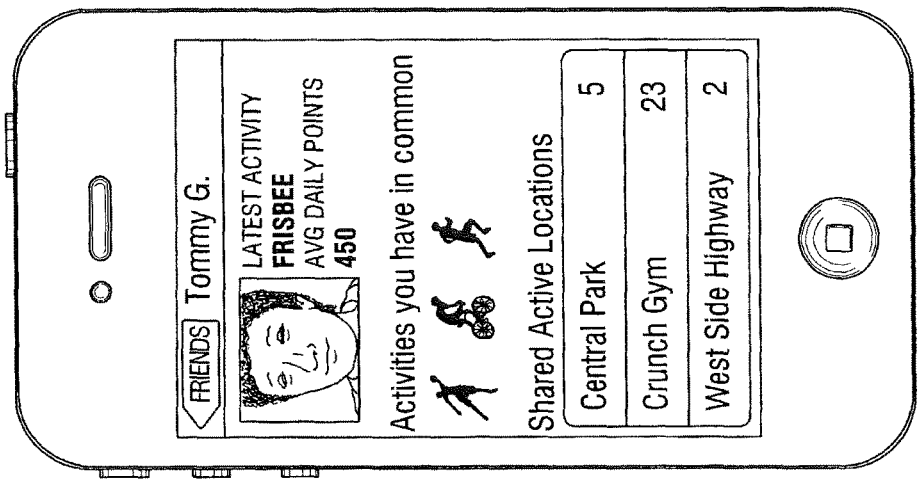
FIGS. 136A-136C illustrate example interfaces for comparing activity of a user with others.
Figure 136B:
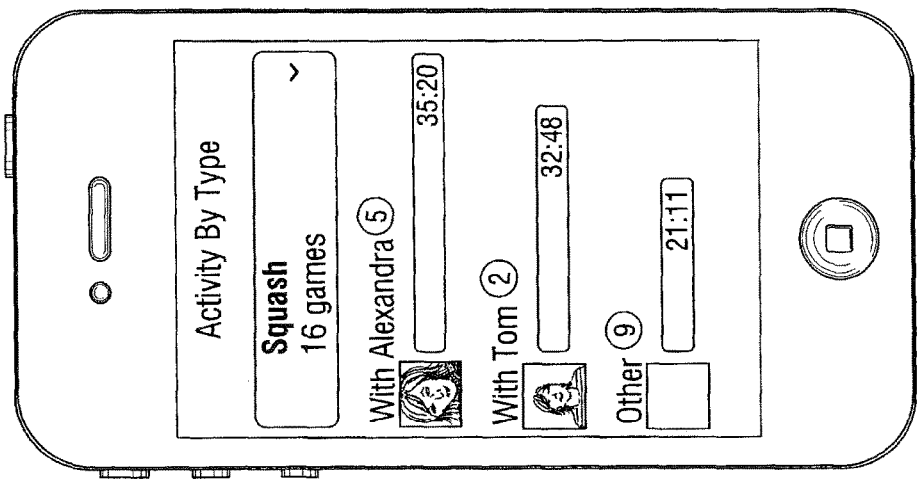
Figure 136A:
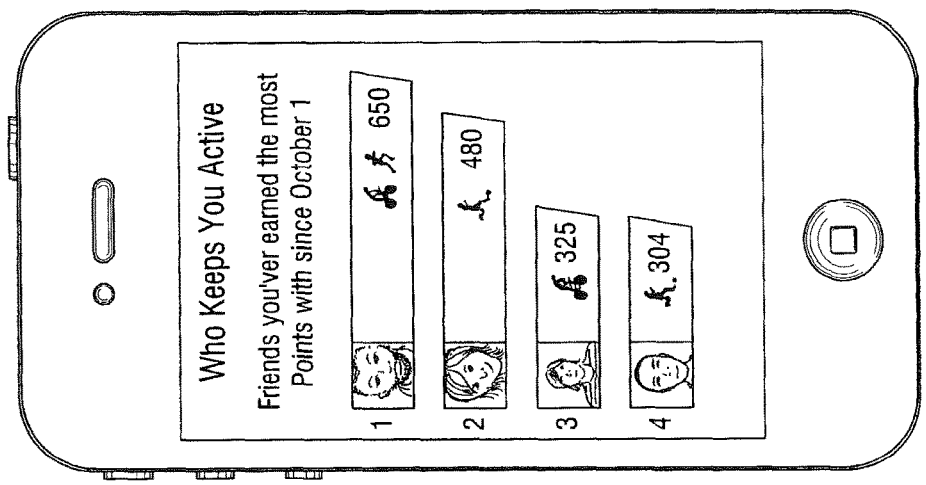

FIGS. 136A-136C illustrate example interfaces for displaying aggregate activity information for activities performed with friends. Friends may be organized according to an amount of activity performed with that friend overall (FIG. 136A) or for a specific type of activity (FIG. 136B). Selecting a friend, as shown in FIG. 136C, may display the user's profile as well as common activity interests and/or shared activity locations.

Figure 137A:
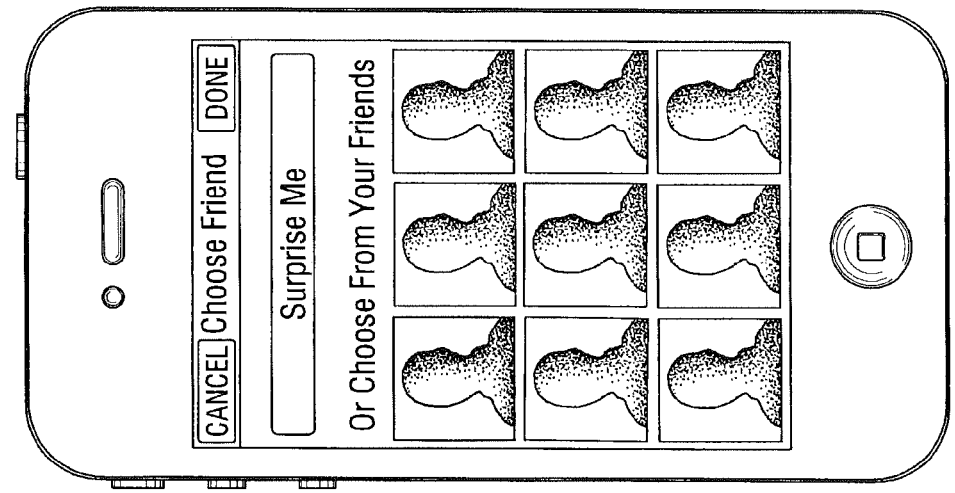
FIGS. 137A, 137B, 138A and 138B illustrate example activity competition interfaces.
Figure 137B:
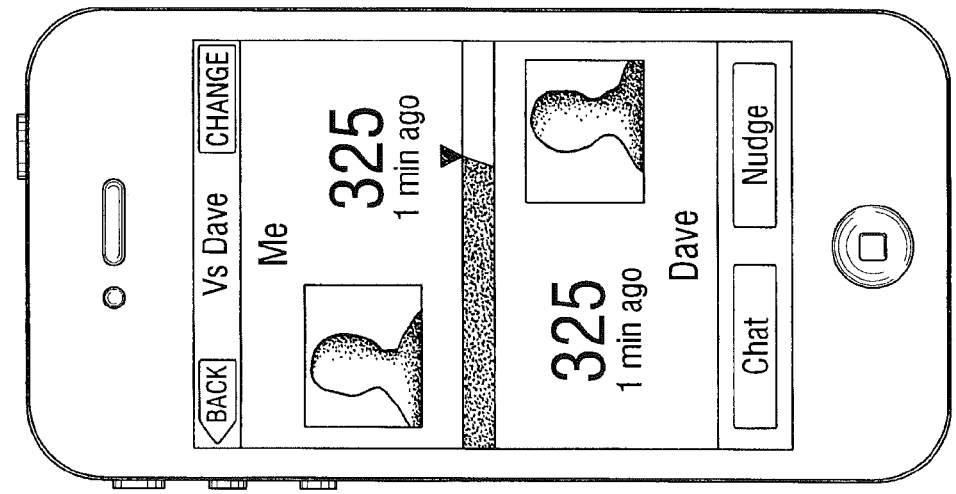

FIGS. 137A and 137B illustrate example competition or game interfaces that may be displayed when a user chooses to compete with a friend. The interfaces may also be used to provide a comparison between the amount of athletic activity performed by the user and another user. Accordingly, a user may select any friend or user with which to compare athletic activity, as shown in FIG. 137B. A graph may then be displayed, as shown in FIG. 137A, illustrating a comparison of athletic activity. A variety of graphs and comparison formats may be used.

Figure 138B:
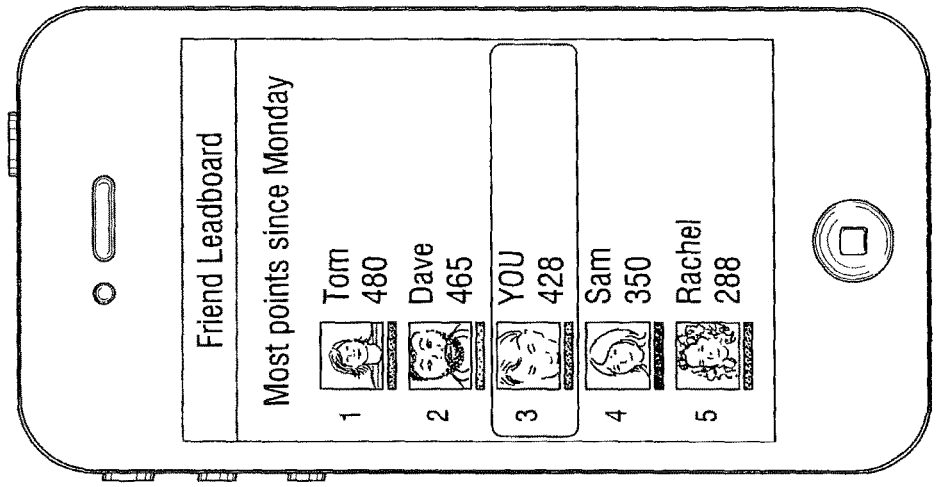
Figure 138A:
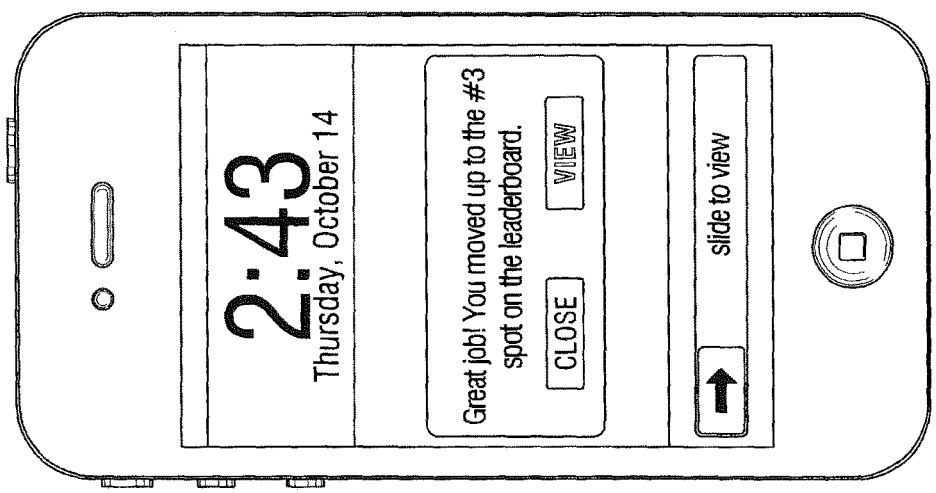

FIGS. 138A and 138B illustrate a series of interfaces through which a user may access a leaderboard identifying where the user places among all friends or users or a group. The user may be highlighted by an indicator such as a rectangular outline or highlighting.

Figure 139B:
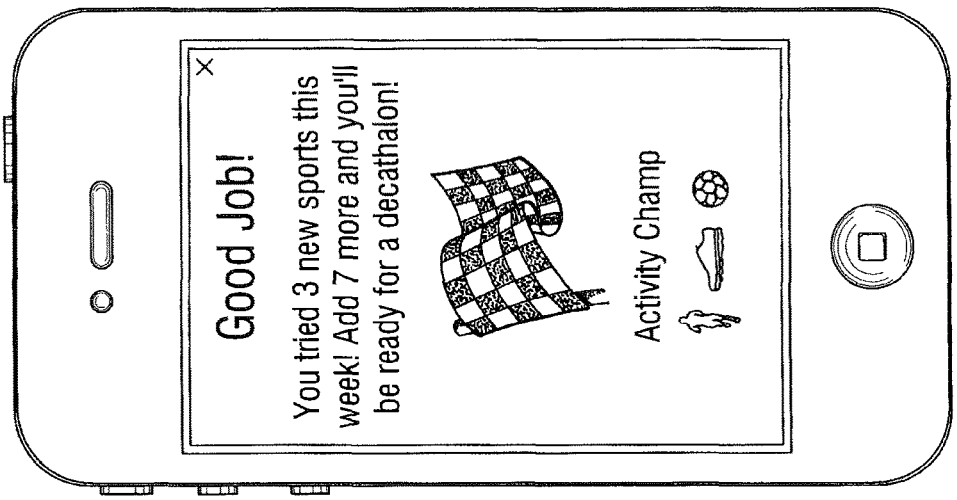
FIGS. 139A, 139B, 140A and 140B illustrate example rewards and achievement notifications for user activity.
Figure 139A:
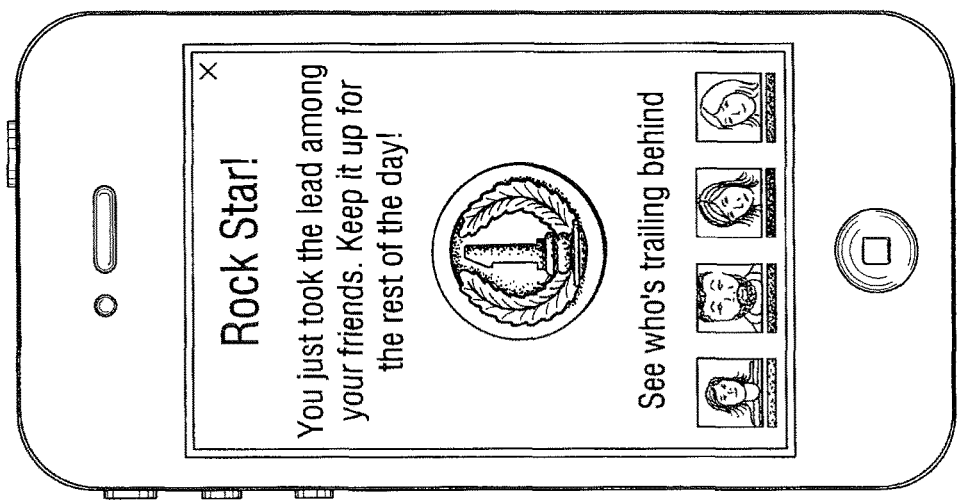

FIGS. 139A and 139B illustrate example achievement interfaces configured to provide a user with encouragement or an indication of some achievement such as a new personal best (e.g., for a 1 mile run) or completion of a goal (e.g., running 10 miles for the first time).

Figure 140B:
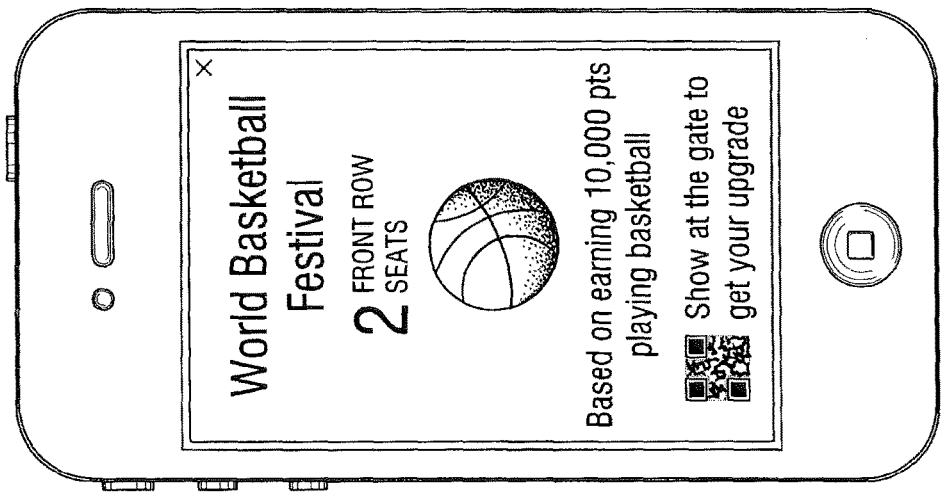
Figure 140A:
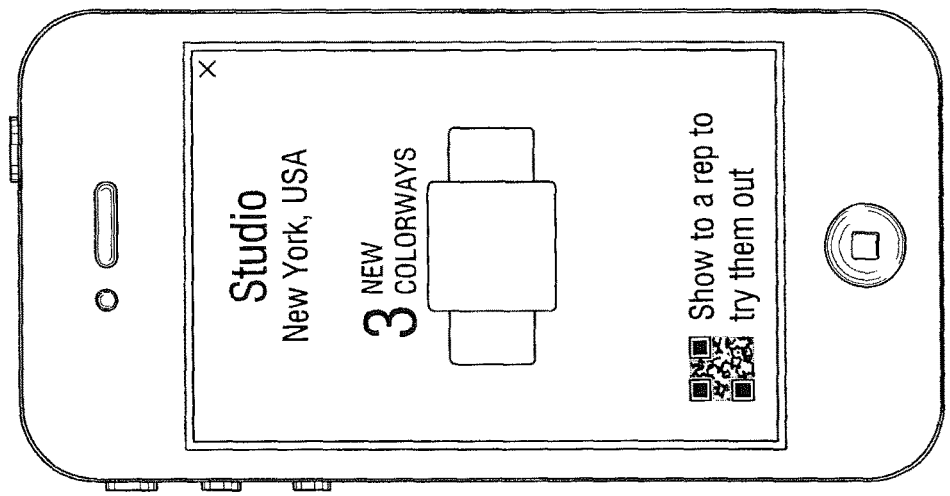

FIGS. 140A and 140B illustrate example interfaces that provide special access to events or locations. The interfaces may include a scanning code or pattern 14001 that may be scanned (on screen) by event or place staff to verify authenticity and admittance. Such interfaces may also include discounts or other special offers for products, services, food items and the like.

According to another aspect, joint or multi-user goals may be defined to provide team-oriented activities. In one example, an overall goal may be defined for a group of users, where each user is required to complete a portion of the overall goal. Activity in excess of one user's portion might not be applied to the overall goal or contribute to completion of another user's portion of the goal so that each user must complete his or her own portion. This may encourage the users to perform the activity required due to peer-pressure or a sense of responsibility if the overall goal is not reached. In other arrangements, excess activity by one user may contribute to the completion of another user's portion of the goal. Limits may be set to an amount of activity that may be contributed to other user's goal portions. In yet other examples, the multi-user goal might not have predefined user portions. Accordingly, users may contribute as much as they would like to the overall goal.

Multi-user goals may include visualizations or user interface elements that celebrate the goal achievement upon completion. For example, the overall goal may be represented by a set of bowling pins. Each user may be responsible for knocking his or her pin down by completion his or her portion of the overall goal. Upon a user completing his or her portion of the goal, an appearance of a corresponding bowling pin may change to appear knocked over. Once all users have completed their goal portions, a celebratory message, visualization or other indicator may be displayed.

Figure 141:
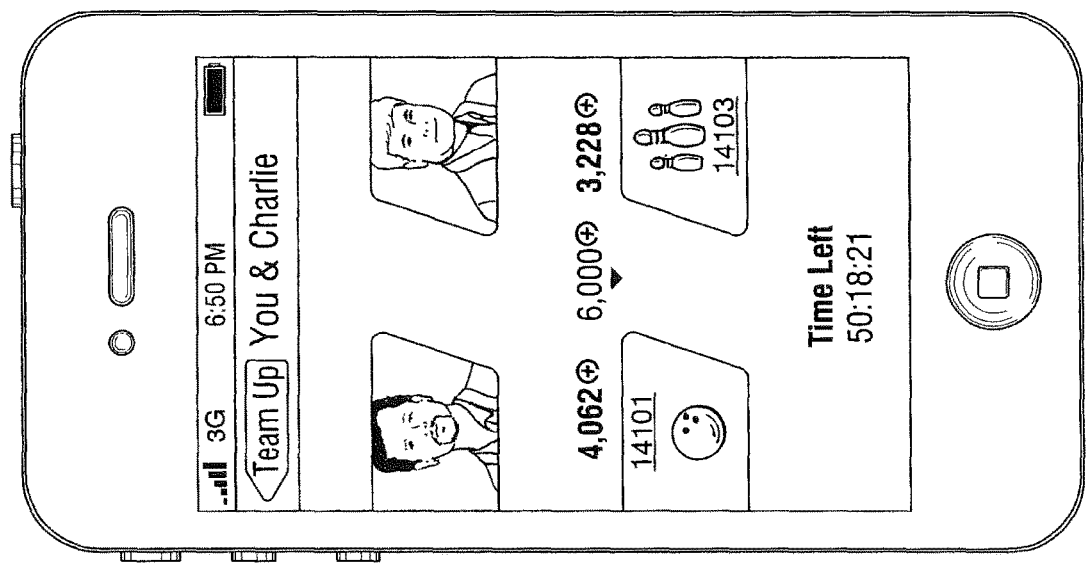
FIG. 141 illustrates an example interface displaying information for tracking progress toward a team oriented goal.

FIG. 141 illustrates another example visualization for a multi-user goal. In this example, two users may be jointly attempting to achieve a goal of accumulating 6,000 activity points. The first user's progress 14101 may be represented by a bowling ball while the second user's progress 14103 may be represented by a set of bowling pins. In order to virtually knock down the bowling pin, the users may be required to move their progress bars to a middle portion where the bowling ball and the bowling pins would meet. Accordingly, the users may be required to complete their own portions in order to achieve the goal. The goal portions, as illustrated, are evenly divided. However, the goal portions might not be evenly divided and one user may be required to perform more activity than the other. Various goal splits may be used and/or defined as selected by a user, a coach, an activity tracking service or the like.

As described, the device 10 or device 4300 (FIG. 43) is capable of interacting with another device 10. Accordingly, a first user wearing the device 10 can compare their activity with the activity of a second user wearing a second device 10. The indicator system 20 on the device can indicate a first level of activity of the first user while also indicating a second level of activity of the second user. Similarly, the indicator system 20 on the second device can indicate the second level of activity of the second user while also indicating the first level of activity of the first user. The activity data of the other user can be communicated to the other device via wireless communication from a mobile device or remote site. In this configuration, the plurality of lights of the respective indicator system can be considered to be divided into a first segment and a second segment. The first segment may comprise a first group of ten of the light members while the second segment may comprise a second group of ten of the light members. Thus, the first user's activity level is displayed on the first segment of the indicator system and the second user's activity level is displayed on the second segment of the indicator system. The indicator system may be illuminated when a user depresses the input button to check progress of each user's activity level. In this aspect of competition between two users, there is no end goal. If one of the users reaches the full meter limit on the indicator system, the system will increase the upper limit and adjust each of the user's progress levels.

In another aspect, a first user and a second user can compete in a "tug of war" competition. Each user's respective indicator system displays both user's activity levels. For example, the first user's activity level is displayed in a first color and the second user's activity level is displayed in a second color. In comparing respective activity levels, each user tries to take over the other user's indicator system by increasing their respective activity levels where more light members of the indicator system is illuminated with their respective color.

In another aspect, the device 10 may be programmed to display activity levels in a particular color for a set period of time. For example, a user may be performing activities and earning activity points for a charity. In such case, the indicator system may illuminate all of the light members in a designated color such as white. Also, if the user was participating in a particularly sponsored event, activity relating to that event could be displayed in another designated color.

In another aspect, one can provide motivational messages to a user such that the message is conveyed via the display or indicator system. For example, a motivational message may be loaded onto a remote site by a first user and directed to a second user. The message may be loaded onto the second user's device such as when the second user plugs the device into the computer. The message may be downloaded to the second user's device 10 stored therein. The second user may not immediately be aware a message has been received. The motivational message could be triggered by an event such when the second user reached a goal. Upon a triggering event, the indicator system of the second user's device may be illuminated in a certain fashion such as all light members blinking. Audible sounds could also be provided or other animated lighting features on the display or indicator system. It is further understood that the triggering event could be based on other parameters such as time, or the motivational message may be provided immediately upon transferring to the device. Finally, it is understood that the motivational message may be delivered wirelessly to the device 10. It is further understood that a message could be delivered to the device for the user to check an associated mobile device for the message.

In another aspect, an alert message can be delivered to the device 10 wherein the indicator system may be illuminated in a certain designated manner. The alert message may be delivered and triggered in any of the manners as described herein. The alert message may indicate that the user should visit a remote site for further information or to look for a message on the user's mobile device. In one exemplary embodiment, the alert message could indicate that a reward is possible for activity performed at a particular time.

In another aspect, the device 10 may provide a message based on inactivity or non-active periods. If the device 10 senses that the user has been in a non-active (e.g., low activity) state for a predetermined amount of time, an alert message may be delivered to the indicator system or display to remind the user to become more active. The alert message can be delivered in any of the manners described herein. The threshold levels of a low activity state and amount of inactive time could also vary and be individually set by the user.

In some arrangements, user non-activity or inactivity may also be detected and affect the user's progress toward completion of an activity goal. For example, inactivity may be detected when a user does not exhibit movement of a particular level or a type of movement for a specified amount of time, does not exhibit a heart rate of at least a threshold level, does not move a sufficient amount of distance over an amount of time and the like and/or combinations thereof. For arrangements in which a user accumulates activity points to reach an activity point goal, points or a value may be deducted from the user's activity point or other activity metric total when an amount of non-activity (e.g., inactivity or sedentary state) is detected. Various conversion rates for converting inactivity to activity point deductions may be used. In a particular example, 10 minutes of inactivity may correspond to a 5 point deduction. In another example, 30 minutes of inactivity may correspond to a 100 point deduction. Loss or deduction of activity points may be linear or may be non-linear, for example, exponential, parabolic and the like.

As noted herein, current progress may be indicated by an indicator system such as system 20. Current progress indication may be triggered not only based on an increase in goal progress, but also a decrease in goal progress. For example, if activity points or a threshold amount of activity points are deducted from the user due to inactivity, a current progress indication may be displayed. For example, a lighting element of system 20 corresponding to a user's current level of progress may be illuminated. Alternatively or additionally, an alert may be displayed in a primary display such as display 18 indicating that points were deducted and/or that the user has been inactive for a specified amount of time. In a particular example, progress may be indicated on an indicator system such as indicator system 20 using intervals of progress. Each interval may represent an amount of activity points and may correspond to a different indicator lighting element in indicator system 20. In such an example, the threshold number of activity points may correspond to a difference between a user's current amount of activity points and an upper activity point boundary for a lower interval of progress. In other examples, any decrease in activity points may cause a current progress indication. Accordingly, the user may receive immediate notification that his or her progress has decreased.

A user's non-active time may include inactive time and sedentary time. Inactivity and sedentary time may be defined by different movement, heart-rate, step or other thresholds or may be defined using the same thresholds. In one example, sedentary time may have a higher threshold (e.g., requiring a higher level of activity) than an inactivity threshold. That is, an individual may be considered sedentary but not inactive. The non-active threshold may correspond to the sedentary threshold or a higher threshold, if desired. Alternatively, an inactivity threshold may be greater than a sedentary threshold. There may also be multiple sedentary thresholds, inactivity thresholds and/or non-active thresholds (e.g., each of the sedentary and inactivity thresholds may be a non-active threshold). Different point deductions or rates of point deductions may also be defined between the multiple thresholds and levels of little to no activity (e.g., non-activity). For example, a user may lose 50 points per hour for inactivity and 30 points per hour for sedentary activity or vice versa. Further, activity point deduction may be triggered at different times depending on if the user is inactive or sedentary. For instance, a user may begin losing activity points after 30 minutes of inactivity or 45 minutes of being sedentary. Additional thresholds (e.g., more than two thresholds) and corresponding rates of activity point loss may also be defined.

In some arrangements, various sensors may be used to detect non-active periods of time. As discussed, non-activity time periods may be defined based on heart-rate, amplitude of a movement signal, step rate (e.g., <10 steps per minute), or the like. Alternatively or additionally, inactivity and sedentary time periods may be measured based on a physical position, body position, body orientation, body posture of or type of activity being performed by the individual. The detrimental effects of various physical inactivity or sedentary body positions or orientations may also differ. Accordingly, 30 minutes of reclining may introduce the same health risks as 45 minutes of sitting. The potential for health risks may also be time-dependent. Accordingly, non-activity (e.g., sleeping) for a specified range of durations and during a specified range of time might not introduce health risks. In one example, sleeping for 7-9 hours between 9 PM and 9 AM might not introduce detrimental health risks and thus, might not contribute to activity point or other activity metric value deduction. Indeed, in some example, a lack of inactivity (such as sleep) for a specified range of durations and/or during a specified range of time may be considered detrimental to a user's health. Thus, activity points may be deducted or activity points may be accumulated at a slower rate during these times.

Alternatively or additionally, the amount by which a value of the activity metric (e.g., an activity points) is decreased may be determined based on time of day, location of the user, physical position of the user, level of inactivity and the like. For example, a user may lose greater value in an activity metric and/or at a faster rate during the afternoon than during the evenings. In another example, if a user is at a gym, the user may lose fewer activity points or other activity metric or lose value in the metric at a slower rate than if the user was located at home.

To account for the variances in types of non-active activity (e.g., below a requisite level of movement to be considered activity), a system may distinguish between physical body positions or orientations including, for example, sleeping, reclining, sitting and standing. Distinguishing between different physical body positions and orientations may include placing sensors at different locations of the user's body to detect the individual positions of each body part. The physical body position of the user may then be determined based on the relative positions of the body parts to one another. For example, when a knee location sensor is within a first threshold distance of a waist or chest sensor, the system may determine that the user is sitting. If the knee location sensor is outside of the first threshold distance, the system may determine that the user is standing. In the above example, the system may use a portion of the distance such as the vertical distance. By using vertical distance alone or in combination with an absolute distance (e.g., straight line distance between the two sensors), the system may further distinguish between when a user is lying down and standing up. For example, a lying down position may correspond to a very low vertical distance between the knee sensor and chest or waist sensor even though the absolute distance may be larger. A standing position may correspond to a larger vertical distance between the knee sensor and the waist or chest sensor but exhibit a similar absolute distance. In other examples, an angle formed by the various sensors may be used to determine an individual's position. Additionally or alternatively, the location of the user's various body parts may be evaluated in conjunction with accelerometer or movement data to determine if the user is exhibiting movement or (e.g., at, above or below) a specified level of movement.

In addition to deductions in activity points, the system may alert a user to inactivity to encourage active lifestyles. In one example, the system may alert the user by displaying a message or indicator on a device such as the wearable device assembly described herein after a specified amount of inactivity such as 2 minutes, 5 minutes, 30 minutes, 1 hour and the like. The amount of inactivity time may be additive over non-consecutive time periods. An amount of consecutive inactivity time may alternatively or additionally be tracked. For example, if the user is inactive between 10:15 and 11:00 AM and then again between 2:00 and 2:30 PM, the total amount of non-active time may be 1 hour and 15 minutes. The message or indicator of inactivity may be provided as a warning prior to deducting activity points. For example, the message may indicate that X amount of activity points will be deducted if the user does not exhibit a sufficient level of activity within a specified amount of time (e.g., 30 minutes, 5 minutes, 10 seconds, 30 seconds, 1 hour, 2 hours, etc.). Accordingly, the device may include an non-active timer to determine the amount of user non-activity. Additionally, the message may provide a suggestion as to a type of activity the user should perform to counter any risks introduced by the inactivity. For example, the system may suggest that the user walk 1 hour at a 10 minute mile pace. When the user has counteracted or accounted for the risks or negative effects of the detected amount of inactivity time, a celebratory message or other indication may be provided.

Warnings, point deductions and/or other notifications may be provided if a user returns to a sedentary or a non-active mode within a specified amount of time of exiting sedentary or a non-active mode. For example, the user may exercise or exhibit a sufficient level of activity to exit the sedentary or a non-active mode for a period of 10 minutes. However, the system or device may require at least 30 minutes of activity to avoid additional warnings for a period of time such as 1 hour, 2 hours, 3 hours, etc. For example, the warnings may indicate that the user did not exhibit activity for a sufficient amount of time or a sufficient level of activity or a combination thereof. Additionally, multiple sedentary periods within short amounts of time (e.g., a threshold amount of time) may require higher or additional levels of activity to counteract potential sedentary effects including health risks and the like. In a particular example, the user may be required to perform a higher level of activity to halt point deduction.

The device or other system may further advise a user as to an amount of non-active time allowed before negative health effects may occur. In one example, the device or system may include a countdown indicating a remaining amount of allowable non-active time before potential health risks may begin taking effect. An amount of permissible non-active time may be earned or accumulated based on an amount of activity performed. Accordingly, the device may also provide suggestions or recommendations as to a type and/or duration of activity that may be performed to earn a specified amount of non-active time (e.g., 1 hour of TV watching). Different types of non-active or sedentary activities may require different types or amounts of activity. For example, 1 hour of reclining may require more strenuous or longer exercise than 1 hour of sitting. In another example, 1 hour of sitting while knitting may require less strenuous or a lower amount of exercise or activity than 1 hour of sitting while watching television. According to one or more arrangements, recommendations may be generated based on empirical data and/or predefined programming and data tables specifying a type and/or duration of activity and a corresponding amount of permissible non-activity.

The device or activity tracking system may further recommend activities based on historical records. For instance, the device or tracking system may determine activity performed by the user in the past and generate recommendations based on those types of activities. Additionally or alternatively, the device or tracking system may generate recommendations for specific workouts performed by the user in the past. For example, a user may need to perform 500 calories worth of activity to counteract 2 hours of TV watching. In such a case, the system may recommend a particular workout performed by the user in the past in which the user burned 500 calories. Combinations of historical activity types and specific historical workouts may be used to generate recommendations. In one example, the system may recommend one of two workouts that the user has performed in the past based on a type of workout that the user appears to prefer. The preference may be determined based on a number of times the user has performed each type of workout. A workout or activity type may also be recommended based on location and time. For example, if a user previously performs a particular type of activity or a particular workout routine at the same location and/or at the same time, the system may recommend that type of activity or workout routine. Other recommendations algorithms and factors may be used.

As disclosed herein, the spine member 24 provides a chassis member that supports various components of the device 10. It is understood that the spine member 24 could be eliminated or combined with other components in other exemplary embodiments. A flexible PCB member could be provided having localized stiffening members. Additional components are attached to the flexible PCB member. In this configuration, the spine member 24 is not used. In constructing the device, an inner portion of the outer encasement member may be formed in an injection molding process and then the flexible PCB member is attached to this inner portion. The remaining outer portion of the outer encasement member is formed over the PCB member.

In another embodiment, the device 10 may have a housing that is substantially rounded. The housing may have a substantially circular cross-section and have a tubular configuration. The housing has similar features as described above wherein the display and/or indicator system is viewable through an outer encasement member that is tubular. Ends of the housing may employ cooperating members in an interference fit and include a data transfer member at one of the device. The data transfer member may take any of the forms previously described such as a micro USB member and may include a further adapter member to a full USB connector. The device may include an integrated PCB member and LED/light pipe assembly as well as a micro piezoelectric accelerometer that may be also three-axis accelerometer. The accelerometer senses activity and the LED/light pipe assembly may be illuminated based on the sensed activity. Other features described above may be incorporated into this embodiment as desired.

The device may also incorporate various other features and alternative structures. The display and/or indicator system may utilize electrophoretic ink devices. The display and/or indicator system may also take other forms such as an electro luminescent/phosphorescent ribbon display, electrochromic ink devices, electrowetting devices, or fiber optic displays. The accelerometers can take various forms including piezoelectric accelerometers or nano accelerometers. The battery employed could be any lithium ion battery cells and may have a tubular configuration as well as other types of power supplies. The housing may include a plurality of interconnected links that are stretchable wherein certain links may include a display segment thereon. The links may be interconnected via an elastic cord having conductive traces. The housing may also utilized dual capacitive touch sensors to activate the display and/or the indicator system. The display may further take the form of a touch-activated screen. The housing may also incorporate a display utilizing an electro-chromatic polymer having a plurality of leads or pipes. Each pipe is wired to an electrode and encapsulates an electro-chromatic polymer than changes color when a change of current is applied from the controller. The housing may further take the form of an elongated strap that can be coiled up to adjust the circumference of the device.

The device 10 provides numerous benefits. The device has a compact design that is easily wearable by a user at all times. The device incorporates a reliable data transfer device in the form of the USB connector to easily transfer data to and from the device. The device is further capable of interacting with other mobile devices and remote sites provide enhanced user experiences that increase activity and performance of the user. The device is also capable of tracking multiple types of activity and can further track a user's activity for an extended period of a day as well as for a complete 24 hour period from day to day. The indicator system provides an easy and enhanced methodology to communicate activity information to the user. Messages communicated via the device 10 provide motivation to the user to increase total activity and provide a healthier lifestyle. The device structure also provides significant benefits. The housing has flexible zones allowing for ease of removing from and placing on a user's wrist while providing sufficient rigidity to protect the components supported by the housing. The spacer member allows for easy size adjustments.

FIGS. 145-178 illustrate different views of additional embodiments of the wearable device assembly 10 of the present invention. It is understood that any of the features of the additional embodiments can be utilized in combination with any of the features described above. It is further understood that similar structures will be designated with identical or similar reference numerals. As discussed, the wearable device assembly 10 generally includes the housing 12, the controller 14, the input button 16, the display 18, and the indicator system 20. The controller 14 has and/or is operably connected to various associated components including power supplies, sensors and associated circuitry. Also similar to prior embodiments, the housing 12 is in the form of a wearable band such as a wristband and generally includes the inner spine member 22 (FIGS. 6-9) having compartments for power supplies, the outer encasement member 24, and the fastening mechanism 26 or latch member 26. In certain exemplary embodiments, the housing 12 may have one or more spacer members 28 to adjust the size of the device 10 to be discussed in greater detail below.

As previously described and shown, the inner spine member 22 is a member having substantially rigid portions and certain flexible portions or zones. The inner spine member 22 shown in FIGS. 145-150 is substantially the same as the spine member 22 shown in FIGS. 7-9 above, but incorporates additional structures in the form of plug members to enhance the overall structure of the wearable device assembly 10 as described herein. The spine member 22 has the general curvilinear configuration and has the outer surface 30 and the inner surface 32. The spine member 22 has the intermediate portion 34 that extends to the first distal end 36 and the second distal end 38. The intermediate portion 34 has a central portion or central segment 40 as well as a first segment 42 and a second segment 44. The intermediate portion 34 further has the first flexible zone 46 or member or portion that connects one end of the central portion 40 to the first segment 42, and has the second flexible zone 48 or member or portion that connects the other end of the central portion 40 to the second segment 44. The flexible zones 46,48 provide for more easy flexing of the spine member 22 at these zones and also the overall device while the first segment 42 and second segment 44, and central portion 40, are considered rigid zones or substantially rigid zones. In an exemplary embodiment, the flexible zones 46,48 may be considered flexible hinge zones and are curved segments in a generally concave shape. Thus, the flexible zones have a central portion or base portion with a pair of members extending away from the base portion, and therefore define an inwardly curved portion, thus having a concave upper facing surface 500. The curved segments have a thinned out thickness at the base or central portion of the concave configuration to enhance the flexible characteristics of the flexible zones 46,48. Thus, the spine member 22 has a general thickness or first thickness along its length (e.g., the rigid central portion and rigid first and second segments) while the flexible zones have a lesser, second thickness to assist in the flexible characteristics of the spine member 22 and overall housing 12. In particular, the base portion of the flexible zone has a lesser thickness than the rigid central portion and first and second rigid segments. The first flexible portion defines a first recessed area A and the second flexible zone defines a second recessed area A. The generally concave-shaped, inwardly curved flexible zones 46,48 define the area A above the base portion and pair of members, which is a U-shaped area in an exemplary embodiment. The areas A have a depth defined between an inner surface at the base extending up to a curvilinear arc AR defined by the outer surfaces of the adjacent central segment and first and second segments.

Figure 146A:
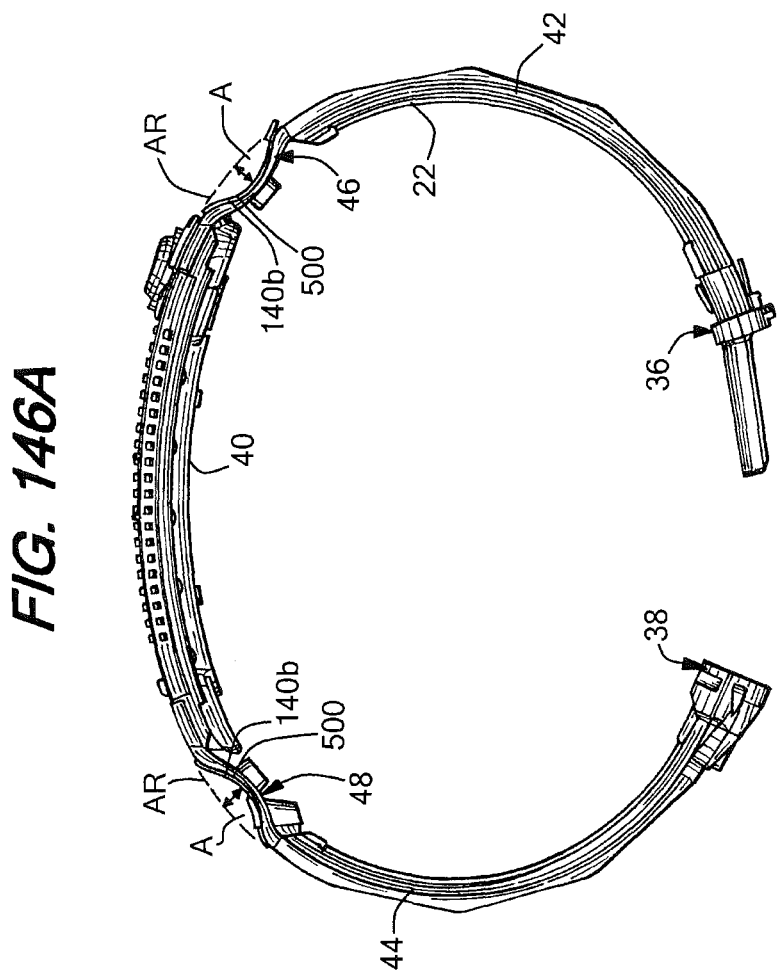
FIG. 146a is side elevation view of a spine member having a PCB member connected thereto.
Figure 145:
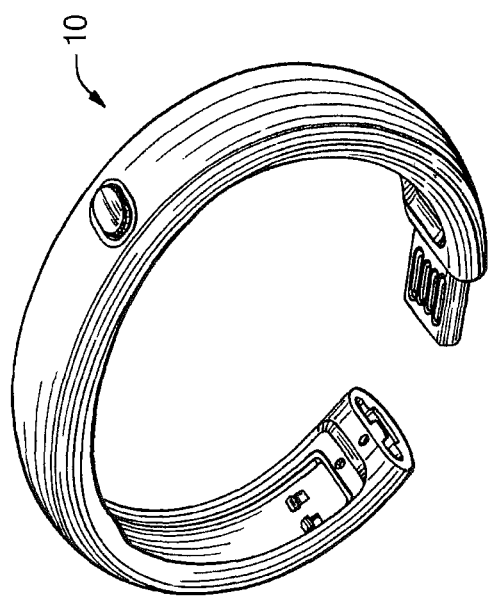
FIG. 145 is a perspective view of an alternative embodiment of the wearable device assembly of the present invention.
Figure 146B:
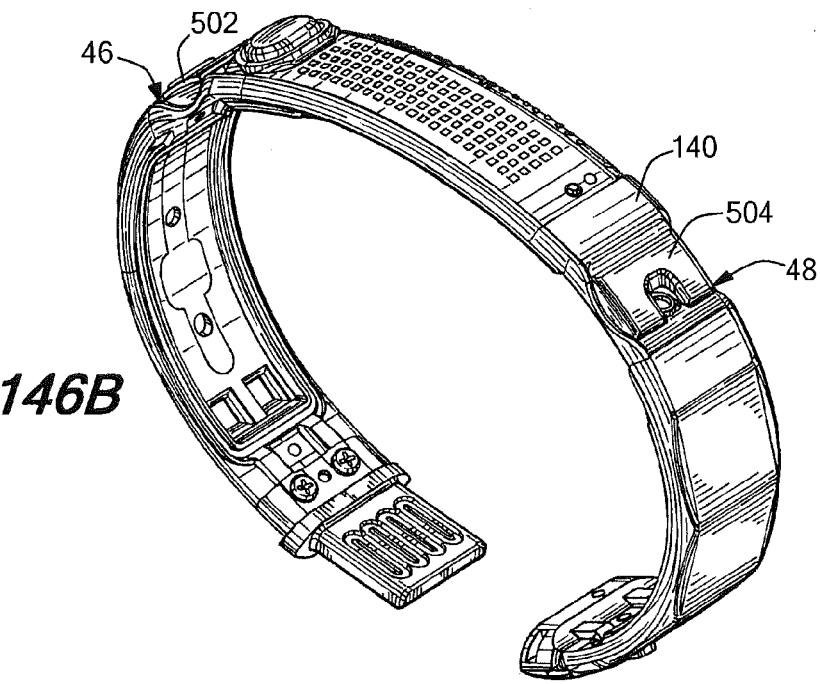
FIG. 146b is a perspective view of the spine member having plug members attached thereto.
Figure 146C:
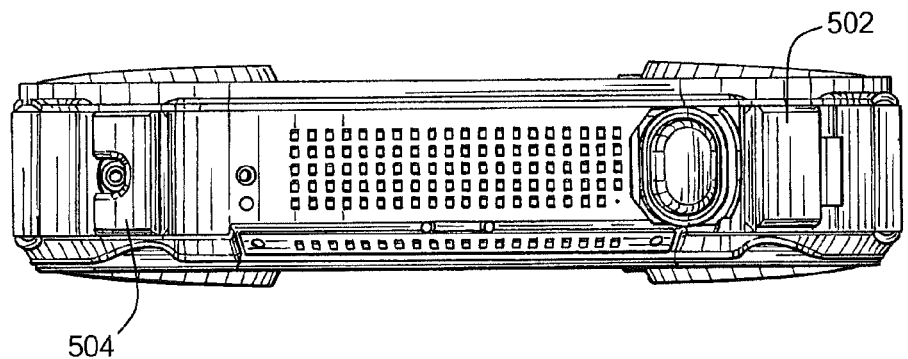
FIG. 146c is a plan view of the spine member having a PCB member and plug members attached thereto.
Figure 146D:
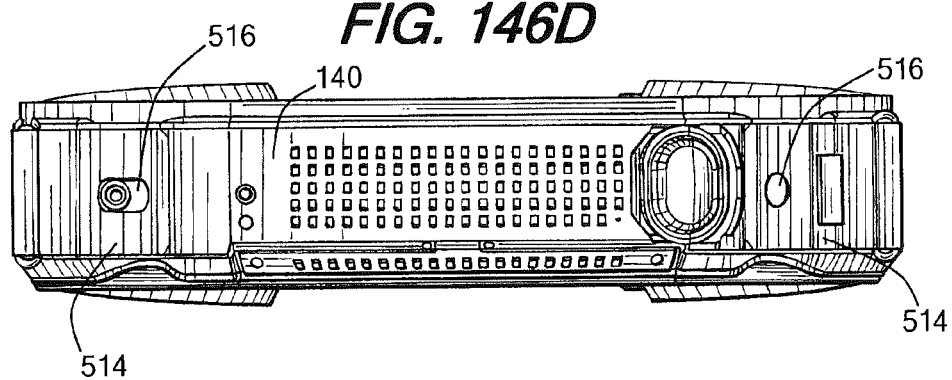
FIG. 146d is a plan view of the spine member and PCB member having plug members removed to expose adhesive members.

As also discussed, the flexible printed circuit board (PCB member) 140 (FIG. 146f) is connected to the inner spine member 22. To this end, the PCB member 140 is in surface-to-surface engagement with the inner spine member 22 including along the first flexible zone 46 and the second flexible zone 48. The PCB member 140 has the flex regions 140b that correspond in position to the flexible zones 46,48 of the spine member 22. As previously described, the PCB member 140 is wrapped around and mounted to the spine member 22. Fasteners may be used to fixedly attach the PCB member to the spine member 22 including mechanical fasteners and adhesives. It is understood that the central region 140a of the PCB member corresponds to the central portion 34 of the spine member 22 when connected. The PCB member 140 generally follows the contours of the spine member 22 including the contours of the flexible zones 46,48. Thus, the flex regions 140b are positioned at the flexible zones 46,48 of the spine member 22 and are in general surface-to-surface engagement. Openings 516 are provided through the PCB member 140 at the flex regions 140b to expose portions of the spine member at the flexible zones 46,48. It is further noted that the indicator system 20 is operably connected to the PCB member 140 as shown in FIG. 146f and extends from the main portion of the member 140. The indicator system 20 is folded into the edge of the spine member 22 as shown in the figures.

As shown in FIGS. 146-150, the spine member 22 utilizes plug members at the flexible zones 46,48 and specifically includes a first plug member 502 and a second plug member 504. The first plug member 502 and the second plug member 504 have a generally convex lower outer surface 506 and a generally smooth upper surface 508. The convex surface 506 is shaped and dimensioned to follow the contours of the base and pair of inwardly curved walls and concave surface 500 of the flexible zones 46,48 of the spine member 22. The first plug member 502 and the second plug member 504 each have a height that generally corresponds to the height of the area A defined by the flexible zones 46,48. It is understood that one or both of the plug members 502,504 may have an opening therein to receive an additional fastener. The plug members 502,504 can be formed from a variety of materials. In one exemplary embodiment, the plug members 502,504 are formed from polypropylene.

As shown in FIGS. 146-150, the first plug member 502 is positioned proximate the first flexible zone 46 and a second plug member 504 is positioned proximate the second flexible zone 48. In particular, the first plug member 502 is adhered via an adhesive to the PCB member 140 at the first flexible zone 46. Openings 516 in the flex regions 140b of the PCB member 140 allow for some direct adherence of the plug member to the spine member 22. In an exemplary embodiment, the adhesive may be a VHB adhesive tape member 514 (FIG. 146d) such as provided by the 3M Company. The tape may have a substrate having the adhesive on both sides of the substrate. The convex surface 506 of the first plug member 502 confronts the flex regions 140b of the PCB member 140 and the concave surface 500 of the first flexible zone 46 and is in surface-to-surface engagement, thus connecting the plug member 502 to the PCB member 140 and the spine member 22. The first plug member 502 generally occupies the area A defined by the first flexible zone 46. As the height of the first plug member 502 generally corresponds to the height of the area A of the first flexible zone 46, the upper surface 508 of the first plug member 502 is positioned generally in line with and proximate the curvilinear arc AR defined by the outer surface of the spine member 22. Similarly, the second plug member 504 is adhered via the adhesive member 514 to the PCB member 140 at the second flexible zone 48. The convex surface 506 of the second plug member 504 confronts the flex regions 140b of the PCB member 140 and the concave surface 500 of the second flexible zone 48 and is in surface-to-surface engagement, thus connecting the plug member 502 to the PCB member 140 and the spine member 22. The second plug member 502 generally occupies the area A defined by the second flexible zone 48. As the height of the second plug member 504 generally corresponds to the height of the area A of the second flexible zone 48, the upper surface 508 of the second plug member 504 is positioned generally in line with and proximate the curvilinear arc AR defined by the outer surface of the spine member 22.

Figure 148A:
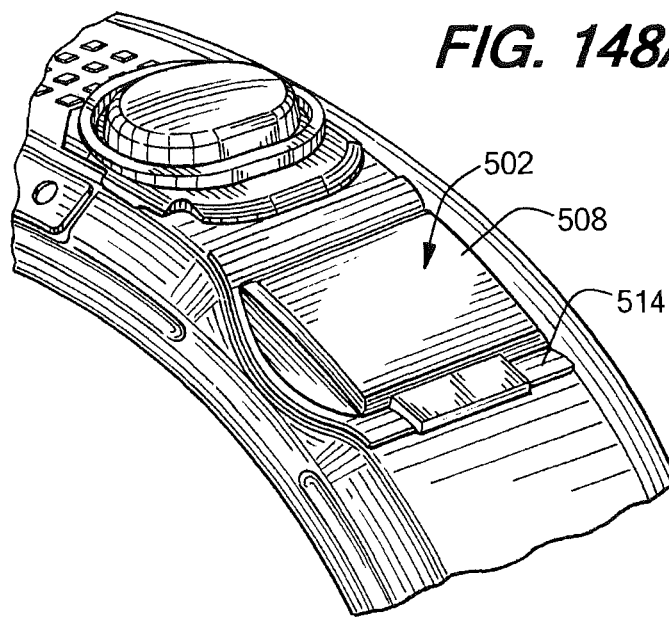
FIG. 148a is a partial perspective view of a first plug member positioned in a first flexible portion.
Figure 148B:
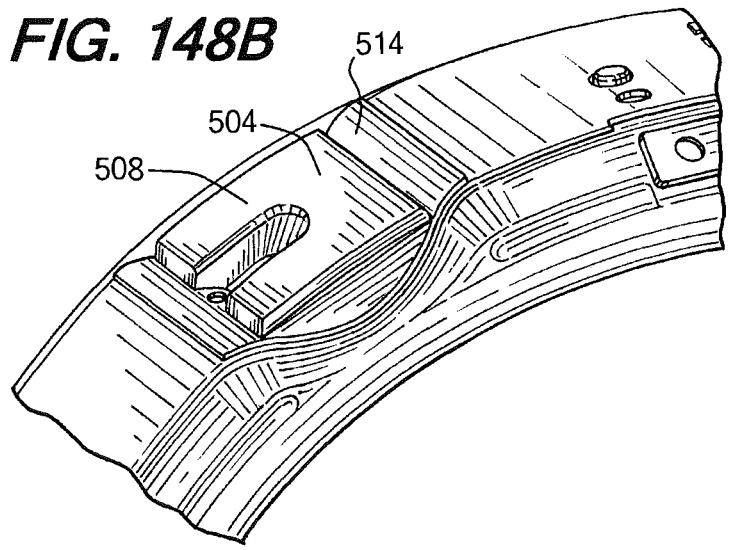
FIG. 148b is a partial perspective view of a second plug member positioned in a second flexible portion.
Figure 149:
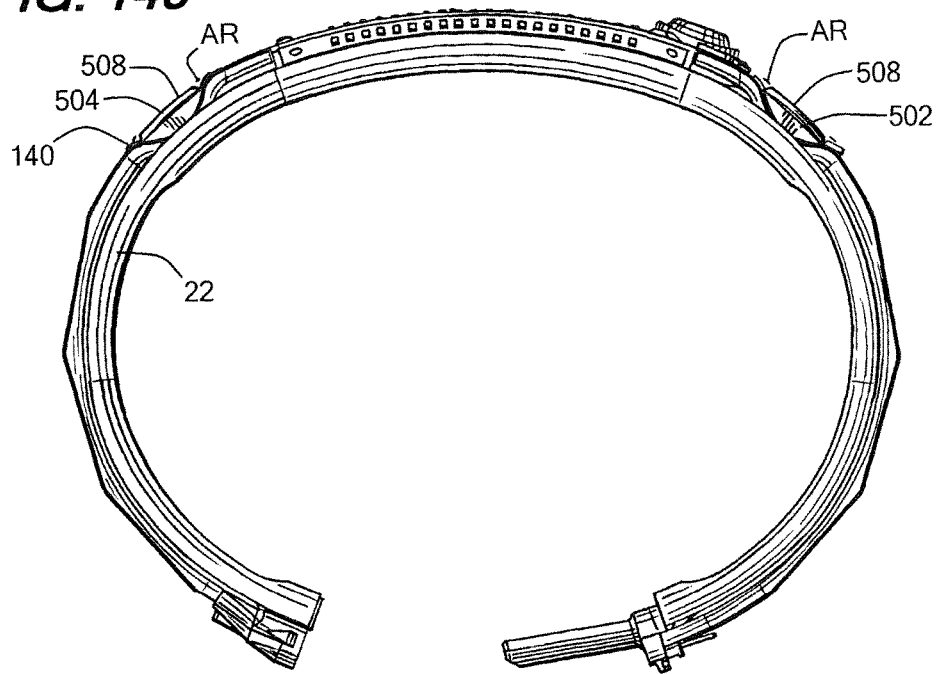
FIG. 149 is a side elevation view of the spine member having the PCB member and plug members attached thereto.
Figure 150:
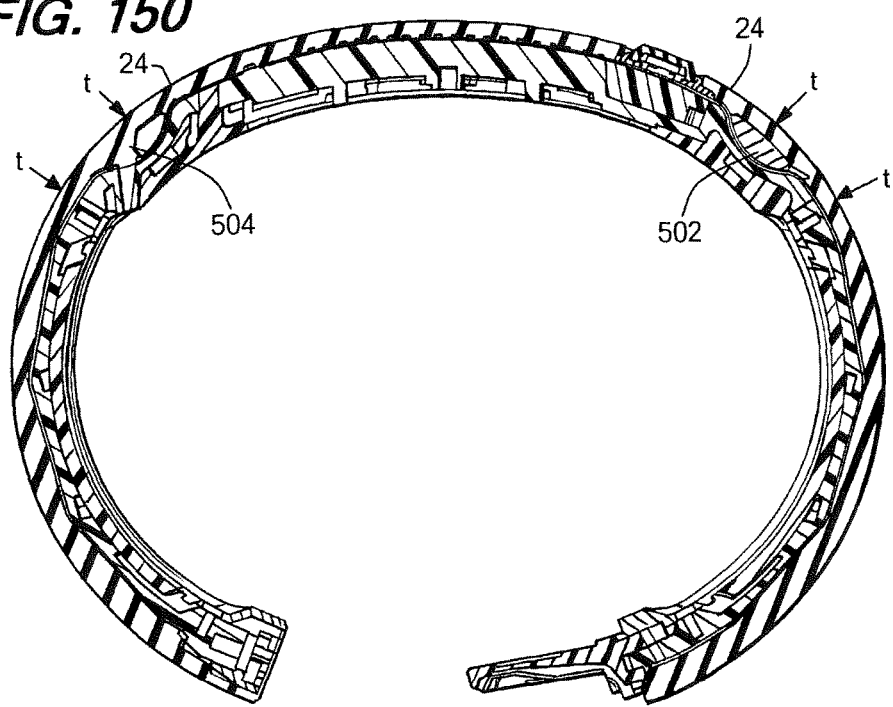
FIG. 150 is a cross-sectional view of the wearable device assembly showing the plug members and outer encasement member.

The first plug member 502 and the second plug member 504 assist in connecting the PCB member 140 to the spine member 22. As there are openings 516 through the PCB member 140 at the flex zones 140b, there is some direct contact with the adhesive between the plug members 502, 504, the PCB member 140 and the spine member 22. Thus, the flexible zones 46,48, adhesive member 514 and plug members 502,504 are in vertical stacked arrangement as shown in FIGS. 148-150). The polypropylene plug members 502,504 still allow sufficient overall flexibility of the wearable device assembly 10. In one or more examples, the flexibility of the zones proximate to the plug members 502,504 may be at or above one or more predefined flex values or thresholds to provide the overall flexibility. Moreover, plug members 502,504 may each have different flexibilities. Still further, in one or more arrangements, the flexible zones 46,48 and plug member 502,504 may have different shapes that correspond to one another.

As can be appreciated from FIG. 150, the plug members 502,504 assist in enhancing the over-molding of the outer polymeric encasement member of the housing. As the encasement member 24 is molded over the assembly, the plug members 502,504 assist in keeping the PCB member 140 down against the spine member 22, thus minimizing the chances for the PCB member 140 to lift off of the spine member 22. The plug members 502,504, therefore, assist in preventing the PCB member 140 from straightening out across the flexible zones 46,48. In addition, as the plug members 502,504 occupy the area defined by the flexible zones 46,48, less polymeric encasement material is required at the flexible zones 46,48. Accordingly, the thickness t (FIG. 150) of the elastomer member 24 at the first flexible portion 46 is approximately the same as the thickness t of the elastomer member 24 adjacent the first flexible portion 46. Similarly, the thickness t of the elastomer member 24 at the second flexible portion 48 is approximately the same as the thickness t of the elastomer member 24 adjacent the second flexible portion 48. This helps prevent any potential sinking or sagging of the outer encasement material at these areas.

This provides an enhanced encasement member 24 of the housing 12 as any potential surface irregularities are minimized. While in an exemplary embodiment the plug members 502,504 are adhered via an adhesive, the plug members 502,504 may also be adhered using mechanical fasteners including one or more threaded screw fasteners. Thus, threaded fasteners can also be used to connect the plug members 502,504 to the PCB member 140 and spine member 22. The plug members 502,504 could also be heat-staked if desired. An alternative reinforcement member may take the form of a clamp member such as shown in FIG. 146e. The clamp member 518 may be fastened to the PCB member 140 and spine member 22 with a screw 519. Clamp members 518 may be positioned on each side of the flexible portions 46,48 and could also be used in conjunction with the plug members 502,504. The clamp members 518 also assist in keeping the PCB member 140 down on the spine member 22.

Figure 151:
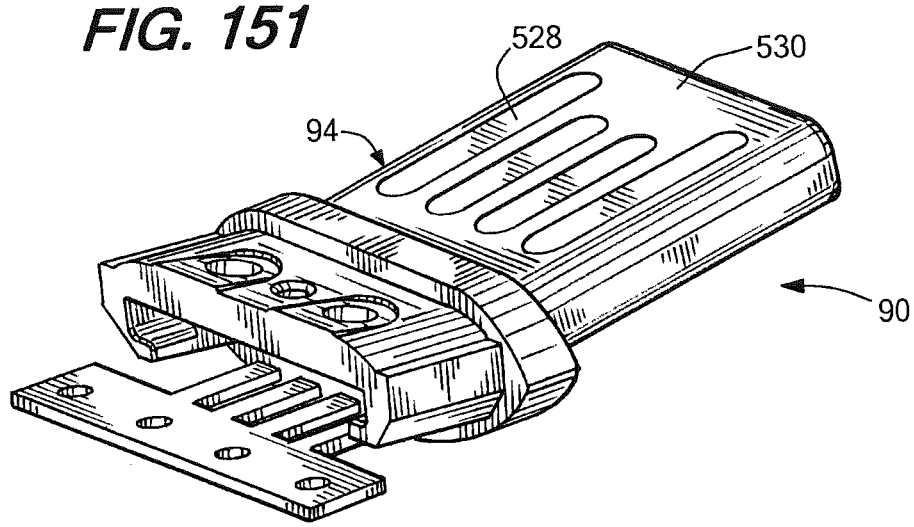
FIG. 151 is a perspective view of an alternative embodiment of a USB connector of the present invention.
Figure 152:
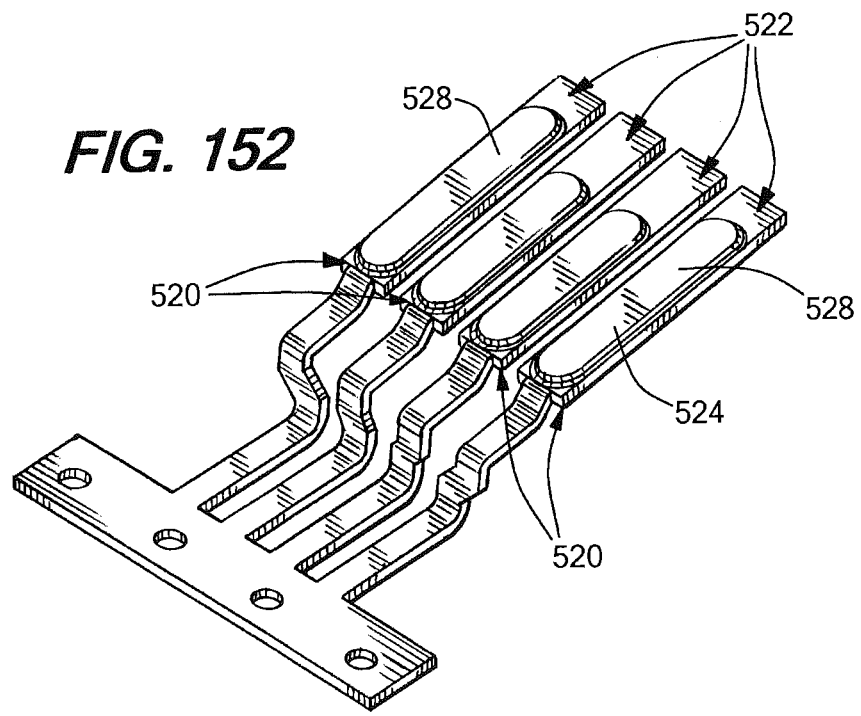
FIG. 152 is a perspective view of USB leads of FIG. 151.
Figure 155:
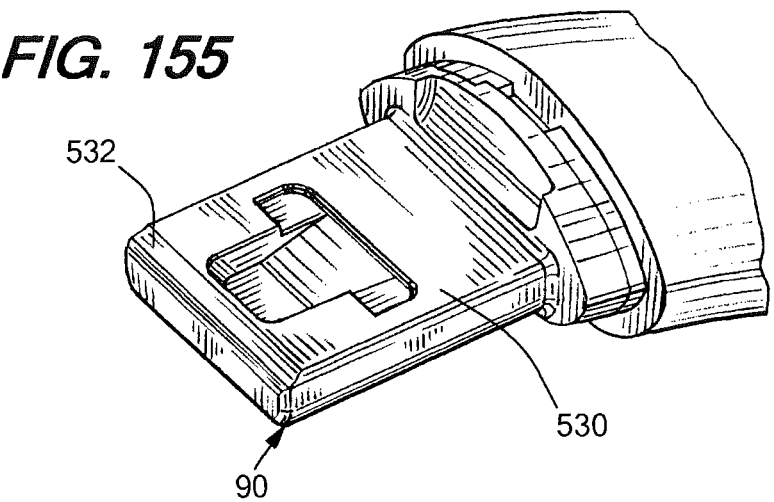
FIG. 155 is an underside perspective view of the USB connector.
Figure 156A:
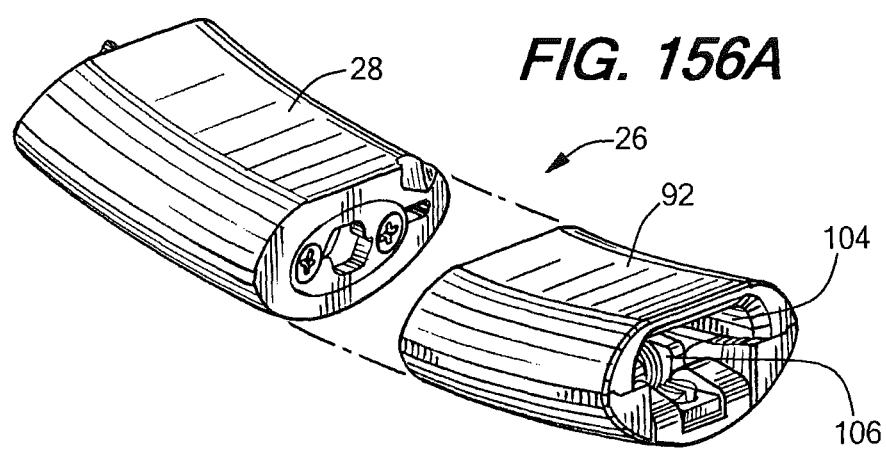
FIGS. 156a-156b are front and rear perspective views of a second receiver member of a fastening mechanism and a spacer member according to an alternative embodiment of the invention.
Figure 156B:
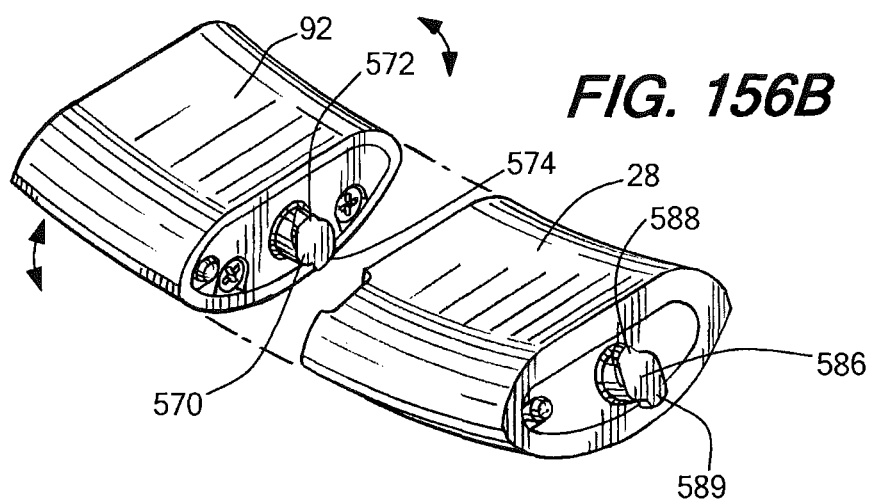
Figure 161:
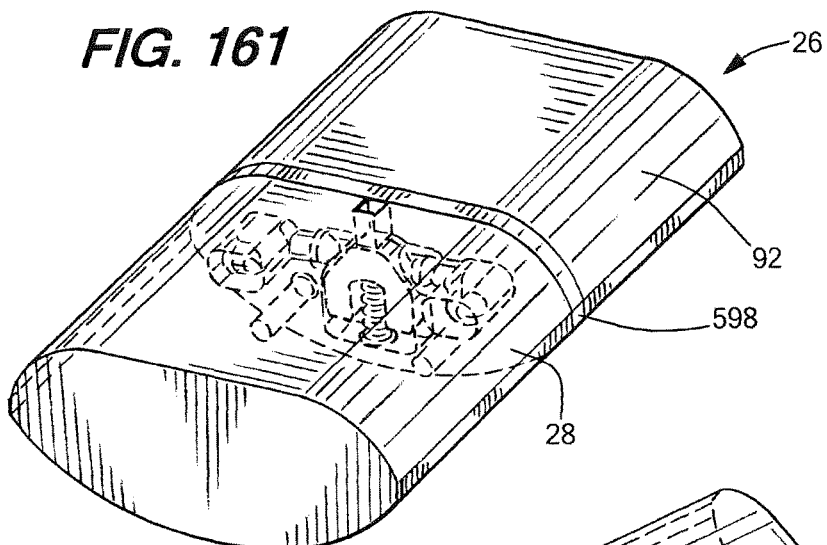
FIG. 161 is a schematic perspective view of a second receiver member of a fastening mechanism and a spacer member according to an alternative embodiment of the invention.
Figure 162:
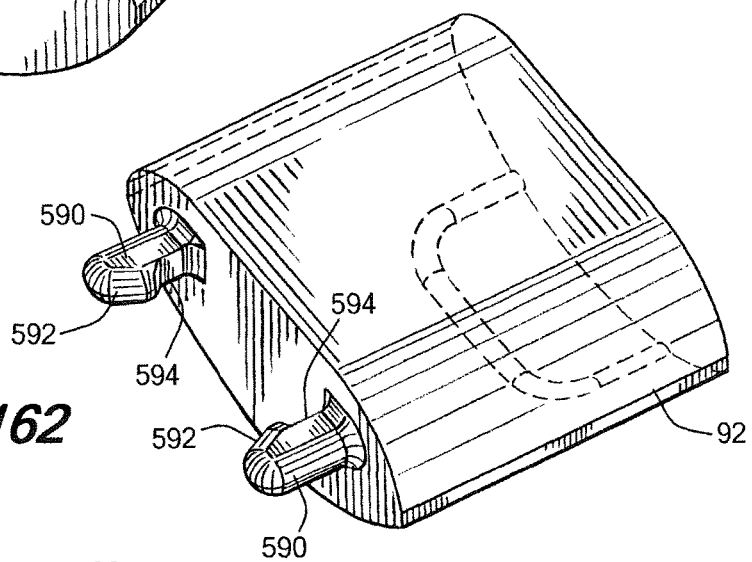
FIG. 162 is a perspective view of the second receiver member of FIG. 161.
Figure 163:
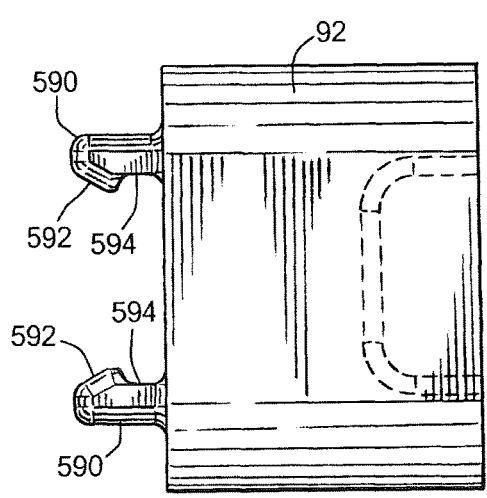
FIG. 163 is a plan view of the second receiver member of FIG. 161.
Figure 164:
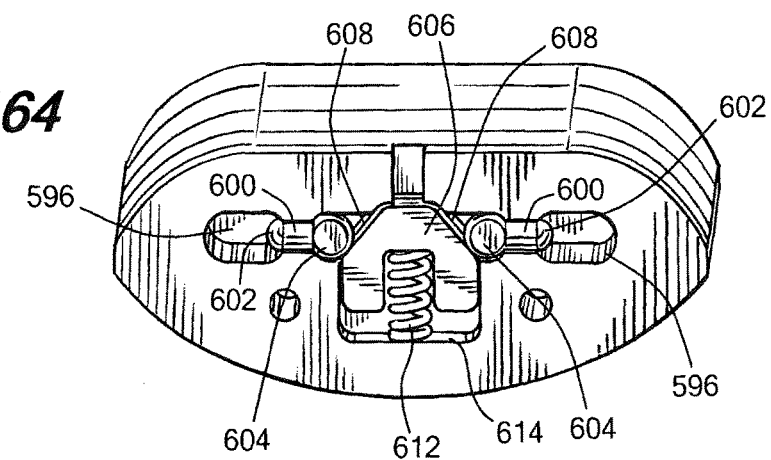
FIG. 164 is an end view of the spacer member of FIG. 161 and having a spacer plate removed for clarity.
Figure 165:
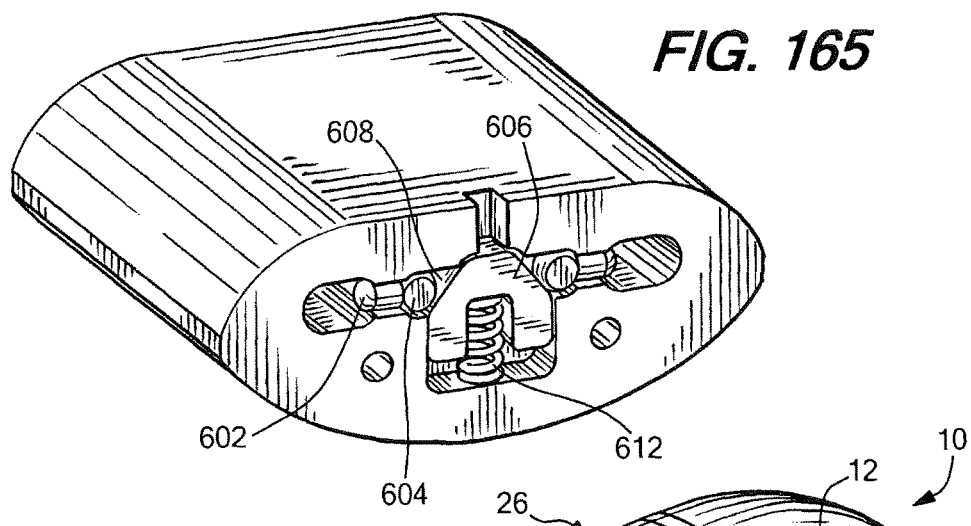
FIG. 165 is a perspective view of the spacer member of FIG. 161 and having a spacer plate removed for clarity.
Figure 166:
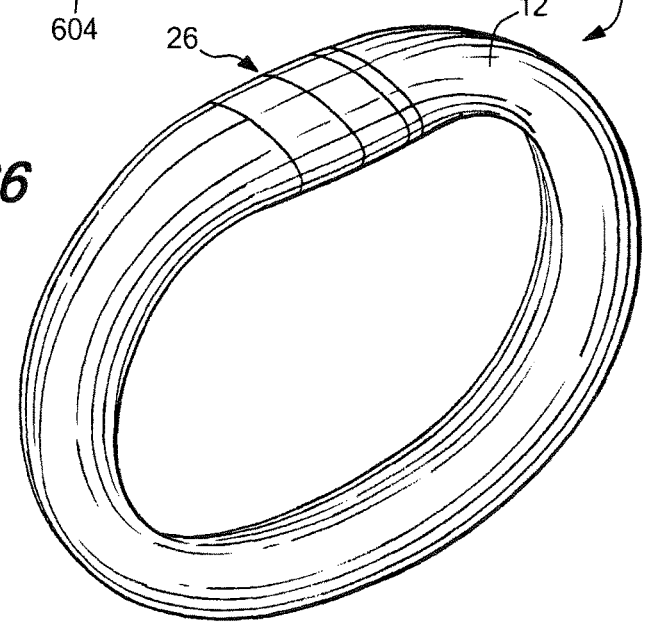
FIG. 166 is a perspective view of an alternative embodiment of a wearable device assembly having an alternative fastening mechanism.
Figure 167:
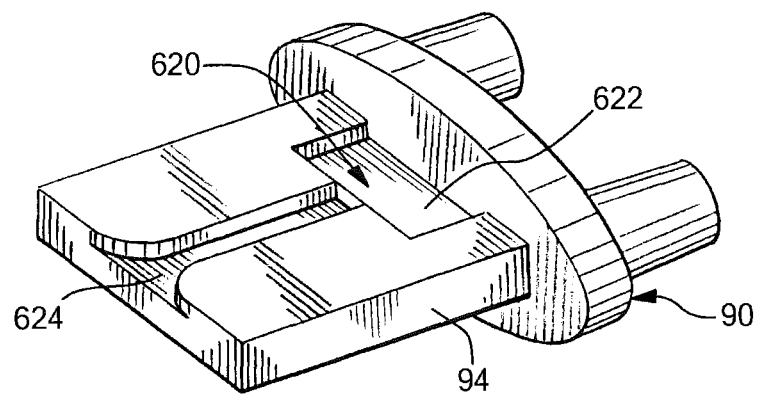
FIG. 167 is a perspective view of a first projection member of the fastening mechanism shown in FIG. 166.
Figure 168:
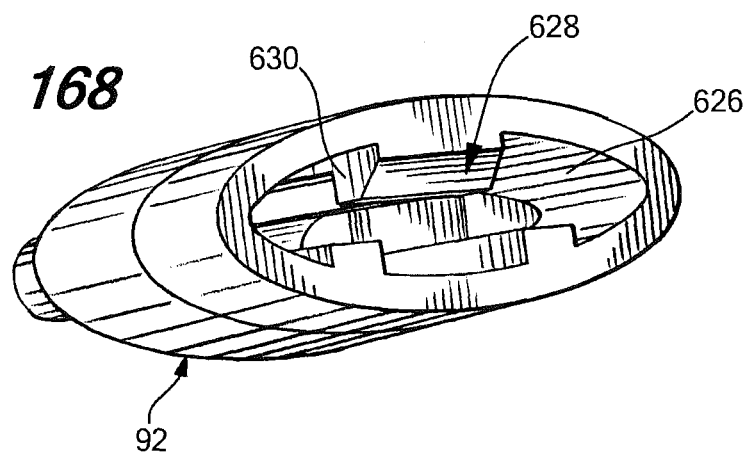
FIG. 168 is a rear perspective view of a second receiver member of the fastening mechanism shown in FIG. 166.
Figure 169:
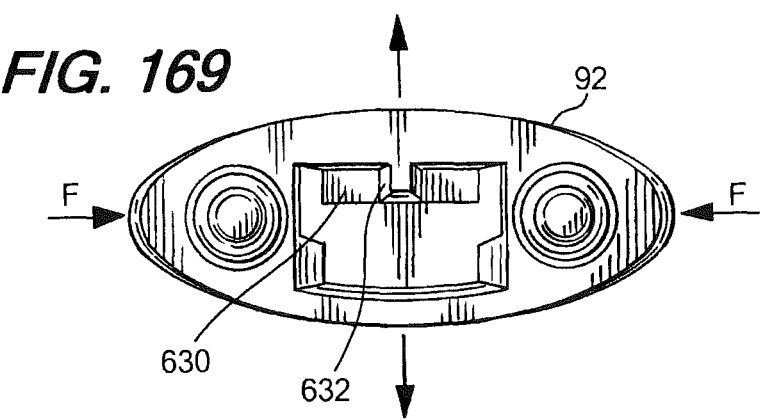
FIG. 169 is a rear elevation view of a second receiver member of the fastening mechanism shown in FIG. 166.
Figure 174:
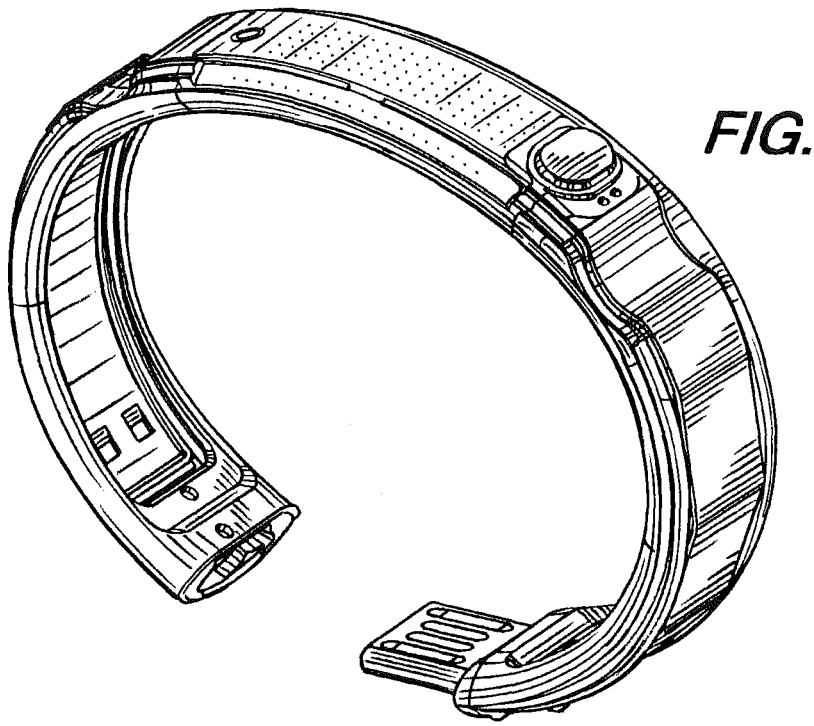
Figure 175:
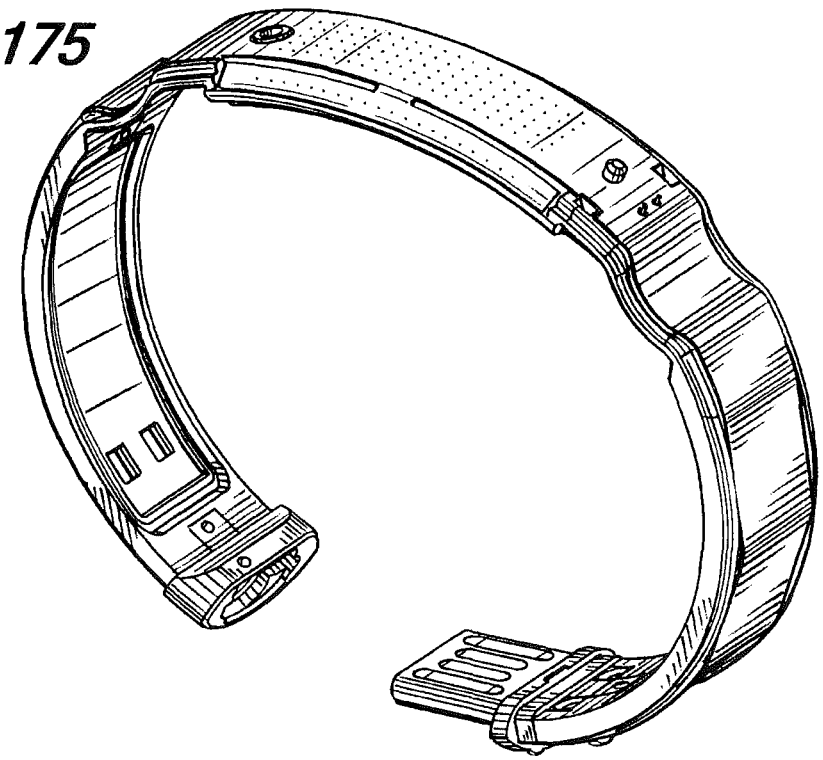

FIGS. 151-154 disclose an alternative embodiment of the first projection member 90 in the form of the USB connector 94 that can be used in the wearable device assembly 10. In this embodiment, the rigid body and the leads of the connector 94 have a generally flush configuration as described in greater detail below. As shown in FIGS. 152-153, the USB connector 94 has a plurality of leads 520. Each lead 520 has a base member 522 that is subjected to a mechanical coining fabrication process. The coining process compresses the leads thereby moving material to form a peripheral support wall 524 defining a peripheral surface 526. The movement of material from the coining process further defines a raised planar platform 528 positioned inwardly from the peripheral support wall 524. With such configuration, the leads 520 are positioned in a mold assembly wherein mold members can be positioned to locations corresponding to the raised planar platforms 528 and beneath the leads 520. Material can then be injected into the mold assembly to form the rigid body 530. Because of the configuration of the mold members, as shown in FIGS. 151 and 154, the rigid body 530 is generally flush with the raised planar platforms 528. Thus, the raised planar platforms 528 are generally at the same level as the top surface of the body 530. Such configuration provides enhanced operable connection with the USB connector 94 is inserted into a USB receptacle such as the computer shown in FIG. 44. Other mechanical fabrication techniques can also be used on the leads 520 to move material as desired including other forging processes and molding operations. As further shown in FIG. 155, the rigid body 530 can be formed with a beveled edge or angled surface 532. In this exemplary embodiment, the beveled edge 532 is positioned on the underside surface having the recess therein. The beveled edge 532 is generally adjacent to the recess as shown in FIG. 155. The beveled edge 532 provides a lead-in structure to allow easier and smoother insertion of the USB connector 94 into the second receiver member 92.

FIGS. 156-173 disclose additional embodiments and features of the fastening mechanism 26 and spacer member 28 of the wearable device assembly 10 of FIG. 1.

As previously discussed, the fastening mechanism 26 or latch member 26 generally includes a first projection member 90 and a second receiver member 92. The first projection member 90 is positioned proximate the first end of the housing 12, and the second receiver member 92 is positioned proximate the second end of the housing 12. It is understood that the members 90,92 could be placed on opposite ends of the housing 12 if desired. The first projection member 90 incorporates an input/output member 94 for data transfer and in an exemplary embodiment, takes the form of the USB connector 94. It is understood that the USB connector 94 as described herein forms part of the alternative fastening mechanisms 26 described herein.

FIGS. 156-160 disclose a second receiver member 92 and a spacer member 28 having alternative connection structures. Similar structures will be designated with like reference numerals. It is understood that the second receiver member 92 could be directly connected to one end of the housing 12, but that the spacer member 28 can be utilized to expand the circumferential size of the device 10 so that device size can be varied. The second receiver member 92 defines the opening 104 therein and supports a pivoting member 106 that cooperates with the first projection member 90 as described herein. As shown in FIGS. 156-159, the second receiver member 92 has a central prong member 570 at an opposite end from the opening 104. The central prong member 570 is a single member and is positioned generally at a mid-portion of the second receiver member 92. The prong member 570 has a first lateral projection 572 and a second lateral projection 574 extending from the prong member 570. The lateral projections 572,574 define engagement surfaces 576 (FIG. 158).

As further shown in FIG. 160, the spacer member 28 has the body 130 having one end having a central opening 580 generally dimensioned to receive the central prong member 570. The central opening 580 has a first peripheral segment 582 and a second peripheral segment 584. Engagement surfaces are defined at backside surfaces adjacent to the central opening 580. The other end of the body 130 has a central prong member 586 (FIG. 156b) having a first lateral projection 588 and a second lateral projection 589 similar to the central prong member 570 on the second receiver member 92.

It is further understood that in this embodiment, the end of the housing 12 will have an opening similar to the central opening 580 in the spacer member 28. Thus, when using a spacer member 28, the second receiver member 92 is rotated (see arrows in FIG. 156b) about an axis extending from the central prong member 570 to a first position wherein the prong member 570 is aligned with the central opening 580. In addition, the first lateral projection 572 is aligned with the first peripheral segment 582 and the second lateral projection 574 is aligned with the second peripheral segment 584. The prong member 570 is fully inserted into the central opening 580 wherein the second receiver member 92 is rotated back to a second position to align the outer surfaces of the second receiver member 92 with the outer surfaces of the spacer member 28. The engagement surfaces 576 of the lateral projections 572,574 then engage the backside engagement surfaces of the spacer member 28 to connect the second receiver member 92 to the spacer member 28. Similarly, the central prong member 586 on the other end of the spacer member 28 is rotated about an axis extending from the prong member 586 and is inserted into a corresponding opening on the end of the housing 12 and rotated back to connect the spacer member 28 and second receiver member 92 to the end of the housing 12. Thus, a rotatable cooperating connection mechanism is provided in the alternative embodiment shown in FIGS. 156-160. It is understood that the first projection member 90 can be inserted into the opening 104 of the second receiver member 92 as previously described herein.

FIGS. 161-165 disclose another alternative latching mechanism 26 along with a spacer member 28. It is understood that FIGS. 161-165 disclose a second receiver member 92 that will cooperate with the first projection member 90 having a USB connector 94 in an exemplary embodiment. As such, the second receiver member 92 will have the opening 104 to receive the USB connector 94. The other end of the second receiver member has a pair of posts 590 extending therefrom. Each post 590 has an inclined cam surface 592 and a slot 594 defined along a length of the post 590. As further shown in FIGS. 164-165, one end of the spacer member 28 has a pair of openings 596 to receive the posts 590 of the second receiver member 92. It is understood that a plate member 598 on the spacer member 28 (FIG. 161) is removed in FIGS. 164-165 to more easily view the additional components. The spacer member 28 further internally supports a pair of fingers 600. Each finger 600 has a distal end 602 and a generally spherical ball-shaped proximal end 604. The fingers 600 are biased outwardly by a central base member 606. The central base member 606 has a pair of inclined surfaces 608 and a slot 610 that receives a biasing spring 612 that is supported by a floor 614 of the spacer member 28. The spring 612 biases the base member 606 upwards wherein the inclined surfaces 608 act against the proximal ends 604 of the fingers 600 to bias the fingers 600 outwardly. It is understood that an opposite end of the spacer member 28 will have a pair of posts similar to the posts 590 on the second receiver member 92 to achieve the daisy chain connecting arrangements as described in the various embodiments herein. Accordingly, the end of the housing 12 will have structures similar to the internal biased fingers just described regarding the spacer member 28.

In operation and as can be appreciated from FIGS. 161-165, it is understood that the one end of the spacer member 28 is connected to the one end of the housing 12. The posts 590 on the second receiver member 92 are inserted into the openings 596 of the spacer member 28. The inclined cam surfaces 592 on the posts 590 push the fingers 600 inwardly wherein the ball-shaped proximal ends 604 move along the inclined surfaces 608 of the base member 606 compressing the biasing spring 612. Upon further insertion, the fingers 600 are biased by the spring 612 into the slots 594 in the posts 590 wherein the second receiver member 92 is connected to the spacer member 28. The opening of the second receiver member 92 can receive the USB connector 94 of the first projection member 90 to connect the ends of the device 10. As discussed, it is understood that the spacer member 28 has similar posts that are connected to the end of the housing 12 having similar biased fingers. If a spacer member 28 was not used, the posts 590 on the second receiver member 92 are inserted directly into the end of the housing 12 wherein similar connection structures are present.

FIGS. 166-169 disclose another alternative fastening mechanism 26. The fastening mechanism 26 utilizes a first projection member 90 and a second receiver member 92 that cooperate with ends of the housing 12. The first projection member 90 may include a USB connector 94 having leads as described herein with the appropriate operable connections. On one end of the rigid body of the USB connector 94, a slot 620 is defined therein. The slot 620 has a first segment 622 and a second segment 624 generally transverse to the first segment 622. The second receiver member 92 has an internal opening 626 and a depending projection 628 therein. The depending projection 628 has a first section 630 and a second section 632 that is generally transverse to the first section 630. When the first projection member 90 is inserted into the second receiver member 92, the projection 628 is received in the slot 620. In particular, the first segment 622 receives the first section 630 and the second segment 624 receives the second section 632. The engagement surface of the first segment 622 cooperates with the engagement surface on the first section 630 of the projection 628 to connect the members 90,92. To disconnect, a user squeezes the second receiver member 92 to provide a force F laterally inwardly as shown by the arrows in FIG. 169. In response, the second receiver member 92 expands upwardly and downwardly as shown by the arrows wherein the projection 628 is removed from the slot 620 wherein the first projection member 90 may be removed from the second receiver member 92.

FIGS. 170-173 disclose another alternative fastening mechanism 26. The first projection member 90 may be similar to prior embodiments and incorporate a body and the USB connector 94 having leads, other structures and the necessary operable connections as described herein. The connector 94 has a pair of notches 638 in lateral sides of the connector 94. The second receiver member 92 has a support body 641 having a central opening 640 (FIG. 173) to receive the USB connector 94. The second receiver member 92 also supports a pair of resiliently flexible fingers 642. Each finger 642 has a first segment 644 and a second segment 646 connected together at an end 648. One end of the first segment 644 is connected to the support body 641 and an intermediate portion 650 of the first segment 644 contacts the support body 641. A distal end of the second segment 646 has a latch member 652. It is understood that a sheath can be provided over the second receiver member 92 or the outer encasement member 24 of the housing 12 can be molded over the second receiver member 92 in an exemplary embodiment. In a connected position such as shown in FIG. 171, the first projection member 90 is inserted through the opening 640 and the latch members 652 are received in the notches 638. To disengage, the fingers 642 are squeezed through the housing 12 at the ends 648 and in the direction of the arrows shown in FIG. 171. This pivots the second segment 646 of the fingers 642 outwardly wherein the latch members 652 are removed from the notches 638. This allows the first projection member 90 to be removed from the second receiver member 92. Similarly when reconnecting, the USB connector 94 is inserted into the opening 640 wherein the second segments 646 are deflected until the latch members 652 are received in the notches 638 as can be appreciated from FIG. 171.

Figure 176:
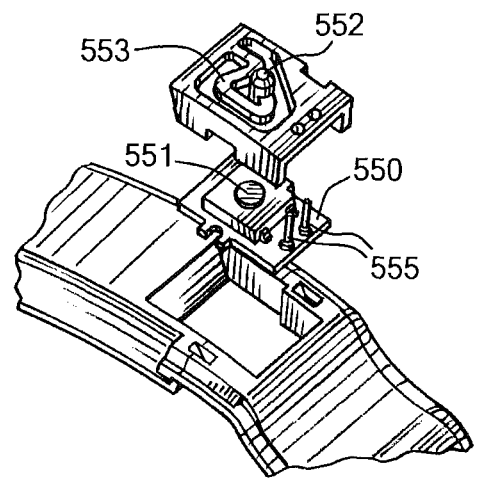
Figure 177:
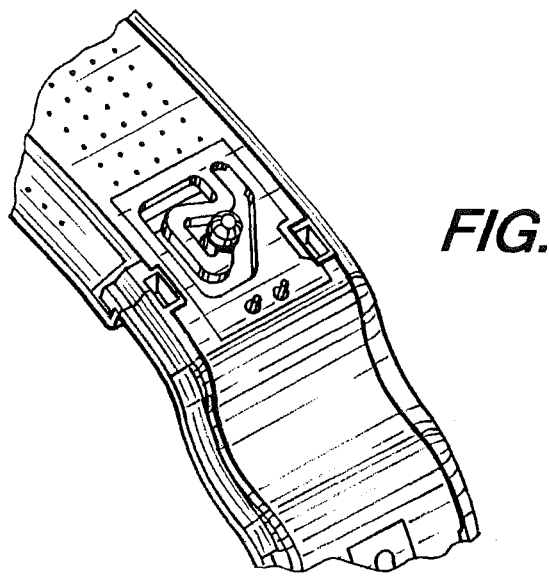
Figure 178:
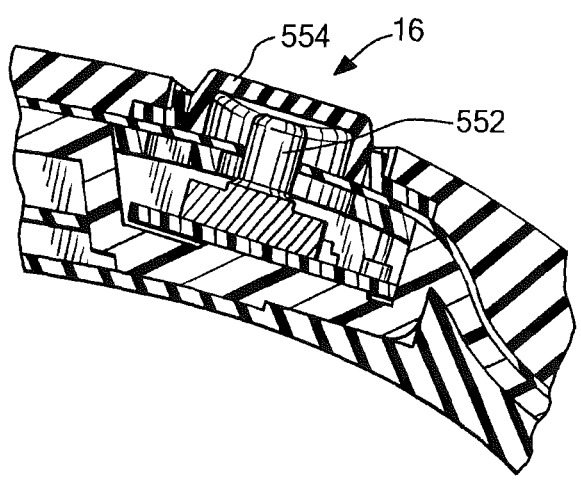

FIGS. 174-178 disclose an alternative embodiment of the input button 16 that can be used in the wearable device assembly 10 of the present invention. As shown in FIG. 176-178, the input button 16 has a base member 550 supporting a contact 551. The button 16 further has an activation post 552 as well as a flexible cap member 554. The activation post member 552 is supported by a resiliently flexible serpentine member 553 that is connected to the base member 550. The base member 550 is generally supported in a well located in the spine member 22 and is operably connected to the PCB member 140 via a pair of leads 555. The activation post 552 is connected onto the base member 550 and positioned over the contact 551. In addition, the activation post 552 has a generally cylindrical configuration and is received through a corresponding circular aperture formed in the PCB member 140. As shown in FIG. 178, the flexible cap member 554 is positioned over the post 552 and is supported on the PCB member 140. The flexible cap member 554 may have similar engagement surfaces as described above that are used when forming the outer encasement member 24 of the housing 12. Upon depression of the flexible cap member 554, the activation post 552 is deflected downward to engage the contact 551 to provide an input to the device 10.

It is further understood that the wearable device assembly 10 described herein can include additional modifications and features. For example, while the inner spine member is a polymeric member in one exemplary embodiment, the spine member may also be made from spring steel or other metallic materials having sufficient resilient flexibility. In another exemplary embodiment, the wearable device assembly 10 may utilize a single battery. In this exemplary embodiment, the spine member may have a single battery compartment. In such a configuration, any inner support member such as the spine member will have additional space and locations to support additional componentry such as additional sensors and larger displays and/or indicator systems. Such configuration further provides increase flexing options for the wearable device assembly 10. In another alternative embodiment, a single battery can be supported at a central location of the device such as at a central location of the inner spine member underneath the display. Such configuration can also provide similar benefits regarding flexibility and space for additional componentry as described above. The outer encasement member of the housing may also include materials having glow-in-the-dark characteristics which can enhance the display abilities of the device 10. The device 10 can also employ a display and/or indicator system utilizing side-firing LED elements. The use of light pipes could also be used in such designs. Such side-firing LED designs could be used with LEDs positioned at a central location of the device 10. In further exemplary embodiments, flexible battery leads may be utilized. For example, the battery may have a pair of leads each having a length extending between opposite ends. One end may be solder-connected to the battery and the other end may be solder-connected to the PCB member. When the battery is positioned in the battery compartment, the length of the battery lead may be folded upon itself, and then the battery closure member is connected over the battery. The batteries may also be subjected to various treatments such as heat treatments to enhance performance. The device 10 utilizes curved batteries and the curvature of the batteries can also be varied as desired. Other latch mechanism arrangements may also be utilized such as a hingedly attached member on the second receiver member pivotally attached to the first projection member. Latch mechanisms using a rotating pawl activated by a push button are also possible. As previously discussed, adhesion promoters can be utilized with the device when forming the outer encasement member over the spine member and PCB member to minimize any chances for air gaps to form between the inner components of the device and the inner surfaces of the outer encasement member. Eliminating any air gaps provides enhanced lighting of the display and indicator system through the housing 12, particularly enhancing the display of colored light through the housing 12. It is understood that the various features and structures of the various embodiments may be used in combination to form the wearable device assembly 10 of the present invention as well as utilize and incorporate the various user interface and experience features described herein.

Data Synchronization

As described herein, data recorded by an athletic activity monitoring device, such as device 10 and/or a mobile communication device (e.g., a smartphone), may be synchronized to one or more other systems (remote or local). In one example, the synchronization destination system may comprise a remote network site and system configured to track physical activity information for a community of users. Synchronization of data with an activity monitoring system may require the user to connect to the activity monitoring system and interact with one or more components thereof such as user interfaces, options, software modules and the like or combinations thereof. The user interfaces may be configured to convey information including product recommendations, informational articles, activity statistics, social networking data, user messages and the like.

According to one aspect, a game or other function of an activity monitoring device may allow a user to compete with another user based on various activity metrics. The game or other function may allow the user to specify a particular activity type, device type specific (e.g., capabilities of the device, device model, device manufacturer, device components) and the. Accordingly, activity data that does not match the specified activity type and/or device type might not be registered for the game or other function. In a particular example, a first portion of a user's activity data stored in the activity monitoring device may include data corresponding to the specified activity type and/or device type and a second portion that does not. Accordingly, only the first portion of the user's activity data may count toward a challenge, competition or game between the user and at least one other user. In some examples, the creator of a competition may specify an amount of activity required to win the competition. The amount of activity may be expressed in different metrics, if desired. Accordingly, the user may manually and individually specify an amount of activity required to win in each of the different metrics. In some examples, the amount of activity in each of the different metrics might not correspond to a direct conversion, while in other examples, the amounts may be direct conversions.

Figure 179:
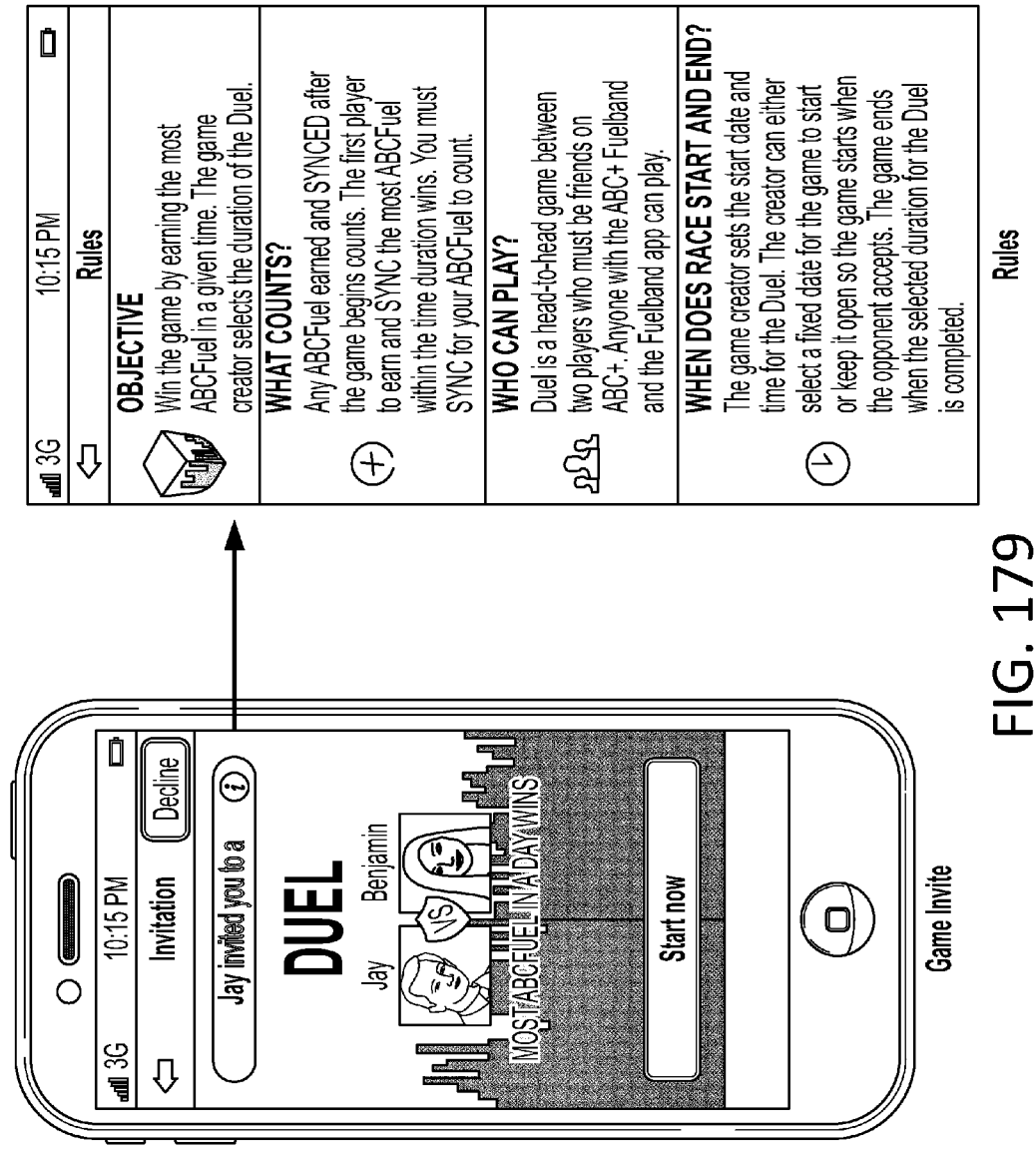
Figure 181D:
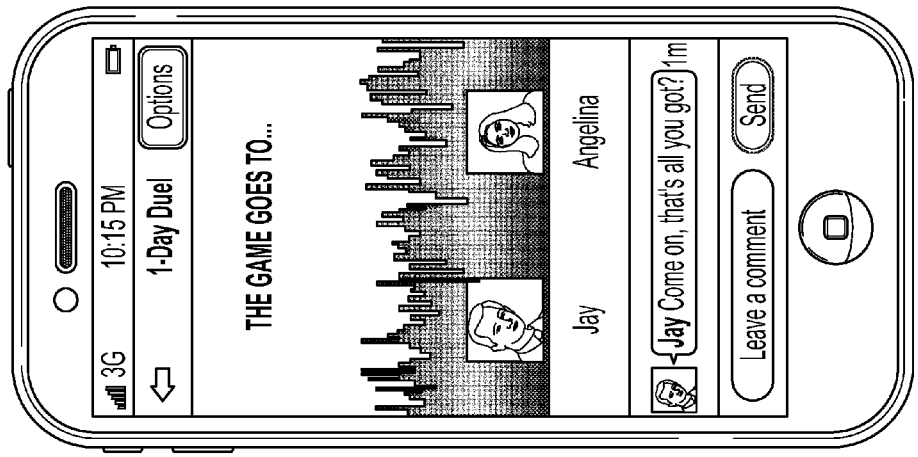
Figure 181E:
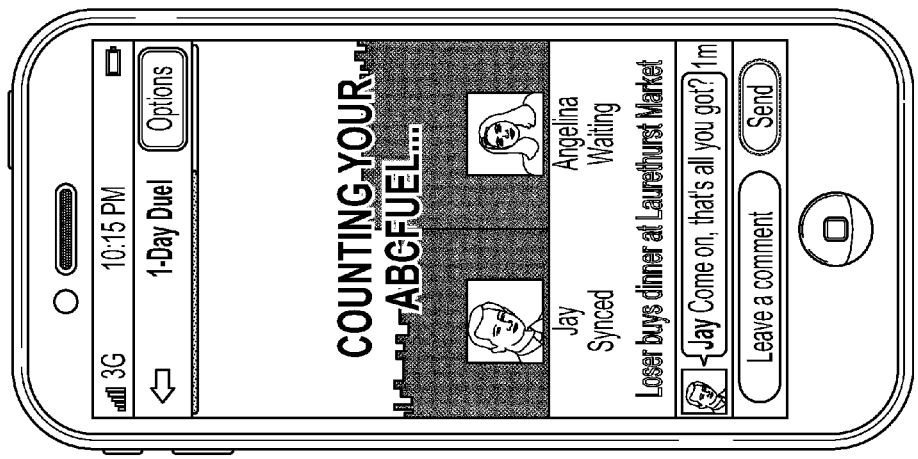
Figure 181F:
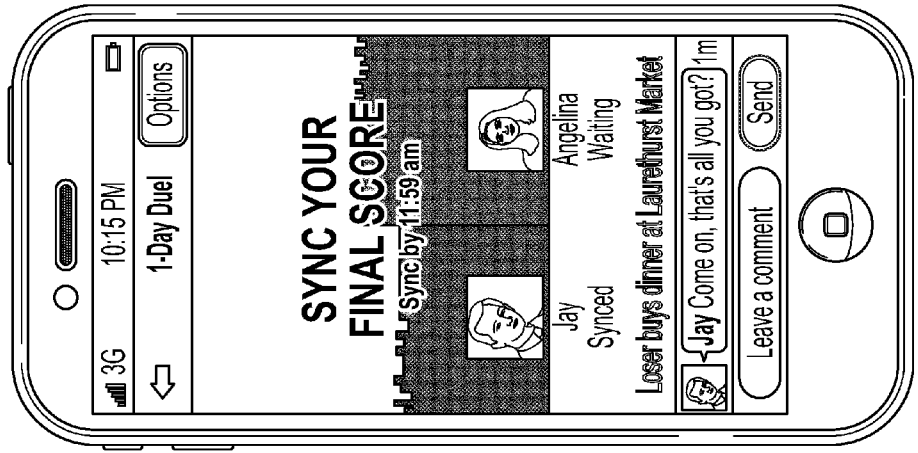

FIG. 179 illustrates an example activity monitoring game in which two or more users may compete to earn a specified amount of activity metric. As noted above, the game may be activity type and/or device type specific. Additionally, activity data might not count toward the game until the user synchronizes his or her data with an activity monitoring system. As such, even if the user records 100 miles on his or her activity monitoring device, the 100 miles will not count toward the game or other competition unless the data is synchronized to an activity monitoring system (e.g., a remote network site). Synchronization may include the transmission and/or storage of the data at the activity monitoring system. In some examples, a confirmation may be required to reflect that the data has been registered toward the game or challenge.

FIG. 180A illustrates an example synchronization interface for an activity challenge.

FIGS. 180B and 180C illustrate examples notification messages that may be provided to a user depending on a current challenge status. For example, if a user is falling behind, the user may be provided with a motivation message, as shown in FIG. 180B. FIG. 180C illustrates an example post-synchronization game status message. After data has been synchronized, the display may reflect a comparison between the competitor's registered activity.

FIGS. 181A-181F illustrate example synchronization interfaces. The interfaces may reflect whether each user has or has not synchronized their data. A final score or winner might only be determined once all users have synchronized their data (e.g., at or after the completion of the game).

In one or more arrangements, an objective of competition or challenge may be to accumulate a certain amount of activity in the shortest time. Such a challenge may encourage a user to synchronize his or her data as frequently as possible. Accordingly, this objective in conjunction with the requirement to synchronize the data for the data to count toward the objective, may allow an activity monitoring system to maximize user interactivity. For example, the activity monitoring system may be provided with more opportunities to convey information (such as product recommendations, reminders, advertisements, fitness advice, etc.) to the user and/or to receive information from the user. The increased frequency of receiving or transmitting data may allow the system to get closer to real-time accuracy of activity data among its community of users. A creator of a game may, in some arrangements, specify characteristics of users that are allowed to participate in the challenge. These characteristics may include location, height, weight, gender, age, level of athleticism (e.g., beginner, novice, intermediate, expert; low, medium, high, etc.) and the like and/or combinations thereof.

In yet other examples, a competition or activity monitoring system may require participants to synchronize data at a specified frequency (e.g., once every 30 minutes, twice every 15 minutes, once every hour, etc.) and/or at specified times. If the user does not synchronize the data accordingly the specified schedule, the user might only be permitted to synchronize data recorded for a next window of time. For example, if a user does not synchronize his or her data during a first 30 minute window for a challenge requiring synchronization every 30 minutes, the unsynchronized data (e.g., activity performed) recorded by the user for that first 30 minute window might not count toward the challenge. In another example, if a user does not synchronize his or her data at specified times (or within an amount of time of the specified times), the user's unsynchronized data prior to and up until the specified time might not count toward the challenge. Various other arrangements may be defined for a challenge.

CONCLUSION

While the invention has been described with respect to specific examples including presently preferred modes of carrying out the invention, those skilled in the art will appreciate that there are numerous variations and permutations of the above described systems and methods. For example, various aspects of the invention may be used in different combinations and various different subcombinations of aspects of the invention may be used together in a single system or method without departing from the invention. In one example, software and applications described herein may be embodied as computer readable instructions stored in computer readable media. Also, various elements, components, and/or steps described above may be changed, changed in order, omitted, and/or additional elements, components, and/or steps may be added without departing from this invention. Thus, the invention should be construed broadly as set forth in the appended claims.

What is claimed is:

1. A non-transitory computer readable medium storing instructions that, when executed, cause an apparatus to:
   detect, from data received from an accelerometer sensor integrated into the apparatus, activity performed by a user for an activity competition;
   determine that the activity performed by the user has been registered toward the activity competition only upon determining that activity data corresponding to the detected activity has been synchronized through a network system with at least one other apparatus;
   determine further activity data;
   determine a required synchronization frequency specified by the activity competition;
   trigger synchronization of the further activity data by movement of the apparatus; and determine whether synchronization of the further activity data was requested in accordance with the required synchronization frequency.

2. The non-transitory computer readable medium of claim 1, wherein the network system is located remotely from the apparatus.

3. The non-transitory computer readable medium of claim 1, wherein detecting activity performed by the user includes:
   receiving data corresponding to the activity performed by the user;
   determining a type of activity specified for the competition; and
   extracting only data corresponding to the determined type of activity as the activity data to be synchronized.

4. The non-transitory computer readable medium of claim 1, wherein detecting activity performed by the user includes:
   receiving data corresponding to the activity performed by the user;
   determining a type of device specified for the competition; and
   extracting only data corresponding to the determined type of device as the activity data to be synchronized.

5. The non-transitory computer readable medium of claim 1, wherein the instructions, when executed, further cause the apparatus to:
   connecting to the at least one other apparatus through a wireless connection; and
   transmitting the activity data to the at least one other apparatus.

6. The non-transitory computer readable medium of claim 1, wherein determining that the activity data corresponding to the detected activity has been synchronized with the at least one other apparatus includes receiving a synchronization confirmation from the at least one other apparatus.

7. The non-transitory computer readable medium of claim 1, wherein the instructions, when executed, further cause the apparatus to:
   determine further activity data;
   determine a required synchronization frequency specified by the activity competition; and
   synchronize the further activity data with the at least one other apparatus based on the required synchronization frequency.

8. The non-transitory computer readable medium of claim 7, wherein synchronizing the further activity data include receiving information from the at least one other apparatus.

9. The non-transitory computer readable medium of claim 1, where in response to determining that the synchronization of the further activity data was not requested in accordance with the required synchronization frequency, preventing the further activity data from being synchronized with the at least one other apparatus.

10. A method comprising:
   detecting, from data received from an accelerometer sensor integrated into an apparatus, activity performed by a user for an activity competition;
   determining that the activity performed by the user has been registered toward the activity competition only upon determining that activity data corresponding to the detected activity has been synchronized through a network system with at least one other apparatus;
   determine further activity data;
   determine a required synchronization frequency specified by the activity competition;

trigger synchronization of the further activity data by movement of the apparatus; and determine whether synchronization of the further activity data was requested in accordance with the required synchronization frequency.

11. The method of claim 10, wherein the network system is located remotely from the apparatus.

12. The method of claim 10, wherein detecting activity performed by the user includes:

receiving data corresponding to the activity performed by the user;

determining a type of activity specified for the competition; and extracting only data corresponding to the determined type of activity as the activity data to be synchronized.

13. The method of claim 10, wherein detecting activity performed by the user includes:

receiving data corresponding to the activity performed by the user;

determining a type of device specified for the competition; and extracting only data corresponding to the determined type of device as the activity data to be synchronized.

14. The method of claim 10, further comprising:

connecting to the at least one other apparatus through a wireless connection; and transmitting the activity data to the at least one other apparatus.

15. The method of claim 10, wherein determining that the activity data corresponding to the detected activity has been synchronized with the at least one other apparatus includes receiving a synchronization confirmation from the at least one other apparatus.

16. The method of claim 10, further comprising:

in response to determining that the synchronization of the further activity data was not requested in accordance with the required synchronization frequency, preventing the further activity data from being synchronized with the at least one other apparatus.

* * * * *